(12) United States Patent
Khan et al.

(10) Patent No.: US 7,645,769 B2
(45) Date of Patent: Jan. 12, 2010

(54) INHIBITORS OF C-JUN N-TERMINAL KINASES FOR THE TREATMENT OF NEURODEGENERATIVE DISORDERS RELATING TO APOPTOSIS AND/OR INFLAMMATION

(75) Inventors: Afzal Khan, London (GB); Darren Peter Medland, London (GB); Gurpreet Singh Bhatia, London (GB)

(73) Assignee: Eisai R & D Management Co., Ltd. (JP)

( * ) Notice: Subject to any disclaimer, the term of this patent is extended or adjusted under 35 U.S.C. 154(b) by 97 days.

(21) Appl. No.: 11/499,334

(22) Filed: Aug. 4, 2006

(65) Prior Publication Data
US 2007/0072896 A1 Mar. 29, 2007

(30) Foreign Application Priority Data
Aug. 5, 2005 (GB) ................................. 0516156.7

(51) Int. Cl.
C07D 471/04 (2006.01)
A61K 31/4375 (2006.01)
(52) U.S. Cl. .................. 514/300; 546/113; 544/126
(58) Field of Classification Search ................ 546/113; 514/300
See application file for complete search history.

(56) References Cited

U.S. PATENT DOCUMENTS

| | | | |
|---|---|---|---|
| 4,719,218 A | 1/1988 | Bender et al. | |
| 5,439,917 A | 8/1995 | Briving et al. | |
| 5,714,495 A | 2/1998 | Viaud et al. | |
| 6,642,375 B2 | 11/2003 | Inomata et al. | |
| 7,291,630 B2 | 11/2007 | Graczyk et al. | |
| 7,314,940 B2 | 1/2008 | Graczyk et al. | |
| 2002/0013354 A1 | 1/2002 | Cheng et al. | |
| 2005/0272761 A1 | 12/2005 | Graczyk et al. | |
| 2006/0235042 A1 | 10/2006 | Graczyk et al. | |
| 2006/0270646 A1 | 11/2006 | Graczyk et al. | |
| 2007/0142366 A1 | 6/2007 | Graczyk et al. | |

FOREIGN PATENT DOCUMENTS

| | | |
|---|---|---|
| EP | 0 509 974 | 10/1992 |
| EP | 0 737 685 | 10/1996 |
| EP | 1 106 621 | 6/2001 |
| JP | 06 247966 A | 9/1994 |
| WO | WO-92/10498 A1 | 6/1992 |
| WO | WO-92/10499 A1 | 6/1992 |
| WO | WO-98/47899 | 10/1998 |
| WO | WO-99/20624 | 4/1999 |
| WO | WO-99/21859 | 5/1999 |
| WO | WO-99/51233 | 10/1999 |
| WO | WO-00/26210 | 5/2000 |
| WO | WO-00/26211 | 5/2000 |
| WO | WO-00/35909 | 6/2000 |
| WO | WO-00/35921 A1 | 6/2000 |
| WO | WO-00/43393 | 7/2000 |
| WO | WO-00/56710 | 9/2000 |
| WO | WO-00/64449 | 11/2000 |
| WO | WO-00/64872 | 11/2000 |
| WO | WO-01/12609 | 2/2001 |
| WO | WO-01/47922 | 7/2001 |
| WO | WO-01/49288 | 7/2001 |
| WO | WO-02/10137 | 2/2002 |
| WO | WO-02/16359 | 2/2002 |
| WO | WO-02/081475 | 10/2002 |
| WO | WO-03/028724 | 4/2003 |
| WO | WO-03/082868 | 10/2003 |
| WO | WO-03/082869 | 10/2003 |
| WO | WO-2004/016609 | 2/2004 |
| WO | WO-2004/016610 | 2/2004 |
| WO | WO-2004/078756 | 9/2004 |
| WO | WO2005085224 | * 3/2005 |

OTHER PUBLICATIONS

Jones, M. Organic Chemistry Norton: New York, 1997, pp. 578-591.*
Nguyen et. al. "The First General Palladium Catalyst for the Suzuki-Miyaura and Carbonyl Enolate Coupling of Aryl Arenesulfonates" Journal of the American Chemical Society 2003, 125,11818-11819.*
Dorwald F. A. Side Reactions in Organic Synthesis, 2005, Wiley: VCH, Weinheim p. IX of Preface.*
Michelotti et. al. "Two classes of p38a MAP kinase inhibitors having a common diphenylether core but exhibiting divergent binding modes" Bioorganic & Medicinal Chemistry Letters 2005, 15, 5274-5279.*
Jiang et. al. "3,5-Disubstituted quinolines as novel c-Jun N-terminal kinase inhibitors." Bioorganic & Medicinal Chemistry Letters 2007, 17, 6378-6382.*
Liu et. al. "Synthesis and SAR of 1,9-dihydro-9-hydroxypyrazolo[3,4-b]quinolin-4-ones as novel, selective c-Jun N-terminal kinase inhibitors" Bioorganic & Medicinal Chemistry Letters 2006, 16, 2590-2594.*
Resnick, et al. "Targeting JNK3 for the Treatment of Neurodegenerative Disorders", Drug Discovery Today, Elsevier Science LTD. 9:21 (2004) pp. 932-939.
European Search Report, 06254089.3.

(Continued)

Primary Examiner—Janet L Andres
Assistant Examiner—David K O'Dell
(74) Attorney, Agent, or Firm—Wilmer Cutler Pickering Hale & Dorr LLP.

(57) ABSTRACT

The present invention provides novel compounds of formula I and their use in the inhibition of c-Jun N-terminal kinases. The present invention further provides the use of these compounds in medicine, in particular in the prevention and/or treatment of neurodegenerative disorders related to apoptosis and/or inflammation.

(I)

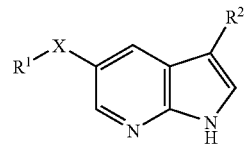

14 Claims, No Drawings

OTHER PUBLICATIONS

U.S. Appl. No. 10/591,551, filed May 1, 2008, Graczyk et al.
U.S. Appl. No. 12/143,231, filed Jun. 20, 2008, Graczyk et al.
Adams et al., Bioorg. Med. Chem. Lett. 2001, 11, 2867-2870.
Alam et al., Synthesis and SAR of aminopyrimidines as novel c-Jun N-terminal kinase (JNK) inibitors:, Bioorg Med Chem Lett, vol. 17, pp. 3463-3467, 2007.
Bundgaard, Design of ProDrugs, Elsevier Science Publishers 1985.
Cao et al., "Distinct Requirements for p38α and c-Jun N-terminal Kinase Stress-activated Protein Kinases in Different Forms of Apoptotic Neuronal Death", *The Journal of Biological Chemistry*, vol. 279, No. 34, pp. 35903-35913, Aug. 20, 2004.
CAS Accession No. 2001:432896, Registry No. 344454-31-1.
CAS Document No. 135:107148.
CAS document No. 135:43132.
Corey, E.Jr., et. al.., A synthetic Method for Formyl-Ethynyl Conversion (RCHO-RC=CH or RC=CR'), Tetrahedron Letters No. 36, Aug. 1972.
Database Beilstein, Beilstein Institute for Organic Chemistry, Citation No. 5563002 (1987).
Denmark et al., "Convergence of Mechanistic Pathways in the Palladium(0)-Catalyzed Cross-Coupling of Alkenylsilacyclobutanes and Alkenylsilanols"*Organic Letters*. vol. 2, No. 16, pp. 2491-2494. (2000).
Denmark et al., "Highly Stereospecific, Palladium-Catalyzed Cross-Coupling of Alkenylsilanols" *Organic Letters* vol. 2, No. 4, pp. 565-568 (2000).
Dhar, et al., "The TosMIC Approach to 3-(Oxazol-5-yl) Indoles: Application to the Synthesis of Indole-Based IMPDH Inhibitors," Bioorganic & Medicainal Chemistry Letters, 2002.
Eilers et al., "Direct Inhibition of c-Jun N-terminal Kinase in Sympathetic Neurones Prevents *c-jun* Promoter Activation and NGF Withdrawal-induced Death", *Journal of Neurochemistry*. vol. 76, pp. 1439-1454, 2001.
Eilers et al., "Role of the Jun Kinase Pathway in the Regulation of c-Jun Expression and Apoptosis in Sympathetic Neurons", *The Journal of Neuroscience*. vol. 18, No. 5, pp. 1713-1724, Mar. 1, 1998.
Estus et al., "Aggregated Amyloid-β Protein Induces Cortical Neuronal Apoptosis and Concomitant "Apoptotic" Pattern of Gene Induction", *The Journal of Neuroscience*, vol. 17, No. 20, pp. 7736-7745, Oct. 15, 1997.
Golub et al., Science, vol. 286, pp. 531-537, Oct. 15, 1999.
Greene, T. and Wuts, P., *Protective Groups in Organic Synthesis* 3rd Edidtion, Wiley, New York (1999).
Guillard, et al., "Synthesis of New Maltonin Analogues from Dimers of Azaindole and Indole by Use of Suzuki Monocoupling", Heterocycles, vol. 60, No. 4, pp. 865-877 (2003).
Ham et al., "A c-Jun Dominant Negative Mutant Protects Sympathetic Neurons against Programmed Cell Death", *Neuron*, vol. 14, pp. 927-939, May, 1995.
Harper and LoGasso, *Drugs of the Future* 2001, 26, 957-973.
Harper et al., "Inhibitors of the JNK Signaling Pathway", *Drugs of the Future*, vol. 26, No. 10, pp. 957-973, 2001.
Hatanaka et al., "Cross-Coupling of Organosilanes with Organic Halides Mediated by Palladium Catalyst and Tris(diethylamino)sulfonium Difluorotrimethylsilicate" *J. Org. Chem* 53 pp. 918-920 (1988).
Hatanaka et al., "Highly Selective Cross-Coupling Reactions of Organosilicon Compounds Mediated by Fluoride Ion and a Palladium Catalyst", *Synlett* pp. 845-853 (1991).
Henry et al, Bioorg. Med. Chem. Lett. 1998, 8, 3335-3340.
Houwing, et al., Preparation of N-Tosylmethylimino Compounds and their Use in the Synthesis of Oxazoles, Imidazoles and Pyrroles, Tetrahedron Letters No. 2, 1976.
International Search Report for PCT/GB2004/002099, mailed Dec. 2, 2004, 4 pages.
International Search Report for PCT/GB2005/000779, mailed Aug. 12, 2005, 4 pages.
Krasnokutskaya et al., *Khim. Geterotsikl. Soed* No. 3 pp. 380-384 (1977).
Kruber, Caplus, Copyright 2007 ACS on STN, 2 pages.
Kumar et al, "Synthesis of 7-Azaindole and 7-Azaoxindole Derivatives through a Palladium-Catalyzed Cross Coupling Reaction", J. Org. Chem, 57, pp. 6995-6998 (1992).
Lecointe, Reach-trhough Claims, International Pharmaceutical (2002)(also available at <http:////www.bakerbotts.com/infocenter/publications/detail.aspx?id=bffe4a7d-5beb-4cf8-a189-15a190f0eb>).
Lisnock et al., "Activation of JNK3α1 Requires Both MKK4 and MKK7: Kinetic Characterization of in Vitro Phosphorylated JNK3α1", *Biochemistry*, vol. 39, pp. 3141-3149, 2000.
Littke et al., "Pd/P(t-Bu)$_3$: A Mild and General Catalyst for Stille Reactions of Aryl Chlorides and Aryl Bromides" *J. Am. Chem. Soc.* 124 pp. 6343-6348 (2002).
Littke et al., "Versatile Catalysts for the Suzuki Cross-Coupling of Arylboronic Acids with Aryl and Vinyl Halides and Triflates under Mild Conditions" *J. Am. Chem. Soc.* 122 pp. 4020-4028 (2000).
Martin et al., "Palladium-Catalyzed Cross-Coupling Reactions of Organoboronic Acids with Organic Electrophiles" *Acta Chemica Scandinavica* 47, pp. 221-230 (1993).
Merour et al., Synthesis and Reactivity of 7-Azaindoles (1H-Pyrrolo[2,3-b]pyridine) *Current Organic Chemistry* 5 pp. 471-506 (2001).
Mettey, et al., "Aloisines, a New Family of CDK/GSK-3 Inhibitors. SAR STudy, Crystal Structure in Complex with CDK2, Enzyme Selectivity and Cellular Effects", J. Med. Chem, 46, pp. 222-236 (2003).
Mitchell, T. "Palladium-Catalysed Reactions of Organotin Compounds" *Synthesis* pp. 803-815 (1992).
Park et al, "A FAcile Synthesis of 2,3-Disubstitute Pyrrolo[2,3-b]pyridines via Palladium-Catalyzed Heteroannulation with Internal Alkynes", Tetrahedron Letters 39, pp. 627-630 (1998).
Pisano et al, "Bis-indols: a Novel Class of Molecules Enhancing the Cytodifferentiating Properties of Retinoids in Myeloid Leukemia Cells", Blood, vol. 100, No. 10, pp. 3719-3730 (2002).
Silva, "Reach through Claims: Bust or Boon?", Intellectual Property Update (available at <http://www.dorsey.com/publlications/legal_detail.aspx?FlashNavID=pubs_legal&pubid=170565003>).
Smulik and Diver, "Synthesis of Cyclosporin A-Derived Affinity Reagents by Olefin Metathesis", Organic Letters, vol. 4, No. 12, pp. 2051-2054, 2002.
Stille, J.K., "The Palladium-Catalyzed Cross-Coupling Reactions of Organotin REagents with Organic Electrophiles" *Angew. Chem. Int. Ed. Engl.* 25 pp. 508-524 (1986).
Suzuki, A. "Synthetic Studies via the Cross-Coupling REaction of Organoboron Derivatives with Organic Halides" *Pure Appl. Chem* vol. 63, No. 3 pp. 419-422 (1991).
Tamao et al., "Palladium-Catalyzed Cross-Coupling REaction of Alkenylalkosysilanes with Aryl and Alkenyl Halides in the Presence of a Fluoride Ion" *Tetrahedron Letters*, vol. 30, No. 44 pp. 6051-6054 (1989).
Taylor et al., "Intramolecular Diels-Alder Reactions of 1,2,4-Triazines" *Tetrahedron*, vol. 43, No. 21 pp. 5145-5158 (1987).
Van Leusen, et al., Chapter 3: Synthetic Uses of Tosylmethyl Isocyanide (TosMIC), Organic Reactions, vol. 57, 2001.
Vippagunta et al., "Crystalline Solids", Advanced Drug Delivery Reviews, vol. 48, No. 1; pp. 3-26, 2001.
Watson et al., "Phosphorylation of c-Jun in Necessary for Apoptosis Induced by Survival Signal Withdrawal in Cerebellar Granule Neurons", *The Journal of Neuroscience*, vol. 18, No. 2, pp. 751-762, Jan. 15, 1998.
West, Anthony R., "Solid State Chemistry and its Applications", Wiley, NY 1988.
Witherington et al., "5-Aryl-pyrazolo [3,4-b]pyridines: Potent Inhibitors of Glycogen Synthase Kinase-3 (GSK-3)", Bioorganic & Medicinal Chemistry Letters 13, pp. 1577-1580 (2003).
Young et al., "Pyridinyl Imidazole Inhibitors of p38 Mitogen-activated Protein Kinase Bind in the ATP Site", *The Journal of Biological Chemistry*, vol. 272, No. 18, pp. 12116-12121, May 2, 1997.
Zevaco, T. et al., Bismuth (III) Pyridine—and Pyrazine-Carboxylates, *New J. Chem..*, vol. 15, pp. 927-930, 1991.

Kontoyiannis et al., "Imparied On/Off Regulation of TNF Biosynthesis in Mice Lacking TNF AU-Rich Elements: Implications for Joint and Gut-Associated Immunopathologies", Immunity, (Mar. 1999) vol. 10, pp. 387-398.

Leroy et al., "Homochiral NADH models in the pyrrolo[2,3-b]pyridine series bearing one or two chiral auxiliaries. Asymmetric reduction of methyl benzoylformate and N-acetyl-enamines. Influence of the magnesium salt concentration on the asymmetric induction of reductions." Tetrahedron: Asymmetry, vol. 8, No. 19, pp. 3309-3318, 1997.

Han, Z. et al., "Jun N-Terminal Kinase in Rheumatoid Arthritis," J. of Pharmacol. Exper. Therap. 291(1): 124-130 (1999).

Kontoyiannis et al., Immunity, (Mar. 1999) vol. 10, No. 3, pp. 387-398.

Leroy et al., Tetrahedron: Asymmetry (1997), 8(19), 3309-3318.

Peng, J. and Andersen, J.K., "The Role of c-Jun N-Terminal Kinase (JNK) in Parkinson's Disease," Life 55(4-5): 267-271, Apr.-May 2003.

* cited by examiner

INHIBITORS OF C-JUN N-TERMINAL KINASES FOR THE TREATMENT OF NEURODEGENERATIVE DISORDERS RELATING TO APOPTOSIS AND/OR INFLAMMATION

The present invention relates to novel compounds, their use in the inhibition of c-Jun N-terminal kinases, their use in medicine and particularly in the prevention and/or treatment of neurodegenerative disorders related to apoptosis and/or inflammation. The invention also provides processes for manufacture of said compounds, compositions containing them and processes for manufacturing such compositions.

c-Jun N-terminal kinases (hereinafter referred to as "JNKs") are members of the mitogen-activated protein kinase (MAPK) family. JNKs are involved in response to various stimuli, including proinflammatory cytokines and environmental stress. JNKs, and JNK3 in particular, play an important role during apoptotic death of cells and therefore have been implicated in various disorders including stroke, traumatic brain injury and other neurodegenerative diseases such as Parkinson's disease, Alzheimer's disease and others. Since JNK activity is a physiological regulator of AP-1 transcriptional activity, JNK inhibitors are expected to reduce inflammatory response.

Apoptosis is a form of cell death in which the cell actively participates in its own destruction in a process involving a characteristic series of biochemical and morphological changes, which are regulated by specific cell death genes. The apoptotic cell death is a process that has been observed in the developing mammalian nervous system. In mice, the inactivation by homologous recombination of genes that encode proteins that promote apoptosis, such as the caspase-3 or the Bax protein, prevents developmental neuronal cell death. The destruction of genes that encode cell death suppressors such as Bcl-x, leads to enhanced neuronal cell death. There is increasing evidence that apoptosis plays an important role in the pathology of acute and chronic neurodegenerative diseases. For example, in transgenic mice overexpressing the anti-apoptotic Bcl-2 protein in the nervous system there is a decrease in infarct volume following cerebral ischemia. Similarly, injection of the caspase inhibitor BAF reduces neuronal cell death following hypoxia/ischaemia in neonatal rats. Another example is spinal muscular atrophy (a motor neuron disease) where loss of function mutations in the SMN gene is associated with the disease. Recent data has shown that the wild type SMN protein binds to Bcl-2 and co-operates with it to inhibit apoptosis. These results suggest that inhibitors of neuronal apoptosis could be beneficial in the treatment of human neurodegenerative diseases. There is increasing evidence that neuronal apoptosis is an important pathological feature of stroke, traumatic brain injury and other neurodegenerative diseases. Therefore, pharmacotherapy using inhibitors of neuronal apoptosis may provide a therapeutic benefit in neurodegenerative conditions.

A number of groups have studied the mechanisms of neuronal cell death using in vitro cell culture systems and the results suggest that in some systems the transcription factor c-Jun is activated by the removal of survival signals and promotes cell death.

Antibodies specific for c-Jun protected NGF-deprived rat sympathetic neurones from apoptosis. Analogous neuroprotection due to expression of a c-Jun dominant negative mutant has been demonstrated, whereas overexpression of wild type c-Jun protein was sufficient to induce apoptosis in the presence of NGF. Estus and co-workers recently showed that an increase in c-Jun RNA levels occurs in cortical neurones undergoing apoptosis after treatment with β-amyloid peptide. It has also been shown that c-Jun is required for apoptosis in cerebellar granule neurones deprived of survival signals.

c-Jun is activated by JNKs, which phosphorylate its transcriptional activation domain. In humans there are three JNK genes: JNK1, JNK2 and JNK3. The RNAs encoding JNK1 and JNK2 are expressed in many tissues, including the brain, but JNK3 is restricted to the nervous system and to a smaller extent the heart and testes.

JNKs are strongly activated in cellular responses to various stresses such as UV radiation, heat shock, osmotic shock, DNA-damaging agents, and proinflammatory cytokines such as TNFα, IL-1β and others. Upstream regulators of the JNK pathway include kinases such as SEK1, MKK7 and MEKK1. There is evidence that Jun kinase activity is required for neuronal apoptosis in vitro. Overexpression of MEKK1 in sympathetic neurones increased c-Jun protein levels and phosphorylation and induced apoptosis in the presence of NGF indicating that activation of the Jun kinase pathway can trigger neuronal cell death. The Jun kinase pathway has been shown to be necessary for the death of differentiated PC12 cells deprived of NGF. Furthermore, compound CEP-1347, which inhibits the c-Jun pathway (upstream of Jun kinase), protects motor neurones against cell death induced by survival factor withdrawal.

In JNK3 homozygous (−/−) knockout mice, epileptic seizures and death of hippocampal CA3 neurones induced by injection of kainic acid is blocked. This indicates that JNK3 is involved in certain forms of neuronal cell death in vivo. It is also a critical component of GluR6-mediated excitotoxicity. Furthermore, JNK3 (−/−) mice appear to develop normally and are viable suggesting that JNK3 is not essential for development or viability.

Strong nuclear JNK3 immunoreactivity in the brain CA1 neurones of patients with acute hypoxia suggests that JNK3 is involved in hypoxia-related neurodegeneration. Transient hypoxia may also trigger apoptosis through JNK signaling pathway in developing brain neurones.

Furthermore, JNK3 immunoreactivity is colocalized with Alzheimer disease-affected neurones. Moreover JNK3 is related to neurofibrillary pathology of Alzheimer disease. In particular, JNK3 induces robust phosphorylation of amyloid precursor protein (APP) thus affecting its metabolism in disease state.

The present inventors have provided compounds, which are inhibitors of c-Jun N-terminal kinases.

The first aspect of the invention therefore relates to a compound of formula (I) as illustrated below:

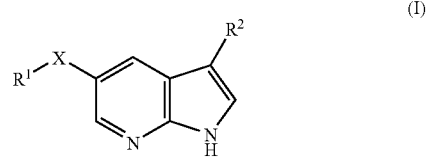

(I)

wherein X is O, S, C(R$^4$)$_2$, SO, SO$_2$, NR$^3$, NR$^3$—C(O)— or NR$^3$—C(O)—O—;

R$^1$ is hydrogen, C$_{1-10}$ alkyl, C$_{2-10}$ alkenyl, C$_{2-10}$ alkynyl, C$_{3-10}$ aryl, C$_{3-10}$ cycloalkyl, C$_{3-10}$ cycloalkenyl or C$_{3-10}$ heterocyclyl;

said R$^1$ group being optionally substituted with one or more of C$_{1-6}$ alkyl, C$_{1-10}$ alkoxy, C$_{3-10}$ cycloalkyl, halo, hydroxy, oxo, CO$_2$R$^5$, C$_{3-10}$aryl, C$_{3-10}$heterocyclyl, C$_{1-6}$alkylC$_{3-10}$ aryl, $NR^6{}_2$ and wherein the $C_{3-10}$ heterocyclyl group can be further optionally substituted with $C_{1-6}$ alkyl; and $R^2$ is a 3-10 membered heterocyclyl; said $R^2$ group being optionally substituted with one or more of $C_{1-6}$ alkyl, $CO_2H$, $C_{3-10}$heterocyclyl, $CO$—$C_{3-10}$heterocyclyl, $C_{1-6}$alkyl$C_{3-10}$heterocyclyl and wherein the heterocyclyl group can be further optionally substituted with a $C_{1-6}$ alkyl group;

wherein
$R^3$ is hydrogen or $C_{1-6}$ alkyl;
$R^4$ is hydrogen or $C_{1-6}$ alkyl;
$R^5$ is hydrogen or $C_{1-6}$ alkyl; and
$R^6$ is hydrogen or $C_{1-6}$ alkyl.

and the pharmaceutically acceptable salts, and other pharmaceutically acceptable biohydrolyzable derivatives thereof, including esters, amides, carbamates, carbonates, ureides, solvates, hydrates, affinity reagents or prodrugs thereof.

$R^1$ is preferably an unbranched alkyl group having 2, 3, 4, 5 or 6 carbon atoms, an unbranched alkenyl or alkynyl group having 2, 3, 4, 5 or 6 carbon atoms, or a $C_5$ or $C_6$ cycloalkyl or a $C_{3-10}$aryl group. $R^1$ can be an aryl or heterocyclyl group having 3, 4, 5, 6, 7, 8, 9 or 10 members, preferably an optionally substituted five or six membered aryl or heteroaryl group wherein the aryl or heterocyclyl group is optionally fused to one or more unsaturated rings. The group $R^1$ is preferably substituted with one or more of $C_{1-6}$ alkyl or a halo group. When $R^1$ is substituted with a $C_{3-10}$heterocyclyl group, the $C_{3-10}$heterocyclyl group is preferably a group

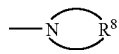

wherein the $R^8$ group is a C4 or C5-alkyl or alkenyl group, preferably an alkyl group which with the nitrogen atom, forms a five or six-membered ring. The alkyl or alkenyl group of $R^8$ can optionally be interrupted with one or more heteroatoms selected from O, S or $NR^9$ wherein $R^9$ is hydrogen or a $C_{1-6}$ alkyl group preferably methyl or ethyl. The alkyl or alkenyl group and/or the heteroatoms can be substituted with $C_{1-6}$ alkyl. The heterocyclyl group is preferably unsaturated and is preferably one or more of piperidine, morpholine and piperazine optionally substituted at the nitrogen atom with a $C_{1-6}$ alkyl group.

$R^1$ is preferably selected from optionally substituted phenyl, acridine, benzimidazole, benzofuran, benzothiophene, benzoxazole, benzothiazole, cyclohexyl furan, imidazole, indole, indoline, isoindole, isoindoline, isoquinoline, isoxazole, isothiazole, morpholine, napthaline, oxazole, phenazine, phenothiazine, phenoxazine, piperazine, piperidine, pyrazole, pyridazine, pyridine, pyrrole, quinoline, quinolizine, tetrahydrofuran, tetrazine, tetrazole, thiophene, thiazole, thiomorpholine, thianaphthalene, thiopyran, triazine, triazole or trithiane.

More preferably $R^1$ is phenyl or optionally substituted phenyl.

As discussed above, $R^1$ can be optionally substituted at any position on the aryl, heterocyclyl or optional fused ring.

Substitution can occur at the ortho, meta or para positions relative to the pyridine ring. When $R^1$ is a six-membered ring, substitution is preferably at the ortho and/or para positions, more preferably at the para position.

When $R^1$ is a five membered ring, the aryl group is preferably substituted at the ortho or para position. $R^1$ is preferably substituted at the ortho or para position with one or more of halogen, or $C_{1-4}$ alkyl.

$R^2$ is preferably a 5-membered heterocycle comprising one or more heteroatoms selected from O, S or N. $R^2$ can be optionally substituted with one or more of $C_{1-6}$ alkyl, $CO_2H$, $C_{3-8}$ heterocyclyl, $C_{1-6}$alkyl$C_{3-8}$ heterocyclyl or $CO$—$C_{3-8}$ heterocyclyl. In particular, one or more of said heteroatoms in $R^2$ can be optionally substituted with $C_{1-6}$ alkyl, The $R^2$ group may be optionally substituted with an alkyl group having 1, 2, 3, 4, 5 or 6 carbon atoms. In particular the optional substitution can occur at one or more of O, S or N in the heterocycle. The $R^2$ group can be substituted with a group $CONR^7R^7$ wherein each $R^7$ can independently be a $C_{1-6}$ alkyl group, preferably methyl or ethyl. Alternatively, the $R^2$ group can be substituted with a group

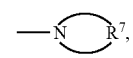

wherein $R^7$ is a C4 or C5-alkyl or alkenyl group, preferably an alkyl group which, with the nitrogen atom, forms a five or six-membered ring. The alkyl or alkenyl group of $R^8$ can optionally be interrupted with one or more heteroatoms selected from O, S or $NR^{10}$ wherein $R^{10}$ is hydrogen or a $C_{1-6}$ alkyl, preferably methyl or ethyl. The alkyl or alkenyl group and/or the heteroatoms can be substituted with $C_{1-6}$ alkyl. The heterocyclyl group is preferably unsaturated and is one or more of piperidine, morpholine and piperazine optionally substituted at an available nitrogen atom with a $C_{1-6}$ alkyl group.

More preferably, $R^2$ is a 5-membered heterocycle comprising two or more heteroatoms selected from O, S or N. $R^2$ may be a 5-membered heterocycle selected from, furan, imidazole, imidazoline, imidazolidine, isoxazole, isothiazole, oxazole, oxadiazole, oxathiazole, oxathiazolidine, pyrazole, pyrazoline, pyrazolidine, pyrrole, tetrahydrofuran, tetrazole, thiophene, thiadiazine, thiazole or triazole.

X is selected from O, S, $C(R^4)_2$, SO, $SO_2$, $NR^3$, $NR^3$—$C(O)$ or $NR^3$—$C(O)$—O wherein $R^3$ is preferably hydrogen or $C_{1-4}$ alkyl, more preferably an alkyl group having 1, 2 or 3 carbon atoms and $R^4$ is preferably hydrogen or $C_{1-4}$ alkyl, more preferably an alkyl group having 1, 2 or 3 carbon atoms.

Preferably X is O, S, $CH_2$, SO, $SO_2$, NH, NH—$C(O)$— or NH—$C(O)$—O.

In particular, the first aspect of the invention includes compound of formula II

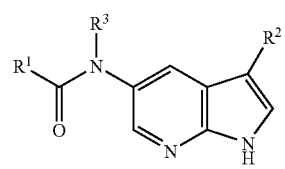

(II)

wherein $R^1$ is $C_{3-8}$ aryl or $C_{1-10}$ alkyl optionally substituted with one or more of halo or $CO_2R^5$;

wherein $R^5$ is hydrogen or $C_{1-6}$ alkyl, $R^3$ is hydrogen or $C_{1-6}$ alkyl, and $R^2$ is a 3-8 membered heterocyclyl optionally substituted with one or more of $C_{1-6}$ alkyl.

Preferably $R^1$ is a branched alkyl having 3, 4, 5 or 6 carbon atoms.

For the avoidance of doubt when a group as defined above contains two or more radicals eg the radical $R^6$ as for example in the groups $NR^6R^6$, the two or more radicals such as $R^6$ may be the same or different.

For the purposes of this invention, alkyl relates to both straight chain and branched alkyl radicals of 1 to 10 carbon atoms, preferably 1 to 8 carbon atoms and most preferably 1 to 4 carbon atoms including but not limited to methyl, ethyl, n-propyl, isopropyl, n-butyl, sec-butyl, isobutyl, tert-butyl n-pentyl, n-hexyl, n-heptyl, n-octyl. The alkyl radical can have 1, 2, 3, 4, 5, 6, 7, 8, 9 or 10 carbon atoms. The term cycloalkyl relates to cycloalkyl radicals of 3 to 12 carbon atoms, preferably 4 to 8 carbon atoms, and most preferably 5 to 6 carbon atoms including but not limited to cyclopropyl, cyclobutyl, $CH_2$-cyclopropyl, $CH_2$-cyclobutyl, cyclopentyl or cyclohexyl. Cycloalkyl groups may be optionally substituted or fused to one or more carbocyclyl or heterocyclyl group. The cycloalkyl radical can have 3, 4, 5, 6, 7, 8, 9 or 10 carbon atoms. The term cycloalkyl also encompasses cycloalkyl-alkyl groups, preferably $C_{4-8}$cycloalkyl-$C_{1-6}$alkyl groups. Particular examples of such groups include —$CH_2$-cyclopropyl, —$CH_2$-cyclobutyl, —$CH_2$-cyclopentyl, —$CH_2$-cyclohexyl. Haloalkyl relates to an alkyl radical preferably having 1 to 8 carbon atoms, preferably 1 to 4 carbon atoms substituted with one or more halide atoms for example $CH_2CH_2Br$, $CF_3$ or $CCl_3$.

The term "alkenyl" means a straight chain or branched alkylenyl radical of 2 to 10 carbon atoms, preferably 2 to 6 carbon atoms and most preferably 2 to 4 carbon atoms, and containing one or more carbon-carbon double bonds and includes but is not limited to ethylene, n-propyl-1-ene, n-propyl-2-ene, isopropylene, etc. The alkenyl radical can have 2, 3, 4, 5, 6, 7, 8, 9 or 10 carbon atoms. The term "cycloalkenyl" relates to cycloalkenyl radicals of 3-12 carbon atoms, preferably 4 to 8 carbon atoms and most preferably 5 to 6 carbon atoms having 1 to 6 double bonds. Preferably the cycloalkenyl group has 1, 2 or 3 double bonds. Cycloalkenyl groups include but are not limited to cyclopropenyl, cyclobutenyl, —$CH_2$-cyclopropenyl, —$CH_2$-cyclobutenyl, cyclopentenyl, or cyclohexenyl. Cycloalkenyl groups may be optionally substituted or fused to one or more carbocyclyl or heterocyclyl group. The cycloalkenyl radical can have 3, 4, 5, 6, 7, 8, 9 or 10 carbon atoms. The term cycloalkenyl also encompasses cycloalkenyl-alkyl or cycloalkenyl-alkenyl groups, preferably $C_{4-8}$ cycloalkenyl-$C_{1-6}$alkyl or $C_{4-8}$cycloalkenyl-$C_{2-6}$alkenyl groups. The term "alkynyl" means a straight chain or branched alkynyl radical of 2 to 12 carbon atoms, preferably 2 to 6 carbon atoms and most preferably 2 to 4 carbon atoms, and containing one or more carbon-carbon triple bonds and includes but is not limited to ethynyl, 2-methylethynyl etc. The alkynyl radical can have 2, 3, 4, 5, 6, 7, 8, 9 or 10 carbon atoms.

"Aryl" means an aromatic 3 to 10 membered hydrocarbon preferably a 6 to 10 membered ring system containing one ring or being fused to one or more saturated or unsaturated rings including but not limited to phenyl, napthyl, anthracenyl or phenanthracenyl.

"Heterocyclyl" means a 3 to 10 membered ring system preferably a 6 to 10 membered ring system containing one or more heteroatoms selected from N, O or S and includes heteroaryl. "Heteroaryl" means an aromatic 3 to 10 membered aryl preferably a 6 to 10 membered ring system containing one or more heteroatoms selected from N, O or S and containing one ring or being fused to one or more saturated or unsaturated rings. The heterocyclyl system can contain one ring or may be fused to one or more saturated or unsaturated rings; the heterocyclyl can be fully saturated, partially saturated or unsaturated and includes but is not limited to heteroaryl and heterocarbocyclyl. Examples of carbocyclyl or heterocyclyl groups include but are not limited to cyclohexyl, phenyl, acridine, benzimidazole, benzofuran, benzothiophene, benzoxazole, benzothiazole, carbazole, cinnoline, dioxin, dioxane, dioxolane, dithiane, dithiazine, dithiazole, dithiolane, furan, imidazole, imidazoline, imidazolidine, indole, indoline, indolizine, indazole, isoindole, isoindoline, isoquinoline, isoxazole, isothiazole, morpholine, napthyridine, oxazole, oxadiazole, oxathiazole, oxathiazolidine, oxazine, oxadiazine, phenazine, phenothiazine, phenoxazine, phthalazine, piperazine, piperidine, pteridine, purine, pyran, pyrazine, pyrazole, pyrazoline, pyrazolidine, pyridazine, pyridine, pyrimidine, pyrrole, pyrrolidine, pyrroline, quinoline, quinoxaline, quinazoline, quinolizine, tetrahydrofuran, tetrazine, tetrazole, thiophene, thiadiazine, thiadiazole, thiatriazole, thiazine, thiazole, thiomorpholine, thianaphthalene, thiopyran, triazine, triazole, and trithiane.

Halogen means F, Cl, Br or I, preferably F.

Representative compounds according to the first aspect of the invention are illustrated below;

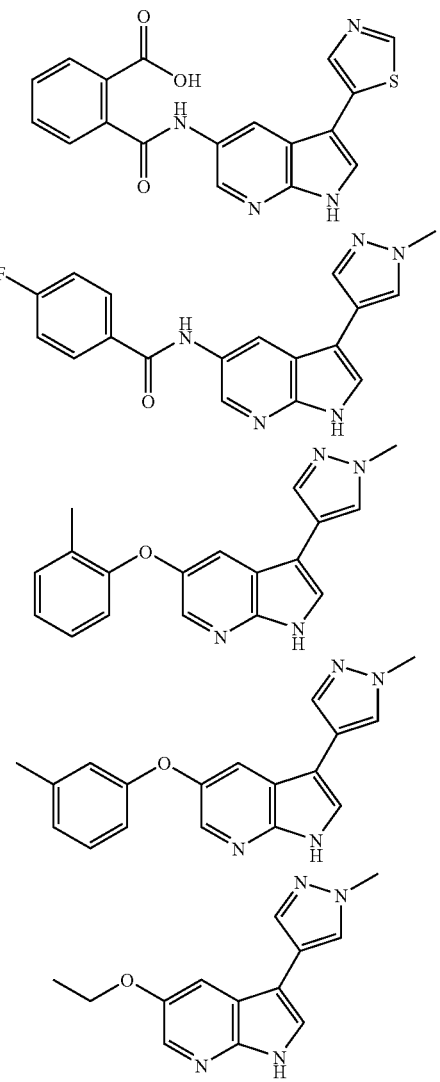

-continued
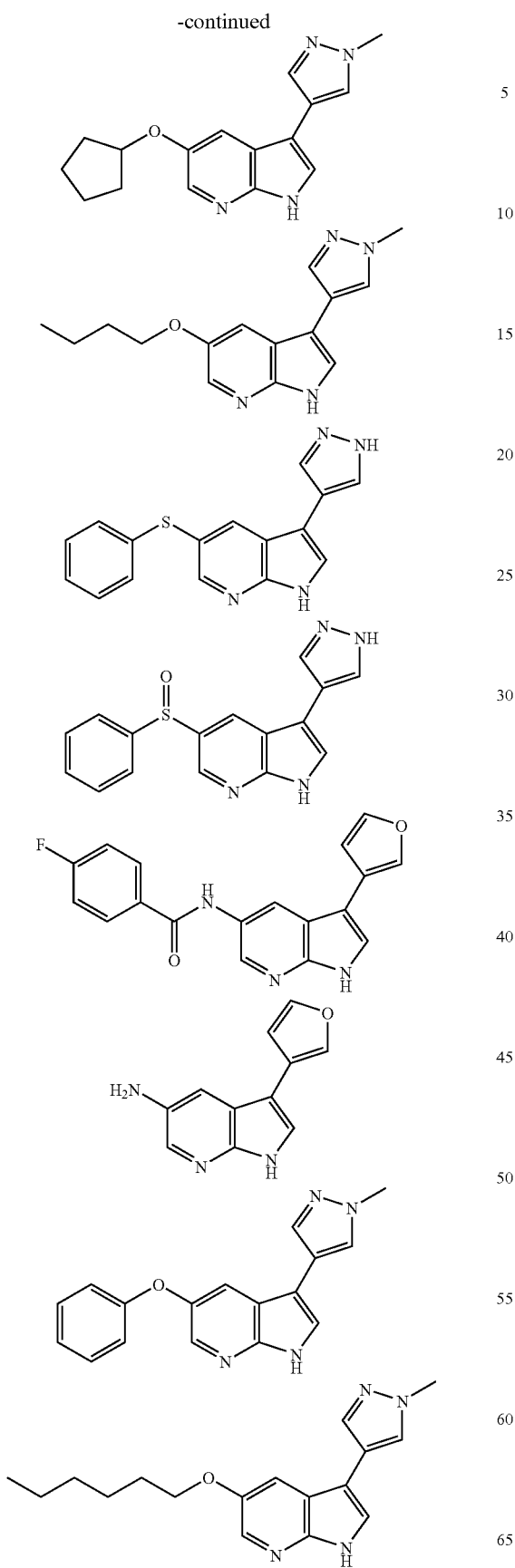
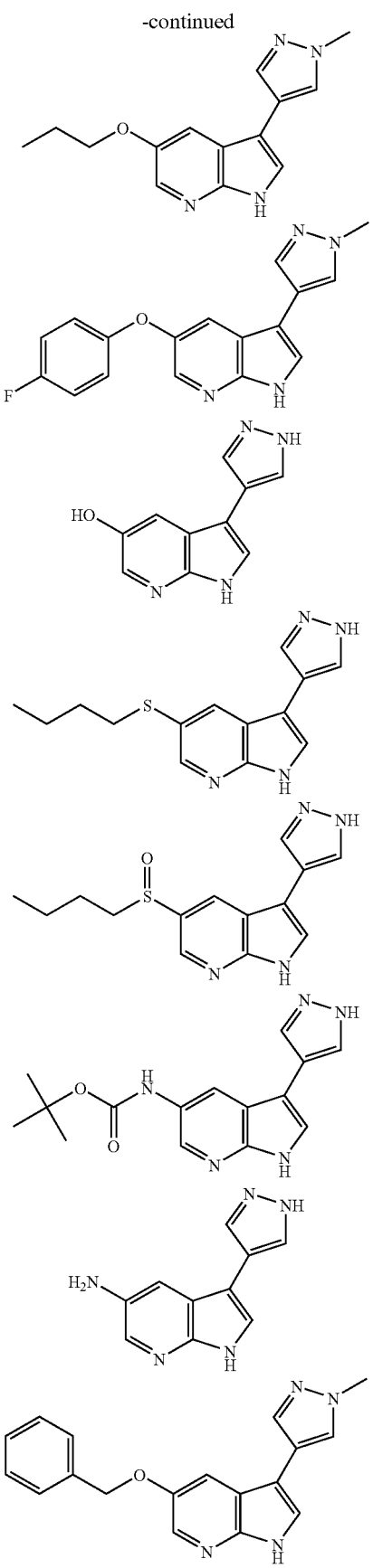

-continued
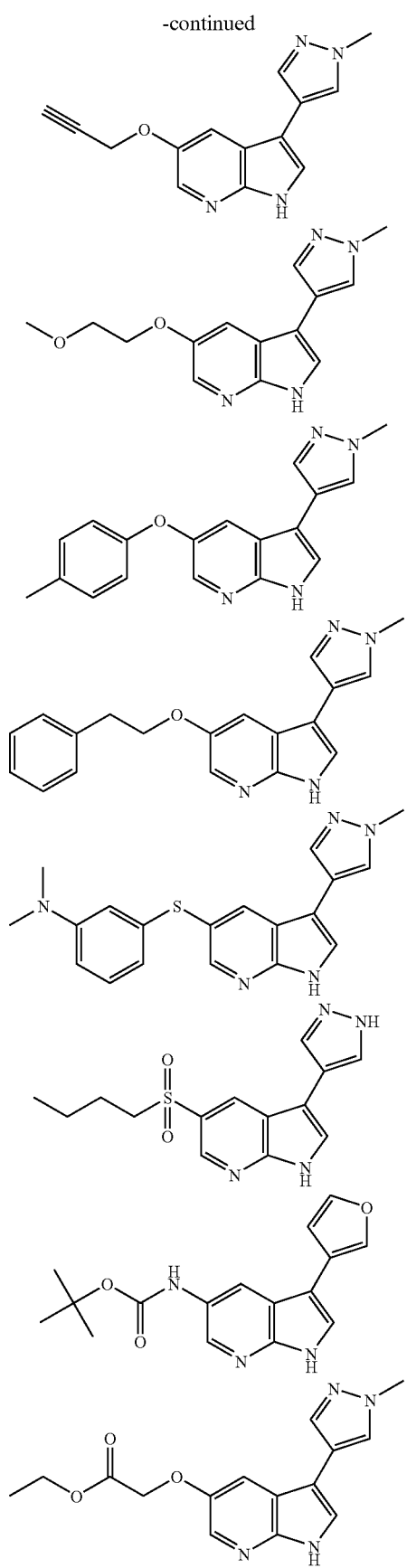
-continued
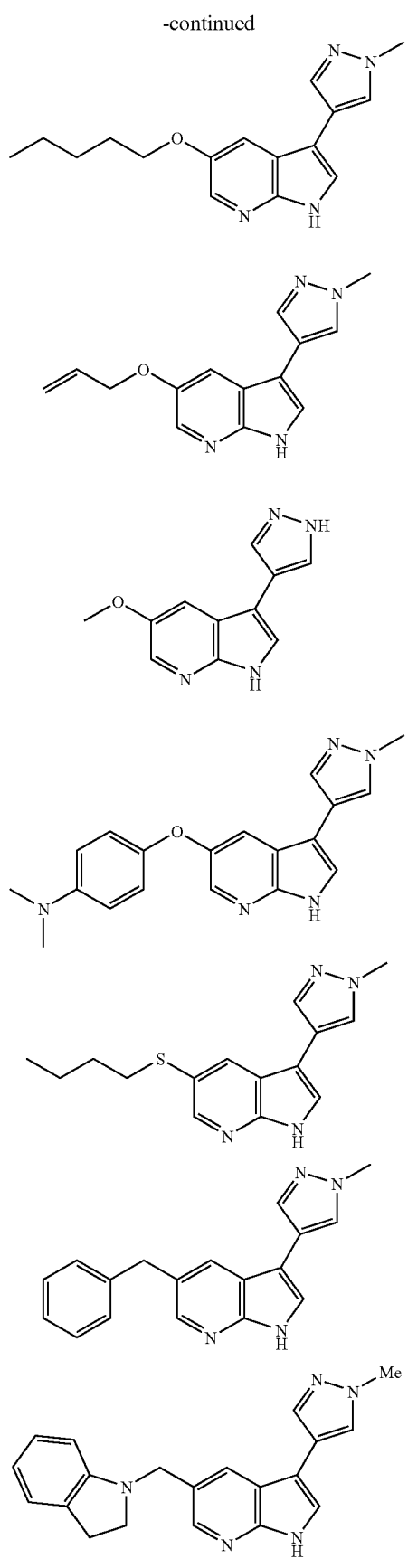

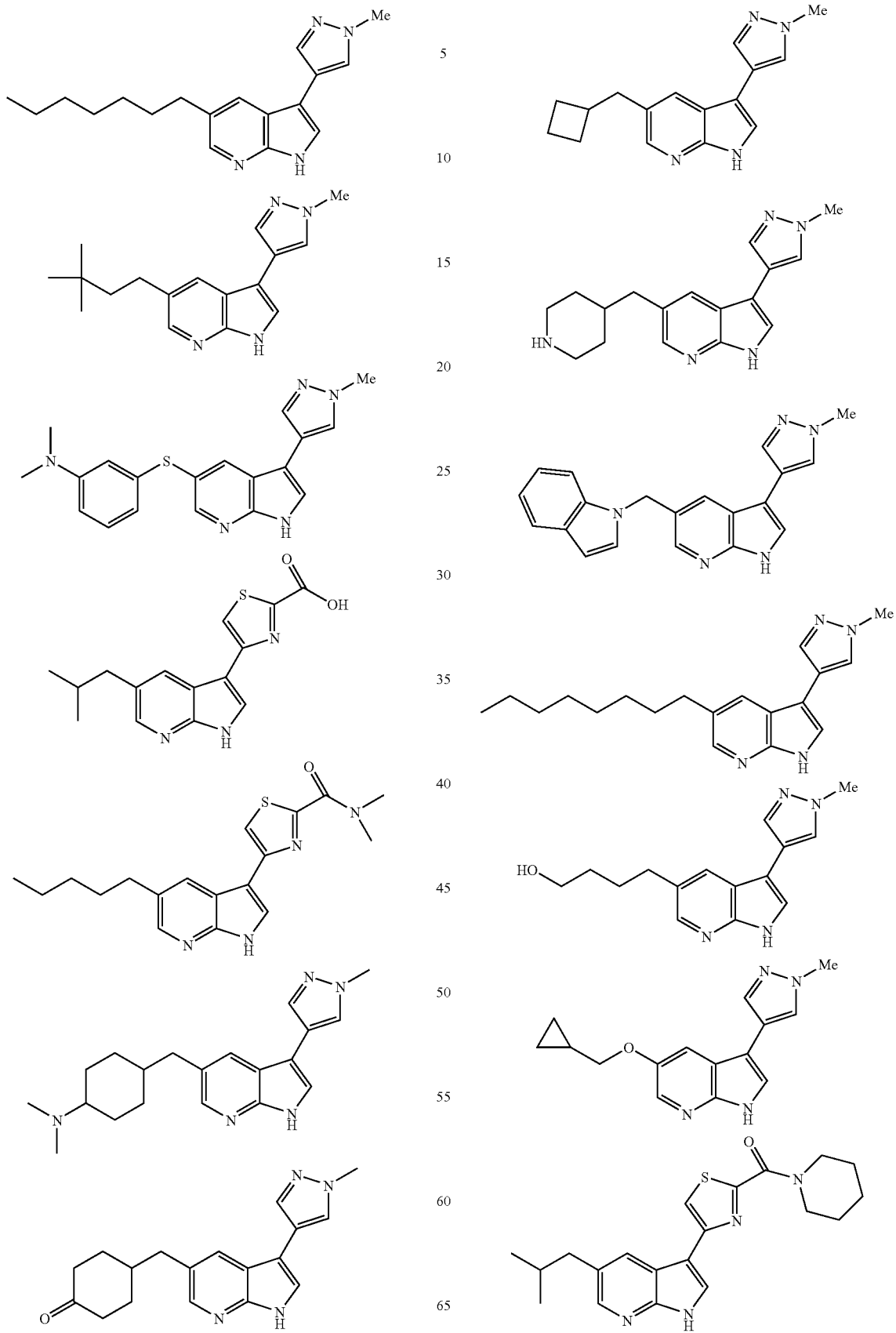

-continued
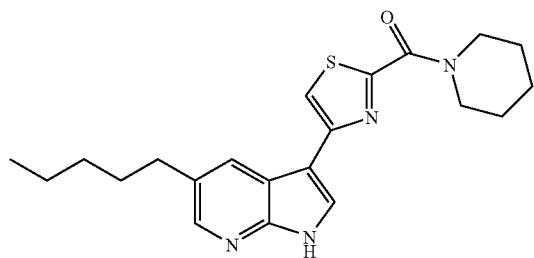
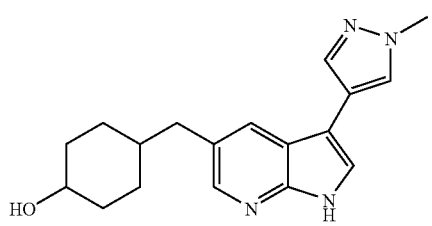
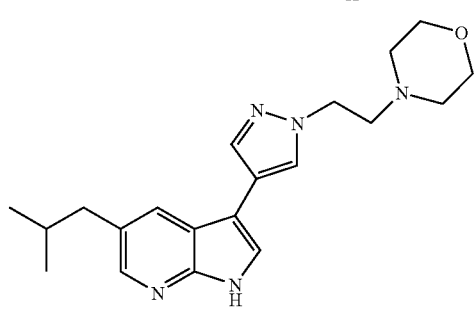
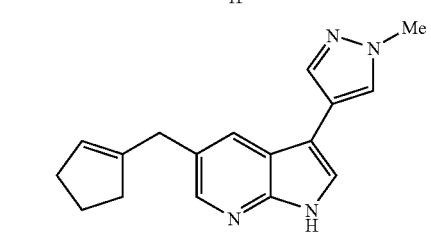
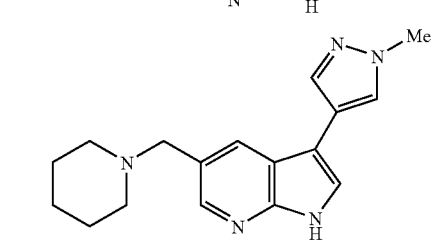
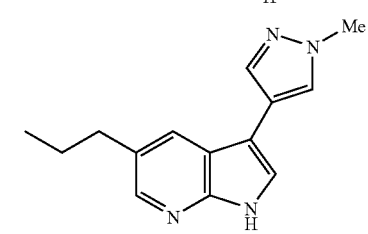
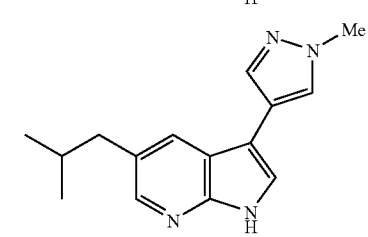
-continued
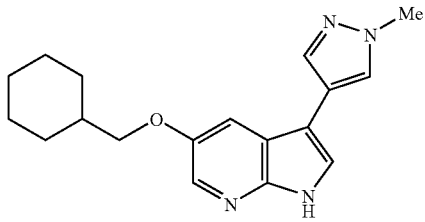
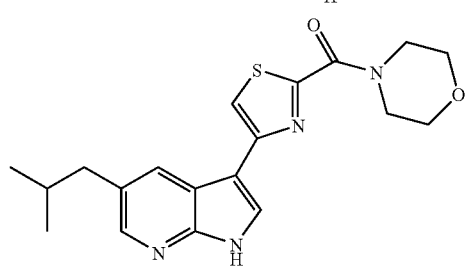
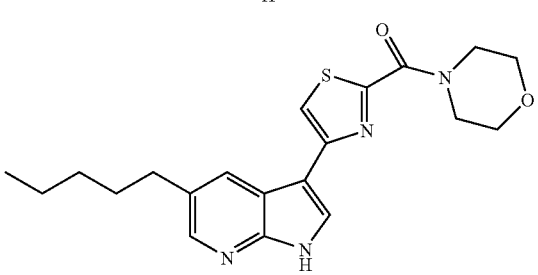
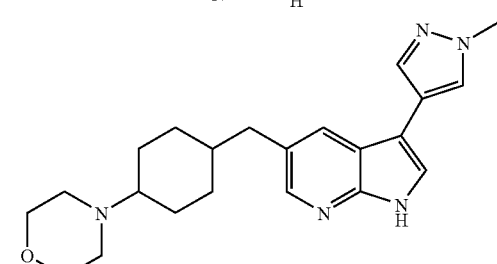
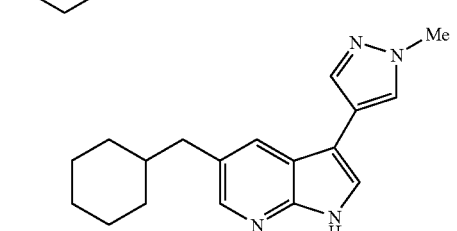
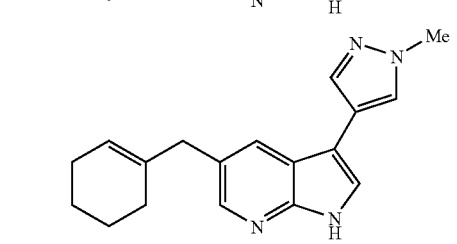
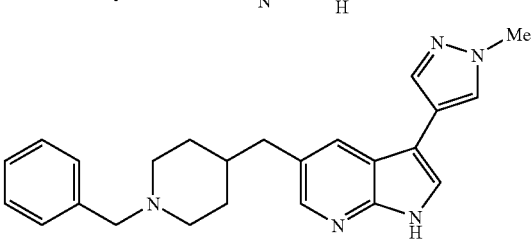

-continued

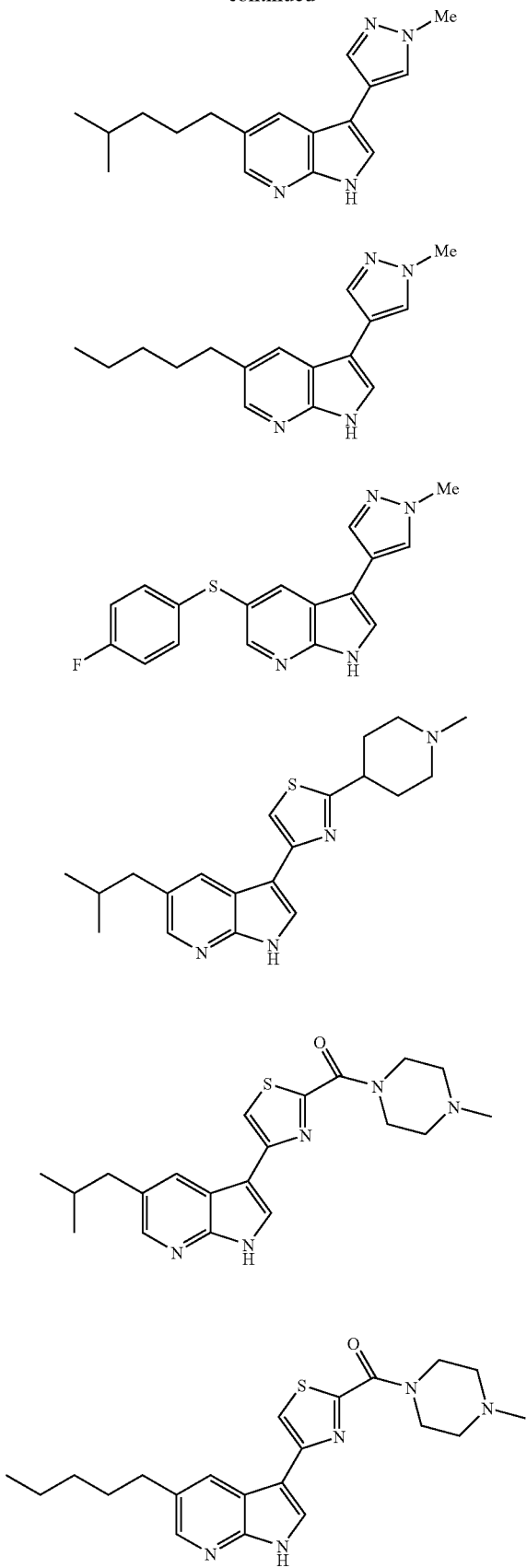

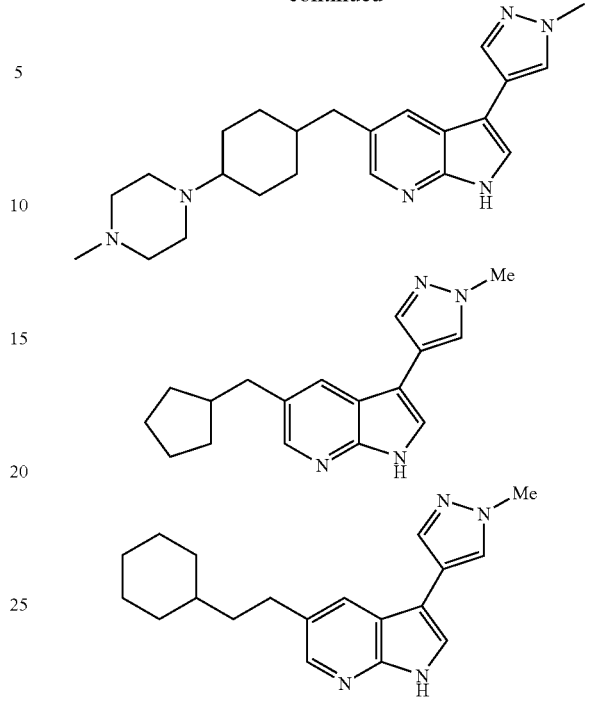

The compounds of the first aspect may be provided as a salt, preferably as a pharmaceutically acceptable salt of compounds of formula (I). Examples of pharmaceutically acceptable salts of these compounds include those derived from organic acids such as acetic acid, malic acid, tartaric acid, citric acid, lactic acid, oxalic acid, succinic acid, fumaric acid, maleic acid, benzoic acid, salicylic acid, phenylacetic acid, mandelic acid, methanesulfonic acid, benzenesulfonic acid and p-toluenesulfonic acid, mineral acids such as hydrochloric and sulfuric acid and the like, giving methanesulfonate, benzenesulfonate, p-toluenesulfonate, hydrochloride and sulphate, and the like, respectively or those derived from bases such as organic and inorganic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds of the present invention include organic bases, which are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl)aminomethane; and the like.

Salts may be prepared in a conventional manner using methods well known in the art. Acid addition salts of said basic compounds may be prepared by dissolving the free base compounds according to the first aspect of the invention in aqueous or aqueous alcohol solution or other suitable solvents containing the required acid. Where a compound of the invention contains an acidic function, a base salt of said compound may be prepared by reacting said compound with a suitable base. The acid or base salt may separate directly or can be obtained by concentrating the solution e.g. by evaporation. The compounds of this invention may also exist in solvated or hydrated forms.

The invention also extends to a prodrug of the aforementioned compounds such as an ester or amide thereof. A prodrug is any compound that may be converted under physiological conditions or by solvolysis to any of the compounds of the invention or to a pharmaceutically acceptable salt of the compounds of the invention. A prodrug may be inactive when administered to a subject but is converted in vivo to an active compound of the invention.

The compounds of the invention may contain one or more asymmetric carbon atoms and may exist in racemic and optically active forms.

The compounds of the invention may exist in trans or cis form. The first aspect of the invention covers all of these compounds.

The compound of the invention may exist in one or more crystalline forms. The invention therefore relates to a single crystal form of a compound of the invention or a mixture of one or more forms.

The second aspect of the invention provides a process for the preparation of a compound of the first aspect of the invention. The compounds of the first aspect of the invention may be prepared by methods known to those skilled in the art for analogous compounds, as illustrated by the general schemes and procedures below and with reference to the examples.

In particular, the compound of the first aspect may be provided by the introduction of a group X—$R^1$ into a compound of formula (X), wherein $Y^1$ is a halogen selected from F, Cl, Br or I.

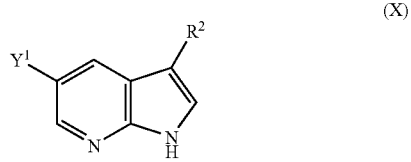
(X)

Introduction of the group X—$R^1$ may be catalysed by a catalyst such as a palladium or copper catalyst, as set out in the examples below.

Alternatively, the group $XR^1$ can be introduced by the initial introduction of the group X,

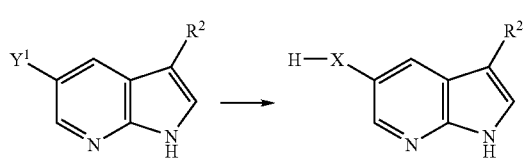

followed by the introduction of the group $R^1$

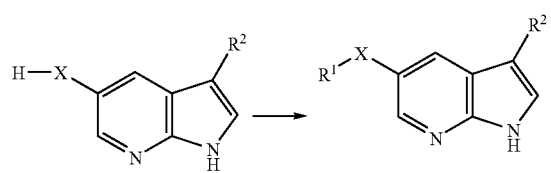

Alternatively, a compound of the invention may be provided by the introduction of the group $R^2$ into a compound of formula (V) wherein $Y^2$ is a halogen or a metal.

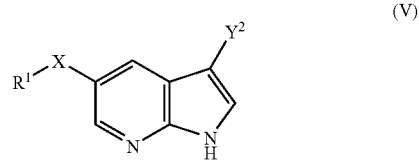
(V)

The group $R^2$ can be introduced directly into a compound of formula

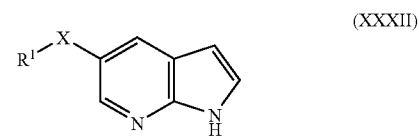
(XXXII)

for example wherein the group $R^2$ is introduced as a cyclic ketone.

The groups $R^1$, $XR^1$ and/or $R^2$ can be introduced into the compounds of the invention as discussed above. Alternatively, a precursor moiety may be introduced into the compounds of the invention. The precursor moiety can then undergo one or more conversions to obtain $R^1$, $XR^1$ or $R^2$. Examples of such precursor moieties include a boronic ester, $CO_2H$, CN, C(NH)O-alkyl, COMe, COH, $NH_2$, NH—$NH_2$, $CONH_2$, $COCHN_2$, $CO_2$-alkyl, CHNOH, $COCH_2N_3$, C(NH)O-alkyl, $CSNH_2$, CONCS, CONHC(S)—$NH_2$, and/or C(NH)$NH_2$.

A compound of formula (V) can be produced from a compound of formula (XXXII) by the addition of a group $Y^2$ as defined above

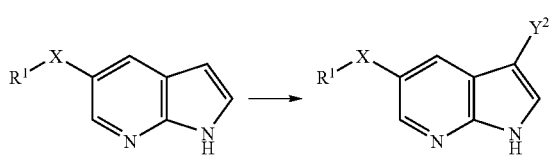

The compound of formula (XXXII) can be produced from a compound of formula (III)

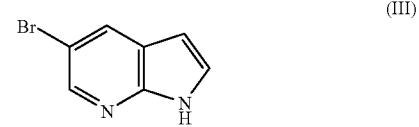
(III)

by the introduction of a group $XR^1$. The compound of formula (XXXII) can also be produced by the introduction of the group X followed by the introduction of the group $R^1$, or by the introduction of a precursor of the group $XR^1$ or $R^1$.

Detailed processes for the production of the compounds of the first aspect are set out in the examples. The reaction conditions set out for the specific reactions in the examples can be applied to the general reaction schemes set out above.

The present invention encompasses the processes for the production of the compounds of the first aspect and the intermediate compounds used in the processes. In particular, the second aspect of the invention provides compounds of general formula (V), (X) and/or (XXXII) wherein the groups $R^1$, $R^2$ and X are as defined for the first aspect of the invention.

The skilled person will appreciate that it may be necessary to protect various functionalities in the compounds of the invention or the intermediate compounds during the processes set out above. In particular, the NH functionality in the azaindole may require protection. Protection and deprotection of functionalities as necessary, in particular the NH functionality in the azaindole group can be carried out using protecting groups, methods of protection and methods of deprotection well known to persons skilled in the art and/or as set out in the examples. The present invention encompasses processes using protected intermediate compounds and including protection and deprotection steps. The invention further encompasses protected intermediate compounds used in the processes described above and with reference to the examples, in particular to protected versions of compounds of general formula (V), (X) and/or (XXXII).

The third aspect of the invention provides a composition comprising a compound according to the first aspect of the invention in combination with a pharmaceutically acceptable carrier, diluent or excipient.

The composition may also comprise one or more additional active agent, such as an anti-inflammatory agent (for example a p38 inhibitor, glutamate receptor antagonist, or a calcium channel antagonist), AMPA receptor antagonist, a chemotherapeutic agent and/or an antiproliferative agent.

Suitable carriers and/or diluents are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration).

The composition according to the invention for use in the aforementioned indications may be administered by any convenient method, for example by oral (including by inhalation), parenteral, mucosal (e.g. buccal, sublingual, nasal), rectal or transdermal administration and the compositions adapted accordingly.

For oral administration, the composition can be formulated as liquids or solids, for example solutions, syrups, suspensions or emulsions, tablets, capsules and lozenges.

A liquid formulation will generally consist of a suspension or solution of the compound or physiologically acceptable salt in a suitable aqueous or non-aqueous liquid carrier(s) for example water, ethanol, glycerine, polyethylene glycol or oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatine capsule; alternatively, a dispersion or suspension can be prepared using any suitable pharmaceutical carrier(s), for example aqueous gums, celluloses, silicates or oils and the dispersion or suspension then filled into a soft gelatine capsule.

Compositions for oral administration may be designed to protect the active ingredient against degradation as it passes through the alimentary tract, for example by an outer coating of the formulation on a tablet or capsule.

Typical parenteral compositions consist of a solution or suspension of the compound or physiologically acceptable salt in a sterile aqueous or non-aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve, which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels, patches and injections including powder injections.

Conveniently the composition is in unit dose form such as a tablet, capsule or ampoule.

The fourth aspect of the invention provides a process for the manufacture of a composition according to the second aspect of the invention. The manufacture can be carried out by standard techniques well known in the art and comprises combining a compound according to the first aspect of the invention and the pharmaceutically acceptable carrier or diluent and optionally one or more additional active agents. The composition may be in any form including a tablet, a liquid, a capsule, and a powder or in the form of a food product, e.g. a functional food. In the latter case the food product itself may act as the pharmaceutically acceptable carrier.

The fifth aspect of the present invention relates to a compound of the first aspect, or a composition of the third aspect, for use in medicine.

The compounds of the present invention are inhibitors of JNK, such as JNK1, JNK2, or JNK3. In particular, the compounds of the present invention are inhibitors of JNK3. Preferably, the compounds of the present invention inhibit JNK3 selectively (i.e. the compounds of the invention preferably show greater activity against JNK3 than JNK1 and 2). For the purpose of this invention, an inhibitor is any compound, which reduces or prevents the activity of the JNK enzyme.

The compounds are therefore useful for conditions for which inhibition of JNK activity is beneficial. Thus, preferably, this aspect provides a compound of the first aspect, or a composition of the second aspect of the present invention, for the prevention or treatment of a JNK-mediated disorder.

The compounds of the first aspect of the invention may thus be used for the inhibition of JNK, more preferably for the inhibition of JNK3.

A "JNK-mediated disorder" is any disease or deleterious condition in which JNK plays a role. Examples include neurodegenerative disorder (including dementia), inflammatory disease, an apoptosis disorder (i.e. a disorder linked to apoptosis) particularly neuronal apoptosis, autoimmune disease, destructive bone disorder, proliferative disorder, cancer, infectious disease, allergy, ischemia reperfusion injury, heart attack, angiogenic disorder, organ hypoxia, vascular hyperplasia, cardiac hypertrophy, thrombin induced platelet aggregation and a prostaglandin endoperoxidase synthase-2 condition (i.e. any condition associated with prostaglandin endoperoxidase synthase-2). The compounds of the present invention may be used for any of these JNK-mediated disorders.

The compounds of the present invention are particularly useful for the prevention or treatment of a neurodegenerative disorder. In particular, the neurodegenerative disorder is an apoptosis neurodegenerative disorder and/or an inflammation neurodegenerative disorder (i.e. the neurodegenerative disorder results from apoptosis and/or inflammation). Examples of neurodegenerative disorders are: dementia; Alzheimer's disease; Parkinson's disease; Amyotrophic Lateral Sclerosis; Huntington's disease; senile chorea; Sydenham's chorea; hypoglycemia; head and spinal cord trauma including traumatic head injury; acute and chronic pain; epilepsy and seizures; olivopontocerebellar dementia; neuronal cell death; hypoxia-related neurodegeneration; acute hypoxia; glutamate toxicity including glutamate neurotoxicity; cerebral ischemia; dementia in a meningitis patient and/or dementia in a neurosis patient; cerebrovascular dementia; or dementia in an HIV-infected patient.

The neurodegenerative disorder may be a peripheral neuropathy, including mononeuropathy, multiple mononeuropathy or polyneuropathy. Examples of peripheral neuropathy may be found in diabetes mellitus, Lyme disease or uremia; peripheral neuropathy for example peripheral neuropathy caused by a toxic agent; demyelinating disease such as acute or chronic inflammatory polyneuropathy, leukodystrophies, or Guillain-Barré syndrome; multiple mononeuropathy secondary to a collagen vascular disorder (e.g. polyarteritis nodosa, SLE, Sjögren's syndrome); multiple mononeuropathy secondary to sarcoidosis; multiple mononeuropathy secondary to a metabolic disease (e.g. diabetes or amyloidosis); or multiple mononeuropathy secondary to an infectious disease (e.g Lyme disease or HIV infection).

The compounds of the invention can also be used to prevent or treat disorders resulting from inflammation. These include, for example, inflammatory bowel disorder, bronchitis, asthma, acute pancreatitis, chronic pancreatitis, allergies of various types, and possibly Alzheimer's disease. Autoimmune diseases which may also be treated or prevented by the compounds of the present invention include rheumatoid arthritis, systemic lupus erythematosus, glumerulonephritis, scleroderma, chronic thyroiditis, Graves's disease, autoimmune gastritis, diabetes, autoimmune haemolytis anaemia, autoimmune neutropaenia, thrombocytopenia, atopic dermatitis, chronic active hepatitis, myasthenia gravis, multiple sclerosis, ulcerative colitis, Crohn's disease, psoriasis or graft vs host disease.

A compound of the present invention may be administered simultaneously, subsequently or sequentially with one or more other active agent, such as an anti-inflammatory agent e.g. p38 inhibitor, AMPA receptor antagonist, glutamate receptor antagonist, calcium channel antagonist, a chemotherapeutic agent or an antiproliferative agent. For example, for acute treatment, a p38 inhibitor may be administered to a patient prior to administering a compound of the present invention.

The compounds of the invention will normally be administered in a daily dosage regimen (for an adult patient) of, for example, an oral dose of between 1 mg and 2000 mg, preferably between 30 mg and 1000 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

The sixth aspect of the invention relates to a method of treating or preventing a JNK-mediated disorder in an individual, which method comprises administering to said individual a compound of the first aspect or a composition of the third aspect. The active compound is preferably administered in a cumulative effective amount. The individual may be in need of the treatment or prevention. Any of the JNK-mediated disorders listed above in relation to the fourth aspect may be the subject of treatment or prevention according to the fifth aspect. One or more other active agent may be administered to the individual simultaneously, subsequently or sequentially to administering the compound. The other active agent may be an anti-inflammatory agent such as a p38 inhibitor, glutamate receptor antagonist, AMPA receptor antagonist, calcium channel antagonist, a chemotherapeutic agent or an antiproliferative agent, but is preferably p38 inhibitor for acute treatment.

The seventh aspect of the present invention provides the use of a compound of the first aspect in the manufacture of a medicament for the prevention or treatment of a JNK-mediated disorder. The medicament may be used for treatment or prevention of any of the JNK-mediated disorders listed above in relation to the fourth aspect. Again, the compound of the present invention may be administered simultaneously, subsequently or sequentially with one or more other active agent, preferably a p38 inhibitor for acute treatment.

In the eighth aspect of the invention, there is provided an assay for determining the activity of the compounds of the present invention, comprising providing a system for assaying the activity and assaying the activity of the compound. Preferably the assay is for the JNK inhibiting activity of the compound, more preferably it is for the JNK3-specific inhibiting activity of the compounds. The compounds of the invention may be assayed in vitro, in vivo, in silico, or in a primary cell culture or a cell line. In vitro assays include assays that determine inhibition of either the kinase activity or ATPase activity of activated JNK. Alternatively, in vitro assays may quantitate the ability of a compound to bind JNK and may be measured either by radiolabelling the compound prior to binding, then isolating the inhibitor/JNK complex and determining the amount of the radiolabel bound or by running a competition experiment where new inhibitors are incubated with JNK bound to known radioligands. An example of an assay, which may be used, is Scintillation Proximity Assay (SPA), preferably using radiolabelled ATP. Another example is ELISA. Any type or isoform of JNK may be used in these assays.

In the ninth aspect, there is provided a method of inhibiting the activity or function of a JNK, particularly JNK3, which method comprises exposing a JNK to a compound or a composition of the first or second aspect of the present invention. The method may be performed in a research model, in vitro, in silico, or in vivo such as in an animal model. A suitable animal model may be a kainic acid model in rat or mice, traumatic brain injury model in rat, or MPTP in mice.

All features of each of the aspects apply to all other aspects *mutatis mutandis*.

The invention will now be illustrated by the following non-limiting examples.

EXAMPLES

General Methods for Synthesis of the Compounds of the Invention

Method 1

5-Bromo-7-azaindole (III)(preparation disclosed in WO2004/078757) is reacted with thiol $R^1$—SH in the presence of palladium catalyst such as $(PPh_3)_4Pd$ and a base such as t-BuONa to afford sulphide (IV) (Migita et al. *Bull. Chem. Soc. Jpn,* 1980, 53, 1385; Kondo and Mitsudo *Chem. Rev.* 2000, 100, 3205). The reaction is carried out under nitrogen atmosphere at elevated temperatures such as 80-100° C., e.g. by refluxing a solution of the reagents in ethanol for an extended time such as 12 to 24 h.

the heteroaryllithium species and subsequent reaction between thiolate and $R^1$—Br affords protected sulfide (IX).

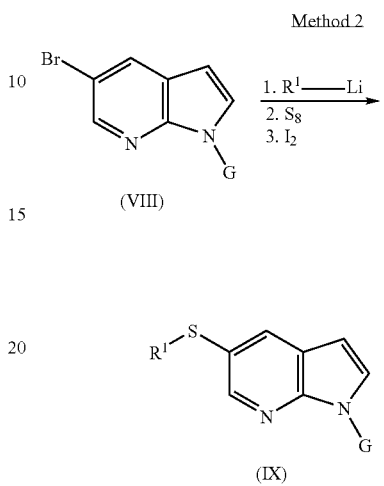

Method 2

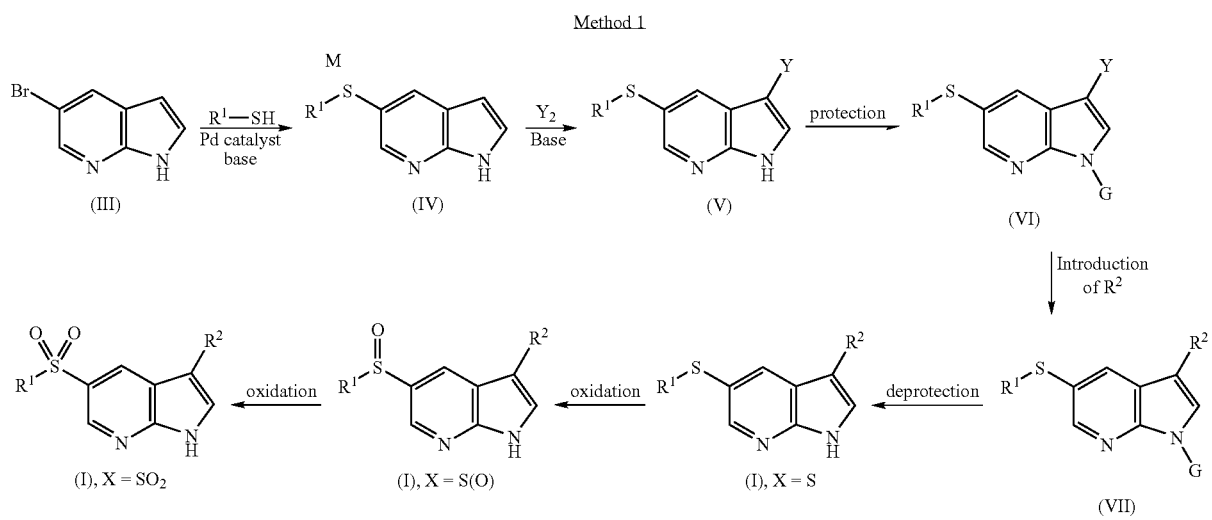

Method 1

Sulfide (IV) is then converted into 3-halo derivative (V) by reaction with halogen $Y_2$ such as iodine in the presence of a strong base, e.g. KOH in appropriate solvent such as DMF by analogy to the protocol developed for analogous indoles by Bocchi and Palla (*Synthesis* 1982, 1096). Standard protection of nitrogen is followed by installation of $R^2$ using one of the processes described in Methods 11-24. Subsequent removal of protecting group affords compound (I) where X=S. This compound can be oxidized in standard way with an oxidizing agent such as e.g. hydrogen peroxide or Oxone® to give sulfoxide (I), X=S(O). Prolonged oxidation and/or using an excess of oxidant leads to sulfone (I), X=$SO_2$.

Method 2

Intermediate (IV) can also be prepared from protected bromide (VIII) (preparation disclosed in WO2004/078757). Halogen-metal exchange followed by the addition of sulfur to -continued

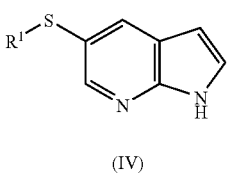

Deprotection of (IX) using methods known in the art produces (IV), which can be converted into (I), X=S, S(O), $SO_2$ as shown in Method 1.

Method 3

Alternatively, the C(5)-alky(aryl)thio group can be introduced after the C(3) substituent has already been installed. This can be achieved in one step process leading to intermediate (VII)(Method 3a) using 5-halo derivative (X) (preparation disclosed in WO2004/078756) and following the protocol by Deng et al. (*Synlett* 2004, 7, 1254).

Method 3 a)

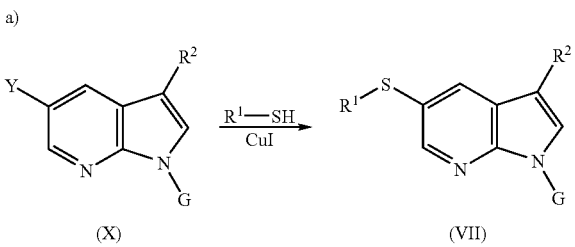

b)

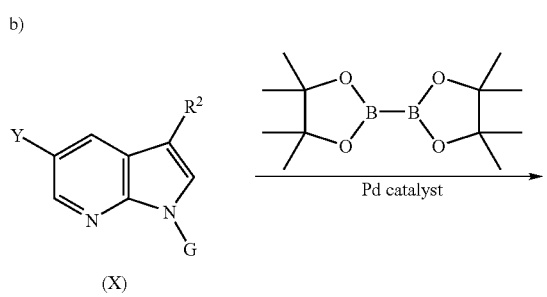

-continued

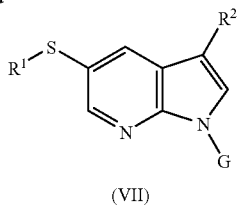

Intermediate (VII) can also be synthesized from (X) in a two-step process (Method 3b). 5-Halo-7-azaindole (X) is converted into pinacol boronic ester (XI) using boronation protocol disclosed in WO2004/078757. Boronic ester (XI) is then reacted with appropriate thiol following the method by Herradura et al. (*Org. Lett.* 2000, 2, 2019) to give (VII). Deprotection of (VII) as described in Method 1 affords (I) X=S.

Compounds (I) with X=O can be prepared using Methods 4 and 5.

Method 4

Boronate (XI) can be converted into the relevant hydroxy derivative (XII) following a modified protocol developed for boronic acids by Simon et al. (*J. Org. Chem.* 2001, 66, 633). It involves acting with hydrogen peroxide solution in acetic acid on boronic ester (XI) at room temperature. Hydroxy derivative (XII) thus obtained can then be reacted with boronic acid $R^1$—$B(OH)_2$ to produce ether (XIII).

Method 4

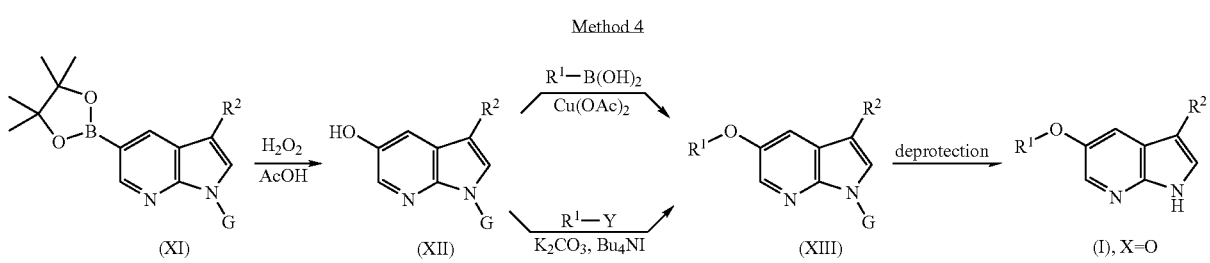

-continued

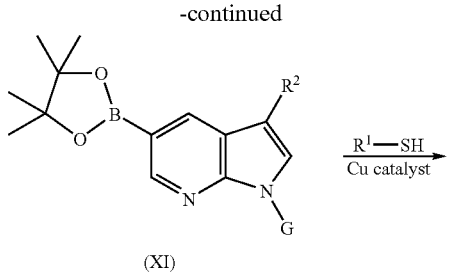

Alternatively, for alkyl-type $R^1$ groups, hydroxy derivative (XII) can be alkylated with $R^1$—Y (Y=halogen) under basic conditions developed by Engler et al. (*J. Org. Chem.* 1996, 61, 9297). Final removal of protecting group G under standard conditions affords (I), X=O.

Method 5

The ether functionality can be introduced directly at C(5) of the 7-azaindole system by using 5-bromo-7-azaindole (III) and following the protocol by Larraya et al. (*Eur. J. Med. Chem.* 2004, 39, 515). This reaction involves heating a mixture of (III), an alkoxide $R^1$—OM' (M'=metal such as e.g. Na), and CuBr in an aprotic solvent such as DMF.

Method 5

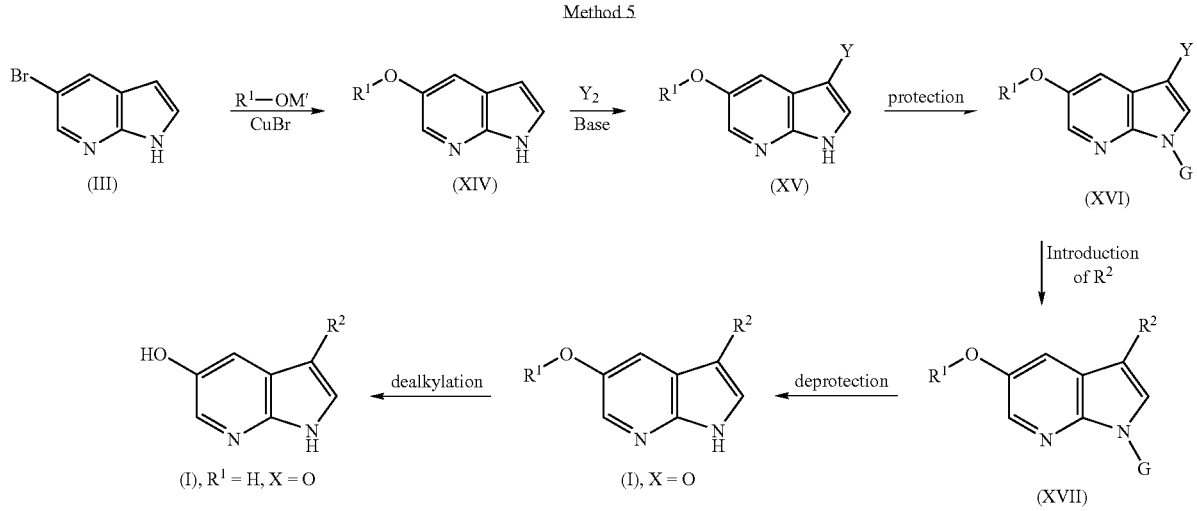

Further transformations leading to (I), X=O are analogous to those shown in Method 1.

Compounds (I) with X=C can be prepared using Method 6.

Method 6

It has been recognized in literature (Viaude et al. *Tetrahedron,* 1997, 53, 5159) that introduction of X=CH$_2$ at C(5) in good yield is difficult as degradation products are observed and yield is only about 20%. This yield can be more than doubled by using Ag(I)-promoted Suzuki-Miaura coupling reaction (Zou et al. *Tetrahedron Lett.* 2001, 42, 7213).

Method 6

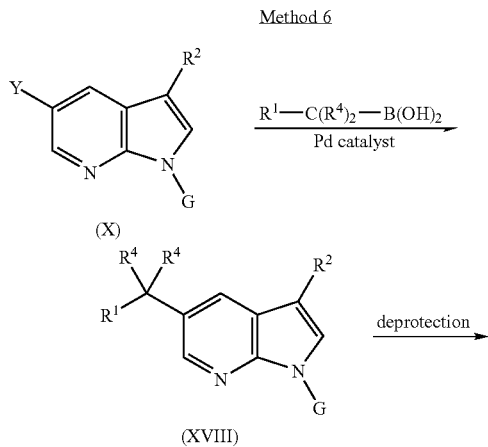

This reaction involves 7-azaindole derivative (X), the relevant benzylboronic acid R$^1$—C(R$^4$)$_2$—B(OH)$_2$, silver oxide, potassium carbonate and a palladium catalyst such as Pd(dppf)Cl$_2$. Reaction is carried at elevated temperature (about 80° C.) over a period of 6-18 hours. Final deprotection of product (XVIII) affords (I), X=CR$^4$R$^4$.

Compounds (I) with X=N can be prepared using Methods 7-10.

Method 7

Formation of a bond between nitrogen (X=N) and carbon atom C(5) of the 7-azaindole system can be performed using Chan-Lam coupling reaction involving (hetero)aryl boronic acid (Quach and Batey *Org. Lett.* 2003, 5, 4397; Chan et al. *Tetrahedron Lett.* 2003, 44, 3863) and NH-containing substrate, which is catalyzed by copper (II) salts, for instance copper (II) acetate.

Method 7

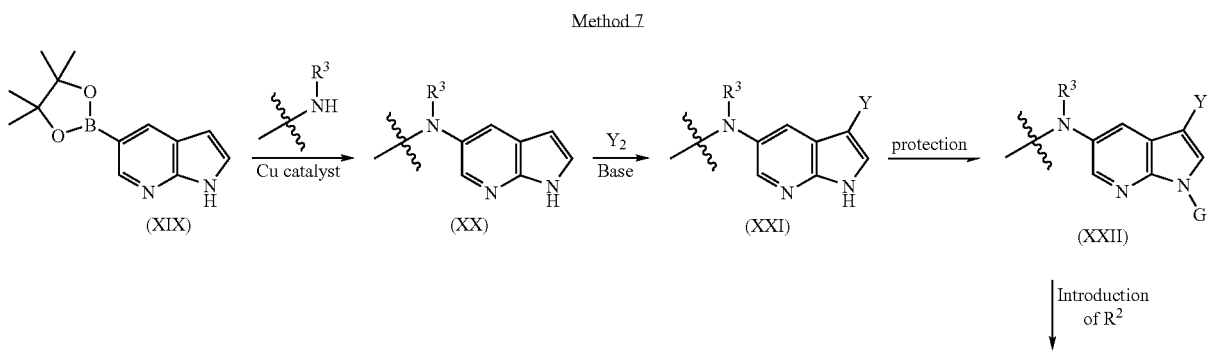

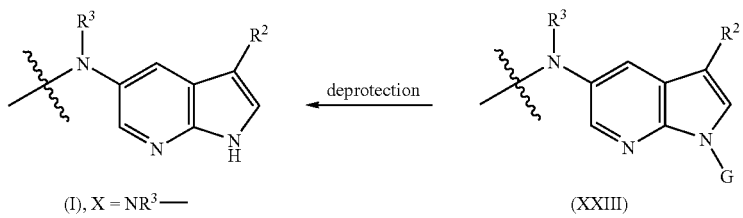

Thus, boronate (XIX)(preparation disclosed in WO2004/078757) can be converted into C(5)-N derivative (XX). Further transformations analogous to those shown in Method 1 lead to inhibitor (I) with X=NR$^3$—, NR$^3$—C(O)— or NR$^3$—C(O)O—.

Method 8

Another alternative is offered by Buchwald-Hartwig methodology (Wolfe et al. *Acc Chem Res* 1998, 31, 805; Zim and Buchwald *Org. Lett.* 2003, 5, 2413) where haloarenes can be coupled with amines using a variety of palladium catalysts such as Pd(dba)$_2$, PdCl$_2$/P(o-tolyl)$_3$, etc.

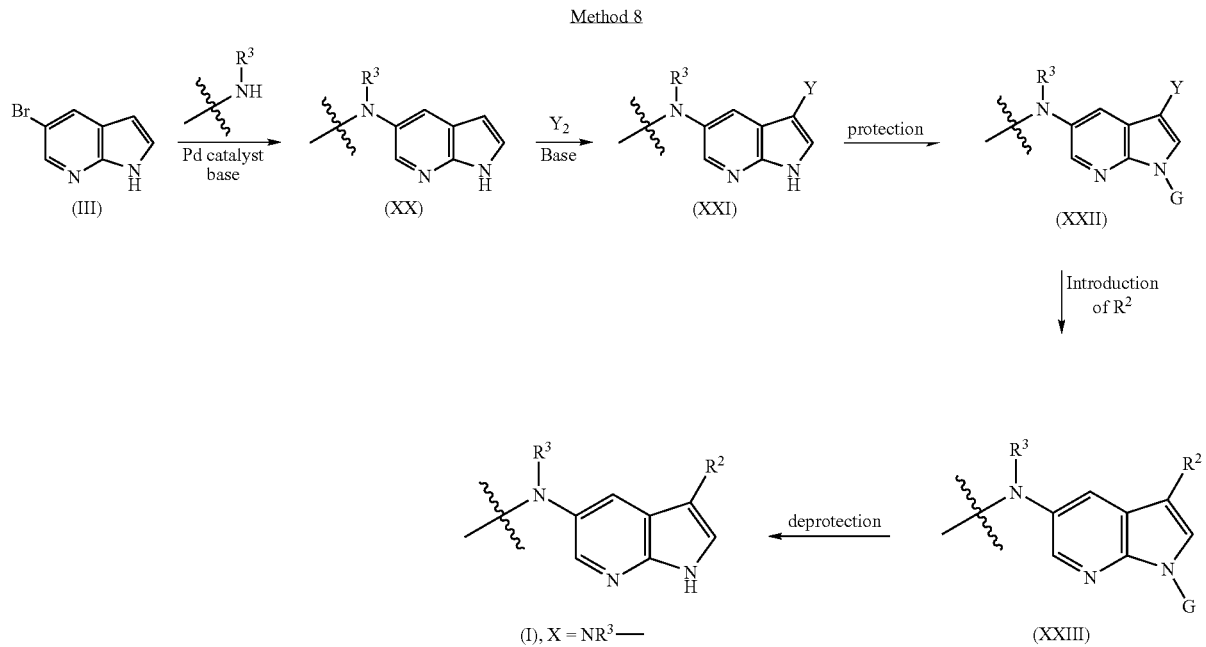

Various bases can be used in the reaction, for instance tBuONa, K$_2$CO$_3$, Et$_3$N, etc. The reaction is usually carried out at elevated temperature, e.g. 60-100° C. in solvent such as toluene.

Method 9

Direct synthesis of primary aryl amines, which are useful for preparation of inhibitors (1) where X=NH—C(O)— or NH—C(O)O— was carried out by the direct conversion of aryl halides into primary amines under mild conditions as developed by Lang et al. (*Tetrahedron Lett.* 2001, 42, 3251).

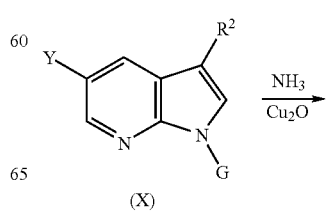

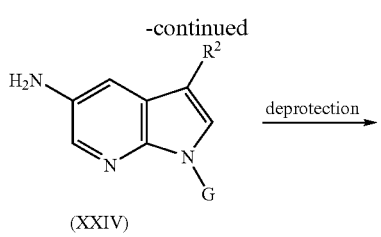

(XXIV)

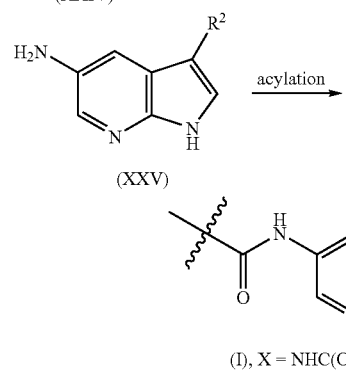

(XXV)

(I), X = NHC(O)—

The primary amine (XXIV) can be converted into (I), X=NRC(O)— or X=NHC(O)O— by deprotection of (XXIV) and acylation of (XXV) with suitable acylating agent such as acid chloride, acid anhydride, or equivalent. In particular, where G is a phenylsulfonyl group, its removal occurs spontaneously prior to the acylation step. Thus, a skilled person will appreciate that the actual synthetic sequence to prepare compound (D) will depend on the type of protecting group G used.

Method 10

Another route to introduce the C(5)-N bond is based on the modified Curtius rearrangement using the relevant carboxylic acid and diphenylphosphoryl azide (DPPA)(Shioiri et al. *J. Am. Chem. Soc.* 1972, 94, 6203; Anquetin et al. *Bioorg. Med. Chem. Lett.* 2004, 14, 2773).

Method 10

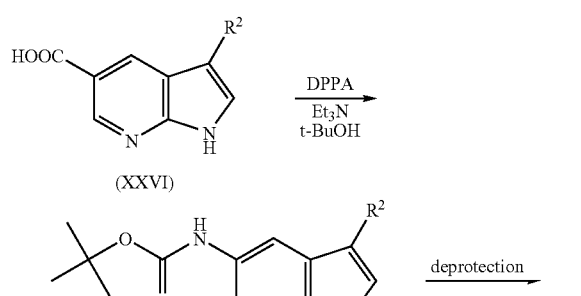

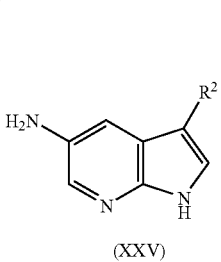

(XXV)

This reaction between acid (XXVI), DPPA, t-BuOH and Et₃N is carried out at elevated temperature (reflux). This procotol can be modified by reacting an intermediate isocyanate with t-BuOH in the presence of CuCl (Kapferer and Vasella *Helv. Chim. Acta* 2004, 87, 2764). Amine (XXV) can then be acylated as shown in Method 9.

Method 11

Substituent $R^2$ can be introduced using an appropriate palladium catalyzed C—C bond-forming reaction between (XXVIII) and appropriate boronic acid or ester, stannane or silane $R^2$-M (M=B, Sn, Si respectively) as taught in WO2004/78756.

Method 11

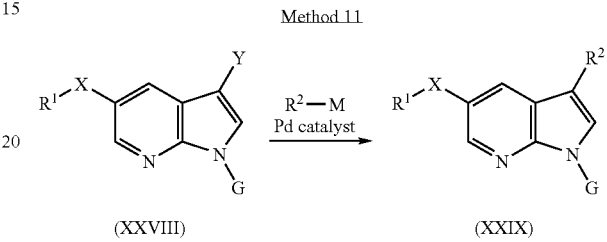

(XXVIII)              (XXIX)

Such method is particularly suitable for attaching rings $R^2$ through an endocyclic sp² carbon atom, which is present in aromatic, heteroaromatic or partially unsaturated rings.

Many boronic acids and esters $R^2$-M (M=B) are commercially available or can be prepared by methods known in the art (Li et al. *J. Org. Chem.* 2002, 67, 5394-5397; Hall, Dennis G. (ed.) *Boronic Acids. Preparation and Applications in Organic Synthesis and Medicine*, Wiley VCH, 2005). Partially saturated boronic acids and esters prepared as taught by Renaud and Ouellet (*J. Am. Chem. Soc.* 1998, 120, 7995) are particularly useful intermediates with regard to installation of partially saturated rings at C(3) of the 7-azaindole system. Unsaturated and (hetero)aromatic stannanes are available using known methods (Pereyre et al. *Tin in Organic Synthesis*; Butterworth: London, 1987; Lee and Dai *Tetrahedron* 1997, 53, 859 and references therein; Smith et al. *Chem. Rev.* 2000, 100, 3257; Evans et al. *J. Am. Chem. Soc.,* 1998, 120, 5921). Synthetic procedures to prepare siloxanes and silacyclobutanes $R^2$-M (M=Si) have been described by Denmark and Choi (*J. Am. Chem. Soc.* 1999, 121, 5821).

The reaction with $R^2$-M (M=B) is a Suzuki reaction which can be carried out according to Suzuki Pure Appl. Chem. 1991, 63, 419 or Littke J. Am. Chem. Soc. 2000, 122, 4020.

It will be appreciated that the reaction with $R^2$-M (M=Sn) is a Stille reaction, which can be carried out according to Stille Angew. Chem., Int.ed, Engl. 1986, 25, 508; Mitchell Synthesis, 1992, 803, or Littke et al. J. Am. Chem. Soc. 2002, 124, 6343.

The reaction with $R^2$-M (M=Si) is a Hiyama reaction which can be carried out according to Hatanaka et al. J. Org. Chem. 1988, 53, 918, Hatanaka et al. Synlett, 1991, 845, Tamao et al. Tetrahedron Lett. 1989, 30, 6051 or Denmark et al. Org. Lett. 2000, 2, 565, ibid. 2491.

Suitable catalysts for the purpose of this invention include $(PPh_3)_2PdCl_2$, $(PPh_3)_4Pd$, $Pd(OAc)_2$, $[PdCl(\eta^3\text{-}C_3H_5)]_2$, $Pd_2(dba)_3$, $Pd(dba)_2$ (dba=dibenzylidenacetone), $Pd/P(t\text{-}Bu)_3$. A variety of coupling conditions for halogenated heterocycles have been reviewed by Schröter et al. *Tetrahedron* 2005, 61, 2245. The C—C bond formation between (hetero)aromatic systems can also be catalyzed by catalysts containing other metals such as copper and nickel (Hassan et al. *Chem. Rev.* 2002, 102, 1359).

Method 12

Introduction of R by means of an appropriate palladium catalyzed C—C bond-forming reaction can also be carried out in a reverse manner using metalloorganic species (XXX) and halide or triflate R²—Y¹ under similar conditions to those used in Method 11.

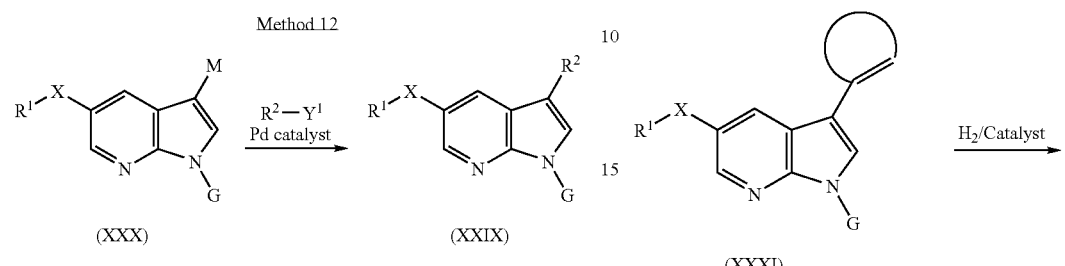

While halides R²—Y¹ (Y¹=I, Br, Cl) are available commercially, the relevant derivatives R²-OTfl containing partially unsaturated rings can be prepared from ketones (Comins and Dehghani *Tetrahedron Letters* 1992, 33, 6299).

Methods for introduction of M=B, Sn, Si at the C(3) position of the 7-azaindole system have been disclosed in WO2004078756 and by Alvarez et al. (*Synthesis* 1999, 4, 615). Analogous reactions on the indole skeleton have also been described for M=Sn by Amat et al. (*J. Org. Chem.* 1994, 59, 10) and Hodson et al. (*Tetrahedron* 1994, 50, 1899), and for M=B by Kawasaki et al. (J. Chem. Soc. Chem. Commun. 1994, 18, 2085) and Claridge et al. *Tetrahedron* 1997, 53, 4035.

Method 13

Compounds (XXXI) with partially saturated rings are accessible using Methods 11 and 12. An alternative protocol involves the reaction of the relevant N-unprotected 7-azaindole (XXXII) with cyclic ketone under basic conditions as described by Fonquerna et al. (*Bioorg. Med. Chem. Len.* 2005, 15, 1165).

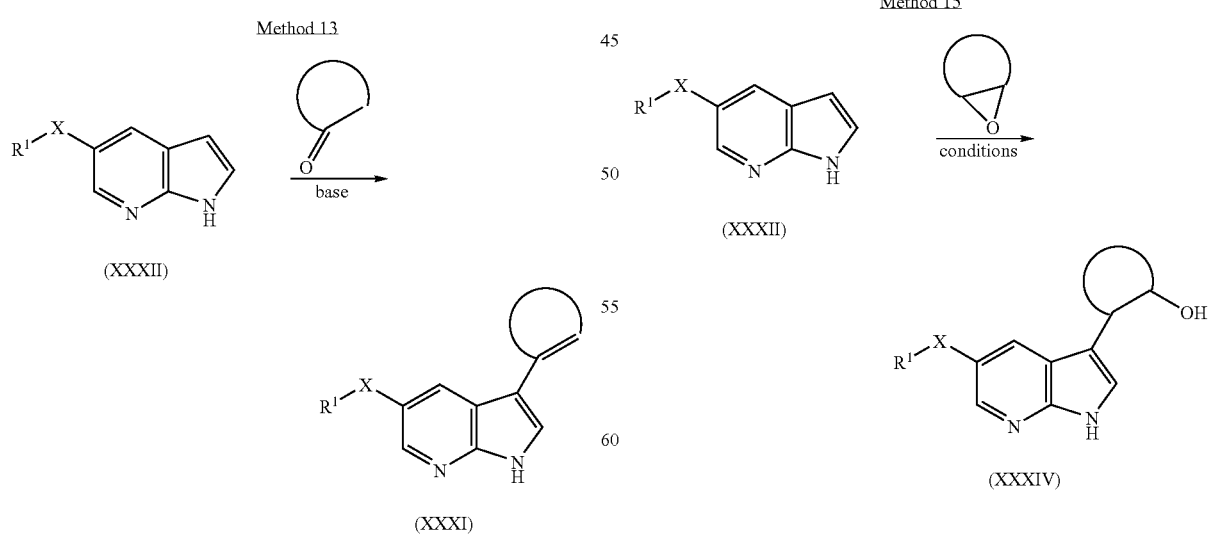

This reaction is carried out at elevated temperature in the presence of base such as KOH.

Method 14

Introduction of saturated rings at the C(3) of the azaindole system to produce (XXXIII) can be achieved by catalytic reduction of compounds (XXXI) containing partially saturated rings.

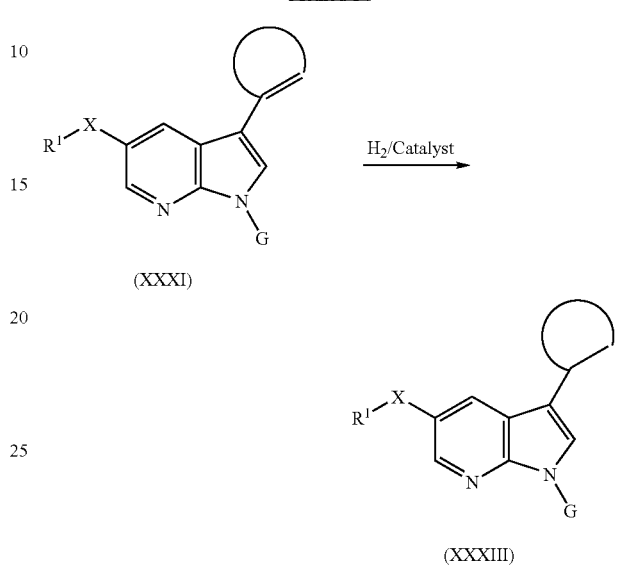

This process can be carried out under the conditions known to those skilled in the art by stirring a solution of (XXXI) in a suitable solvent such as MeOH or AcOH in an atmosphere of $H_2$ and in the presence of a catalyst such as Pd, $Pd(OH)_2$, or $PtO_2$, as illustrated for the relevant indole-based systems by Fonquerna et al. (*Bioorg. Med. Chem. Lett.* 2005, 15, 1165).

Method 15

Saturated rings can be introduced directly at the C(3) carbon atom by the reaction between the relevant epoxide and (XXXII).

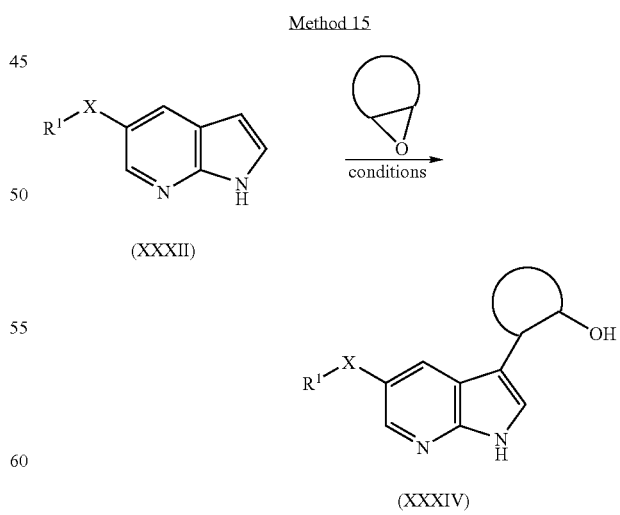

This transformation can be carried out under a variety of conditions. The reaction can be promoted by bases such as EtMgBr or MeMgBr following the conditions developed by Heath-Brown and Philpott (*J. Chem. Soc.* 1965, 7165) and Macor and Ryan (*Heterocycles* 1990, 31, 1497) for the indole system. It can also be catalyzed by silica gel and occur under high pressure as shown by Kotsuki et al. (*J. Org. Chem.* 1996, 61, 984). Other possible catalysts for opening the epoxide ring include $TiCl_4$, $InCl_3$, $InBr_3$, $LiClO_4$, and $[Cr(salen)]SbF_6$.

Heterocyclic rings at C(3), can also be formed by the means of cyclization (Gilchrist *J. Chem. Soc. Perkin Trans* 1 2001, 2491). Preparation of pyrroles via cyclization is known (e.g. Haubmann et al. *Bioorg. Med. Chem. Lett.* 1999, 9, 3143). The following are methods applicable to heterocycles containing two or more heteroatoms:

Method 16

Imidazole

The imidazole ring can be constructed following the method of Matthews et al. (*Synthesis* 1986, 336).

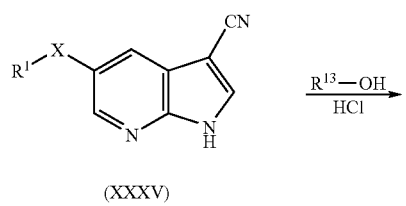

(XXXV)

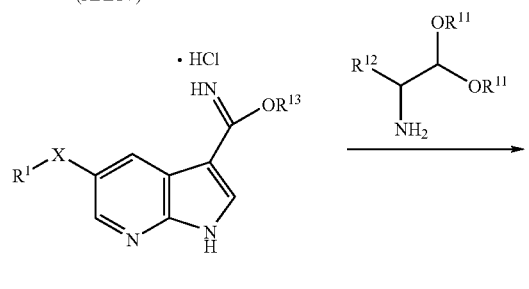

(XXXVI)

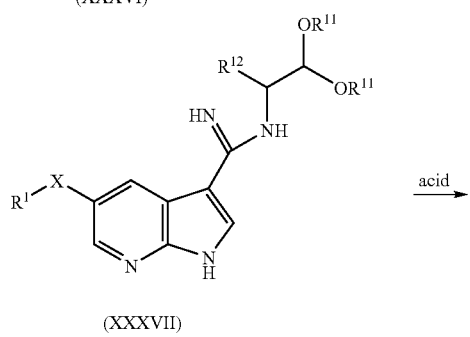

(XXXVII)

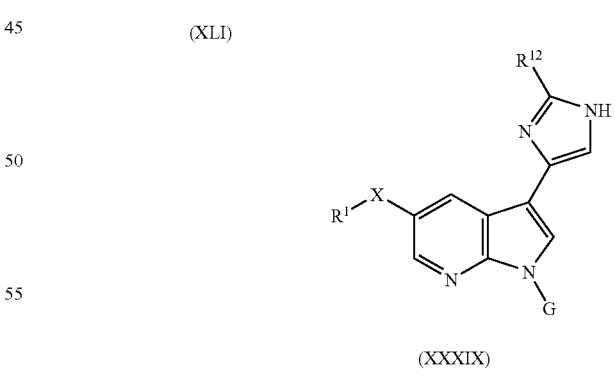

(XXXVIII)

Nitrile (XXXV) which can be produce according to methods disclosed in WO2004101565, is first converted to imidate (XXXVI) using the Pinner method (Nielson, D. G. In *The Chemistry of Amidines and Imidates*; S. Patai Ed.: John Wiley and Sons: New York, 1975, p 443) by reacting (XXXV) with alcohol $R^{13}OH$ ($R^{13}$=alkyl group, preferably Me, Et) in the presence of anhydrous acid such as HCl. Imidate (XXXVI) is then reacted with acetal $H_2NCH(R^{12})CH_2CH(OR^{11})_2$ ($R^{11}$=alkyl group, preferably Me, Et; $R^{12}$=the relevant substituent such as H, alkyl, $COOR^{14}$; $R^{14}$=alkyl) to give amidine (XXXVII), which cyclizes under acidic condition to afford imidazol-2-yl derivative (XXXVIII). In particular, the use of substituted acetals ($R^{12}\neq H$) has been demonstrated by Franchetti et al. (*Bioorg. Med. Chem. Lett.* 2001, 11, 67).

Imidazole derivatives (XXXIX) are accessible (Li et al. *Org. Synth.* 2004, 81, 105) by condensation of amidines (XL) [prepared from nitriles (XXXV) according to Boeré et al. *J. Organomet. Chem.* 1987, 331, 161; Thurkauf et al. *J. Med. Chem.* 1995, 38, 2251], with α-halo ketones (XLI).

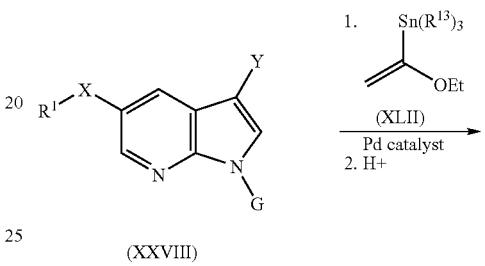

(XXVIII)

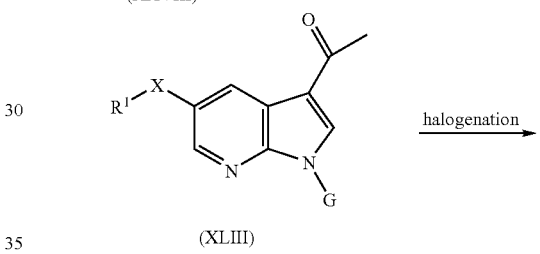

(XLIII)

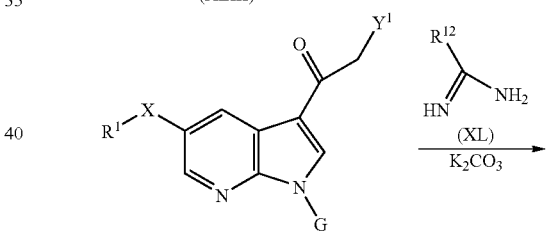

(XLI)

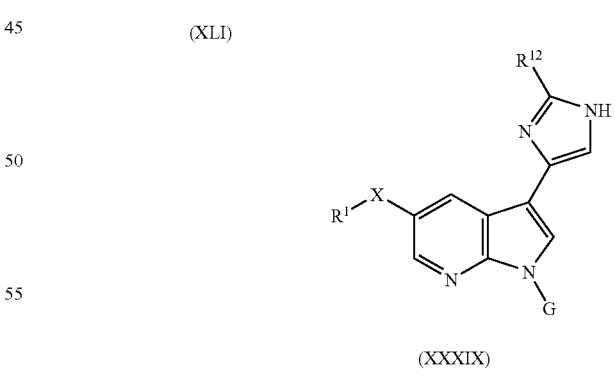

(XXXIX)

The relevant α-halo ketones (XLI) are available by halogenation of ketones (XLIII). In particular Y'=Br can be introduced by direct bromination (Gaudry and Marquet Org. Synth. 1988, VI, 193) or by using $PhNMe_3Br_3$ (Javed and Kahlon *J. Heterocycl. Chem.* 2002, 39, 627), pyridine $HBr_3$ (Zaidlewicz et al. *Heterocycles* 2001, 55, 569) or $CuBr_2$ (Gu et al. *Bioorg. Med. Chem. Lett.* 1999, 9, 569). The relevant iodides (Y'=I) are available following the protocols of Jereb et al. (*Synthesis* 2003, 6, 853) or Lee and Jin (*Synth. Commun.* 1999, 29, 2769) or Bekaert et al (*Tetrahedron Lett.* 2000, 41, 2903) by using the $I_2/SeO_2$ system. Chlorides can be synthesized using $SO_2Cl_2$ as chlorinating agent (Lopez et al. *Farmaco* 2000, 55, 40).

Regiospecific halogenation of an unsymmetrical ketone (XLIII) to afford (XLI)(Y'=Cl, Br, I) can also be executed stepwise by generating silyl enol ether (XLIV) followed by its halogenation. Chlorinating agents include t-BuOCl (Dubac et al. *Synth. Commun.* 1991, 21, 11), $SO_2Cl_2$ (Olah et al. *J. Org. Chem.* 1984, 49, 2032), $CH_3Li/N$-chlorosuccinimide (Denmark and Dapper *J. Org. Chem.* 1984, 49, 798). $CuCl_2$ (Ito et al. *J. Org. Chem.* 1980, 45, 2022), $Ph_3P.Cl_2/(TMSO)_2$ (Shibata et al. *Bull. Chem. Soc. Jpn.* 1991, 64, 3749), and $TiCl_2$ (Oi-Pr)$_2$/t-BuOOH (Krohn et al. *J. Prakt. Chem.* 1999, 341, 62). Bromination can be conducted with $Br_2$ (Blanco et al. *Synthesis* 1976, 194), $PhNMe_3Br_3$ (Baldwin et al. *J. Org. Chem.* 2001, 66, 2588) and N-bromosuccinimide (Paquette et al. *Tetrahedron Lett.* 1985, 26, 1611). Iodine can be introduced using $I_2$/mCPBA (Sha et al. J. Org. Chem. 1987, 52, 3919), $I_2/CrO_3/Me_3SiCl$ (Aizpurua et al. *Tetrahedron* 1985, 41, 2903), $I_2/PCC$ (Scettri et al. *Synth. Commun.* 1982, 12, 11270, $I_2/CH_3COOAg$ (Rubottom and Mott *J. Org. Chem.* 1979, 44, 1731), $I_2Cu(NO_3)_2$ (Dalla Cort *J. Org. Chem.* 1991, 56, 6708) and NaI/N-chlorosuccinimide (Vankar and Kumaravel *Tetrahedron Lett.* 1984, 25, 233.

2001, 66, 2588), or tertiary amine (e.g. $i$-Pr$_2$Net; Kraus et al. *J. Org. Chem.* 1990, 55, 1624).

Introduction of the ketone functionality at C(3) of the 7-azaindole system to provide ketone (XLIII) can be carried out by methods known in the art. These include reacting 3-halo-7-azaindole (XXVIII)(prepared as (V) in Method 1) with α-ethoxyvinyl)trialkyltin (XLII)(Cheney and Paquette *J. Org. Chem.* 1989, 54, 3334) in the presence of palladium catalyst such as $PdCl_2(PPh_3)_2$ followed by acid-catalyzed hydrolysis (Molina et al. *Tetrahedron Lett.* 2002, 43, 1005). Direct introduction of the ketone functionality at C(3) of the 7-azaindole system was demonstrated by Yeung et al. (*Tetrahedron Lett.* 2002, 43, 5793) via Friedel-Crafts methodology.

Method 17

Pyrazole

Ketone (XLIII) may also serve as a starting material for the preparation of pyrazole (XLVII).

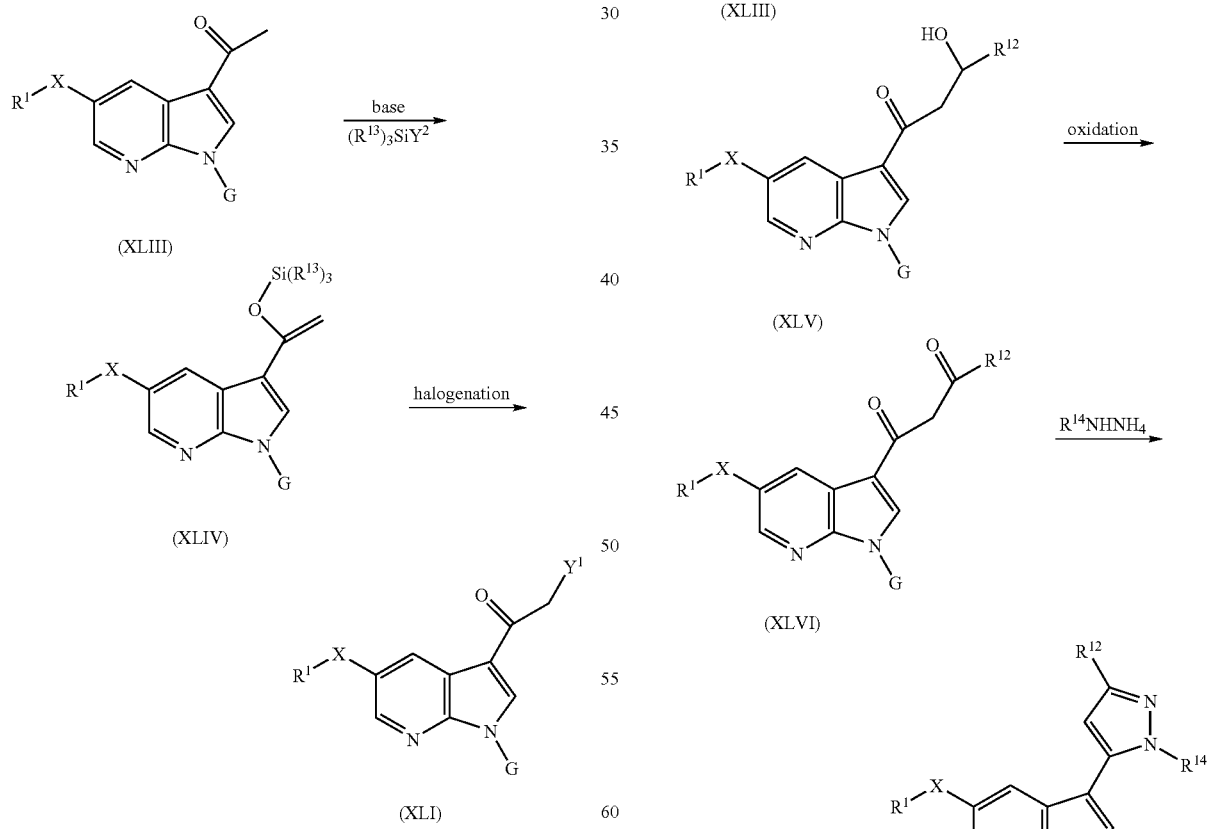

Silyl enol ether (XLIV) needed for this reaction may be formed from ketone (XLIII) using methods known in the art by acting on (XLIII) with silyl halide or triflate $(R^{13})_3SiY^2$ ($Y^2$=Cl, Br, I, $OSO_2CF_3$) and base such as lithium hexamethyldisilylamide (LiHMDS; Baldwin et al. *J. Org. Chem.*

Standard condensation of ketone (XLIII) with aldehyde R[12]CHO affords hydroxyketone (XLV), which can be oxidized by methods known in the art, e.g. Swern oxidation, to α,γ-dicarbonyl system (XLVI). Reaction of (XLVI) with hydrazine R[14]NHNH$_2$ affords pyrazole (XLVII)(R[14]=H; Shoji et al. *Chem. Pharm. Bull.* 1973, 21, 2639; R[14]=Ph; Bendaas et al. *J. Heterocycl. Chem.* 1999, 36, 1291). Regioselective character of this condensation for R[14]=Me was demonstrated by Timmermans et al. (*J. Heterocycl. Chem.* 1972, 9, 1373). Similarly, the use of semicarbazide H$_2$NNHC (O)NH$_2$ leads to amide (XLVII), R[14]=C(O)NH$_2$ (Kumari, et al. *Indian J. Chem., Sect. B* 1996, 35, 846). Pyrazole derivatives (XLVII) where R[12]=OH can be obtained from esters (XLVI)(R[12]=OMe)(Samanta et al. *J. Chem. Res., Synop.* 1995, 11, 429).

Pyrazole (XLVI) can also be prepared from the relevant α,β-unsaturated compound (XLVII) following the method developed for the indole-based systems by Dandia et al. (R[12]=p-F—C$_6$H$_4$; *Indian J. Chem., Sect B.: Org. Chem. Incl. Med. Chem.* 1993, 32, 1288).

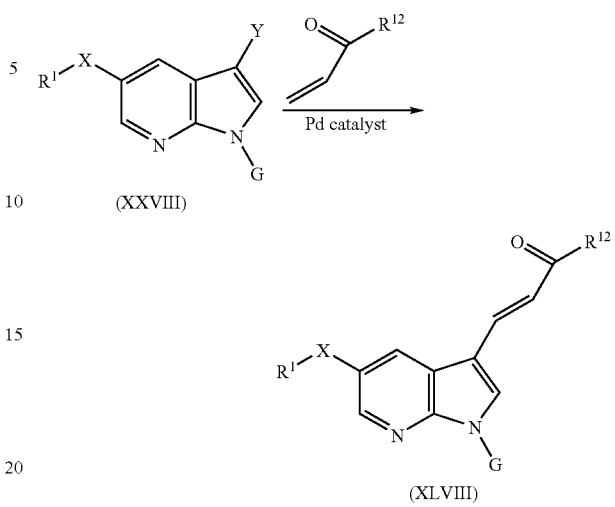

(XXVIII)

(XLVIII)

This reaction is carried out in the presence of tertiary amine such as i-Pr$_2$NEt and with Pd(PPh$_3$)$_2$Cl$_2$ or Pd(OAc)$_2$PPh$_3$ as catalyst. Pyrazole (XLVII) is available from ketone (XLIII) in two steps, as shown below (Speake et al. *Bioorg. Med. Chem. Lett.* 2003, 13, 1183).

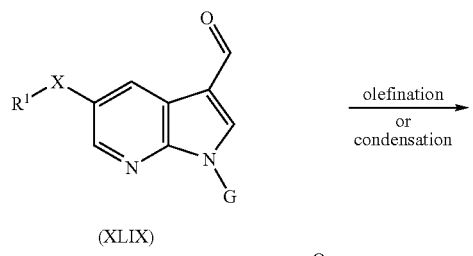

(XLIX)

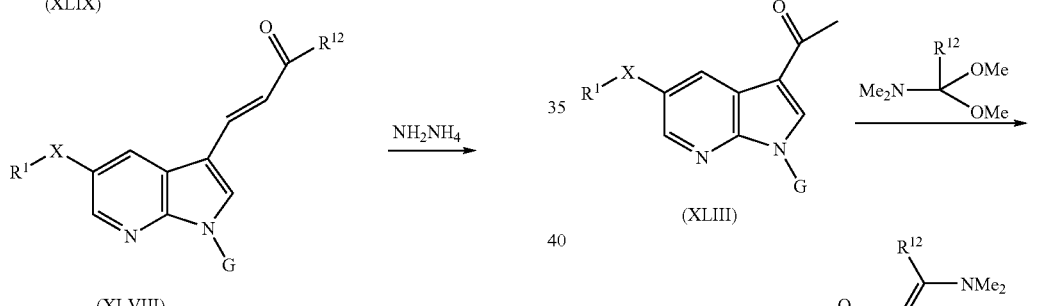

(XLIII)

(XLVIII)

(XLVII)

Compound (XLVII) is available from aldehyde (XLIX; preparation of analogous systems disclosed in WO2004101565) using Horner-type olefination (Willette *Adv. Heterocycl. Chem.* 1968, 9, 27) or base-catalyzed aldol condensation with methylketones (Pailer et al. *Monatsh. Chem.* 1979, 110, 589).

Compound (XLVIII) can also be prepared from the relevant halide (XXVIII)(Y=Br; Brown and Kerr *Tetrahedron Lett.* 2001, 42, 983) or triflate (Y=CF$_3$SO$_3$; Gribble and Conway *Synth. Commun.* 1992, 22, 2129) using Heck methodology.

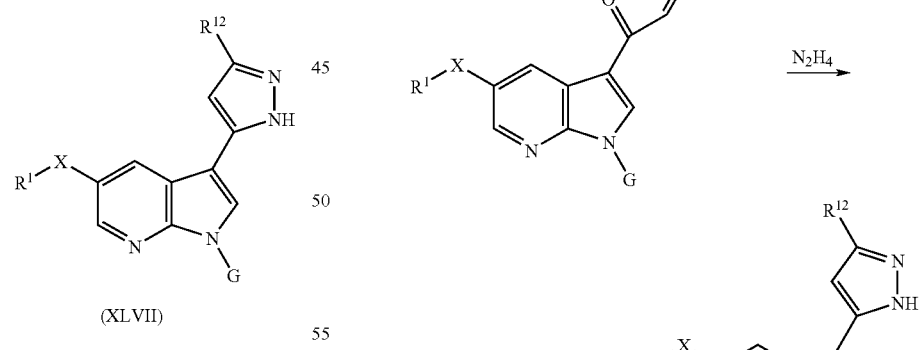

(XLVII)

Pyrazole derivative (L) in which the pyrazole ring is linked to the 7-azaindole C(3) via endocyclic nitrogen could be synthesized by modification of method leading to (XLVII) (see above) and using hydrazine derivative (LI).

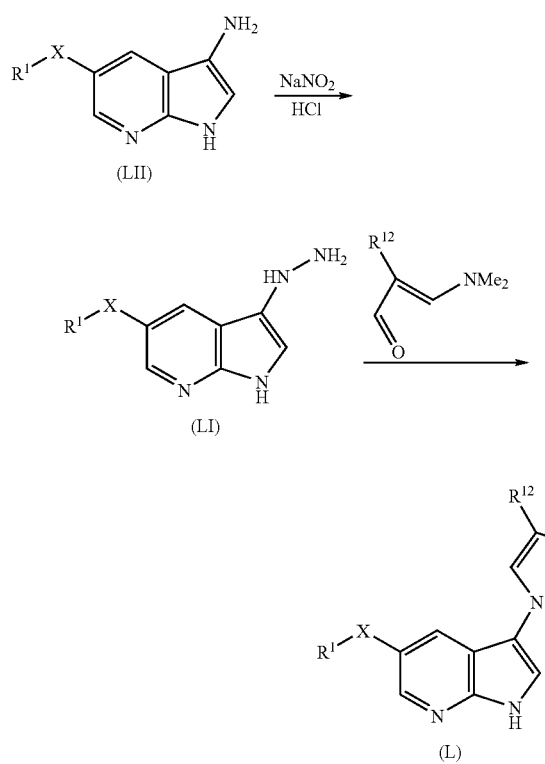

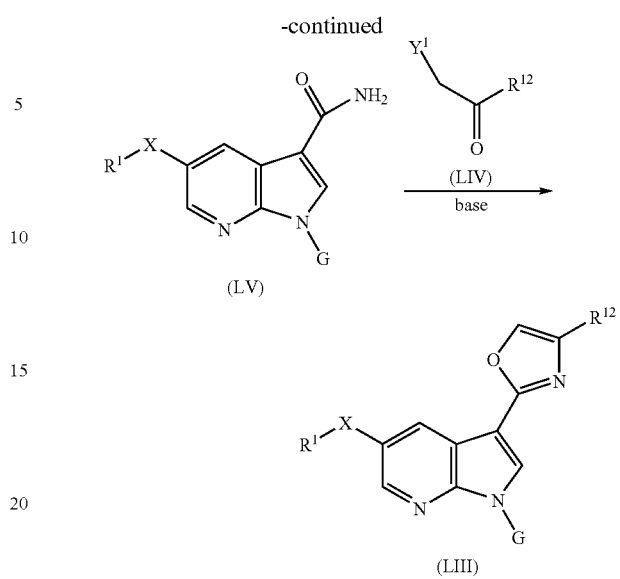

This hydrazine can be prepared in a standard way (Hiremath et al. *Indian J. Chem., Sect. B* 1980, 19, 767) from the relevant amine (LII). Preparation of 3-amino-substituted 7-azaindoles is known in the art (Herbert and Wibberley *J. Chem. Soc. C* 1969, 1505).

Method 18

Oxazole

Oxazole derivatives (LIII) are available via the reaction between amide (LV) and α-haloketone (LIV) using the method of Kelly and Lang (*J. Org. Chem.* 1996, 61, 4623).

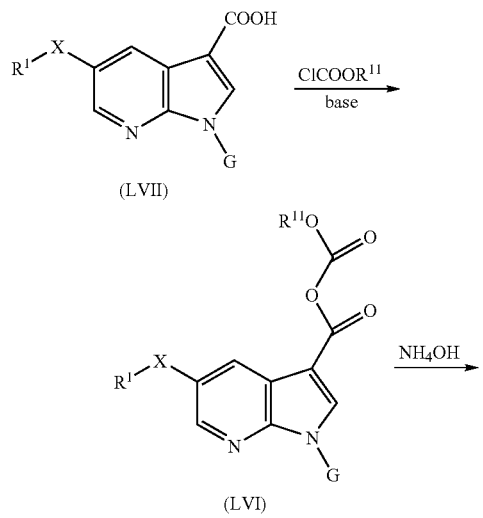

The α-haloketone (LIV) can be prepared in a way analogous to that described for (XLI)(see above, Method 16). Amide (LV) can readily be synthesized from the relevant acid (LVII) via mixed anhydride (LVI)($R^{11}$=alkyl) using standard procedure known to those skilled in the art (preparation of analogous acids and amides was disclosed in WO2003082868).

Reversal of functionalities allows synthesis of oxazoles (LVIII) following the procedure by Kelly and Lang (*J. Org. Chem.* 1996, 61, 4623) as shown below ($R^{12}$=alkyl, alkenyl). Compounds with $R^{12}$=$NH_2$ can be prepared following the method used for the indole series by Bansal et al (*Indian J. Chem., Sect. B: Org. Chem. Incl. Med. Chem.* 2000, 39, 357).

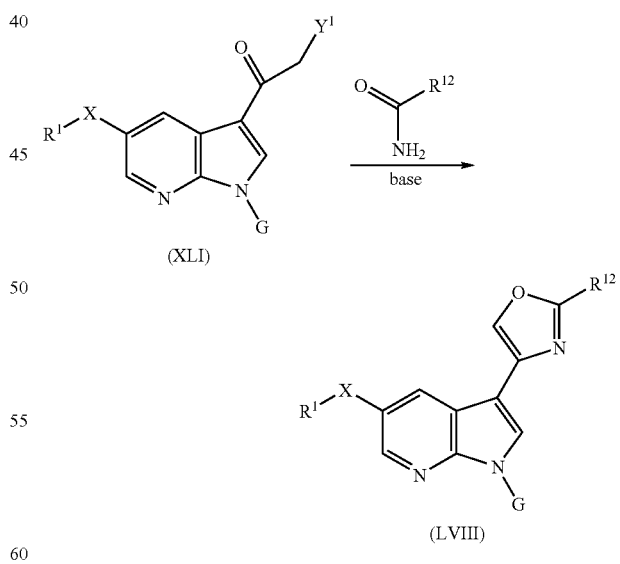

The reaction between α-haloketone (XLI)(preparation described above, Method 16) and amide $R^{12}C(O)NH_2$ is usually carried out at elevated temperature in neutral solvent such as tetrahydrofuran. A large variety of amides $R^{12}C(O)NH_2$ are available commercially or can be prepared using methods known to those skilled in the art.

The remaining regioisomeric oxazole (LIX)($R^{12}$=alkyl, aryl) may be synthesized from α-haloketone (XLI) following the method of Molina et al. (*Synthesis* 1993, 54). The azide (LX) is reacted with acyl halide $R^{12}C(O)Y^2$ ($Y^2$=halogen) in the presence of tertiary phosphine such as tributylphosphine.

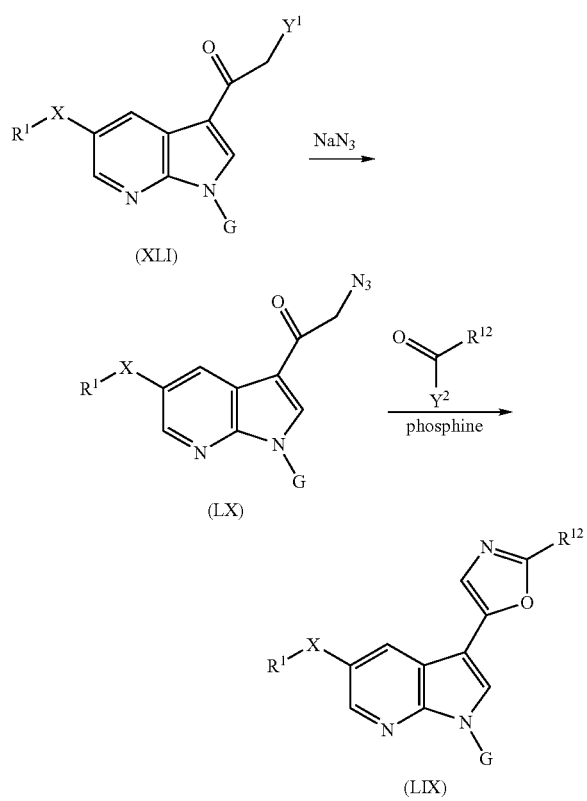

Reacting azide (LX) in the above reaction with the relevant isothiocyanide $R^{14}$—NCS ($R^{14}$=alkyl aryl, heteroaryl) instead of acyl halide $R^{12}C(O)Y^2$ leads to oxazole derivatives (LIX) where $R^{12}$=$NHR^{14}$ (Dhar et al. *Bioorg. Med. Chem. Lett.* 2002, 12, 3305).

An alternative cyclization (Doyle and Moody *Synthesis* 1994, 1021) utilizes diazoketone (LXI), nitrile $R^{12}$CN and $Rh_2(NHCOCF_3)_4$ as catalyst.

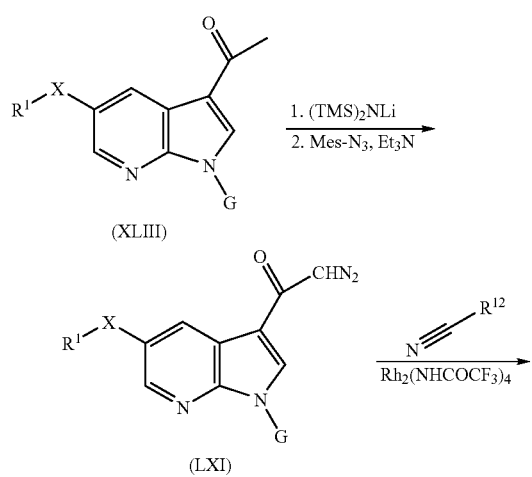

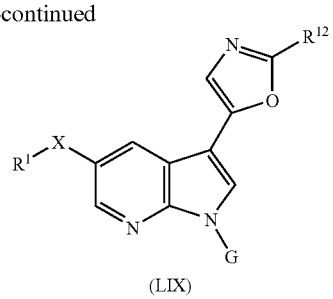

Diazoketones (LXI) can be synthesized from the relevant methyl ketones (XLI)(Moody et al. *J. Chem. Soc., Perkin Trans.* 1 1997, 2413).

The oxazole ring may also be formed by oxidative cyclization as demonstrated by Oikawa et al. (*Heterocycles* 1979, 12, 1457).

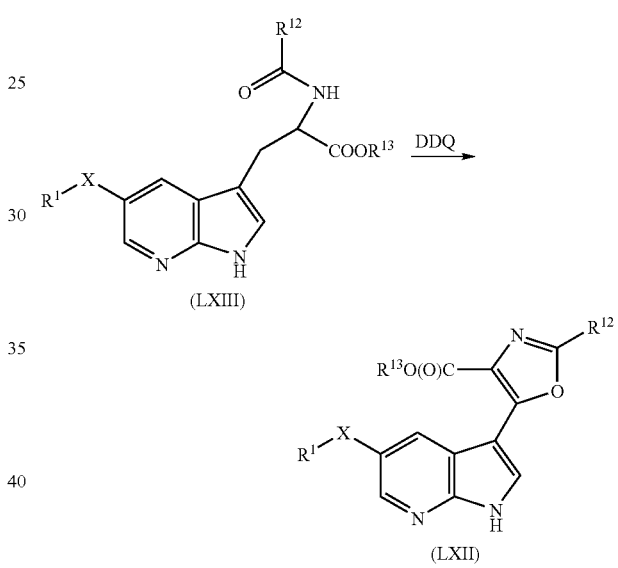

Derivative (LXIII) can be prepared from 7-azatryptophan (commercially available) following the approach presented for tryptophan by Nishida et al. (*Tetrahedron Lett.* 1998, 39, 5983).

The TOSMIC methodology offers a convenient way to convert aldehyde (XLIX) into oxazole (LIX)($R^{12}$=H) using tosylmethyl isocyanide $MeC_6H_4SO_2CH_2NC$ (commercially available) and base such as MeONa (Haubmann et al. *Bioorg. Med. Chem. Lett.* 1999, 9, 3143) or DBU (Dhar et al. *Bioorg. Med. Chem. Lett.* 2002, 12, 3305).

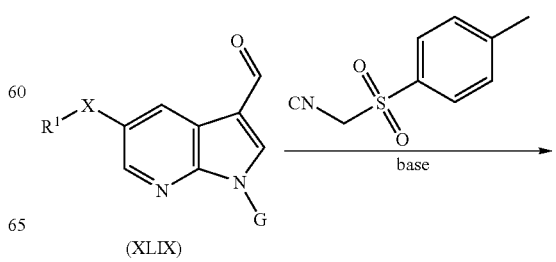

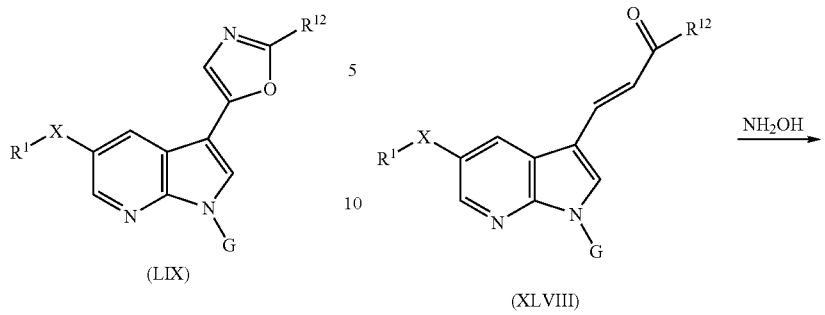

Another method utilizing reactivity of the isocyanide group is based on the Schöllkopf reaction of ester (LXV) (preparation of analogous esters was disclosed in WO2003082868) with LiCH$_2$NC by analogy to the synthesis by Vedejs and Barda (Org. Lett. 2000, 2, 1033) of oxazoles linked to the indole system.

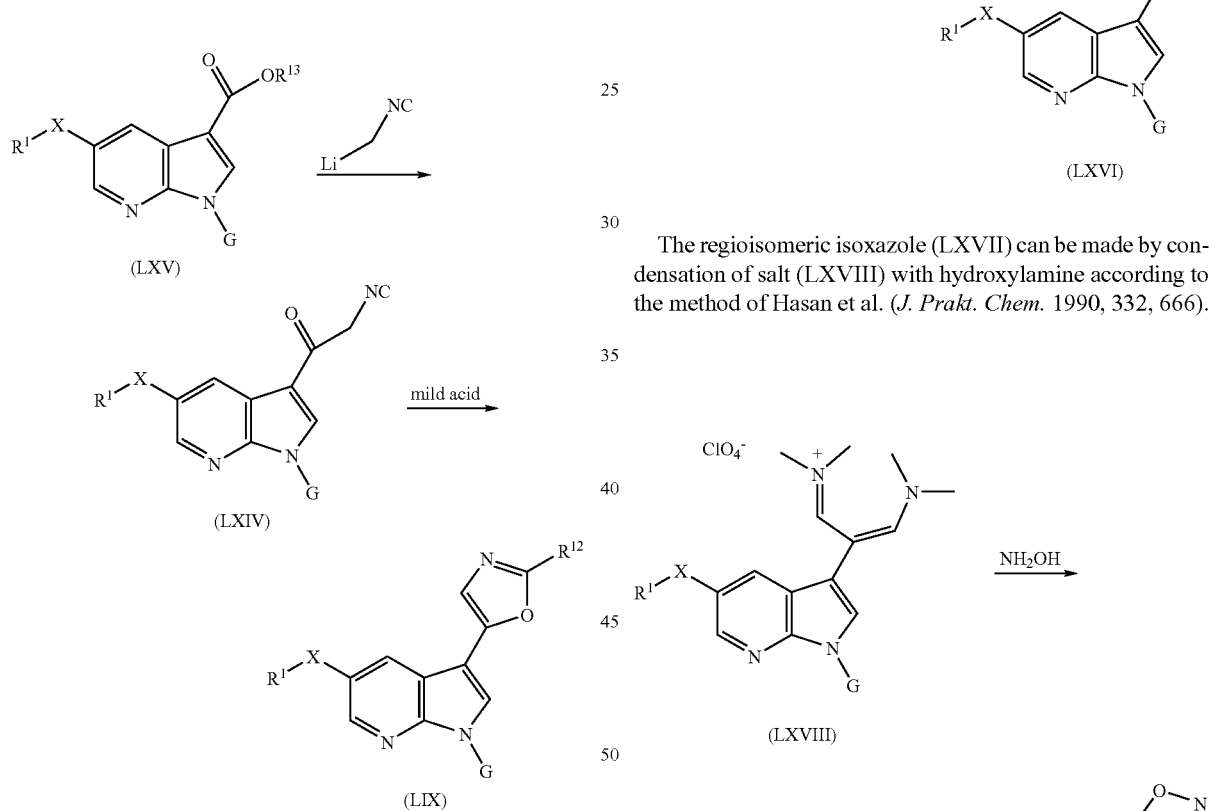

The isocyanide (LXIV) may undergo spontaneous cyclization to afford (LIX)(R$^{12}$=H). In some cases this process may need to be catalyzed by mild acid such as pyridinium toluenesulfonate.

Method 19

Isoxazole

Isoxazole derivatives (LXVI) are available by condensation of unsaturated ketone (XLVIII) with hydroxylamine, following the method used by Roeder and Pigulla (*Arch Pharm* (*Weinheim, Ger*) 1978, 311, 817) for an analogous indole system.

The regioisomeric isoxazole (LXVII) can be made by condensation of salt (LXVIII) with hydroxylamine according to the method of Hasan et al. (*J. Prakt. Chem.* 1990, 332, 666).

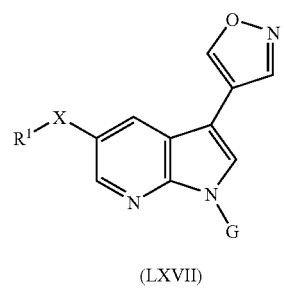

Disubstituted isoxazoles (LXIX) can be synthesized following the method by Kidwai and Sapra (*Org. Prep. Proced. Int.* 2001, 33, 381) using aldehyde (XLIX) as starting material.

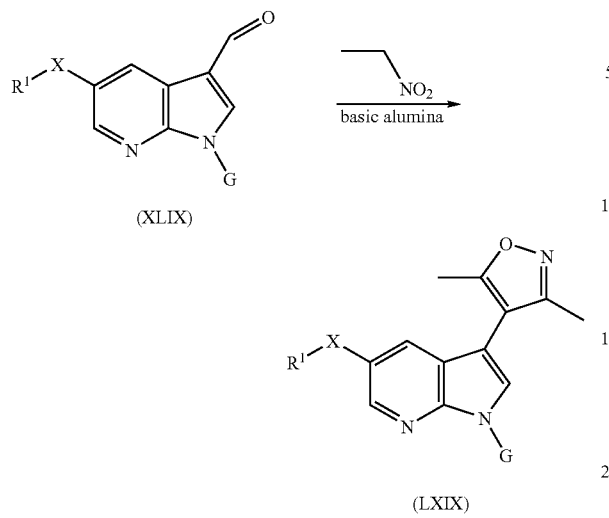

(XLIX)

(LXIX)

The remaining isoxazole regioisomer (LXX) is available from the relevant oxime (LXXI) by halogenation followed by the reaction with alkyne $R^{12}$—C≡CH($R^{12}$=alkyl, aryl). Suitable halogenating agents include NBS (Baruah, et al. *Heterocycles* 1988, 27, 1127) and NaOCl (Jedlovska et al. *Collect. Czech. Chem. Commun.* 1990, 55, 2481). Oxime (LXXI) can be prepared in standard way from the corresponding aldehyde (XLIX).

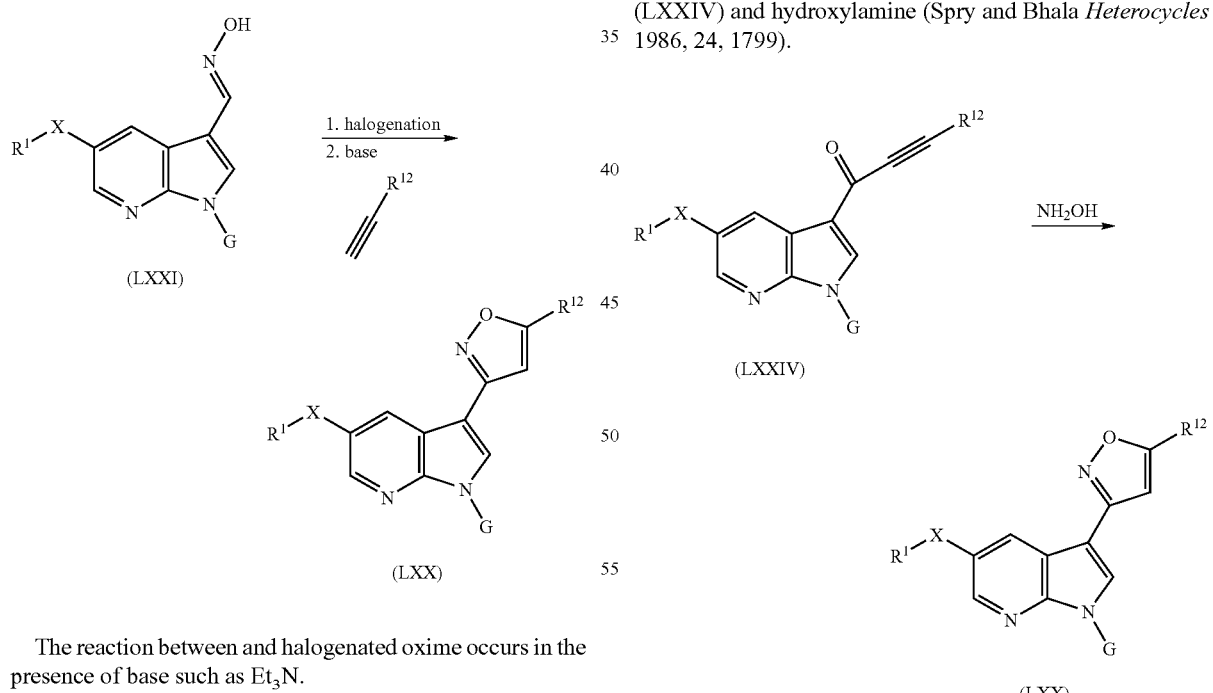

(LXXI)

(LXX)

The reaction between and halogenated oxime occurs in the presence of base such as $Et_3N$.

Propargyloxime (LXXIII)($R^{14}$=alkyl, aryl) [available from α-haloketone (XLI) following conventional methods, e.g. Cory et al. *Helv. Chim. Acta* 1977, 60, 2294; Ben-Basset et al. *J. Med. Chem.* 1976, 19, 928; Hassner and Alexanian *J. Org. Chem.* 1079, 44, 3861] can be cyclized under mild basic conditions to afford isoxazole (LXXII)(Short and Ziegler *Tetrahedron Lett.* 1993, 34, 75).

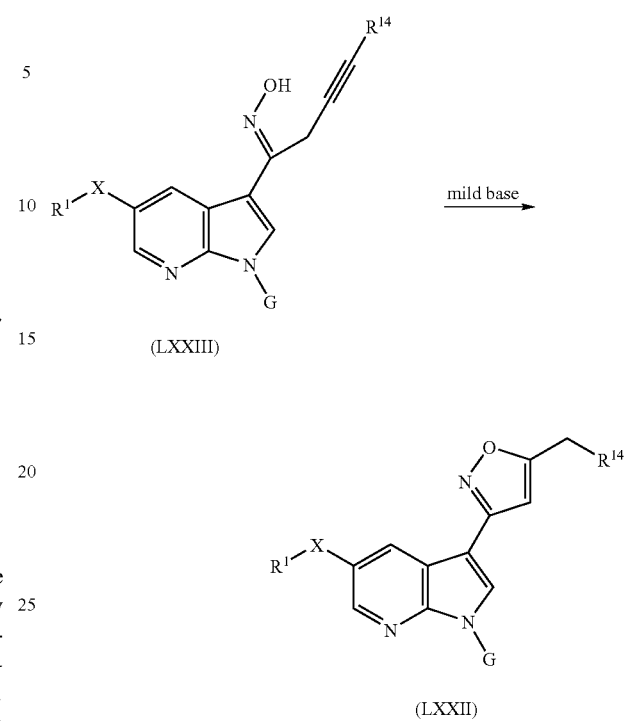

(LXXIII)

(LXXII)

Isoxazole (LXX)($R^{12}$=H) can be synthesized from ketone (LXXIV) and hydroxylamine (Spry and Bhala *Heterocycles* 1986, 24, 1799).

(LXXIV)

(LXX)

Similarly, monosubstituted isoxazole (LXXV) is available from ketone (LXXVI), which can be prepared from methylketone (XLIII)(El-Taweel and Elnagdi *J. Heterocycl. Chem.* 2001, 38, 981).

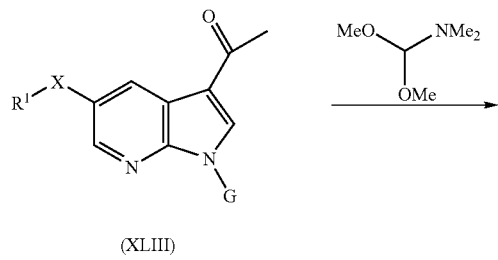
(XLIII)
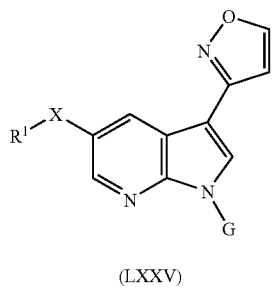
(LXXV)
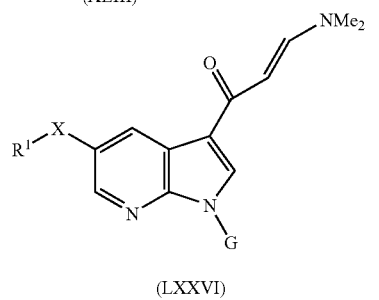
(LXXVI)
Method 20
Thiazole
Methods for synthesis of thiazoles are analogous to those used for oxazoles (cf Method 18). Thus, thiazole (LXXVII) is available by condensation of thioamide (LXXVIII) with α-haloketone (LIV)(Schwarz *Org. Synth.* 1955, *III*, 332; Gu et al. *Bioorg. Med. Chem. Lett.* 1999, 9, 569).

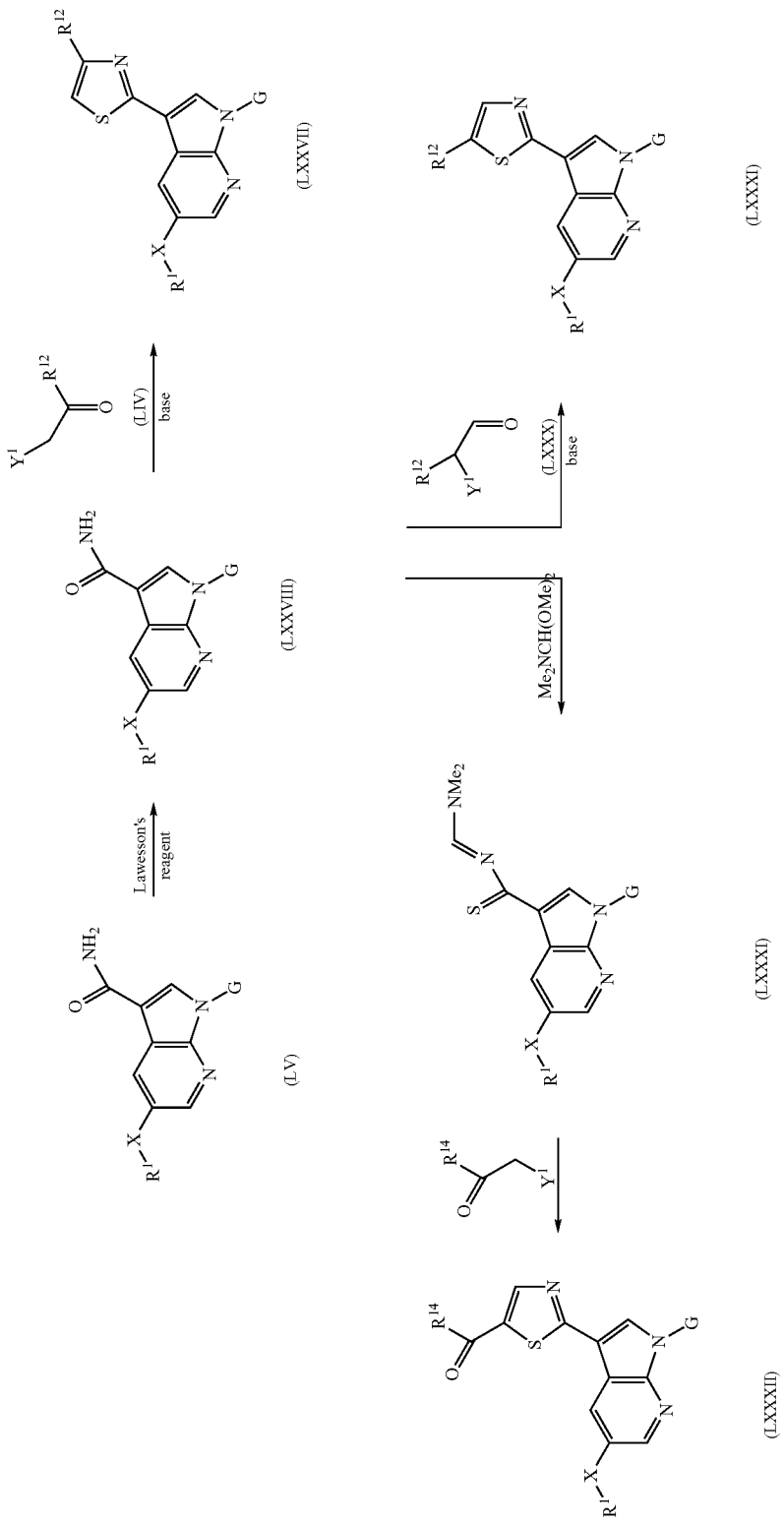

In order to prepare differently substituted thiazole (LXXIX), aldehyde (LXXX) may be applied (Thompson et al. *Bioorg. Med. Chem. Lett.* 1994, 4, 2441). Alkylcarbonyl groups $R^{14}C(O)$ can be installed a to the sulphur atom by converting thioamide (LXXVIII) into amidine (LXXXI) followed by reaction with α-haloketone $R^{14}C(O)CH_2Y^1$ (Thompson et al. *Bioorg. Med. Chem. Lett.* 1994, 4, 2441). Thioamide (LXXVIII) used in these reactions can be readily prepared from amide (LV) using methods known in the art, such as acting on (LV) with the Lawesson's reagent. Alternatively, it can be formed from nitrile (XXXV) and $H_2S$ under basic conditions (Bhattacharya et al. *J. Chem. Soc., Perkin Trans.* 1 1995, 1543; Krawczyk et al. *J. Med. Chem.* 1995, 38, 4115), nitrile (XXXV) and thioacetamide under acidic conditions (Gu et al. *Bioorg. Med. Chem. Lett.* 1999, 9, 569), nitrile (XXXV) and sodium hydrogen sulfide and magnesium chloride in dimethylformamide (DMF)(Manaka and *Sato Synth. Commun.* 2005, 35, 761), or nitrile (XXXV) and the $(Me_3Si)_2S/MeONa$ system (Lin et al. *Synthesis* 1992, 1219; Qiao et al. *Org. Lett.* 2001, 3, 3655)

Isomeric thiazole (LXXXIII) can be synthesized from α-haloketone (XLI)($Y^1$=Cl, Zawistoski *J. Heterocycl. Chem.* 1990, 27, 519; $Y^1$=Br, Di Fabio and Pentassuglia *Synth. Commun.* 1998, 28, 51).

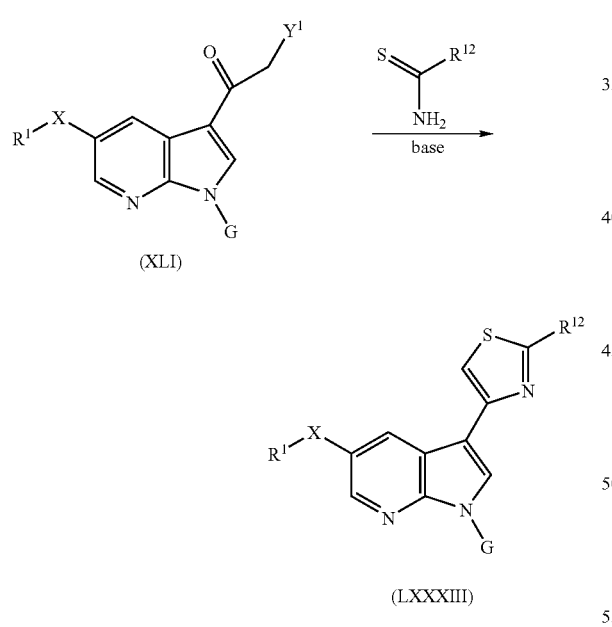

(XLI)

(LXXXIII)

Reaction works for $R^{12}$=$NH_2$ (Hayashi et al. *Heterocycles* 1999, 51, 1233; Bansal et al. *Indian J. Chem., Sect. B: Org. Chem. Incl. Med. Chem.* 2000, 39, 357), $R^{12}$=NH-Aryl (Di Fabio and Pentassuglia *Synth. Commun.* 1998, 28, 51) $R^{12}$= (substituted)alkyl (Zawistoski *J. Heterocycl. Chem.* 1990, 27, 519) and $R^{12}$=aryl (Baldwin et al. *J. Org. Chem.* 2001, 66, 2588). Opposite regiochemistry of this reaction ($Y^1$=Cl, $R^2$=Me, $NH_2$) to produce (LXXXIV) has also been suggested (Arya et al. *Indian J. Chem., Sect. B* 1977, 15, 473).

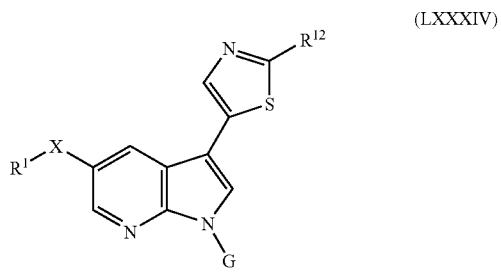

Based on the precedent in the indole series (Saleh *Nucleosides, Nucleotides Nucleic Acids* 2002, 21, 401), thiazole (LXXXV) is available from isothiocyanate $R^{14}$NCS ($R^{14}$=alkyl, heterocyclyl) and α-aminoketone (LXXXVI), which in turn can be prepared by reduction of azide (LX) under acidic conditions (Jiang and Gu *Heterocycles* 2000, 53, 1559).

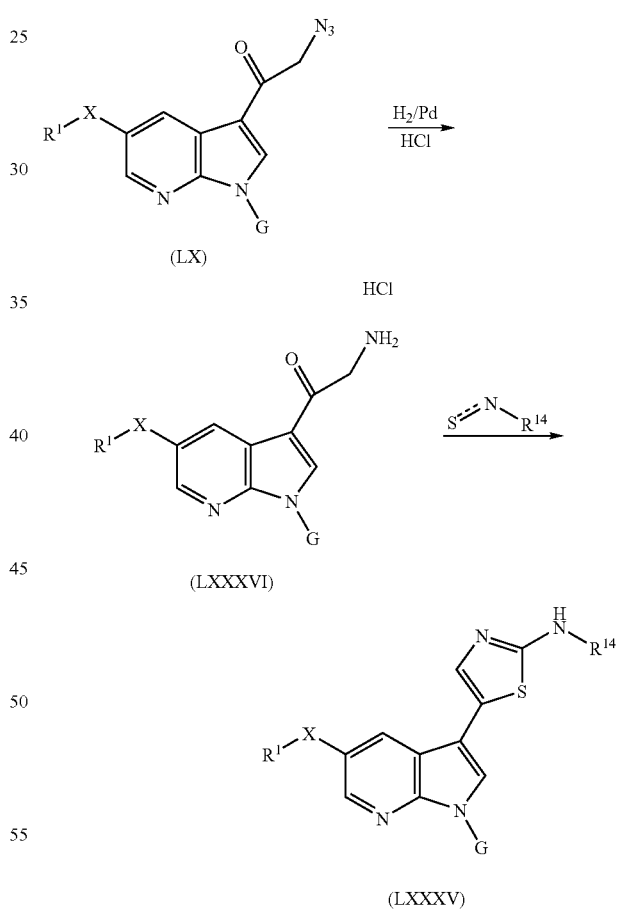

Method 21

Triazole

Triazoles (LXXXVII)($R^{12}$=H, alkyl, aryl, heteroaryl) are available from the relevant imidate (XXXVI)(see Method 16) and hydrazide (LXXXVIII)(Kelarev et al. *Khim. Geterotsikl. Soedin.* 1993, 189).

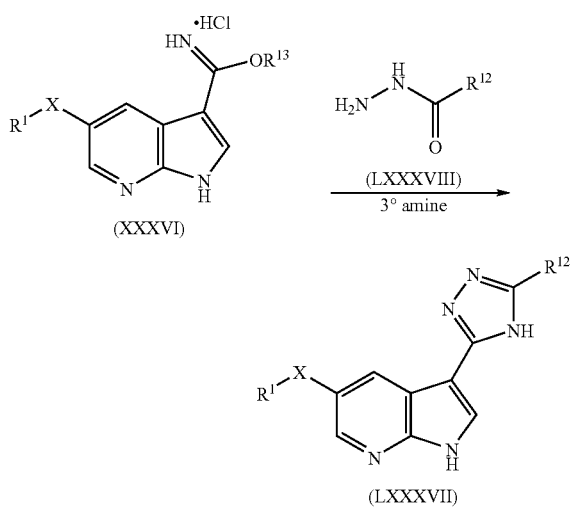

This reaction is carried out in the presence of tertiary amine such as Et$_3$N. The reacting functionalities can also be reversed as shown below:

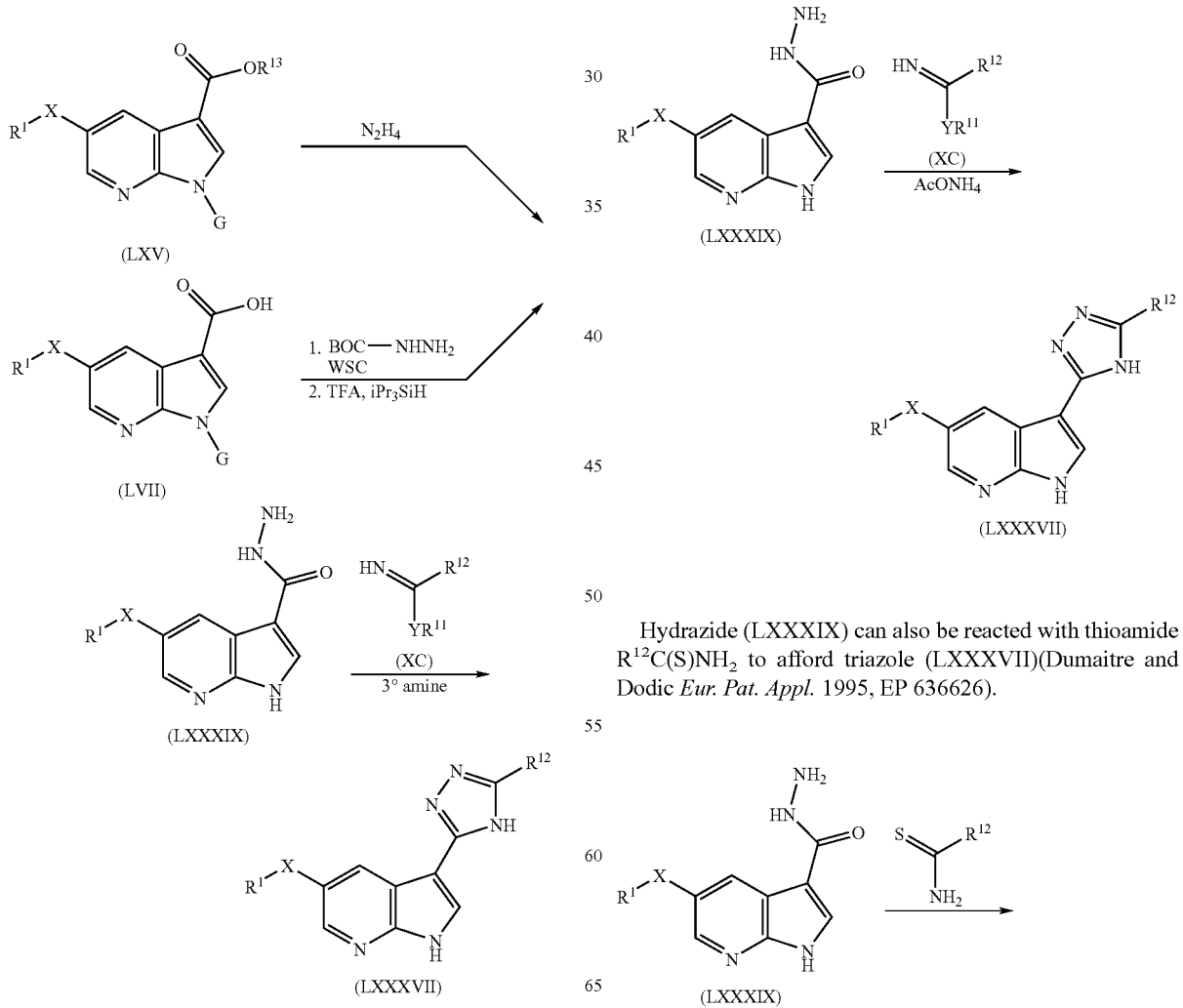

The reaction tolerates a wide range of functionalities incorporated into imidate (XC)(Y=O): R$^{12}$=(hetero)aryl (Omodei-Sale et al. *J. Med. Chem.* 1983, 26, 1187), R$^{12}$=COOEt (McKillop et al. *Tetrahedron Lett.* 1982, 23, 3357), and R$^{12}$=alkyl (Hunter and Neilson *J. Chem. Soc. Perkin Trans. 1: Org. Bio-Org. Chem.* 1988, 1439).

The required hydrazide (LXXXIX) can be prepared from the relevant ester (LXV)(G=H, protecting group) by acting with hydrazine. Alternatively, hydrazine derivative such as BOC—NHNH$_2$ or PhCH$_2$OC(O)NHNH$_2$ is coupled with acid (LVII)(G=H, protection) under usual conditions for amide bond formation. The BOC and PhCH$_2$OC(O) protections can then be removed under appropriate conditions such as TFA/i-Pr$_3$SiH and H$_2$/Pd—C, respectively.

An alternative way to convert hydrazide (LXXXIX) into (LXXXVII) involves three component condensation reaction of (LXXXIX), thioimidate (XC)(Y=S), and ammonium acetate on the surface of silica gel under microwave irradiation as shown below (Rostamizadeh et al. *Synth. Commun.* 2003, 33, 113).

Hydrazide (LXXXIX) can also be reacted with thioamide R$^{12}$C(S)NH$_2$ to afford triazole (LXXXVII)(Dumaitre and Dodic *Eur. Pat. Appl.* 1995, EP 636626).

-continued

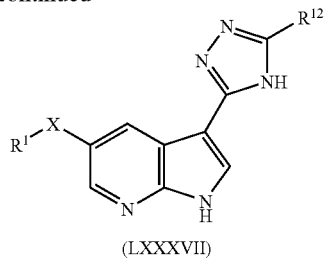

(LXXXVII)

Preparation of a compound where $R^{12}$=H is achieved by the reversal of the functionalities as shown below, and using thioamide (LXXVIII)(G=H) (Vanek et al. *Collect. Czech. Chem. Commun.* 1984, 49, 2492).

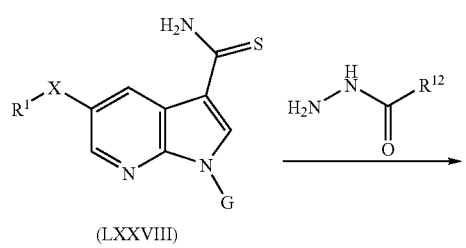

(LXXVIII)

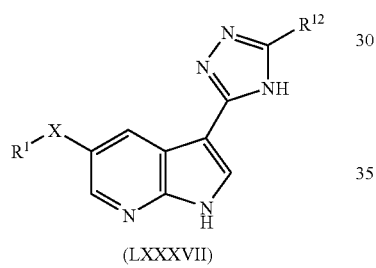

(LXXXVII)

N-Substituted triazole (XCI) is available in three steps from hydrazide (LXXXIX) following the method developed by Gautun and Carlsen (*Molecules* 2001, 6, 969).

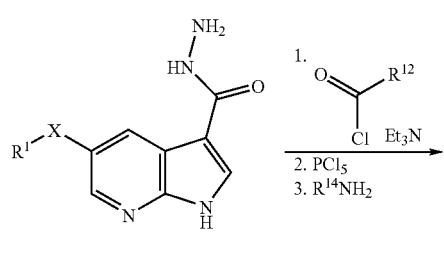

(LXXXIX)

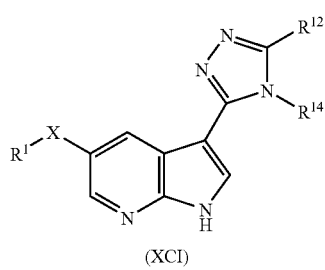

(XCI)

In the last step alcoholic solution of ammonia ($R^{14}$=H) or a primary aliphatic amine $R^{14}NH_2$ can be used.

A variety of heteroatom-substituted triazoles (XCII) are available by condensation of imides (XCIII) with hydrazine.

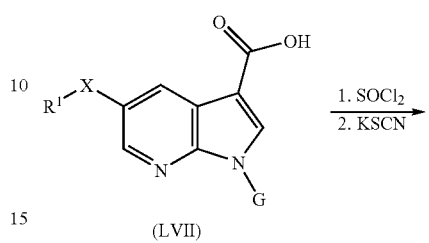

(LVII)

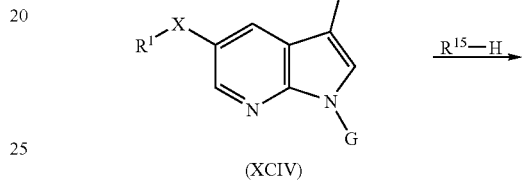

(XCIV)

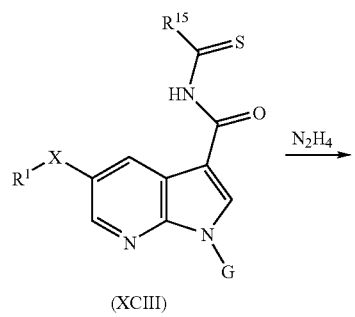

(XCIII)

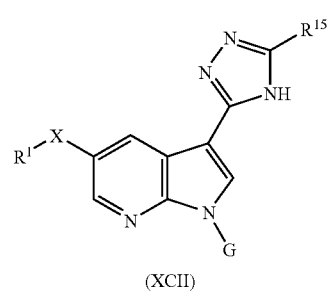

(XCII)

Thus, $R^{15}$=$OR^{13}$ ($R^{13}$=alkyl; Whitfield and Papadopoulos *Synthesis* 1985, 423), $R^{15}$=amino (Whitfield and Papadopoulos *J. Heterocyclic Chem.* 1981, 18, 1197), $R^{15}$=NC(S)— (Saczewski and Foks *Synthesis* 1986, 751), $R^{15}$=NH-aryl (Okajima and Okada *J. Heterocyclic Chem.* 1991, 28, 177). Imides (XCIV) can readily be prepared from the relevant acids (LVII) by sequential formation of acid isothiocyanate (XCIV) and subsequent reaction with alcohol, amine or amide (Whitfield and Papadopoulos Synthesis 1985, 423). A modification of this method ($R^{15}$=amino) using S-methyl derivative (XCV) has recently been described by Chen et al. (*Bioorg. Med. Chem. Lett.* 2001, 11, 3165).

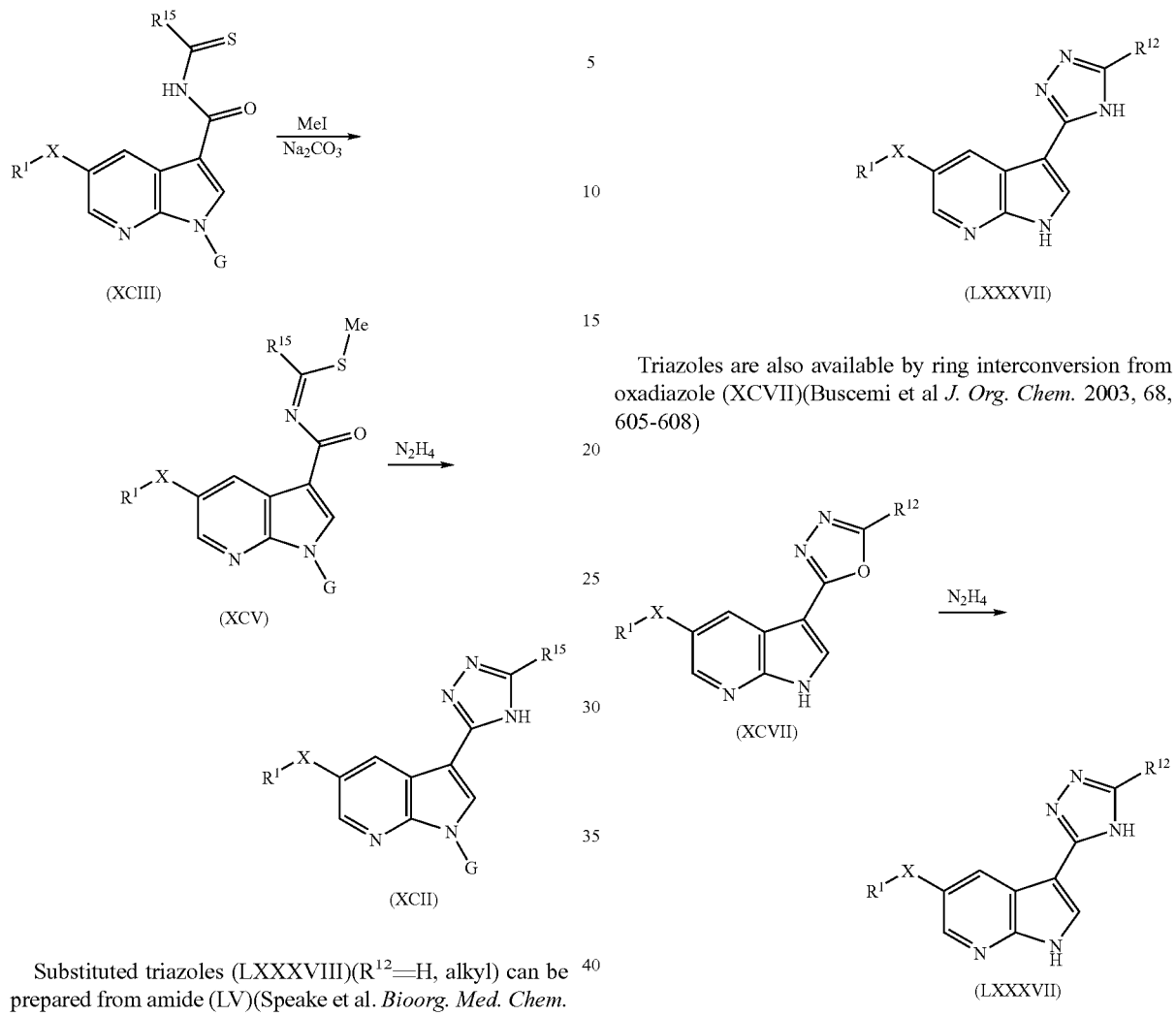

Substituted triazoles (LXXXVIII)(R[12]=H, alkyl) can be prepared from amide (LV)(Speake et al. *Bioorg. Med. Chem. Lett.* 2003, 13, 1183).

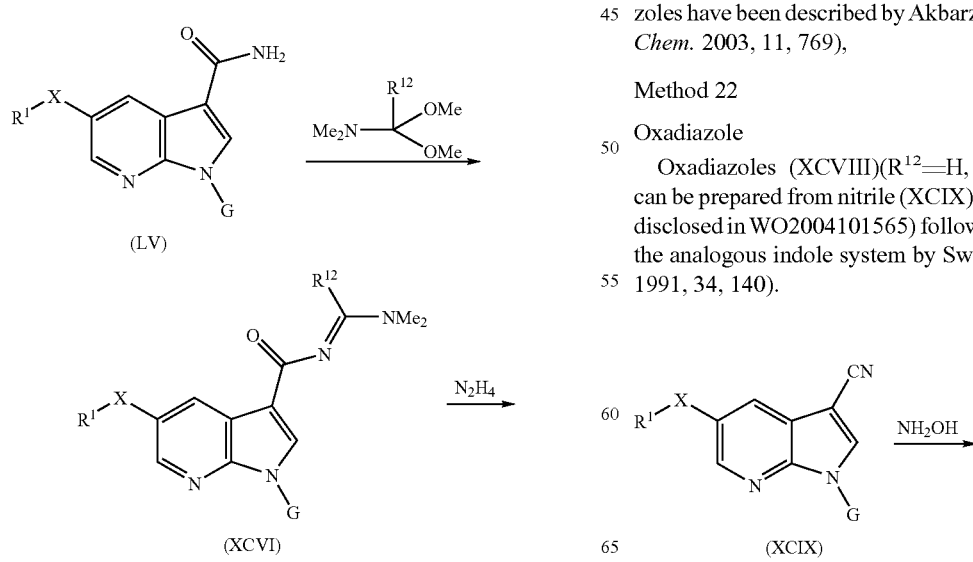

Triazoles are also available by ring interconversion from oxadiazole (XCVII)(Buscemi et al *J. Org. Chem.* 2003, 68, 605-608)

Additional methods to create heteroatom-substituted triazoles have been described by Akbarzadeh et al. (*Bioorg. Med. Chem.* 2003, 11, 769), Method 22

Oxadiazole

Oxadiazoles (XCVIII)(R[12]=H, alkyl, aryl, heteroaryl) can be prepared from nitrile (XCIX)(available using methods disclosed in WO2004101565) following the protocol used for the analogous indole system by Swain et al. (*J. Med. Chem.* 1991, 34, 140).

-continued

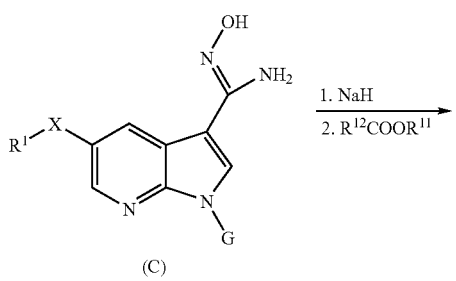

(C)

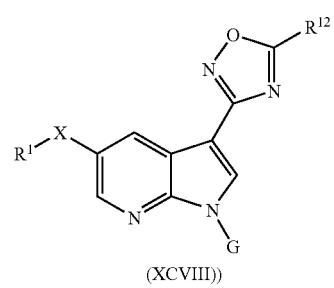

(XCVIII)

Nitrile (XCIX) is first converted into amide oxime (C), salt of which is then reacted with ester R¹²COOR¹¹. The last step may alternatively involve acid anhydride (R¹²CO)₂O, mixed anhydride, acid chloride R¹²COCl or imidate R¹²C(=NH)OR¹¹ (Shvekhgeimer et al. *Khim. Geterotsikl. Soedin.* 1984, 1609).

Oxime (LXXI) may also serve as a substrate to prepare oxadiazole (XCVIII)(Corsaro et al. *J. Chem. Res. Synop.* 1989, 246).

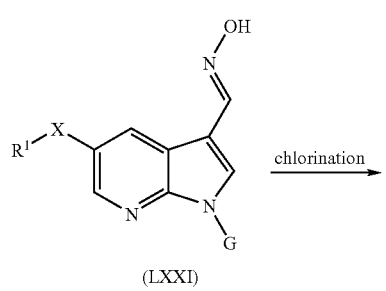

(LXXI)

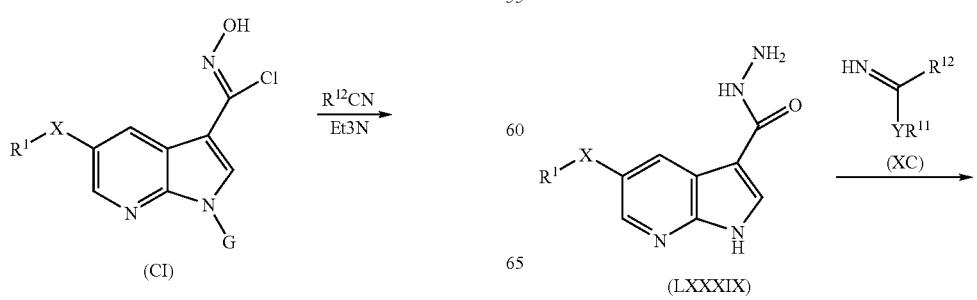

(CI)

-continued

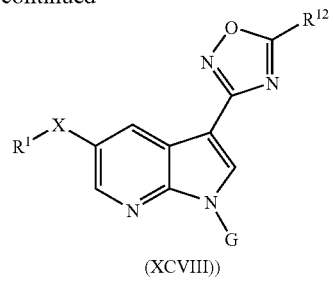

(XCVIII)

Chlorination to produce (CI) can be carried out using Cl₂ (Rajagopalan and Advani *J. Org. Chem.* 1965, 30, 3369), NaNO₂/HCl (Kocevar et al. *Synth. Commun.* 1988, 18, 1427), N-chlorosuccinimide (Bedford et al. *J. Med. Chem.* 1986, 29, 2174), t-BuOCl (Peake and Strickland *Synth. Commun.* 1986, 16, 763), and NOCl (Iwakura et al. *Bull Chem. Soc. Jpn.* 1968, 41, 2954).

Reversal of functionalities in the approaches presented above allows synthesis of regiosiomeric oxadiazole (CII), as shown below.

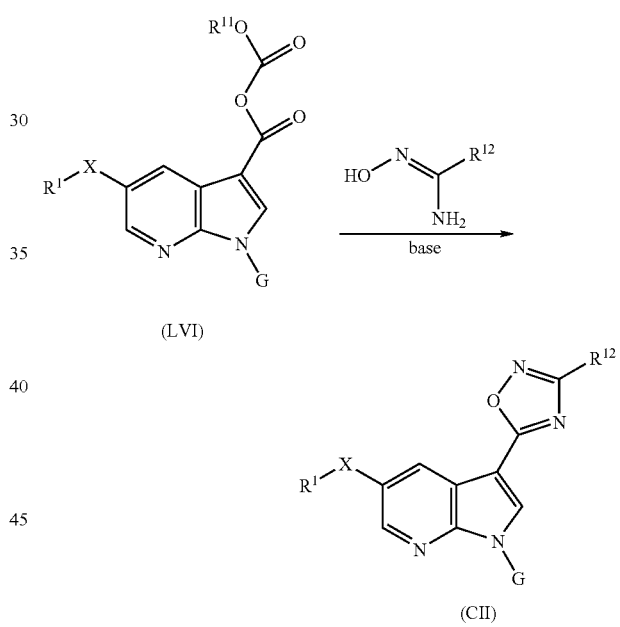

Usually, pyridine is used as base.

Isoxazole regioisomer (XCVII) can be synthesized from hydrazone (LXXXIX) and imidate (XC)(Y=O)(Kelarev et al. *Chem. Heterocycl. Comp.* (*New York*) 2000, 36, 207).

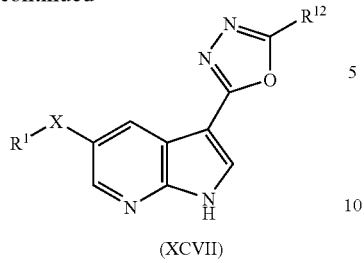

Instead of imidate (XC)(Y=O), the relevant acid anhydride, amide (Kovalenko et al. *Molecules* 2000, 5, 1146) or acid followed by treatment with POCl₃ can be used (Monge Vega et al. *Bol. Soc. Quim. Peru* 1983, 49, 120). Alternatively, orthoformate $R^{12}C(OR^{11})_3$ may be applied ($R^{12}$=H; Hiremath et al. *Indian J. Chem., Sect. B: Org. Chem. Incl. Med. Chem.* 1980, 19B, 1031).

Similarly, after reversal of reacting functionalities isoxazole regioisomer (XCVII) can be formed from imidate (XXXVI) and hydrazone (LXXXVIII)(Reynaud et al. *J. Heterocycl. Chem.* 1992, 29, 991; Swain et al. *J. Med. Chem.* 1991, 34, 140).

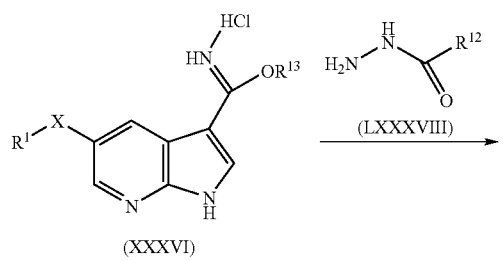

Method 23

Pyrimidine

Pyrimidine (CIII) can be obtained from ketone (LXXVI) and imidate (XC)($R^{11}Y=R^{12}=NH_2$; Molina et al. *Tetrahedron Lett.* 2002, 43, 1005).

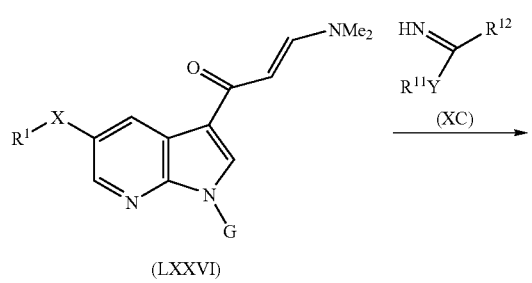

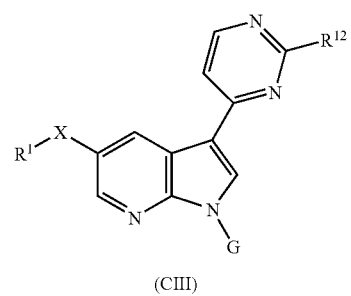

Instead of ketone (LXXVI), ketone (CIV) can be used ($R^{11}Y=H_2N$, R=aryl, S-alkyl; Taboada et al. *J. Carbohyd. Chem.* 2004, 23, 325). It is prepared by oxidation of alcohol (CV)(preparation of analogous systems was disclosed in WO2004101565).

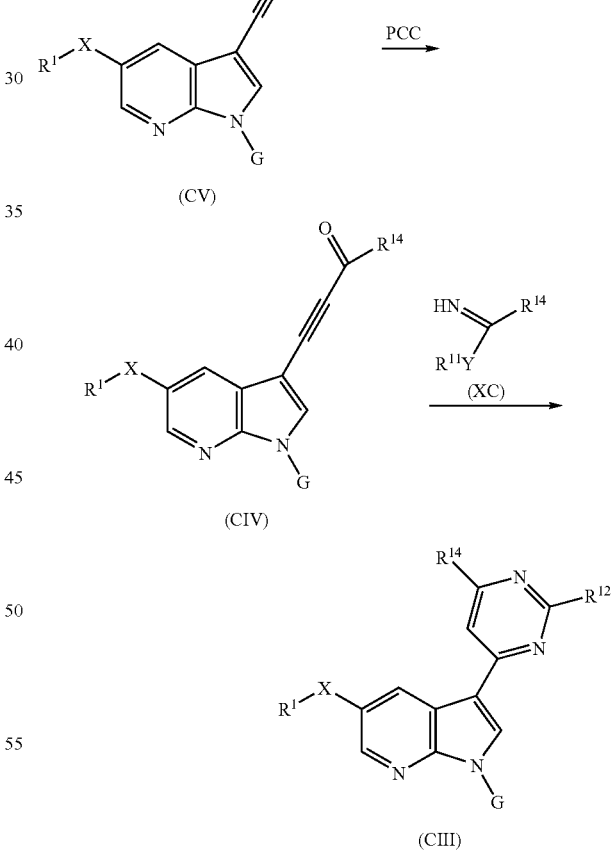

Pyrimidine regioisomer (CVI) is available by modification of the methods presented above. Thus, imidate (CVII) treated with α,β-unsaturated ketone (CVIII) in the presence of base affords pyrimidine (CVI)($R^{14}$=NHC(O)Ph; Bratusek et al *ARKIVOC* 2003, 5, 77, $R^{12}$=heterocycle; El-Taweel et al. *J. Heterocycl. Chem.* 2001, 38, 981).

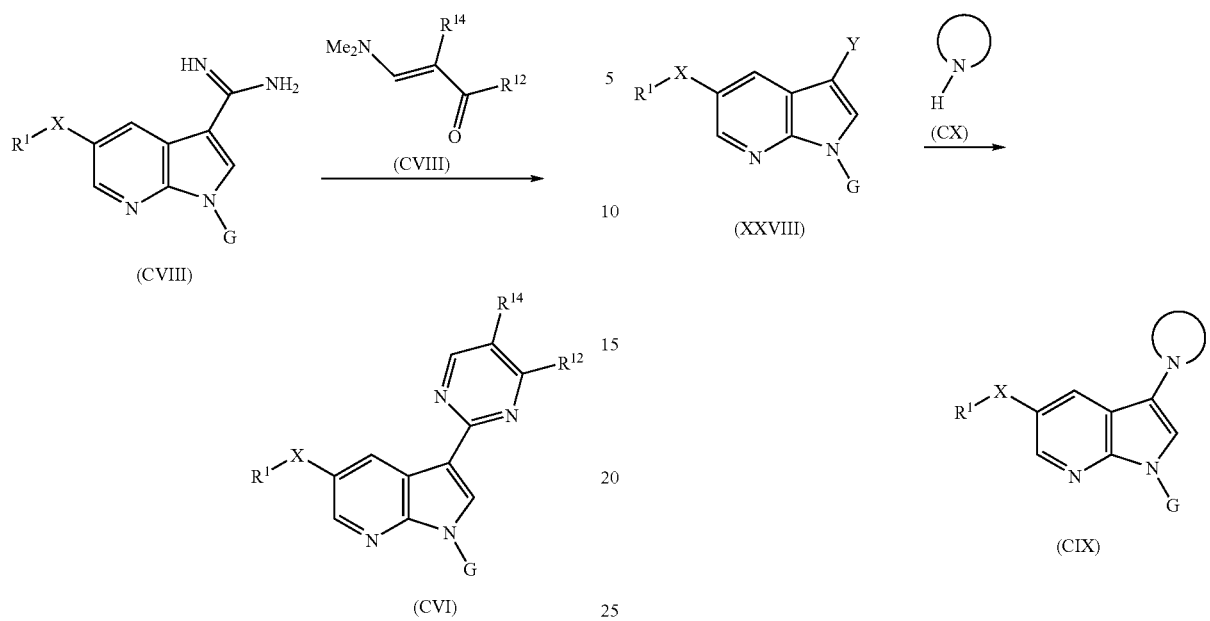

Use of highly functionalized ketone (CVIII) allows preparation of variously substituted pyrimidine derivatives (Westman and Lundin *Synthesis* 2003, 1025; Chhabria and Shishoo *Heterocycles* 1999, 51, 2723).

Method 24

Rings Linked Via Nitrogen

Heteroaromatic rings can also be attached to the C(3) carbon of 7-azaindole system via endocyclic nitrogen atom using C—N couplings.

Thus, (CIX) containing the pyrazolyl group can be prepared using (CX)=pyrazol or imidazole, Y=I and CuI as well as trans-N,N'-dimethylcyclohexanediamine as catalyst (Enguehard et al. *J. Org. Chem.* 2003, 68, 5614). Different set of conditions (Y=Br, Cu$_2$O and salicylaldoxime as catalyst) was proposed by Cristau et al. *Eur. J. Org. Chem.* 2004, 695).

Synthetic Methods for Synthesis of Compounds of the Invention

Synthesis of Example Inhibitors 8 and 9

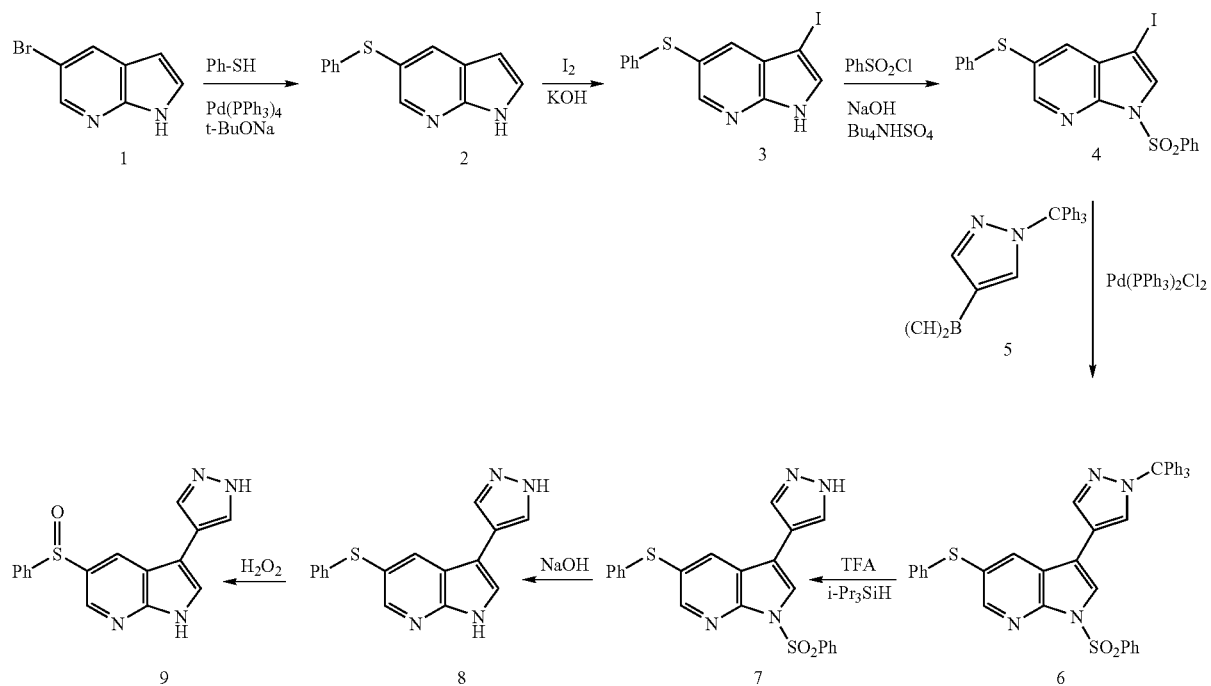

5-Phenylsulfanyl-1H-pyrrolo[2,3-b]pyridine (2)

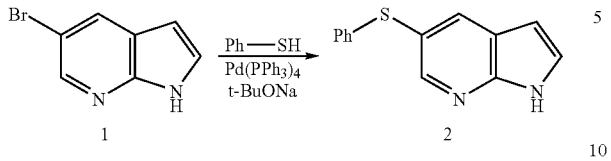

A mixture of 5-bromo-7-azaindole (1)(0.5 g, 2.54 mmol; preparation disclosed in WO2004/078757), benzenethiol (274 µL, 2.66 mmol), sodium t-butoxide (488 mg, 5.07 mmol) and Pd(PPh$_3$)$_4$ (235 mg, 0.20 mmol) in EtOH (25 mL) was heated at reflux for 19 h. More benzenethiol (274 µL, 2.66 mmol), sodium t-butoxide (488 mg, 5.07 mmol) and Pd(PPh$_3$)$_4$ (235 mg, 0.20 mmol) were added and reflux continued for a further 24 h. The reaction mixture was filtered, concentrated, and the residue was extracted with CH$_2$Cl$_2$: hexane=1:1 (v/v). The extract was concentrated and purified by preparative LCMS (column LUNA 10 µ C18(2) 00G-4253-V0 250×50 mm) using water—acetonitrile (0.1% AcOH) as eluent (in gradient; flow 80 mL/min) to afford 2 as a white solid (142 mg, 25%); $^1$H NMR (400 MHz, CDCl$_3$) δ 6.53 (dd, J=3.5, 2.0 Hz, 1H), 7.10-7.30 (m, 5H), 7.41 (dd, J=5.9, 2.5 Hz, 1H), 8.16 (dd, J=2.0, 0.6 Hz, 1H), 8.48 (d, J=2.0 Hz, 1H), 10.00-10.20 (bs, NH).

3-Iodo-5-phenylsulfanyl-1H-pyrrolo[2,3-b]pyridine (3)

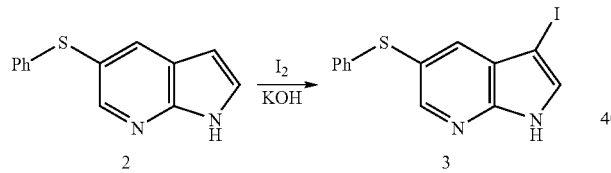

To a solution of 2 (135 mg, 0.60 mmol) in DMF (1.5 mL) was added solid KOH (124 mg, 2.21 mmol) and the reaction mixture stirred for 20 min. Iodine (167 mg, 0.66 mmol) was then added and the stirring continued for 40 min. A mixture of water (8.8 mL) and sat. aq. Na$_2$S$_2$O$_3$ (1.3 mL) was added rapidly, and the resulting solid filtered off, washed with water (2×) and dried in vacuum to give iodide 3 as a creamy solid (205 mg, 98%); $^1$H NMR (400 MHz, CDCl$_3$+2 drops CD$_3$OD) δ 7.10-7.30 (m, 5H), 7.45 (s, 1H), 7.94 (d, J=2.0 Hz, 1H), 8.35 (d, J=1.9 Hz, 1H).

1-Benzenesulfonyl-3-iodo-5-phenylsulfanyl-1H-pyrrolo[2,3-b]pyridine (4)

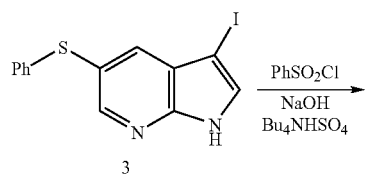

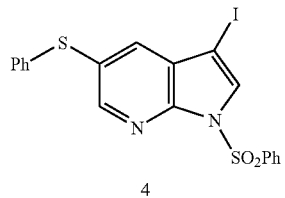

A mixture of 3 (200 mg, 0.57 mmol), benzenesulfonyl chloride (109 µL, 0.85 mmol), n-BuNHSO$_4$ (25 mg, 0.074 mmol) and 50% aqueous NaOH (108 µL) in CH$_2$Cl$_2$ (3.5 mL) were stirred for 0.5 h. The mixture was partitioned between sat. aq. NaHCO$_3$/CH$_2$Cl$_2$. The organic layer was separated and the aqueous phase extracted with CH$_2$Cl$_2$. The combined organic solutions were dried (MgSO$_4$) and concentrated to give 4 as an orange oil (336 mg, 120

1-Benzenesulfonyl-5-phenylsulfanyl-3-(1-trityl-1H-pyrazol-4-yl)-1H-pyrrolo[2,3-b]pyridine (6)

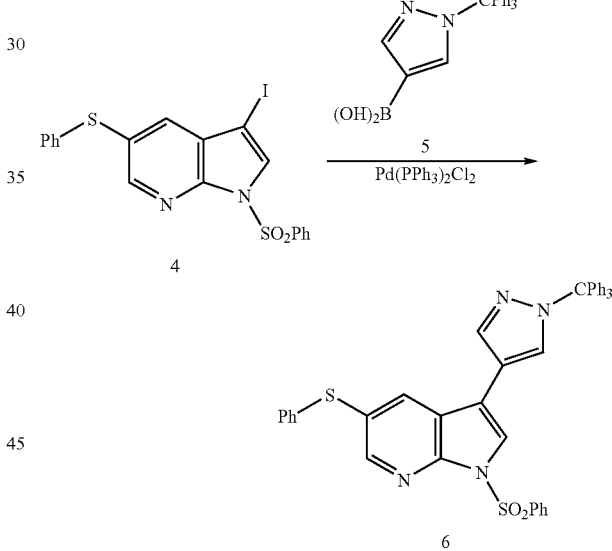

A mixture of iodide 4 (280 mg, 0.57 mmol), boronic acid 5 (302 mg, 0.85 mmol), PdCl$_2$(PPh$_3$)$_2$ (39.9 mg, 0.057 mmol), LiCl (72.3 mg, 1.71 mmol), 1.0 M aq. Na$_2$CO$_3$ (1.4 mL, 1.4 mmol), EtOH (2.7 mL) and toluene (2.7 mL) were heated at reflux for 0.5 h. The mixture was cooled, partitioned between brine/AcOEt, the layers separated and the aqueous phase extracted with more AcOEt (3×), dried (MgSO$_4$) and concentrated. The residue was separated by means of silicagel chromatography (SGC) using AcOEt:hexane as eluent in gradient up to 85:15 (v/v) to give 6 as a light orange foam (353 mg, 92%); $^1$H NMR (400 MHz, CDCl$_3$) δ 7.10-7.40 (m, 20H), 7.49 (t, J=8.1 Hz, 2H), 7.59 (m, 2H), 7.75 (s, 1H), 7.86 (d, J=0.8 Hz, 1H), 7.89 (d, J=2.1 Hz, 1H), 8.19 (m, 2H), 8.46 (d, J=2.0 Hz, 1H).

1-Benzenesulfonyl-5-phenylsulfanyl-3-(1H-pyrazol-4-yl)-1H-pyrrolo[2,3-b]pyridine (7)

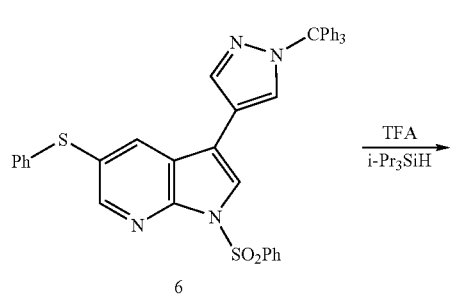

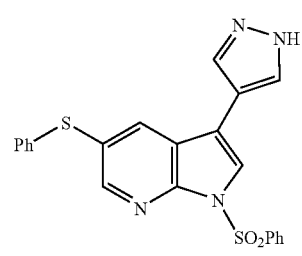

A mixture of 6 (346 mg, 0.51 mmol), CH₂Cl₂ (4.4 mL), CF₃COOH (410 μL), H₂O (41 μL) and i-Pr₃SiH (207 μL) were stirred for 0.5 h then added dropwise to a stirred mixture of CH₂Cl₂/sat. aq. NaHCO₃. The layers were separated and the aqueous phase extracted with more CH₂Cl₂ (3×), dried (MgSO₄) and concentrated. The residue was separated by means of silicagel chromatography (SGC) using AcOEt:hexane as eluent in gradient up to 65:35 (v/v) to give 7 as a white solid (160 mg, 72%); ¹H NMR (400 MHz, CDCl₃+6 drops CD₃OD) δ 7.10-7.28 (m, 5H), 7.47 (t, J=7.7 Hz, 2H), 7.56 (t, J=7.5 Hz, 1H), 7.75 (s, 2H), 7.78 (s, 1H), 8.01 (d, J=2.1 Hz, 1H), 8.13 (d, J=1.4 Hz, 1H), 8.16 (s, 1H), 8.42 (d, J=2.0 Hz, 1H).

5-Phenylsulfanyl-3-(1H-pyrazol-4-yl)-1H-pyrrolo[2,3-b]pyridine (8)

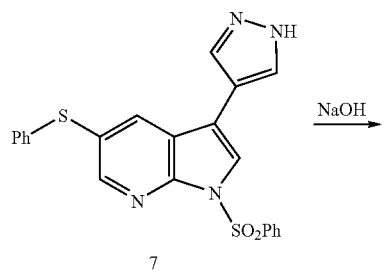

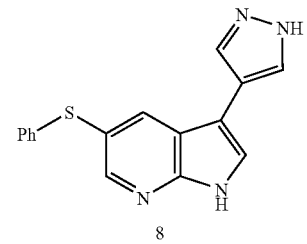

A mixture of 7 (130 mg, 0.30 mmol) and 10% aq. sodium hydroxide (2.8 mL) in EtOH (5.8 mL) were heated at 90° C. for 1 h. The solution was cooled, partitioned between CH₂Cl₂/brine, the layers separated and the aqueous phase extracted with more CH₂Cl₂ (3×). The combined organic extracts were dried (MgSO₄), concentrated and the residue purified by preparative LCMS (column LUNA 10 μ C18(2) 00G-4253-V0 250×50 mm) using water—acetonitrile (0.1% AcOH) as eluent (in gradient; flow 80 mL/min) to give 8 as a white solid (52 mg, 59%); ¹H NMR (400 MHz, CDCl₃+6 drops CD₃OD) δ 7.13 (m, 3H), 7.22 (m, 2H), 7.47 (s, 1H), 7.80 (s, 2H), 8.27 (d, J=2.0 Hz, 1H), 8.38 (d, J=2.0 Hz, 1H).

5-Benzenesulfinyl-3-(1H-pyrazol-4-yl)-1H-pyrrolo[2,3-b]pyridine (9)

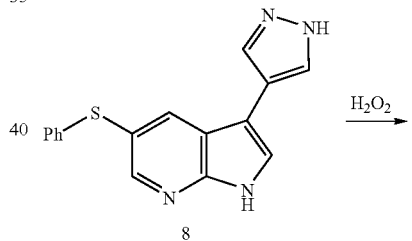

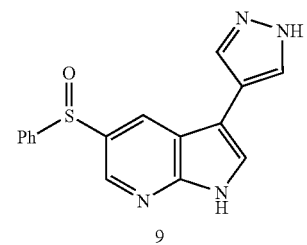

A mixture of sulfide 8 (20 mg, 0.068 mmol) and 30% aqueous H₂O₂ (10.5 μL, 0.103 mmol) in glacial acetic acid (224 μL) was stirred for 72 h then purified by preparative LCMS (column LUNA 10 μl C18(2) 00G-4253-V0 250×50 mm) using water—acetonitrile (0.1% AcOH) as eluent (in gradient; flow 80 mL/min) to give sulfoxide 9 as a white solid (13.6 mg, 64%); ¹H NMR (400 MHz, CDCl₃+6 drops CD₃OD) δ 7.35-7.50 (m, 4H), 7.60 (m, 2H), 7.78 (s, 2H), 8.35 (d, J=2.0 Hz, 1H), 8.40 (d, J=2.0 Hz, 1H).

Synthesis of example inhibitors 17, 18 and 19
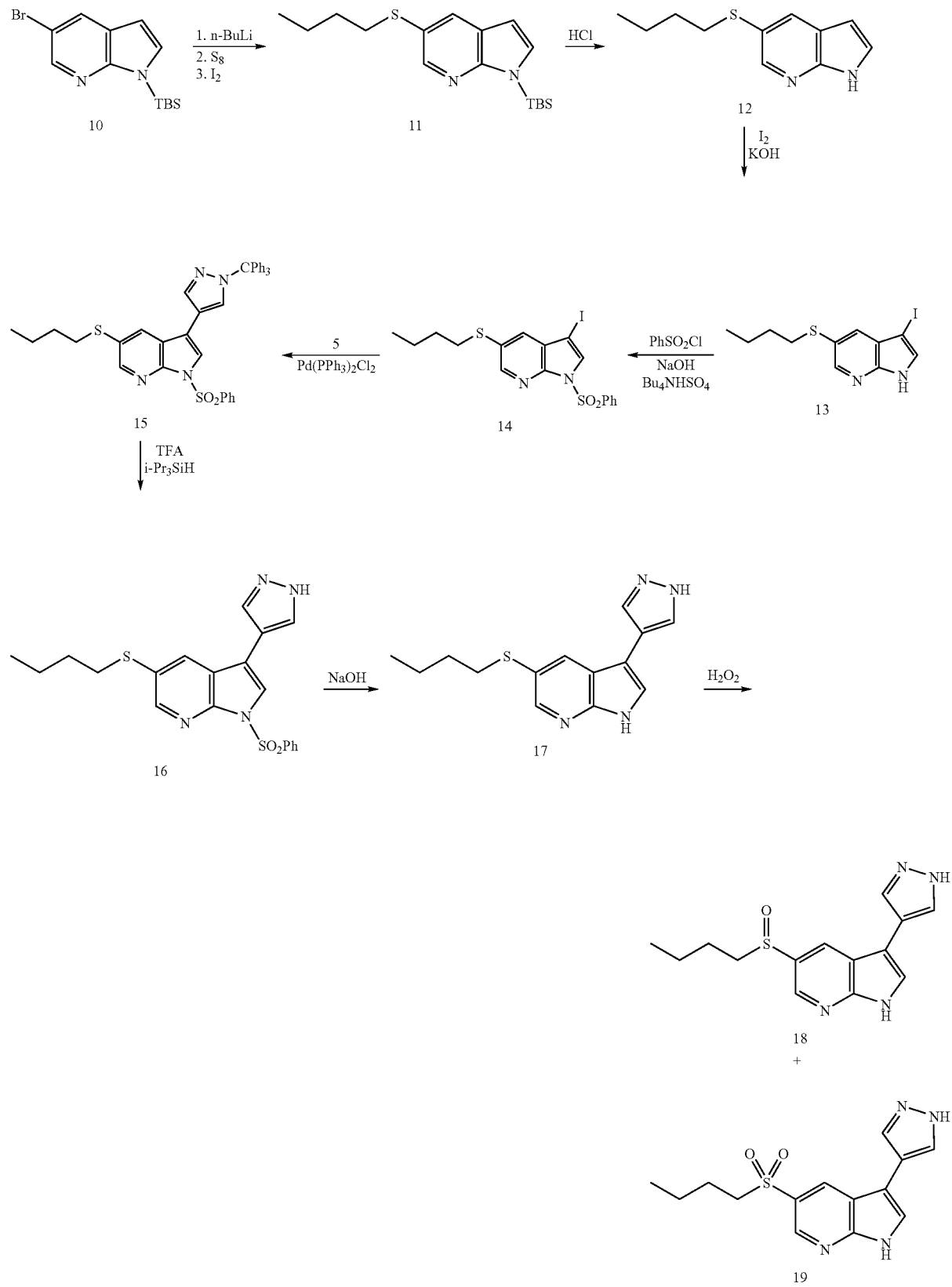

1-(tert-Butyl-dimethyl-silanyl)-5-butylsulfanyl-1H-pyrrolo[2,3-b]pyridine (11)

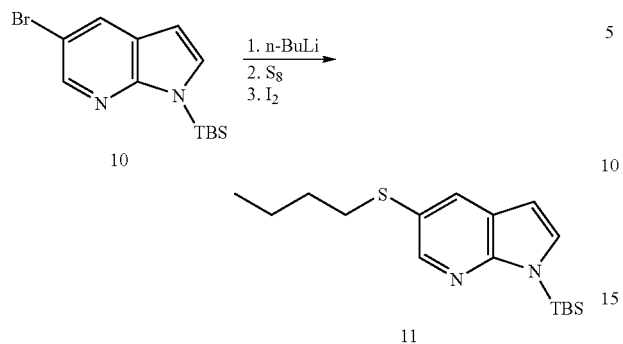

To n-BuLi (13.5 mL, 33.7 mmol, 2.5M in THF) in THF (50 mL), cooled to −78° C., was added a solution of 10 (5.00 g, 16.1 mmol; preparation disclosed in WO2004/078757) in THF (25 mL) dropwise. When the addition was complete the reaction mixture was stirred at −78° C. for 10 min. Solid dry elemental sulfur (618 mg, 2.41 mmol $S_8$) was added and stirring continued at −78° C. for 2 h. Elemental iodine (4.28 g, 16.9 mmol) was added and the reaction mixture stirred at −78° C. for 1.5 h, and at room temperature for 1 h. It was then partitioned between AcOEt/brine, the layers were separated and the aqueous phase extracted with more AcOEt (2×). The combined organic extracts were dried ($MgSO_4$) and concentrated to give crude 11 as a brown oil (5.38 g). This mixture of several compounds was directly used in the next step.

5-Butylsulfanyl-1H-pyrrolo[2,3-b]pyridine (12)

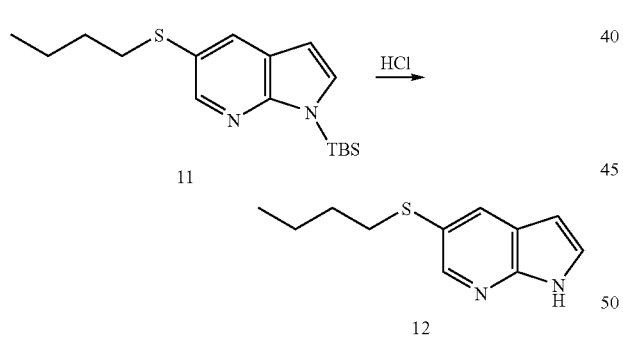

The crude mixture containing 11 (5.38 g) was treated with MeOH (48 mL) and 10% aq. HCl (97 mL) for 0.5 h. The acid was neutralised by dropwise addition of sat. aqueous $NaHCO_3$. The resulting solid was filtered off, washed with water (3×), dried in vacuum and extracted with $CH_2Cl_2$. The extracts were concentrated to afford a dark red oil, which was purified by SGC with $CH_2Cl_2$:MeOH as eluent (gradient elution up to 99:1, v/v) to give 12 as a brown oil (1.23 g, 37% over 2 steps); $^1$H NMR (400 MHz, $CDCl_3$) δ 0.90 (t, J=7.3 Hz, 3H), 1.35-1.50 (m, 2H), 1.52-1.65 (m, 2H), 2.87 (t, J=7.4 Hz, 2H), 6.49 (dd, J=3.5, 1.8 Hz, 1H), 7.41 (dd, J=3.4, 2.3 Hz, 1H), 8.10 (d, J=2.0 Hz, 1H), 8.43 (d, J=2.0 Hz, 1H), 10.90-11.10 (bs, NH).

5-Butylsulfanyl-3-iodo-1H-pyrrolo[2,3-b]pyridine (13)

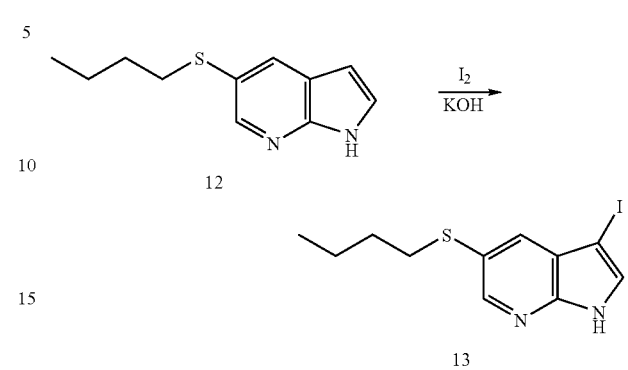

Iodide 13 was synthesized following the method described for preparation of 3 using: 12 (1.00 g, 4.85 mmol), DMF (12.1 mL), KOH (897 mg, 16.0 mmol), iodine (1.35 mg, 5.33 mmol). Reaction time: 40 min. Obtained: 13 as tan solid (1.29 g, 80%).

1-Benzenesulfonyl-5-butylsulfanyl-3-iodo-1H-pyrrolo[2,3-b]pyridine (23)

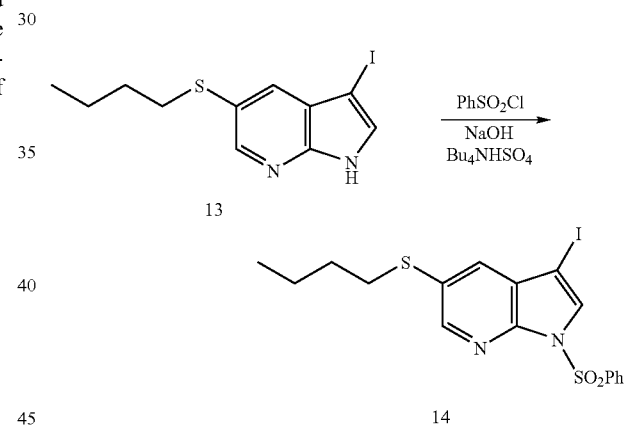

Sulfonamide 14 was synthesized following the method described for preparation of 4 using: 13 (1.20 g, 3.61 mmol), $PhSO_2Cl$ (691 μL, 5.42 mmol), n-$Bu_4NHSO_4$ (159 mg, 0.47 mmol), 50% aq. NaOH (686 μL), $CH_2Cl_2$ (23 mL). Reaction time: 0.5 h. Obtained 14 as a red oil (2.24 g, 131%).

1-Benzenesulfonyl-5-butylsulfanyl-3-(1-trityl-1H-pyrazol-4-yl)-1H-pyrrolo[2,3-b]pyridine (15)

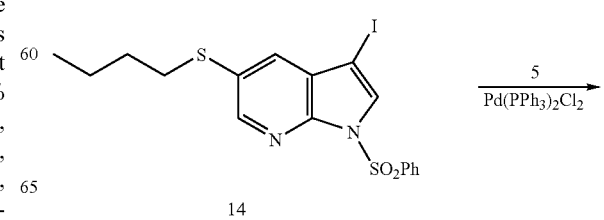

-continued

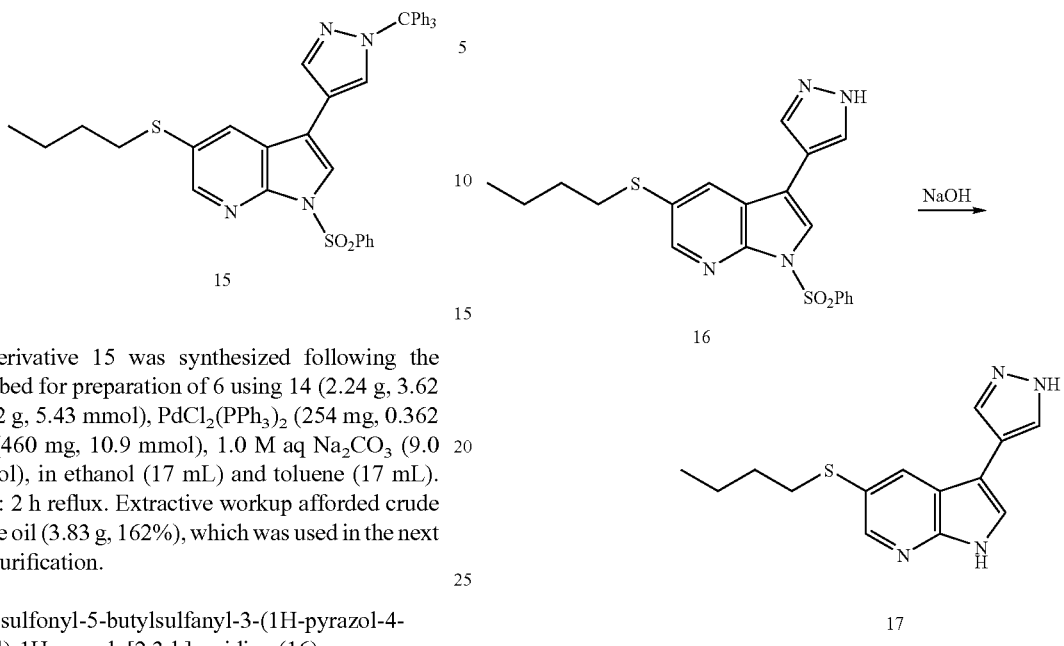

Pyrazole derivative 15 was synthesized following the method described for preparation of 6 using 14 (2.24 g, 3.62 mmol), 5 (1.92 g, 5.43 mmol), PdCl$_2$(PPh$_3$)$_2$ (254 mg, 0.362 mmol), LiCl (460 mg, 10.9 mmol), 1.0 M aq Na$_2$CO$_3$ (9.0 mL, 9.05 mmol), in ethanol (17 mL) and toluene (17 mL). Reaction time: 2 h reflux. Extractive workup afforded crude 15 as an orange oil (3.83 g, 162%), which was used in the next step without purification.

1-Benzenesulfonyl-5-butylsulfanyl-3-(1H-pyrazol-4-yl)-1H-pyrrolo[2,3-b]pyridine (16)

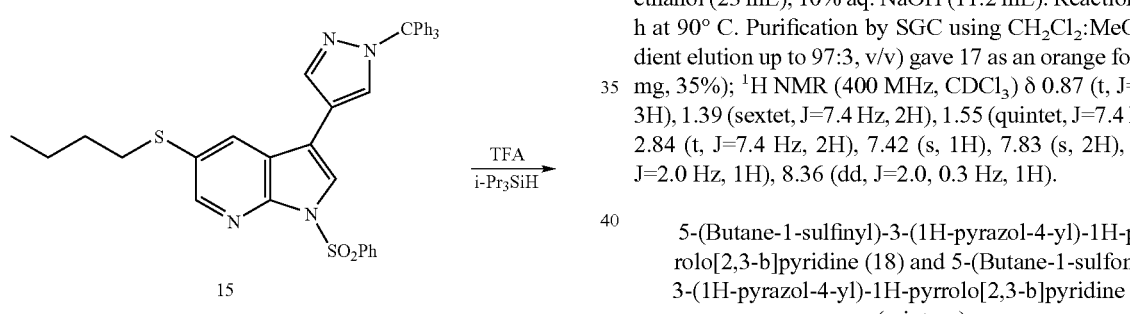

Removal of trityl group leading to 16 was performed by analogy to the method described for preparation of 7 using 15 (3.80 g, crude), CF$_3$COOH (2.9 mL), H$_2$O (288 µL), i-Pr$_3$SiH (1.46 mL) in CH$_2$Cl$_2$ (31 mL). Reaction time: 40 min. Purification by SGC using CH$_2$Cl$_2$:MeOH (gradient elution up to 98:2, v/v) afforded 16 as brown foam (1.14 g, 76%); $^1$H NMR (400 MHz, CDCl$_3$) δ 0.89 (t, J=7.3 Hz, 3H), 1.41 (sextet, J=7.5 Hz, 2H), 1.58 (quintet, J=7.6 Hz, 2H), 2.89 (t, J=7.4 Hz, 2H), 7.45-7.75 (m, 3H), 7.82 (s, 1H), 7.89 (s, 2H), 8.02 (d, J=2.1 Hz, 1H), 8.22 (m, 2H), 8.51 (d, J=2.2 Hz, 1H).

5-Butylsulfanyl-3-(1H-pyrazol-4-yl)-1H-pyrrolo[2,3-b]pyridine (17)

Inhibitor 17 was synthesized following the method described for preparation of 8 using 16 (0.50 g, 1.21 mmol), ethanol (23 mL), 10% aq. NaOH (11.2 mL). Reaction time: 1 h at 90° C. Purification by SGC using CH$_2$Cl$_2$:MeOH (gradient elution up to 97:3, v/v) gave 17 as an orange foam (116 mg, 35%); $^1$H NMR (400 MHz, CDCl$_3$) δ 0.87 (t, J=7.3 Hz, 3H), 1.39 (sextet, J=7.4 Hz, 2H), 1.55 (quintet, J=7.4 Hz, 2H), 2.84 (t, J=7.4 Hz, 2H), 7.42 (s, 1H), 7.83 (s, 2H), 8.19 (d, J=2.0 Hz, 1H), 8.36 (dd, J=2.0, 0.3 Hz, 1H).

5-(Butane-1-sulfinyl)-3-(1H-pyrazol-4-yl)-1H-pyrrolo[2,3-b]pyridine (18) and 5-(Butane-1-sulfonyl)-3-(1H-pyrazol-4-yl)-1H-pyrrolo[2,3-b]pyridine (19) (mixture)

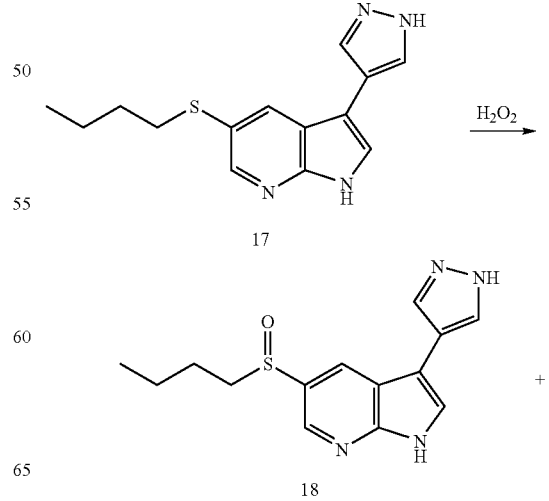

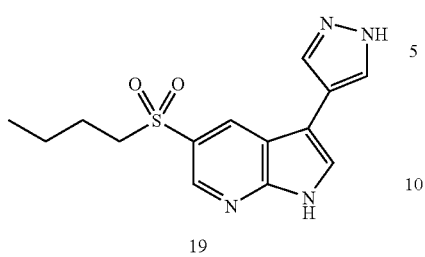

Oxidation of 17 was performed in a way analogous to that used for 9 using 17 (20 mg, 0.073 mmol), 30% aqueous $H_2O_2$ (11.3 µL, 0.11 mmol) and glacial acetic acid (239 µL). Reaction time: 72 h. Obtained:

Sulfoxide 18 as a white solid (7.1 mg, 33%); $^1$H NMR (400 MHz, CDCl$_3$+3 drops CD$_3$OD) δ 0.89 (t, J=7.3 Hz, 3H), 1.35-1.50 (m, 2H), 1.53-1.73 (m, 2H), 2.85 (m, 1H), 2.99 (m, 1H), 7.53 (s, 1H), 7.87 (s, 2H), 8.41 (d, J=2.0 Hz, 1H), 8.44 (d, J=2.0 Hz, 1H).

Sulfone 19 as a white solid (2.1 mg, 9%); $^1$H NMR (400 MHz, CDCl$_3$+6 drops CD$_3$OD) δ 0.84 (t, J=7.3 Hz, 3H), 1.36 (sextet, J=7.4 Hz, 2H), 1.67 (m, 2H), 7.55 (s, 1H), 7.82 (s, 2H), 8.51 (d, J=2.1 Hz, 1H), 8.71 (d, J=2.1 Hz, 1H).

5-(Butane-1-sulfonyl)-3-(1H-pyrazol-4-yl)-1H-pyrrolo[2,3-b]pyridine (19)

Sulfone 19 could be prepared selectively when oxidation of 17 was performed in a way analogous to that used for 9 using 17 (20 mg, 0.073 mmol), 30% aqueous solution of hydrogen peroxide (37.5 µL, 0.37 mmol) and glacial acetic acid (239 µL). After stirring for 22 h, more 30% aqueous $H_2O_2$ (37.5 µL, 0.37 mmol) was added and stirring continued for 45 h to give 19 as a white solid (13 mg, 58%). The $^1$H NMR spectrum of this product was identical with that of the product described earlier.

An alternative method of synthesis of example inhibitor 8

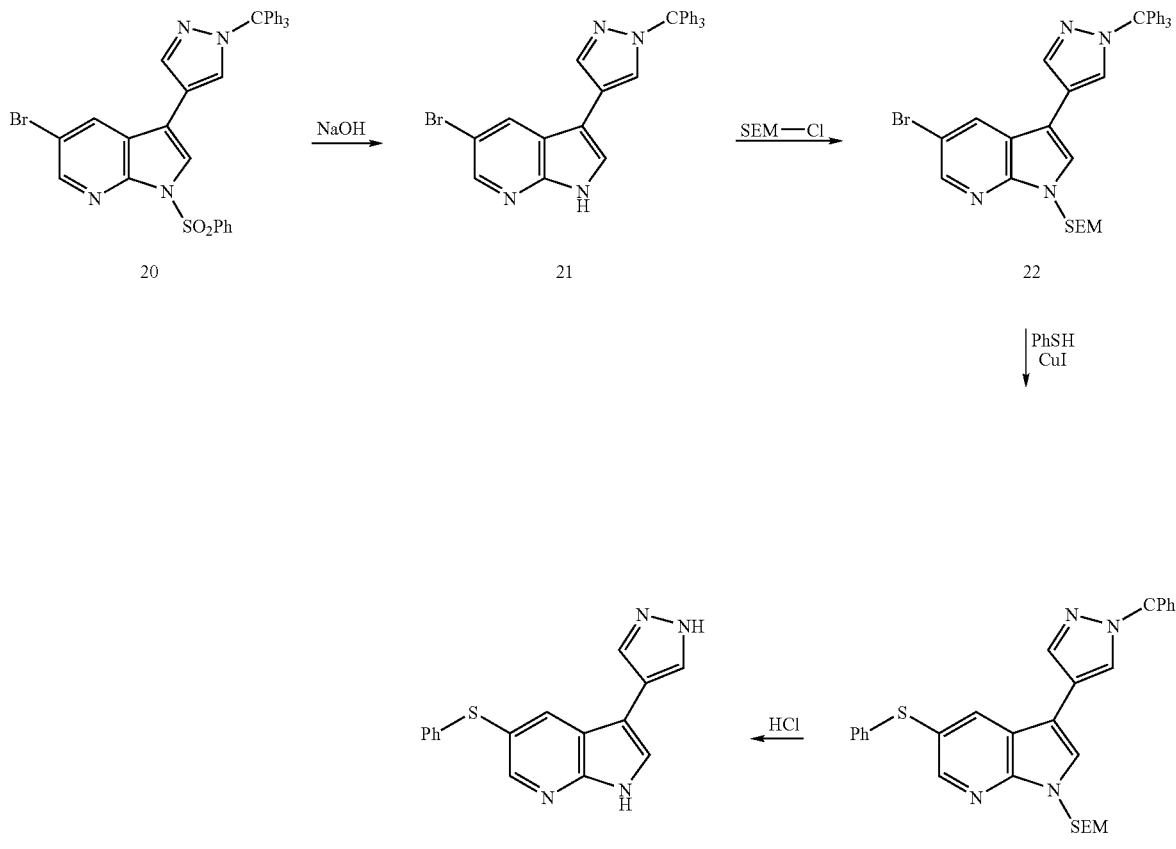

1-Benzenesulfonyl-5-bromo-3-(1-trityl-1H-pyrazol-4-yl)-1H-pyrrolo[2,3-b]pyridine (21)

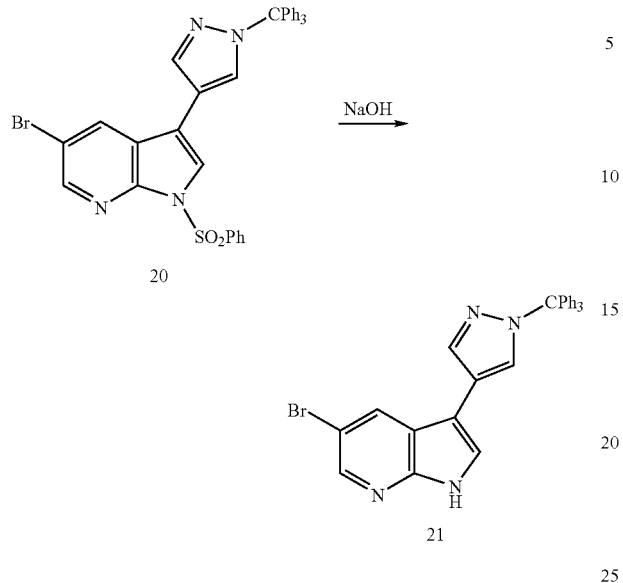

A mixture of 20 (1.50 g, 2.32 mmol; preparation disclosed in WO2004/078756) and 10% aq. NaOH (22 mL) in EtOH (45 mL) were heated at 100° C. for 8 h. The reaction mixture was cooled, poured onto a mixture of brine (100 mL) and AcOEt (50 mL). The aqueous layer was extracted with AcOEt (4×50 mL), and the combined organic extracts washed with brine (50 mL), dried (MgSO$_4$) and concentrated. The aqueous layer was then extracted with 3% MeOH in CH$_2$Cl$_2$ (3×50 mL), and the combined organic extracts concentrated without drying. The residual solid was washed with 30% AcOEt in hexane (5×) to give 21 as an orange solid (0.96 g, 82%).

5-Bromo-1-(2-trimethylsilanyl-ethoxymethyl)-3-(1-trityl-1H-pyrazol-4-yl)-1H-pyrrolo[2,3-b]pyridine (22)

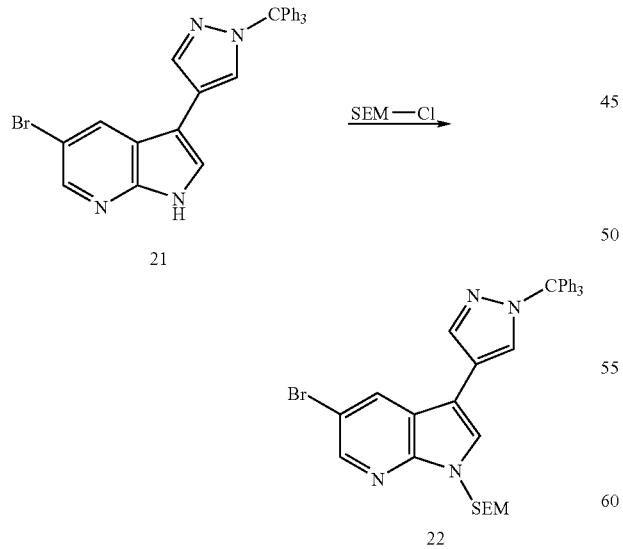

To a solution of 21 (0.5 g, 0.99 mmol) in DMF (2.5 mL) was added NaH (60% w/w in mineral oil, 59.4 mg, 1.48 mmol) portionwise. Then the reaction mixture was stirred for 0.5 h. SEM-Cl (263 µL, 1.48 mmol) was then added and the reaction mixture stirred overnight. It was poured cautiously onto a stirred mixture of ethyl acetate (20 mL)/sat. aq. NH$_4$Cl (20 mL) and the layers separated. The aqueous layer was extracted with AcOEt (2×30 mL), the combined organic extracts dried (MgSO$_4$) and concentrated. The residue was purified by SGC using AcOEt:hexane (gradient elution up to 8:92, v/v) to give 22 as a white foam (345 mg, 55%); $^1$H NMR (400 MHz, CDCl$_3$) δ 0.002 (9H, s), 0.97 (t, J=8.3 Hz, 2H), 3.58 (t, J=8.3 Hz, 2H), 5.69 (s, 2H), 7.30 (m, 6H), 7.40 (m, 9H), 7.46 (s, 1H), 7.65 (s, 1H), 7.98 (d, J=0.7 Hz, 1H), 8.06 (d, J=2.1 Hz, 1H), 8.41 (d, J=2.2 Hz, 1H).

3-(1-Methyl-1H-pyrazol-4-yl)-5-phenylsulfanyl-1-(2-trimethylsilanyl-ethoxymethyl)-1H-pyrrolo[2,3-b]pyridine (23)

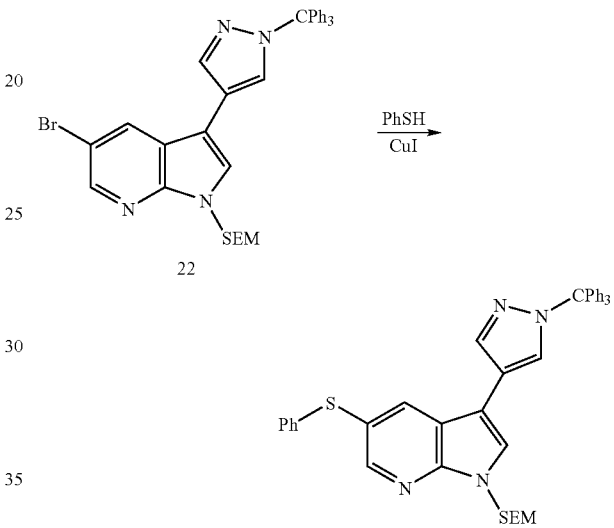

A mixture of 22 (50 mg, 0.079 mmol), benzenethiol (13.0 mg, 0.118 mmol), copper (I) iodide (3.0 mg, 0.016 mmol), N,N-dimethylglycine (1.62 mg, 0.016 mmol) and potassium phosphate (41.8 mg, 0.197 mmol) in DMF (0.5 mL) were heated at 120° C. for 69 h. The reaction mixture was cooled and partitioned between AcOEt/brine, the layers separated and the aqueous phase extracted with more AcOEt (2×). The combined organic extracts were dried (MgSO$_4$) and concentrated. The resulting crude residue containing 23 was used for the subsequent deprotection step.

3-(1-Methyl-1H-pyrazol-4-yl)-5-phenylsulfanyl-1H-pyrrolo[2,3-b]pyridine (8)

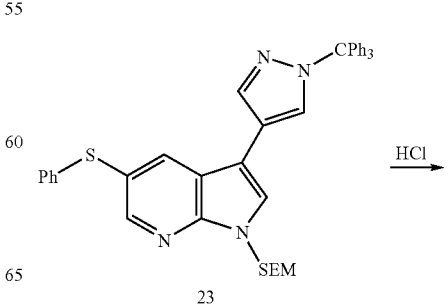

3-(1-Methyl-1H-pyrazol-4-yl)-5-(4,4,5,5-tetramethyl-[1,3,2]dioxaborolan-2-yl)-1-(2-trimethylsilanyl-ethoxymethyl)-1H-pyrrolo[2,3-b]pyridine (25)

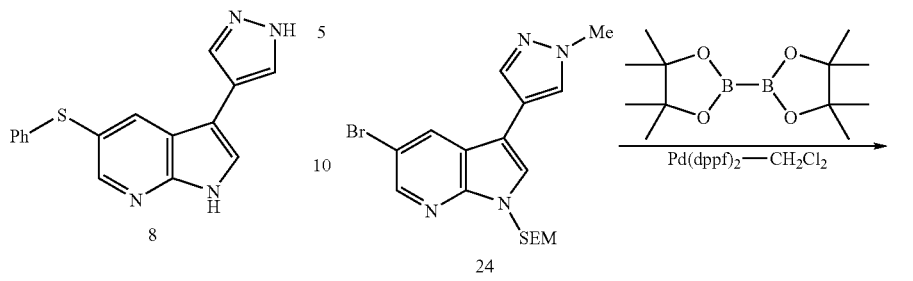

The crude 23 from the previous reaction was heated at 90° C. in EtOH (0.5 mL) and 10% aq. HCl (0.5 mL) for 3 h 10 min. The reaction mixture was cooled, saturated aqueous NaHCO$_3$ was added dropwise to neutralise the acid, and the mixture was extracted with AcOEt (4×). The combined organic extracts were dried (MgSO$_4$), concentrated and the residue purified by preparative TLC (PTLC) using 10% MeOH in CH$_2$Cl$_2$ as eluent to give 8 as a white solid (8.9 mg, 39% over 2 steps). $^1$H NMR of this compound was identical with 8 synthesised above.

Synthesis of SEM-protected sulfide 26

A mixture of 24 (0.5 g, 1.23 mmol; synthesized in analogous way to 22), bis(pinacolato)diboron (468 mg, 1.84 mmol), AcOK (361 mg, 3.68 mmol) and PdCl$_2$(dppf)$_2$·CH$_2$Cl$_2$ (35.1 mg, 0.043 mmol) in DMF (7.8 mL) were heated at 80° C. for 31 h. It was then cooled, partitioned between AcOEt/brine, the layers separated and the aqueous phase extracted with more AcOEt (2×). The combined organic extracts were dried (MgSO$_4$), concentrated and purified by SGC using hexane:AcOEt (gradient elution up to 70:30 v/v) to give boronic ester 25 as a light orange oil (339 mg, 61%); $^1$H NMR (400 MHz, CDCl$_3$) δ−0.062 (s, 9H), 0.92 (m, 2H), 1.39 (s, 12H), 3.55 (m, 2H), 4.01 (s, 3H), 5.72 (s, 2H), 7.41 (s, 1H), 7.71 (s, 1H), 7.78 (d, J=0.7 Hz, 1H), 8.45 (d, J=1.5 Hz, 1H), 8.73 (d, J=1.5 Hz, 1H).

3-(1-Methyl-1H-pyrazol-4-yl)-5-propylsulfanyl-1-(2-trimethylsilanyl-ethoxymethyl)-1H-pyrrolo[2,3-b]pyridine (26)

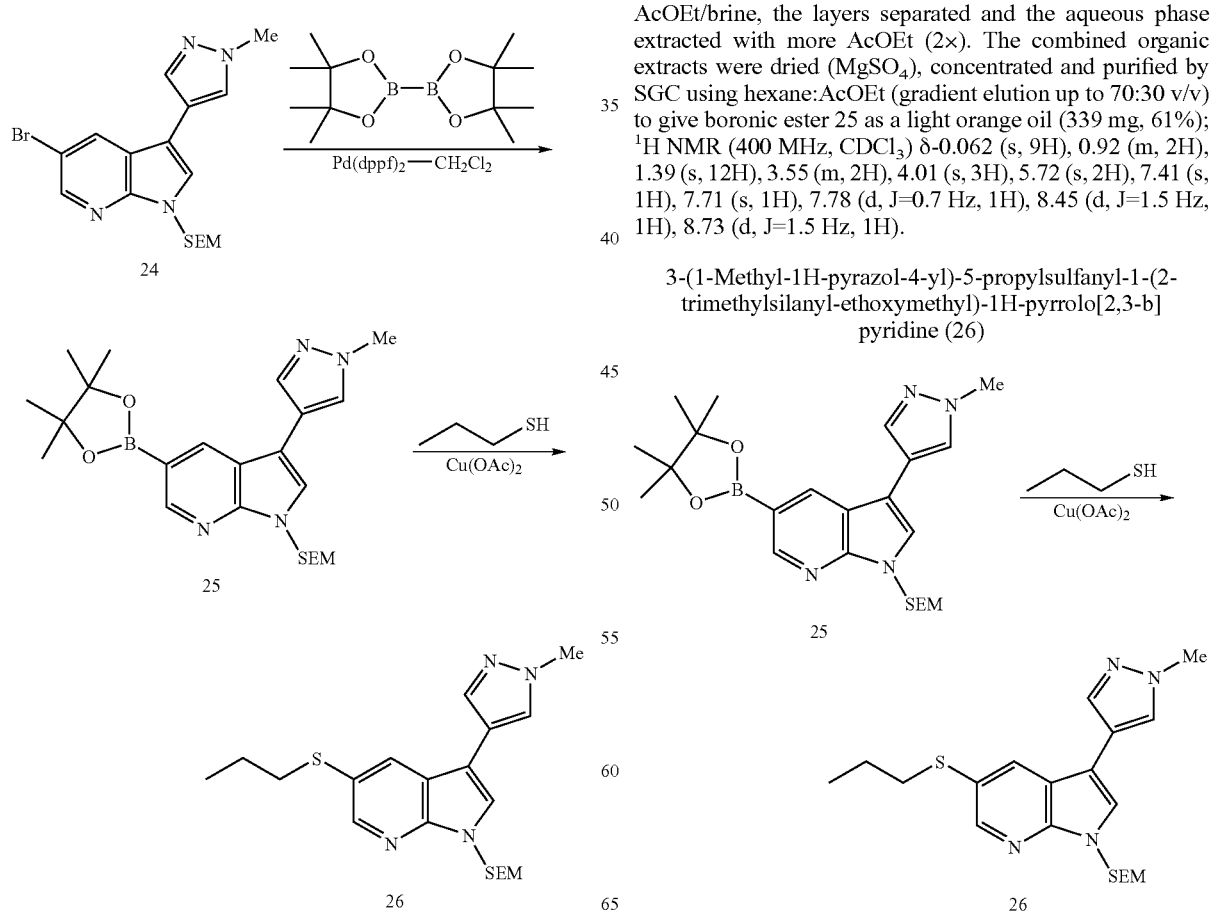

A mixture of 25 (60 mg, 0.132 mmol), n-propanethiol (21.1 mg, 0.264 mmol), copper (II) acetate (36 mg, 0.198 mmol), pyridine (32 μL, 0.396 mmol) and 4A molecular sieves (50 mg) in DMF (1.5 mL) were heated at 110° C. for 25 h. More n-propanethiol (21.1 mg, 0.264 mmol), copper (II) acetate (36 mg, 0.198 mmol) and pyridine (32 μL, 0.396 mmol) were added and heating continued for 20.5 h. More n-propanethiol (21.1 mg, 0.264 mmol), copper (II) acetate (36 mg, 0.198 mmol), pyridine (32 μL, 0.396 mmol) and 4A sieves were added again and the heating continued at 130° C. overnight. The reaction mixture was cooled, diluted with AcOEt, filtered and washed with brine. The aqueous layer was extracted with AcOEt (2×), and the combined organic extracts dried (MgSO$_4$) and concentrated. The residue was purified by preparative LCMS (column LUNA 10 μ C18(2) 00G-4253-V0 250×50 mm) using water—acetonitrile (0.1% AcOH) as eluent (in gradient; flow 80 mL/min) to give 26 as an orange oil (6.7 mg, 13%); $^1$H NMR (400 MHz, CDCl$_3$) δ-0.056 (s, 9H), 0.93 (t, J=8.3 Hz, 2H), 1.00 (t, J=7.3 Hz, 3H), 1.61 (sextet, J=7.4 Hz, 2H), 2.84 (t, J=7.3 Hz, 2H), 3.57 (t, J=8.3 Hz, 2H), 4.00 (s, 3H), 5.68 (s, 2H), 7.43 (s, 1H), 7.64 (s, 1H), 7.76 (s, 1H), 8.15 (d, J=2.0 Hz, 1H), 8.45 (d, J=2.0 Hz, 1H).

Synthesis of example inhibitors 29a-29f.

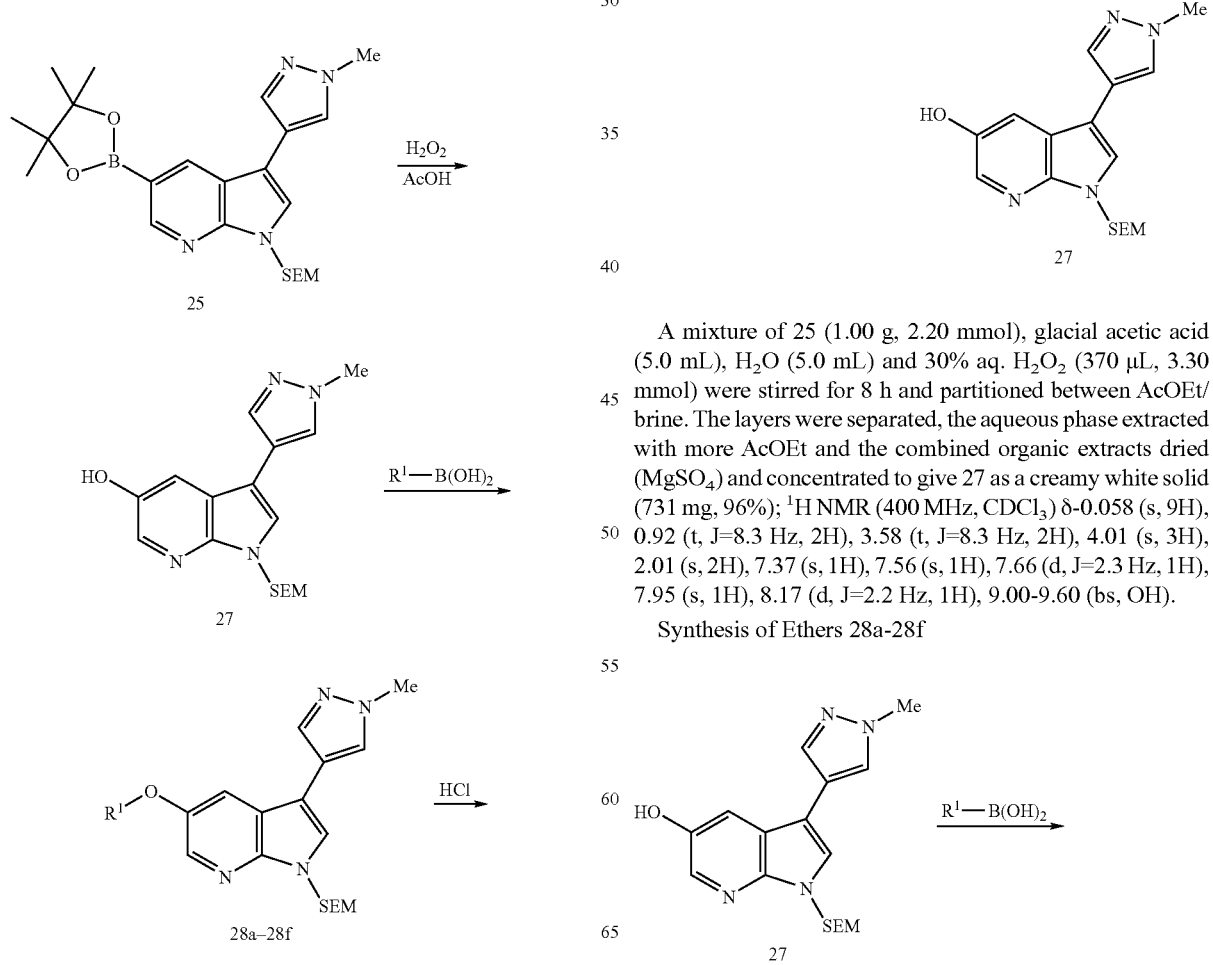

3-(1-Methyl-1H-pyrazol-4-yl)-1-(2-trimethylsilanyl-ethoxymethyl)-1H-pyrrolo[2,3-b]pyridin-5-ol (27)

A mixture of 25 (1.00 g, 2.20 mmol), glacial acetic acid (5.0 mL), H$_2$O (5.0 mL) and 30% aq. H$_2$O$_2$ (370 μL, 3.30 mmol) were stirred for 8 h and partitioned between AcOEt/brine. The layers were separated, the aqueous phase extracted with more AcOEt and the combined organic extracts dried (MgSO$_4$) and concentrated to give 27 as a creamy white solid (731 mg, 96%); $^1$H NMR (400 MHz, CDCl$_3$) δ-0.058 (s, 9H), 0.92 (t, J=8.3 Hz, 2H), 3.58 (t, J=8.3 Hz, 2H), 4.01 (s, 3H), 2.01 (s, 2H), 7.37 (s, 1H), 7.56 (s, 1H), 7.66 (d, J=2.3 Hz, 1H), 7.95 (s, 1H), 8.17 (d, J=2.2 Hz, 1H), 9.00-9.60 (bs, OH).

Synthesis of Ethers 28a-28f

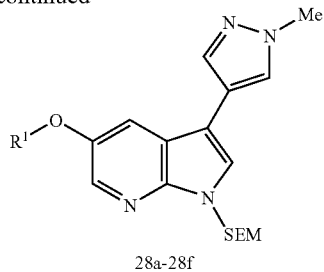

28a-28f

3-(1-Methyl-1H-pyrazol-4-yl)-5-phenoxy-1-(2-trimethylsilanyl-ethoxymethyl)-1H-pyrrolo[2,3-b]pyridine (28a)

General procedure: A mixture of 27 (50 mg, 0.145 mmol), phenylboronic acid (35.6 mg, 0.29 mmol), copper (II) acetate (26.4 mg, 0.145 mmol), Et$_3$N (102 µL, 0.726 mmol) and activated 4A molecular sieves in CH$_2$Cl$_2$ (1.5 mL) were stirred for 65 h. The reaction mixture was filtered and the filtrate concentrated. The residue was purified by PTLC using AcOEt:hexane=60:40 (v/v) as eluent to give 28a as a clear oil (34 mg, 56%); $^1$H NMR (400 MHz, CDCl$_3$) δ -0.0373 (s, 9H), 0.95 (t, J=8.3 Hz, 2H), 3.60 (t, J=8.3 Hz, 2H), 3.95 (s, 3H), 5.69 (s, 2H), 6.98 (d, J=7.9 Hz, 2H), 7.07 (t, J=7.4 Hz, 1H), 7.32 (t, J=8.0 Hz, 2H), 7.48 (s, 1H), 7.57 (s, 1H), 7.71 (s, 1H), 7.73 (d, J=2.5 Hz, 1H), 8.23 (d, J=2.5 Hz, 1H).

3-(1-Methyl-1H-pyrazol-4-yl)-5-o-tolyloxy-1-(2-trimethylsilanyl-ethoxymethyl)-1H-pyrrolo[2,3-b]pyridine (28b)

According to the general procedure using: 27 (50 mg, 0.145 mmol), ortho-methylphenylboronic acid (39 mg, 0.29 mmol), copper (II) acetate (26.4 mg, 0.145 mmol), Et$_3$N (102 µL, 0.726 mmol) and activated 4A molecular sieves in CH$_2$Cl$_2$ (1.5 mL) were stirred for 47 h. The crude 28b was used for preparation of 29b.

3-(1-Methyl-1H-pyrazol-4-yl)-5-m-tolyloxy-1-(2-trimethylsilanyl-ethoxymethyl)-1H-pyrrolo[2,3-b]pyridine (28c)

According to the general procedure using: 27 (50 mg, 0.145 mmol), meta-methylphenylboronic acid (39 mg, 0.29 mmol), copper (II) acetate (26.4 mg, 0.145 mmol), Et$_3$N (102 µL, 0.726 mmol) and activated 4A molecular sieves in CH$_2$Cl$_2$ (1.5 mL) were stirred for 47 h. The crude 28c was used for preparation of 29c.

3-(1-Methyl-1H-pyrazol-4-yl)-5-p-tolyloxy-1-(2-trimethylsilanyl-ethoxymethyl)-1H-pyrrolo[2,3-b]pyridine (28d)

According to the general procedure using: 27 (50 mg, 0.145 mmol), para-methylphenylboronic acid (39 mg, 0.29 mmol), copper (II) acetate (26.4 mg, 0.145 mmol), Et$_3$N (102 µL, 0.726 mmol) and activated 4A molecular sieves in CH$_2$Cl$_2$ (1.5 mL) were stirred for 47 h. The crude 28d was used for preparation of 29d.

5-(4-Fluoro-phenoxy)-3-(1-methyl-1H-pyrazol-4-yl)-1-(2-trimethylsilanyl-ethoxymethyl)-1H-pyrrolo[2,3-b]pyridine (28e)

According to the general procedure using: 27 (50 mg, 0.145 mmol), para-fluorophenylboronic acid (40.6 mg, 0.29 mmol), copper (II) acetate (26.4 mg, 0.145 mmol), Et$_3$N (102 µL, 0.726 mmol) and activated 4A molecular sieves in CH$_2$Cl$_2$ (1.5 mL) were stirred for 17 h. The crude 28e was used for preparation of 29e.

Dimethyl-{4-[3-(1-methyl-1H-pyrazol-4-yl)-1-(2-trimethylsilanyl-ethoxymethyl)-1H-pyrrolo[2,3-b]pyridin-5-yloxy]-phenyl}-amine (28f)

According to the general procedure using: 27 (50 mg, 0.145 mmol), para-(dimethylamino)phenylboronic acid (47.9 mg, 0.29 mmol), copper (II) acetate (26.4 mg, 0.145 mmol), Et$_3$N (102 µL, 0.726 mmol) and activated 4A molecular sieves in CH$_2$Cl$_2$ (1.5 mL) were stirred for 18 h. The crude 28f was used for preparation of 29f.

Synthesis of Inhibitors 29a-29f

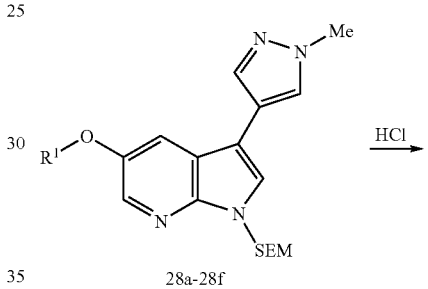

3-(1-Methyl-1H-pyrazol-4-yl)-5-phenoxy-1H-pyrrolo[2,3-b]pyridine (29a)

Following the method used for conversion of 23 into 8, synthesis of 29a was carried out using: 28a (33 mg, 78 µmol), EtOH (1.0 mL) and 10% aq. HCl (1.0 mL) with heating at 90° C. for 17 h. Isolation by PTLC using CH$_2$Cl$_2$:MeOH=19:1 (v/v) as eluent gave 29a as a white solid (17.2 mg, 75%); $^1$H NMR (400 MHz, CDCl$_3$+2 drops CD$_3$OD) δ 3.93 (s, 3H), 6.96 (m, 2H), 7.06 (m, 1H), 7.31 (m, 2H), 7.45 (s, 1H), 7.58 (s, 1H), 7.68 (s, 1H), 7.77 (d, J=2.5 Hz, 1H), 8.12 (d, J=2.5 Hz, 1H).

3-(1-Methyl-1H-pyrazol-4-yl)-5-o-tolyloxy-1H-pyrrolo[2,3-b]pyridine (29b)

Following the method used for conversion of 23 into 8, synthesis of 29b was carried out using: 28b (crude), EtOH (1.0 mL) and 10% aq. HCl (1.0 mL) with heating at 90° C. for 16 h. Isolation by PTLC using AcOEt as eluent gave 29b as a white solid (15 mg, 34%); $^1$H NMR (400 MHz, CDCl$_3$) δ 2.39

(s, 3H), 3.96 (s, 3H), 6.78 (d, J=6.78 Hz, 1H), 7.03 (t, J=7.1 Hz, 1H), 7.13 (t, J=7.0 Hz, 1H), 7.28 (d, J=8.6 Hz, 1H), 7.47 (d, J=2.3 Hz, 1H), 7.57 (s, 1H), 7.70 (d, J=2.4 Hz, 1H), 7.71 (s, 1H), 8.20 (d, J=2.4 Hz, 1H), 10.50 (bs, NH).

3-(1-Methyl-1H-pyrazol-4-yl)-5-m-tolyloxy-1H-pyrrolo[2,3-b]pyridine (29c)

Following the method used for conversion of 23 into 8, synthesis of 29c was carried out using: 28c (crude), EtOH (1.0 mL) and 10% aq. HCl (1.0 mL) with heating at 90° C. for 16 h. Isolation by PTLC using AcOEt as eluent gave 29c as a white solid (15 mg, 34%); $^1$H NMR (400 MHz, CDCl$_3$) δ 2.33 (s, 3H), 3.97 (s, 3H), 6.80 (m, 2H), 6.90 (d, J=7.5 Hz, 1H), 7.21 (t, J=8.1 Hz, 1H), 7.50 (d, J=2.2 Hz, 1H), 7.59 (s, 1H), 7.73 (s, 1H), 7.80 (d, J=2.2 Hz, 1H), 8.23 (d, J=2.3 Hz, 1H), 10.63 (bs, NH).

(s, 3H), 6.50-7.10 (m, 4H), 7.49 (d, J=2.4 Hz, 1H), 7.57 (s, 1H), 7.72 (s, 1H), 7.75 (d, J=2.4 Hz, 1H), 8.21 (d, J=2.4 Hz, 1H), 10.62 (bs, NH).

Dimethyl-{4-[3-(1-methyl-1H-pyrazol-4-yl)-1H-pyrrolo[2,3-b]pyridin-5-yloxy]-phenyl}-amine (29f)

Following the method used for conversion of 23 into 8, synthesis of 29f was carried out using: 28f (crude), EtOH (1.0 mL) and 10% aq. HCl (1.0 mL) with heating at 90° C. for 20 h. Isolation by PTLC using AcOEt as eluent gave 29f as a white solid (10.1 mg, 58%); $^1$H NMR (400 MHz, CDCl$_3$) δ 2.93 (s, 6H), 3.96 (s, 3H), 6.74 (m, 2H), 6.97 (m, 2H), 7.43 (d, J=2.5 Hz, 1H), 7.56 (d, J=0.3 Hz, 1H), 7.69 (d, J=2.5 Hz, 1H), 7.70 (d, J=0.7 Hz, 1H), 8.20 (d, J=2.5 Hz, 1H), 9.99 (bs, NH).

Synthesis of Inhibitors 29g-29t

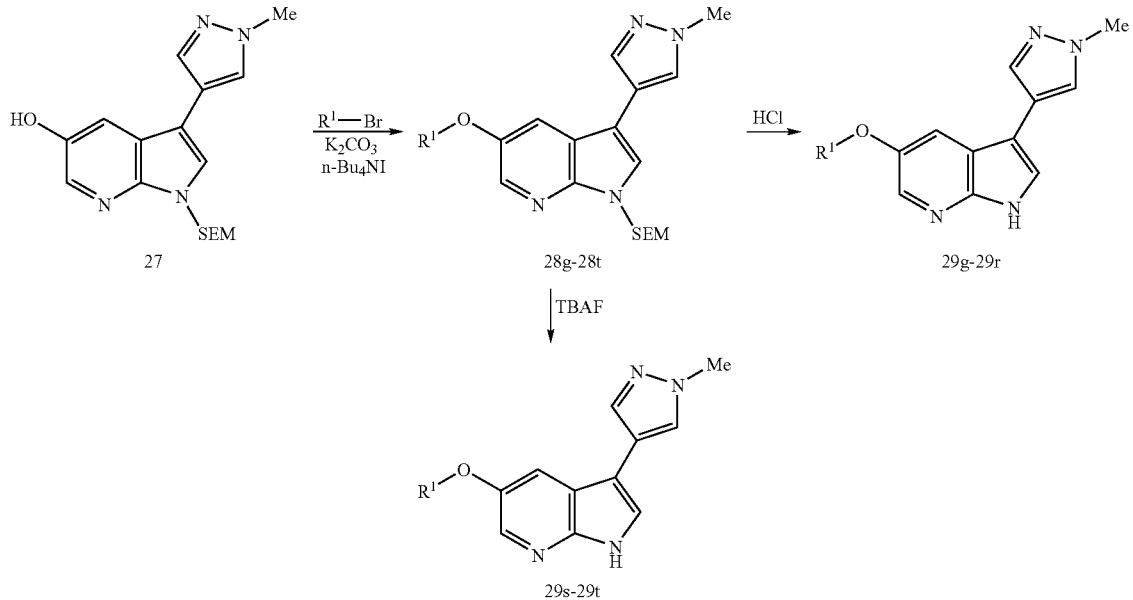

3-(1-Methyl-1H-pyrazol-4-yl)-5-p-tolyloxy-1H-pyrrolo[2,3-b]pyridine (29d)

Following the method used for conversion of 23 into 8, synthesis of 29d was carried out using: 28d (crude), EtOH (1.0 mL) and 10% aq. HCl (1.0 mL) with heating at 90° C. for 16 h. Isolation by PTLC using AcOEt as eluent gave 29d as a white solid (18.1 mg, 41%); $^1$H NMR (400 MHz, CDCl$_3$) δ 2.34 (s, 3H), 3.96 (s, 3H), 6.91 (d, J=8.5 Hz, 2H), 7.13 (d, J=8.4 Hz, 2H), 7.48 (d, J=2.4 Hz, 1H), 7.56 (s, 1H), 7.71 (s, 1H), 7.77 (d, J=2.4 Hz, 1H), 8.23 (d, J=2.5 Hz, 1H), 10.62 (bs, NH).

5-(4-Fluoro-phenoxy)-3-(1-methyl-1H-pyrazol-4-yl)-1H-pyrrolo[2,3-b]pyridine (29e)

Following the method used for conversion of 23 into 8, synthesis of 29e was carried out using: 28e (crude), EtOH (1.0 mL) and 10% aq. HCl (1.0 mL) with heating at 90° C. for 17 h. Isolation by PTLC using AcOEt as eluent gave 29e as a white solid (18 mg, 40%); $^1$H NMR (400 MHz, CDCl$_3$) δ 3.97

5-Benzyloxy-3-(1-methyl-1H-pyrazol-4-yl)-1-(2-trimethylsilanyl-ethoxymethyl)-1H-pyrrolo[2,3-b]pyridine (28g)

General procedure: A mixture of 27 (60 mg, 0.174 mmol), benzyl bromide (124 μL, 1.05 mmol), K$_2$CO$_3$ (241 mg, 1.74 mmol) and n-Bu$_4$NI (6.4 mg, 17 μmol) in acetone (4.0 mL) were heated at reflux for 22.5 h. The reaction mixture was cooled, filtered and the filtrate concentrated. The residue was purified by PTLC using AcOEt:hexane=6:4 (v/v) as eluent to give 28g as a light orange oil (24.3 mg, 32%); $^1$H NMR (400 MHz, CDCl$_3$) δ-0.054 (s, 9H), 0.93 (t, J=8.3 Hz, 2H), 3.56 (t, J=8.3 Hz, 2H), 3.99 (s, 3H), 5.16 (s, 2H), 5.65 (s, 2H), 7.30-7.45 (m, 4H), 7.49 (d, J=7.1 Hz, 2H), 7.56 (s, 1H), 7.58 (d, J=2.7 Hz, 1H), 7.77 (s, 1H), 8.21 (d, J=2.6 Hz, 1H).

5-Ethoxy-3-(1-methyl-1H-pyrazol-4-yl)-1-(2-trimethylsilanyl-ethoxymethyl)-1H-pyrrolo[2,3-b]pyridine (28h)

According to the general procedure using: 27 (60 mg, 0.174 mmol), bromoethane (114 mg, 1.05 mmol), K$_2$CO$_3$ (241 mg, 1.74 mmol) and n-Bu$_4$NI (6.4 mg, 17 μmol) in acetone (4.0 mL) were heated at reflux for 18 h. Purification by PTLC using AcOEt:hexane=6:4 (v/v) as eluent gave 28h as a clear oil (39 mg, 60%).

3-(1-Methyl-1H-pyrazol-4-yl)-5-propoxy-1-(2-trimethylsilanyl-ethoxymethyl)-1H-pyrrolo[2,3-b]pyridine (28i)

According to the general procedure using: 27 (60 mg, 0.174 mmol), 1-bromopropane (129 mg, 1.74 mmol), K$_2$CO$_3$ (241 mg, 1.74 mmol) and n-Bu$_4$M (6.4 mg, 17 μmol) in acetone (4.0 mL) were heated at reflux for 18 h. Purification by PTLC using AcOEt:hexane=6:4 (v/v) as eluent gave 28i as a clear oil (40 mg, 59%).

5-Butoxy-3-(1-methyl-1H-pyrazol-4-yl)-1-(2-trimethylsilanyl-ethoxymethyl)-1H-pyrrolo[2,3-b]pyridine (28j)

According to the general procedure using: 27 (60 mg, 0.174 mmol), 1-bromobutane (143 mg, 1.05 mmol), K$_2$CO$_3$ (241 mg, 1.74 mmol) and n-Bu$_4$NI (6.4 mg, 17 μmol) in acetone (4.0 mL) were heated at reflux for 22.5 h. Purification by PTLC using AcOEt:hexane=6:4 (v/v) as eluent gave 28j as a clear oil (48.7 mg, 70%).

3-(1-Methyl-1H-pyrazol-4-yl)-5-pentyloxy-1-(2-trimethylsilanyl-ethoxymethyl)-1H-pyrrolo[2,3-b]pyridine (28k)

According to the general procedure using: 27 (60 mg, 0.174 mmol), 1-bromopentane(129 μL, 1.05 mmol), K$_2$CO$_3$ (241 mg, 1.74 mmol) and n-Bu$_4$NI (6.4 mg, 17 μmol) in acetone (4.0 mL) were heated at reflux overnight. Purification by PTLC using AcOEt:hexane=6:4 (v/v) as eluent gave 28k as a clear oil (38 mg, 51%).

5-Hexyloxy-3-(1-methyl-1H-pyrazol-4-yl)-1-(2-trimethylsilanyl-ethoxymethyl)-1H-pyrrolo[2,3-b]pyridine (28l)

According to the general procedure using: 27 (60 mg, 0.174 mmol), 1-bromohexane (117 μL, 1.74 mmol), K$_2$CO$_3$ (241 mg, 1.74 mmol) and n-Bu$_4$NI (6.4 mg, 17 μmol) in acetone (4.0 mL) were heated at reflux overnight. Purification by PTLC using AcOEt:hexane=6:4 (v/v) as eluent gave 28l as a clear oil (36 mg, 48%).

3-(1-Methyl-1H-pyrazol-4-yl)-5-prop-2-ynyloxy-1-(2-trimethylsilanyl-ethoxymethyl)-1H-pyrrolo[2,3-b]pyridine (28m)

According to the general procedure using: 27 (60 mg, 0.174 mmol), 80% wt in toluene propargyl bromide (116 μL, 1.05 mmol), K$_2$CO$_3$ (241 mg, 1.74 mmol) and n-Bu$_4$NI (6.4 mg, 17 μmol) in acetone (4.0 mL) were heated at reflux for 16 h and the product 28m used crude for the next step.

5-(2-Methoxy-ethoxy)-3-(1-methyl-1H-pyrazol-4-yl)-1-(2-trimethylsilanyl-ethoxymethyl)-1H-pyrrolo[2,3-b]pyridine (28n)

According to the general procedure using: 27 (60 mg, 0.174 mmol), 1-bromo-2-methoxyethane (98 μL, 1.05 mmol), K$_2$CO$_3$ (241 mg, 1.74 mmol) and n-Bu$_4$NI (6.4 mg, 17 μmol) in acetone (4.0 mL) were heated at reflux for 16 h and the product 28n used crude for the next step.

5-Allyloxy-3-(1-methyl-1H-pyrazol-4-yl)-1-(2-trimethylsilanyl-ethoxymethyl)-1H-pyrrolo[2,3-b]pyridine (28o)

According to the general procedure using: 27 (60 mg, 0.174 mmol), 1-bromoprop-2-ene (90 μL, 1.05 mmol), K$_2$CO$_3$ (241 mg, 1.74 mmol) and n-Bu$_4$NI (6.4 mg, 17 μmol) in acetone (4.0 mL) were heated at reflux for 17 h and the product 28o used crude for the next step.

[3-(1-Methyl-1H-pyrazol-4-yl)-1-(2-trimethylsilanyl-ethoxymethyl)-1H-pyrrolo[2,3-b]pyridin-5-yloxy]-acetic acid methyl ester (28p)

According to the general procedure using: 27 (60 mg, 0.174 mmol), Bromo-acetic acid ethyl ester (99 μL, 1.05 mmol), K$_2$CO$_3$ (241 mg, 1.74 mmol) and n-Bu$_4$NI (6.4 mg, 17 μmol) in acetone (4.0 mL) were heated at reflux for 18 h and the product 28p used crude for the next step.

5-Cyclopentyloxy-3-(1-methyl-1H-pyrazol-4-yl)-1-(2-trimethylsilanyl-ethoxymethyl)-1H-pyrrolo[2,3-b]pyridine (28q)

According to the general procedure using: 27 (60 mg, 0.174 mmol), bromocyclopentane (112 μL, 1.05 mmol), K$_2$CO$_3$ (241 mg, 1.74 mmol) and n-Bu$_4$NI (6.4 mg, 17 μmol) in acetone (4.0 mL) were heated at reflux for 20 h and the product 28q used crude for the next step.

3-(1-Methyl-1H-pyrazol-4-yl)-5-phenethyloxy-1-(2-trimethylsilanyl-ethoxymethyl)-1H-pyrrolo[2,3-b]pyridine (28r)

According to the general procedure using: 27 (60 mg, 0.174 mmol), (2-bromo-ethyl)-benzene (143 μL, 1.05 mmol), K$_2$CO$_3$ (241 mg, 1.74 mmol) and n-Bu$_4$NI (6.4 mg, 17 μmol) in acetone (4.0 mL) were heated at reflux overnight. Standard workup and purification by PTLC using AcOEt:hexane=6:4 (v/v) as eluent gave 28r as a clear oil (39 mg, 50%).

5-(cyclopropylmethoxy)-3-(1-methyl-1H-pyrazol-4-yl)-1-((2-(trimethylsilyl)ethoxy)methyl)-1H-pyrrolo[2,3-b]pyridine (28s)

According to the general procedure using: 27 (60 mg, 0.174 mmol), (bromomethyl)cyclopropane (101 μL, 1.05 mmol), K$_2$CO$_3$ (241 mg, 1.74 mmol) and n-Bu$_4$NI (6.4 mg, 17 μmol) in acetone (4.0 mL) were heated at reflux overnight. Standard workup and purification by PTLC using 5% MeOH in CH$_2$Cl$_2$ gave 28s as a clear oil (41 mg, 59%); $^1$H NMR (400 MHz, CDCl$_3$) δ-0.066 (s, 9H), 0.38 (q, J=4.68 Hz, 2H), 0.68 (m, 2H), 0.91 (m, 2H), 1.31 (m, 1H), 3.55 (t, J=8.3 Hz, 2H), 3.89 (d, J=7.0 Hz, 2H), 3.98 (s, 3H), 5.64 (s, 2H), 7.36 (s, 1H), 7.51 (d, J=2.6 Hz, 1H), 7.58 (s, 1H), 7.74 (d, J=0.3 Hz, 1H), 8.16 (d, J=2.6 Hz, 1H).

5-(cyclohexylmethoxy)-3-(1-methyl-1H-pyrazol-4-yl)-1-((2-(trimethylsilyl)ethoxy)methyl)-1H-pyrrolo[2,3-b]pyridine (28t)

According to the general procedure using: 27 (60 mg, 0.174 mmol), (bromomethyl)cyclohexane (146 μL, 1.05 mmol), K$_2$CO$_3$ (241 mg, 1.74 mmol) and n-Bu$_4$M (6.4 mg, 17 μmol) in acetone (4.0 mL) were heated at reflux for 24 h. Standard workup and purification by PTLC using 80% AcOEt in hexane gave 28t as a clear oil (40 mg, 52%); $^1$H NMR (400 MHz, CDCl$_3$) δ-0.059 (s, 9H), 0.93 (t, J=8.2 Hz, 2H), 1.09 (dq, J=12.2 Hz, J=3.3 Hz, 2H), 1.17-1.40 (m, 2H), 1.65-1.95 (m, 7H), 3.56 (t, J=8.3 Hz, 2H), 3.84 (d, J=6.3 Hz, 2H), 3.99 (s, 3H), 5.64 (s, 2H), 7.38 (s, 1H), 7.49 (d, J=2.6 Hz, 1H), 7.59 (s, 1H), 7.75 (d, J=0.3 Hz, 1H), 8.13 (d, J=2.6 Hz, 1H).

5-Benzyloxy-3-(1-methyl-1H-pyrazol-4-yl)-1H-pyrrolo[2,3-b]pyridine (29g)

Following the method used for conversion of 23 into 8, synthesis of 29g was carried out using 28g (24 mg, 55 µmol), EtOH (0.5 mL), 10% aq. HCl (0.5 mL) and heating for 19.5 h to give 29g as a white solid (6.0 mg, 36%); $^1$H NMR (400 MHz, CDCl$_3$) δ 3.99 (s, 3H), 5.17 (s, 2H), 7.36 (m, 2H), 7.42 (t, J=7.3 Hz, 2H), 7.50 (d, J=7.2 Hz, 2H), 7.56 (s, 1H), 7.62 (d, J=2.6 Hz, 1H), 7.72 (s, 1H), 8.20 (d, J=2.6 Hz, 1H), 9.38 (bs, NH).

5-Ethoxy-3-(1-methyl-1H-pyrazol-4-yl)-1H-pyrrolo[2,3-b]pyridine (29h)

Following the method used for conversion of 23 into 8, synthesis of 29h was carried out using 28h (38 mg, 0.102 mmol), EtOH (1.0 mL), 10% aq. HCl (1.0 mL) and heating for 17 h to give 29h as a white solid (16 mg, 65%); $^1$H NMR (400 MHz, CDCl$_3$+6 drops CD$_3$OD) δ 1.41 (t, J=7.0 Hz, 3H), 3.92 (s, 3H), 4.08 (q, J=7.0 Hz, 2H), 7.32 (s, 1H), 7.52 (d, J=2.6 Hz, 1H), 7.56 (s, 1H), 7.67 (s, 1H), 7.99 (d, J=2.7 Hz, 1H).

3-(1-Methyl-1H-pyrazol-4-yl)-5-propoxy-1H-pyrrolo[2,3-b]pyridine (29i)

Following the method used for conversion of 23 into 8, synthesis of 29i was carried out using 28i (39 mg, 0.101 mmol), EtOH (1.0 mL), 10% aq. HCl (1.0 mL) and heating for 17 h to give 29i as a white solid (19 mg, 73%); $^1$H NMR (400 MHz, CDCl$_3$+6 drops CD$_3$OD) δ 1.03 (t, J=7.4 Hz, 3H), 1.80 (sextet, J=7.1 Hz, 2H), 3.93 (s, 3H), 3.98 (t, J=6.6 Hz, 2H), 7.32 (s, 1H), 7.52 (d, J=2.5 Hz, 1H), 7.56 (s, 1H), 7.67 (s, 1H), 8.00 (bs, 1H).

5-Butoxy-3-(1-methyl-1H-pyrazol-4-yl)-1H-pyrrolo[2,3-b]pyridine (29j)

Following the method used for conversion of 23 into 8, synthesis of 29j was carried out using 28j (48 mg, 0.12 mmol), EtOH (1.0 mL), 10% aq. HCl (1.0 mL) and heating for 20.5 h to give 29j as a white solid (25 mg, 77%); $^1$H NMR (400 MHz, CDCl$_3$) δ 1.01 (t, J=7.4 Hz, 3H), 1.54 (sextet, J=7.5 Hz, 2H), 1.83 (quintet, J=7.0 Hz, 2H), 4.00 (s, 3H), 4.07 (t, J=6.5 Hz, 2H), 7.38 (d, J=2.5 Hz, 1H), 7.55 (d, J=2.5 Hz, 1H), 7.60 (s, 1H), 7.75 (s, 1H), 8.13 (d, J=2.6 Hz, 1H), 9.59 (bs, NH).

3-(1-Methyl-1H-pyrazol-4-yl)-5-pentyloxy-1H-pyrrolo[2,3-b]pyridine (29k)

Following the method used for conversion of 23 into 8, synthesis of 29k was carried out using 28k (38 mg, 92 µmol), EtOH (1.0 mL), 10% aq. HCl (1.0 mL) and heating for 16 h to give 29k as a white solid (21 mg, 81%); $^1$H NMR (400 MHz, CDCl$_3$) δ 0.96 (t, J=7.2 Hz, 3H), 1.30-1.60 (m, 4H), 1.85 (quintet, J=7.0 Hz, 2H), 4.00 (s, 3H), 4.06 (t, J=6.6 Hz, 2H), 7.40 (d, J=2.5 Hz, 1H), 7.56 (d, J=2.6 Hz, 1H), 7.60 (s, 1H), 7.76 (s, 1H), 8.14 (d, J=2.6 Hz, 1H), 10.28 (bs, NH).

5-Hexyloxy-3-(1-methyl-1H-pyrazol-4-yl)-1H-pyrrolo[2,3-b]pyridine (29l)

Following the method used for conversion of 23 into 8, synthesis of 29l was carried out using 28l (36 mg, 84 µmol), EtOH (1.0 mL), 10% aq. HCl (1.0 mL) and heating for 16 h to give 29l as a white solid (21 mg, 84%); $^1$H NMR (400 MHz, CDCl$_3$) δ 0.92 (t, J=7.1 Hz, 3H), 1.30-1.45 (m, 4H), 1.51 (m, 2H), 1.83 (quintet, J=7.1 Hz, 2H), 3.99 (s, 3H), 4.06 (t, J=6.5 Hz, 2H), 7.39 (d, J=2.4 Hz, 1H), 7.55 (d, J=2.6 Hz, 1H), 7.59 (s, 1H), 7.75 (s, 1H), 8.13 (d, J=2.6 Hz, 1H), 10.18 (bs, NH).

3-(1-Methyl-1H-pyrazol-4-yl)-5-prop-2-ynyloxy-1H-pyrrolo[2,3-b]pyridine (29m)

Following the method used for conversion of 23 into 8, synthesis of 29m was carried out using 28m (crude), EtOH (1.0 mL), 10% aq. HCl (1.0 mL) and heating for 16 h to give 29m as a white solid (21 mg, 48%); $^1$H NMR (400 MHz, CDCl$_3$+6 drops CD$_3$OD) δ 2.56 (t, J=2.2 Hz, 1H), 3.92 (s, 3H), 4.73 (d, J=2.3 Hz, 2H), 7.34 (s, 1H), 7.56 (s, 1H), 7.66 (d, J=2.6 Hz, 1H), 7.67 (s, 1H), 8.04 (d, J=2.6 Hz, 1H).

5-(2-Methoxy-ethoxy)-3-(1-methyl-1H-pyrazol-4-yl)-1H-pyrrolo[2,3-b]pyridine (29n)

Following the method used for conversion of 23 into 8, synthesis of 29n was carried out using 28n (crude), EtOH (1.0 mL), 10% aq. HCl (1.0 mL) and heating for 16 h to give 29n as a white solid (16.7 mg, 35%); $^1$H NMR (400 MHz, CDCl$_3$) δ 3.50 (s, 3H), 3.81 (t, J=4.6 Hz, 2H), 3.99 (s, 3H), 4.23 (t, J=4.6 Hz, 2H), 7.40 (d, J=2.4 Hz, 1H), 7.59 (s, 1H), 7.62 (d, J=2.6 Hz, 1H), 7.75 (s, 1H), 8.18 (d, J=2.6 Hz, 1H), 10.23 (bs, NH).

5-Allyloxy-3-(1-methyl-1H-pyrazol-4-yl)-1H-pyrrolo[2,3-b]pyridine (29o)

Following the method used for conversion of 23 into 8, synthesis of 29o was carried out using 28o (crude), EtOH (1.0 mL), 10% aq. HCl (1.0 mL) and heating for 16 h to give 29o as a white solid (17.1 mg, 39%); $^1$H NMR (400 MHz, CDCl$_3$) δ 3.99 (s, 3H), 4.64 (dt, J=5.3, 1.4 Hz, 2H), 5.34 (dq, J=10.5, 0.9 Hz, 1H), 5.48 (dq, J=17.2, 1.5 Hz, 1H), 6.05-6.20 (m, 1H), 7.41 (d, J=2.4 Hz, 1H), 7.59 (s, 2H), 7.75 (s, 1H), 8.17 (d, J=2.6 Hz, 1H), 10.31 (bs, NH).

[3-(1-Methyl-1H-pyrazol-4-yl)-1H-pyrrolo[2,3-b]pyridin-5-yloxy]-acetic acid ethyl ester (29p)

Following the method used for conversion of 23 into 8, synthesis of 29p was carried out using 28p (crude), EtOH (1.0 mL), 10% aq. HCl (1.0 mL) and heating for 16 h to give 29p as an orange oil (7.3 mg, 14%). Note: due to trans-esterification the methyl ester was converted into the ethyl ester; $^1$H NMR (400 MHz, CDCl$_3$) δ 1.32 (t, J=7.1 Hz, 3H), 4.00 (s, 3H), 4.30 (q, J=7.1 Hz, 2H), 4.72 (s, 2H), 7.41 (d, J=2.4H, 1H), 7.59 (s, 1H), 7.61 (d, J=2.6 Hz, 1H), 7.23 (s, 1H), 8.20 (d, J=2.6 Hz, 1H), 9.67 (bs, NH).

5-Cyclopentyloxy-3-(1-methyl-1H-pyrazol-4-yl)-1H-pyrrolo[2,3-b]pyridine (29q)

Following the method used for conversion of 23 into 8, synthesis of 29q was carried out using 28q (crude), EtOH (1.0 mL), 10% aq. HCl (1.0 mL) and heating for 16 h to give 29q as a white solid (20.8 mg, 42%); $^1$H NMR (400 MHz, CDCl$_3$) δ 1.55-1.75 (m, 2H), 1.80-2.00 (m, 6H), 3.99 (s, 3H), 4.83 (quintet, J=4.1 Hz, 1H), 7.40 (d, J=1.8 Hz, 1H), 7.57 (d, J=2.2 Hz, 1H), 7.59 (s, 1H), 7.75 (s, 1H), 8.10 (d, J=2.3 Hz, 1H), 10.38 (bs, NH).

3-(1-Methyl-1H-pyrazol-4-yl)-5-phenethyloxy-1H-pyrrolo[2,3-b]pyridine (29r)

Following the method used for conversion of 23 into 8, synthesis of 29r was carried out using 28r (39 mg, 87 μmol), EtOH (1.0 mL), 10% aq. HCl (1.0 mL) and heating for 20 h to give 29r as a white solid (18.5 mg, 67%); $^1$H NMR (400 MHz, CDCl$_3$+6 drops CD$_3$OD) δ 3.08 (t, J=7.0 Hz, 2H), 3.91 (s, 3H), 4.21 (t, J=7.1 Hz, 2H), 7.20-7.35 (m, 6H), 7.47 (d, J=2.6 Hz, 1H), 7.53 (s, 1H), 7.65 (d, J=0.6 Hz, 1H), 7.97 (d, J=2.6 Hz, 1H).

5-(cyclopropylmethoxy)-3-(1-methyl-1H-pyrazol-4-yl)-1H-pyrrolo[2,3-b]pyridine (29s)

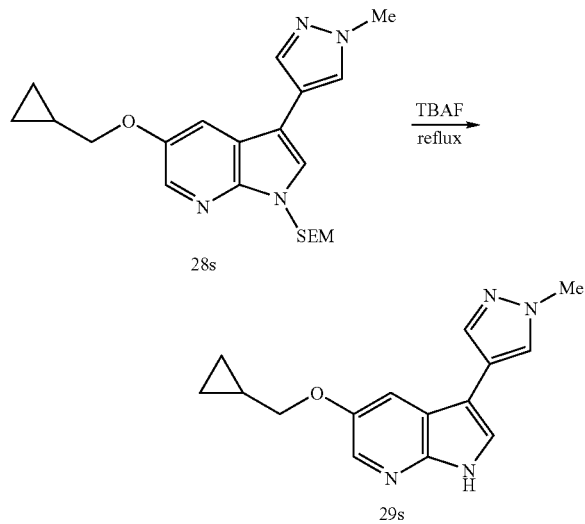

A mixture of 28s (40 mg, 0.10 mmol) and 1.0 M TBAF in THF (3 mL) was heated at reflux for 7 h. The reaction mixture was then cooled, poured onto a mixture of AcOEt and saturated aqueous NaHCO$_3$. The layers were separated, the aqueous phase extracted with more AcOEt (2×) then the combined organic extracts dried (MgSO$_4$) and concentrated. The residue was purified by PTLC using 5% MeOH in CH$_2$Cl$_2$ as eluent) to give 29s as a white solid (25.0 mg, 62%); $^1$H NMR (400 MHz, CDCl$_3$) δ 0.40 (q, J=4.7 Hz, 2H), 0.69 (m, 2H), 1.33 (m, 1H), 3.91 (d, J=7.0 Hz, 2H), 4.00 (s, 3H), 7.36 (d, J=2.5 Hz, 1H), 7.56 (d, J=2.5 Hz, 1H), 7.60 (s, 1H), 7.75 (s, 1H), 8.15 (d, J=2.6 Hz, 1H), 9.14 (bs, NH).

5-(cyclohexylmethoxy)-3-(1-methyl-1H-pyrazol-4-yl)-1H-pyrrolo[2,3-b]pyridine (29t)

Following the method used for conversion of 28s into 29s, synthesis of 29t was carried out using 28t (38 mg, 0.086 mmol), 1.0 M TBAF in THF (2 mL) with heating at reflux for 7 h. The product was purified by preparative LCMS (column LUNA 10 μ C18(2) 00G-4253-V0 250×50 mm) using water—MeCN (0.1% AcOH) as eluent (in gradient; flow 80 mL/min) to 29t as a white solid (10.6 mg, 40%); $^1$H NMR (400 MHz, CDCl$_3$) δ 1.12 (dq, J=15.1 Hz, J=3.3 Hz, 2H), 1.18-1.40 (m, 4H), 1.68-2.00 (m, 5H), 3.86 (d, J=6.3 Hz, 2H), 4.00 (s, 3H), 7.39 (d, J=2.48 Hz, 1H), 7.54 (d, J=2.6 Hz, 1H), 7.60 (s, 1H), 7.76 (d, J=0.6 Hz, 1H), 8.13 (d, J=2.6 Hz, 1H), 9.84 (bs, NH); m/z (CI$^+$) 311.1(MH$^+$).

Synthesis of Inhibitors 35 and 36

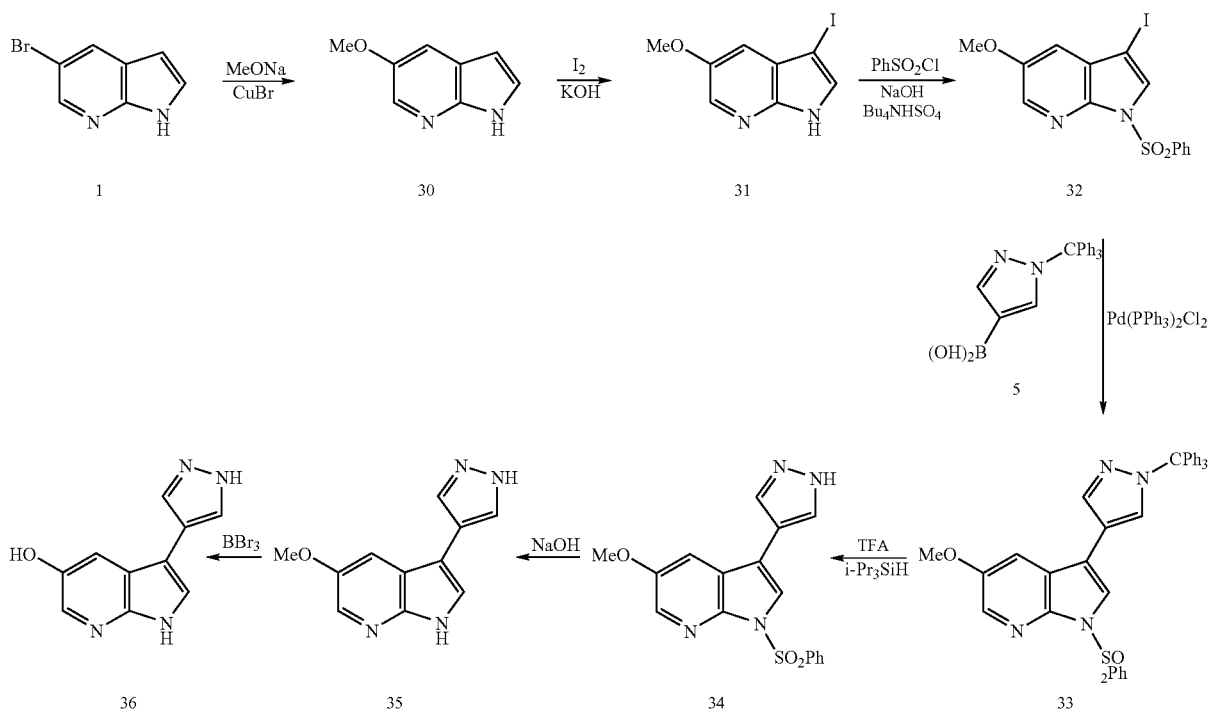

5-Methoxy-1H-pyrrolo[2,3-b]pyridine (30)

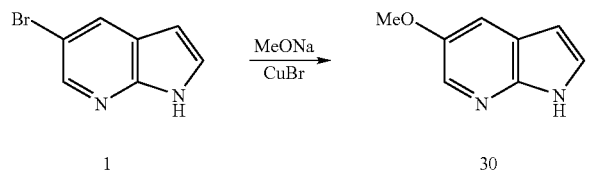

To 5-bromo-7-azaindole 1 (0.98 g, 5.0 mmol) in DMF (32 mL) was added 25% (w/w) MeONa (48 mL, 210 mmol) followed by copper (1) bromide (1.43 g, 10.0 mmol), and the reaction mixture was heated at 140° C. for 2.5. It was then cooled and concentrated to remove DMF. Water (100 mL) was added followed by saturated aqueous $NaHCO_3$ (20 mL). The mixture was extracted with AcOEt (3×), the combined organic extracts dried ($MgSO_4$) and concentrated. The solid residue was purified by SGC using AcOEt:hexane (gradient elution up to 30:70) to give 30 as a green solid (0.58 g, 78%); $^1$H NMR (400 MHz, $CDCl_3$) δ 3.90 (s, 3H), 6.45 (d, J=2.3 Hz, 1H), 7.33 (d, J=2.8 Hz, 1H), 7.48 (d, J=2.2 Hz, 1H), 8.00-8.20 (bs, 1H); 10.60-10.80 (bs, NH).

3-Iodo-5-methoxy-1H-pyrrolo[2,3-b]pyridine (31)

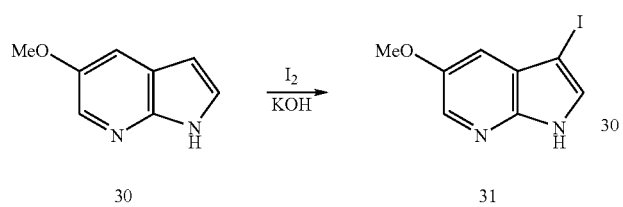

Following the method used for conversion of 2 into 3, synthesis of 31 was carried out using 30 (0.50 g, 3.37 mmol), DMF (8.4 mL), KOH (701 mg, 12.5 mmol), 12 (942 mg, 3.71 mmol) with stirring for 40 min. to give 31 as a creamy solid (850 mg, 92%); $^1$H NMR (400 MHz, $CDCl_3$) δ 3.94 (s, 3H), 7.23 (d, J=2.6 Hz, 1H), 7.46 (d, J=2.2 Hz, 1H), 8.10 (d, J=2.6 Hz, 1H), 9.40-9.60 (bs, NH).

1-Benzenesulfonyl-3-iodo-5-methoxy-1H-pyrrolo[2,3-b]pyridine (32)

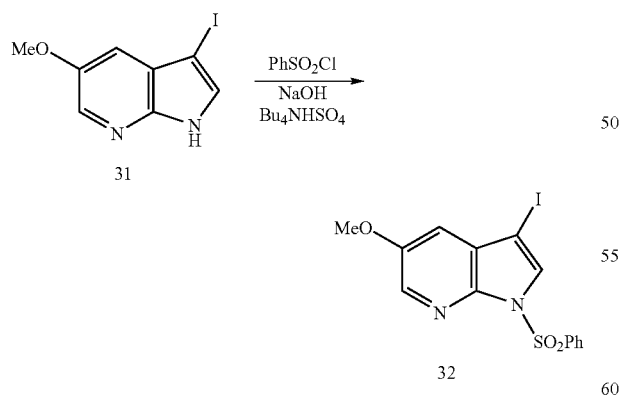

Following the method used for conversion of 3 into 4, synthesis of 32 was carried out using 31 (700 mg, 2.55 mmol), $PhSO_2Cl$ (489 μL, 3.83 mmol), n-$Bu_4NHSO_4$ (113 mg, 0.33 mmol) and 50% aq. NaOH (485 μL) in $CH_2Cl_2$ (16 mL) with stirring for 1 h 15 min. The concentrated residue was washed with a small amount of methanol (3×) to give 32 as a white solid (833 mg, 79%); $^1$H NMR (400 MHz, $CDCl_3$) δ 3.89 (s, 3H), 7.10 (d, J=2.7 Hz, 1H), 7.48 (t, J=2.5 Hz, 2H), 7.60 (tt, J=7.4, 1.3 Hz, 1H), 7.83 (d, J=0.4 Hz, 1H), 8.14 (m, 2H).

1-Benzenesulfonyl-5-methoxy-3-(1-trityl-1H-pyrazol-4-yl)-1H-pyrrolo[2,3-b]pyridine (33)

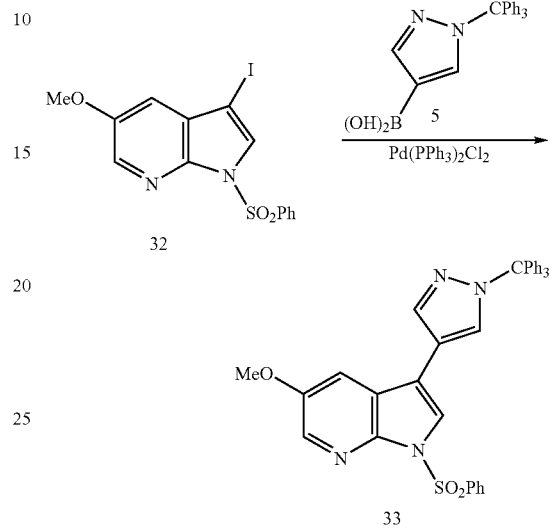

Following the method used for conversion of 4 into 6, synthesis of 33 was carried out using 32 (260 mg, 0.63 mmol), 5 (333 mg, 0.94 mmol), $PdCl_2(PPh_3)_2$ (44 mg, 0.063 mmol), LiCl (80 mg, 1.88 mmol), 1M aq. $Na_2CO_3$ (1.57 mL, 1.57 mmol) in EtOH (2.9 mL) and toluene (2.9 mL). Reaction time: 0.5 h at reflux. The crude product was used in the subsequent reaction.

1-Benzenesulfonyl-5-methoxy-3-(1H-pyrazol-4-yl)-1H-pyrrolo[2,3-b]pyridine (34)

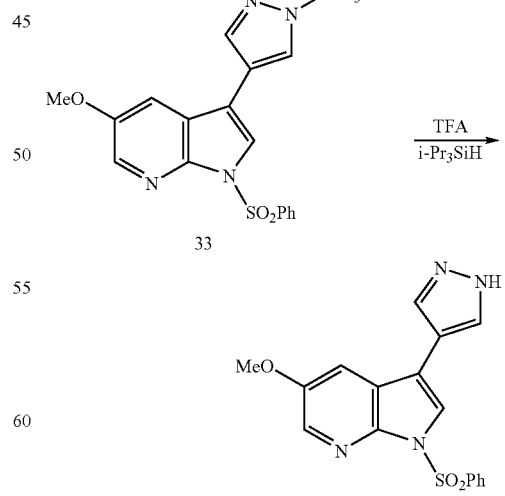

Following the method used for conversion of 6 into 7, synthesis of 34 was carried out using 33 (crude), TFA (501

μM), H₂O (50 μL) and i-Pr₃SiH (254 μL) in CH₂Cl₂ (5.3 mL) with stirring for 0.5 h. Isolation of product by means of SGC using CH₂Cl₂:MeOH as eluent (gradient elution up to 97:3, v/v) afforded 34 as a brown solid (176 mg, 79%); ¹H NMR (400 MHz, CDCl₃+6 drops CD₃OD) δ 3.82 (s, 3H), 7.38 (d, J=2.7 Hz, 1H), 7.43 (t, J=7.3 Hz, 2H), 7.52 (tt, J=7.5, 1.3 Hz, 1H), 7.70 (s, 1H), 7.77 (s, 2H), 8.08 (m, 2H), 8.12 (d, J=2.7 Hz, 1H).

5-Methoxy-3-(1H-pyrazol-4-yl)-1H-pyrrolo[2,3-b]pyridine (35)

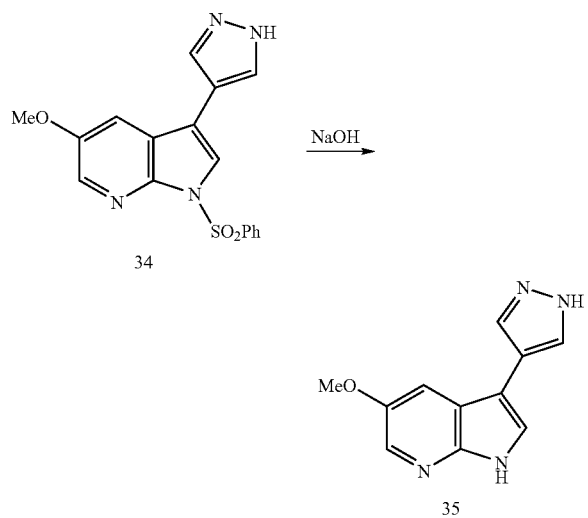

Following the method used for conversion of 7 into 8, synthesis of 35 was carried out using 34 (150 mg, 0.42 mmol), EtOH (8.2 mL), 10% aq. NaOH (3.9 mL) with heating at 90° C. for 4 h 20 min. TLC showed unreacted 34 so more 10% aq. NaOH (3.9 mL) was added and the reaction continued for 1 h. Extraction was performed using CH₂Cl₂ (1×) then 3% MeOH in CH₂Cl₂ (3×) and the residue purified by preparative LCMS (column LUNA 10 μ C18(2) 00G-4253-V0 250×50 mm) using water—MeCN (0.1% AcOH) as eluent (in gradient; flow 80 mL/min) to give 35 as a white solid (31.7 mg, 35%); ¹H NMR (400 MHz, CDCl₃+8 drops CD₃OD) δ 3.84 (s, 3H), 7.34 (s, 1H), 7.51 (d, J=2.7 Hz, 1H), 7.74 (s, 2H), 7.95 (d, J=2.7 Hz, 1H).

3-(1H-Pyrazol-4-yl)-1H-pyrrolo[2,3-b]pyridin-5-ol (36)

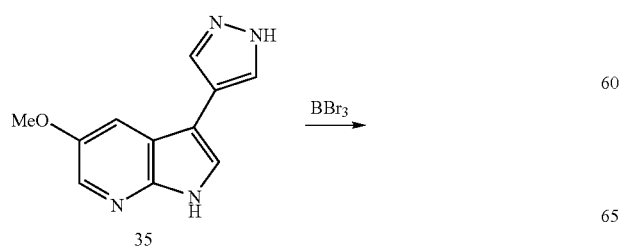

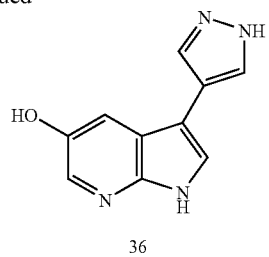

To a suspension of 35 (25 mg, 0.12 mmol) in CH₂Cl₂ (2.0 mL), cooled to 0° C., was added a 1M solution of BBr₃ (467 μL, 0.48 mmol) in CH₂Cl₂ and the reaction mixture stirred for 2 h at room temperature. More CH₂Cl₂ (2.0 mL) and BBr₃ (467 μL) was added at r.t. and the stirring continued for 65 h. The reaction mixture was partitioned between AcOEt and saturated aqueous NaHCO₃ and the layers separated. The aqueous phase was extracted with more AcOEt (4×), the combined organic extracts dried (MgSO₄) and concentrated. The residue was purified by preparative LCMS (column LUNA 10 μ C18(2) 00G-4253-V0 250×50 mm) using water—MeCN (0.1% AcOH) as eluent (in gradient; flow 80 mL/min) to give 36 as a white solid (9.1 mg, 39%); ¹H NMR (400 MHz, DMSO-d₆) δ 7.49 (d, J=2.5 Hz, 1H), 7.57 (d, J=2.5 Hz, 1H), 7.86 (d, J=2.5 Hz, 1H), 7.90 (s, 2H), 9.05-9.20 (bs, 1H), 11.32 (bs, NH).

Synthesis of Inhibitor 39

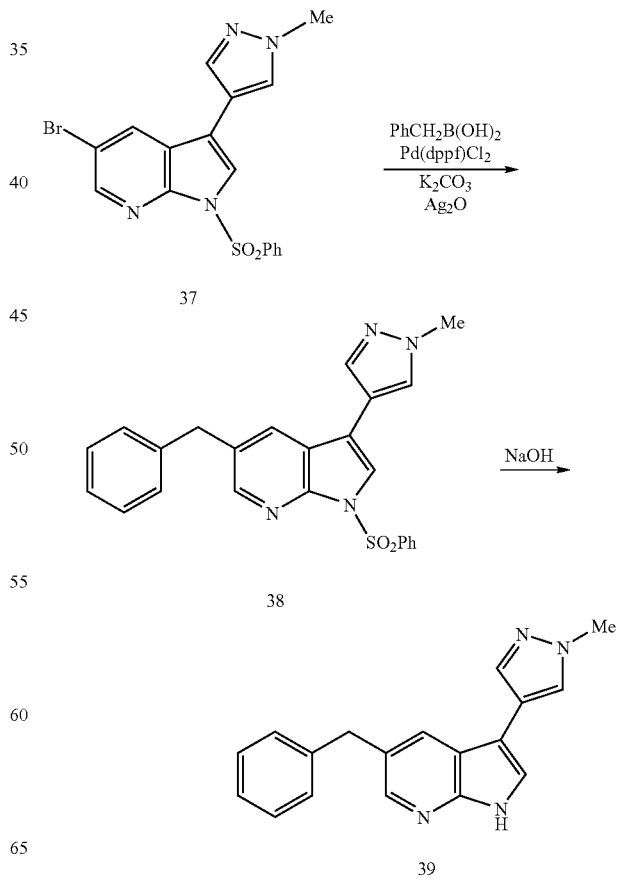

1-Benzenesulfonyl-5-benzyl-3-(1-methyl-1H-pyrazol-4-yl)-1H-pyrrolo[2,3-b]pyridine (38)

5-Benzyl-3-(1-methyl-1H-pyrazol-4-yl)-1H-pyrrolo[2,3-b]pyridine (39)

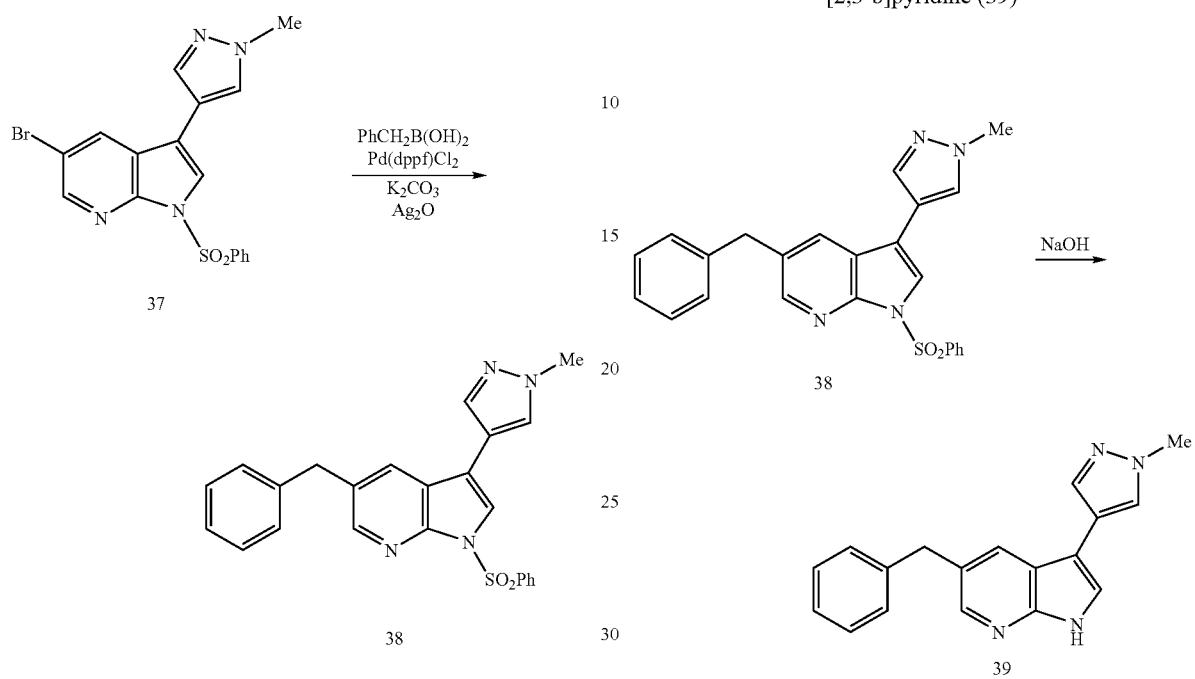

Bromide 37 (80 mg, 0.19 mmol; prepared in analogous way to 20), benzyl boronic acid (29 mg, 0.21 mmol), Ag$_2$O (111 mg, 0.48 mmol), K$_2$CO$_3$ (80 mg, 0.58 mmol), [1,1'-bis(diphenylphosphino)ferrocene]dichloropalladium(II) complex with CH$_2$Cl$_2$ (1:1)(16 mg, 0.019 mmol) in THF (2.5 mL) were heated at 80° C. for 17.5 h. The mixture was allowed to cool to r.t., diluted with AcOEt and a solution of 30% H$_2$O$_2$ and 10% NaOH (1:1, v/v) and partitioned. The aqueous layer was extracted with AcOEt (3×). The combined organic extracts were dried (MgSO$_4$), filtered and concentrated. The crude residue was purified by LCMS (column LUNA 10 μ C18(2) 00G-4253-V0 250×50 mm) using water—MeCN (0.1% AcOH) as eluent (in gradient; flow 80 mL/min) to afford 38 (36 mg, 44%). $^1$H NMR (400 MHz; CDCl$_3$) δ 3.97 (s, 3H), 4.07 (s, 2H), 7.15-7.22 (m, 3H), 7.26-7.30 (m, 2H), 7.46-7.51 (m, 2H), 7.55-7.59 (m, 2H), 7.70 (d, J=0.73 Hz, 1H), 7.73-7.75 (m, 2H), 8.18-8.22 (m, 2H), 8.35 (d, J=2.0 Hz, 1H). MS (CI) m/z 429 (MH$^+$).

A mixture of benzyl derivative 38 (36 mg, 0.08 mmol) and 10% NaOH solution (0.80 mL) in EtOH (2.5 mL) was heated at 90° C. After 1 h the mixture was cooled to r.t., diluted with AcOEt and saturated brine and partitioned. The aqueous layer was extracted with AcOEt (3×). The combined organic extracts were dried (MgSO$_4$), concentrated and the residue was purified by LCMS (column LUNA 10 μ C18(2) 00G-4253-V0 250×50 mm) using water—MeCN (0.1% AcOH) as eluent (in gradient; flow 80 mL/min) to afford 39 (17 mg, 70%). $^1$H NMR (400 MHz; CDCl$_3$) δ 3.97 (s, 3H), 4.12 (s, 2H), 7.19-7.36 (m, 6H), 7.58 (s, 1H), 7.71 (s, 1H), 7.86 (brs, 1H), 8.24 (m, 1H), 8.79 (brs, 1H). MS (CI) m/z 289 (MH$^+$).

Synthesis of Example Inhibitor 45

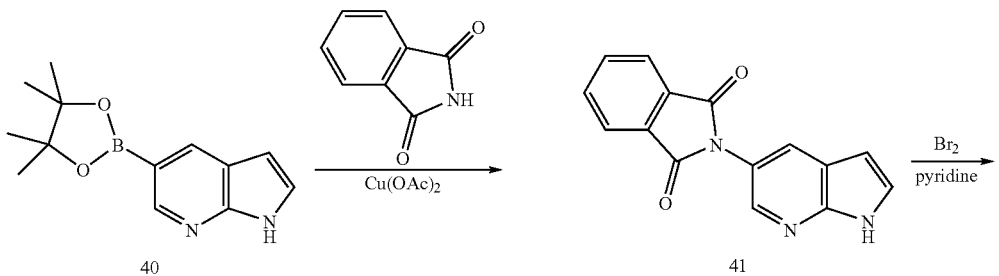

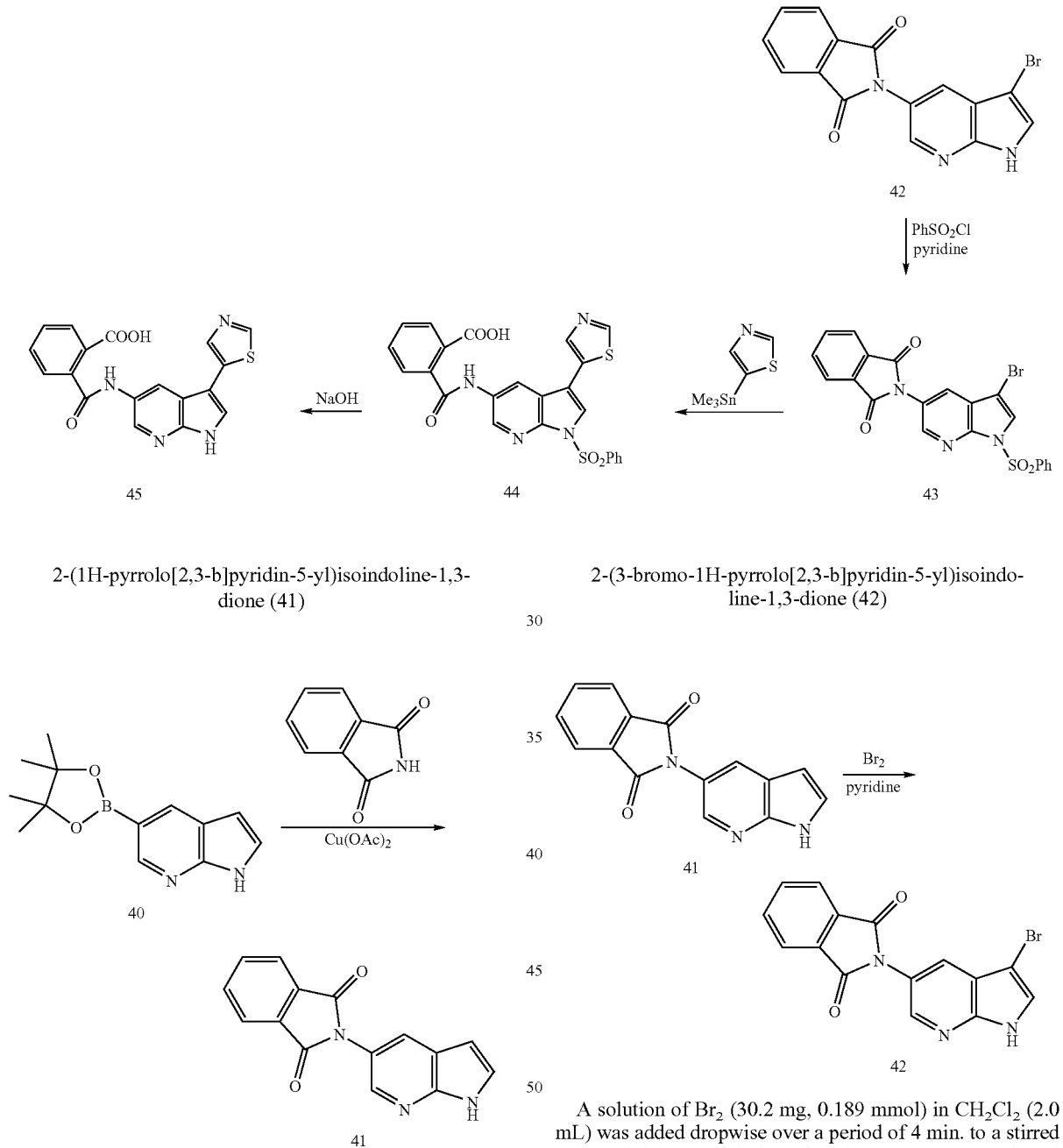

2-(1H-pyrrolo[2,3-b]pyridin-5-yl)isoindoline-1,3-dione (41)

2-(3-bromo-1H-pyrrolo[2,3-b]pyridin-5-yl)isoindoline-1,3-dione (42)

A mixture of boronic ester 40 (3.80 g, 15.6 mmol; preparation disclosed in WO2004/078757), phtalimide (0.951 g, 15.6 mmol), Cu(OAc)$_2$ (1.56 g, 8.59 mmol) and Et$_3$N (2.11 g, 20.8 mmol) in CH$_2$Cl$_2$ (152 mL) was stirred at r.t. for 5 d. The mixture was then concentrated, dissolved in DMF and separated by LCMS (column LUNA 10 μ C18(2) 00G-4253-V0 250×50 mm) using water—MeCN (0.1% AcOH) as eluent (in gradient; flow 80 mL/min) to afford 41 (205 mg, 5%). $^1$H NMR (400 MHz; CDCl$_3$) δ 6.58 (dd, J=2.0, 3.5 Hz, 1H), 7.39 (dd, J=2.5, 3.5 Hz, 1H), 7.80-7.84 (m, 2H), 7.96-8.01 (m, 3H), 8.34 (d, J=2.2 Hz, 1H), 8.98 (bs, 1H). MS (ES) m/z 305 (MH$^+$+MeCN).

A solution of Br$_2$ (30.2 mg, 0.189 mmol) in CH$_2$Cl$_2$ (2.0 mL) was added dropwise over a period of 4 min. to a stirred and cooled (0° C.) solution of 41 (50 mg, 0.189 mmol) and pyridine (18.0 mg, 0.23 mmol) in CH$_2$Cl$_2$ (2 mL). After additional stirring at 0° C. for 26 min. the reaction mixture was treated with a 1:1 (v/v) solution of saturated aqueous NaHCO$_3$ and saturated aqueous Na$_2$S$_2$O$_3$. Stirring continued for 30 min at 0° C. and the organic phase was separated. The aqueous layer was extracted with CH$_2$Cl$_2$. The combined organic solutions were dried (MgSO$_4$), concentrated and the residue was separated by LCMS (column LUNA 10 μ C18(2) 00G-4253-V0 250×50 mm) using water—MeCN (0.1% AcOH) as eluent (in gradient; flow 80 mL/min) to afford 42 (64.7 mg, quant.). $^1$H NMR (400 MHz; CDCl$_3$+3 drops of CD$_3$OD) δ 7.40 (s, 1H), 7.81 (dd, J=3.1, 5.4 Hz, 2H), 7.94 (d, J=2.3 Hz, 1H), 7.96 (dd, J=5.5, 3.1 Hz, 2H), 8.29 (d, J=2.3 Hz, 1H); MS (ES) m/z 383 (MH$^+$+MeCN).

2-(3-bromo-1-(phenylsulfonyl)-1H-pyrrolo[2,3-b]pyridin-5-yl)isoindoline-1,3-dione (43)

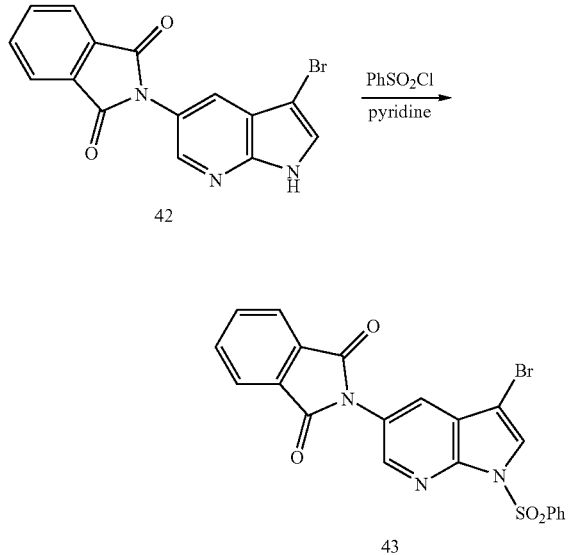

PhSO₂Cl (24 mg, 0.136 mmol) was added dropwise over a period of 3 min. to a stirred solution of 42 (31 mg, 0.090 mmol) and pyridine (11.4 mg, 0.144 mmol) in CH₂Cl₂. The mixture was stirred at r.t. overnight. Additional portion of PhSO₂Cl (24 mg, 0.136 mmol) was added, followed by DMAP (3 mg, 0.025 mmol). After additional stirring for 1.5 h, the mixture was partitioned between saturated aqueous NaHCO₃:CH₂Cl₂. The aqueous layer was extracted with CH₂Cl₂. The combined organic solutions were washed with brine, dried (MgSO₄) and concentrated. Purification by PTLC using AcOEt:hexane=1:1 (v/v) as eluent afforded 43 as orange powder (15 mg, 35%). ¹H NMR (400 MHz; CDCl₃) δ 7.55 (tt, J=6.6, 1.6 Hz, 2H), 7.62 (tt, J=5.3, 2.0 Hz, 1H), 7.84 (dd, J=5.4, 3.0 Hz, 2H), 7.88 (s, 1H), 7.92 (d, J=2.3 Hz, 1H), 7.98 (dd, J=5.4, 3.0 Hz, 2H), 8.23 (dd, J=4.0, 1.3 Hz, 2H), 8.55 (d, J=1.9 Hz, 1H).

2-(1-(phenylsulfonyl)-3-(thiazol-5-yl)-1H-pyrrolo[2,3-b]pyridin-5-ylcarbamoyl)benzoic acid (44)

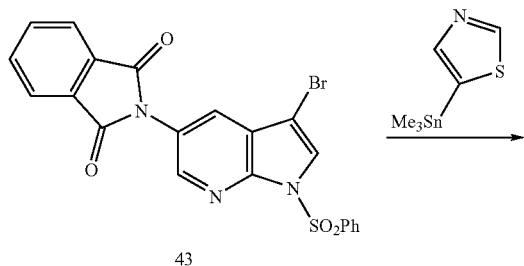

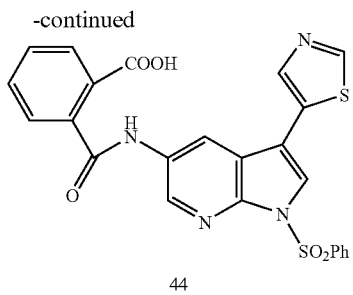

A mixture of bromide 43 (50 mg, 0.104 mmol), 5-(trimethylstannyl)thiazole (51.1 mg, 0.21 mmol), PdCl₂(MeCN)₂ (2.67 mg, 10 μmol), and P(o-tolyl)₃ (6.27 mg, 21 μmol) in toluene (5 mL) was heated in darkness at 85° C. overnight and then refluxed for 2 d. The mixture was concentrated and the product isolated by LCMS (column LUNA 10 μ C18(2) 00G-4253-V0 250×50 mm) using water—MeCN (0.1% AcOH) as eluent (in gradient; flow 80 mL/min) to afford 44 (20 mg, 38%). ¹H NMR (400 MHz; CDCl₃+3 drops of CD₃OD) δ 7.30 (dd, J=4.5, 2.0 Hz, 2H), 7.35 (t, J=7.4 Hz, 2H), 7.44-7.50 (m, 2H), 7.61-7.63 (m, 1H), 7.80 (s, 1H), 7.98 (d, J=1.4 Hz, 1H), 8.00 (s, 2H), 8.42 (d, J=2.3 Hz, 1H), 8.59 (d, J=2.3 Hz, 1H), 8.70 (s, 1H). MS (ES) m/z 505 (MH⁺).

2-(3-(thiazol-5-yl)-1H-pyrrolo[2,3-b]pyridin-5-ylcarbamoyl)benzoic acid (45)

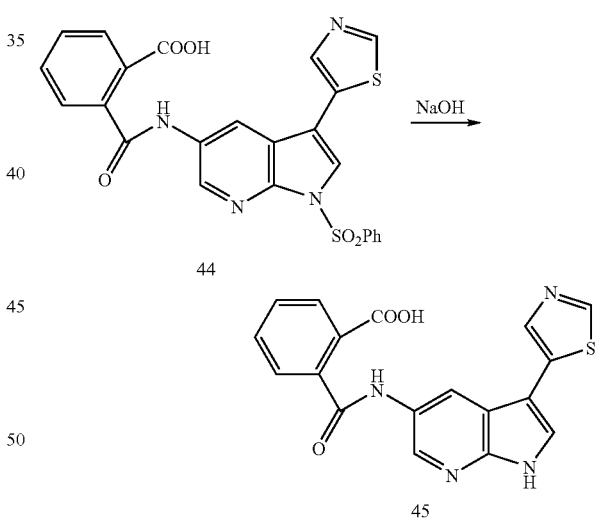

Sulfonamide 44 (20 mg, 40 μmol), 10% aqueous NaOH solution (0.36 mL, 0.9 mmol) in EtOH (1.0 mL) was refluxed for 30 min. The mixture was cooled, concentrated, treated with glacial acetic acid (0.72 mL, 12 mmol), and concentrated again. The residue was separated by LCMS (column LUNA 10 μ C18(2) 00G-4253-V0 250×50 mm) using water—MeCN (0.11% AcOH) as eluent (in gradient; flow 80 mL/min) to afford 45 (3.88 mg, 27%). ¹H NMR (400 MHz; CDCl₃+3 drops of CD₃OD) δ 7.36 (dd, J=7.5, 2.5 Hz, 1H), 7.57 (s, 2H), 7.78 (s, 1H), 8.02 (d, J=2.0 Hz, 1H), 8.15 (d, J=1.8 Hz, 1H), 8.20 (d, J=1.9 Hz, 1H), 8.39 (d, J=2.1 Hz, 1H), 8.50 (s, 1H); MS (ES) m/z 406.3 (MH⁺+MeCN).

Synthesis of Example Inhibitor 49

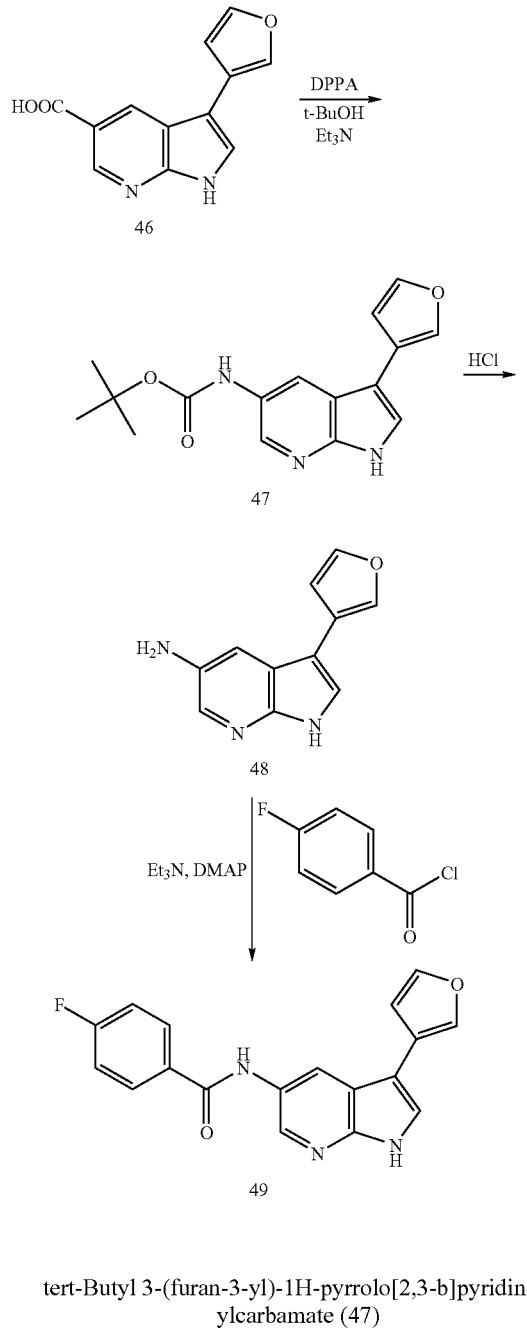

tert-Butyl 3-(furan-3-yl)-1H-pyrrolo[2,3-b]pyridin-5-ylcarbamate (47)

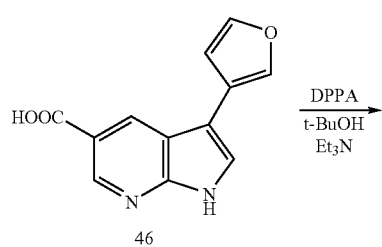

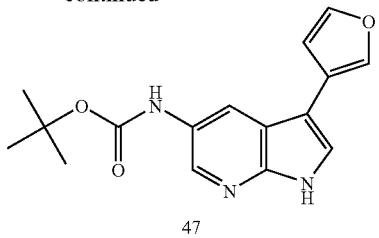

A mixture of acid 46 (200 mg, 088 mmol; preparation disclosed in WO2005085244), DPPA (254.28 mg, 0.92 mmol) and Et₃N (93.5 mg, 0.92 mmol) in 2-methylpropan-2-ol (20.6 mL) was stirred at r.t. for 30 min. and gradually raised to 100° C. over a period of 2 h. After additional 6 h stirring at 100° C. the mixture was cooled, concentrated in vacuum, and dissolved in AcOEt-water. The aqueous layer was extracted with AcOEt. Combined organic solutions were washed with saturated aqueous NaHCO₃, brine, dried (MgSO₄) and concentrated. The residue was separated by PTLC using CH₂Cl₂:MeOH=19:1 (v/v) as eluent to afford 47 (97.29 mg, 37%). ¹H NMR (400 MHz; CDCl₃) δ 1.56 (s, 9H), 6.62 (bs, 1H), 6.68 (dd, J=1.8, 0.9 Hz, 1H). 7.26 (s, 1H), 7.42 (d, J=2.4 Hz, 1H), 7.51 (dd, J=3.3, 1.5 Hz, 1H), 7.79 (s, 1H), 8.23 (d, J=2.2 Hz, 1H), 8.25 (bs, NH); MS (ES) m/z 341 (MH⁺+MeCN).

3-(Furan-3-yl)-1H-pyrrolo[2,3-b]pyridin-5-amine (48)

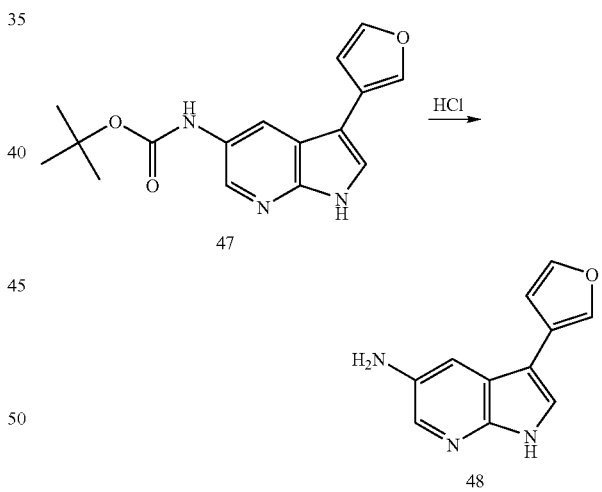

4.0 M aqueous HCl (0.83 mL, 3.32 mmol) was added to a suspension of 47 (90 mg, 0.30 mmol) in MeOH (0.17 mL) and the mixture was stirred at r.t. overnight. Concentrated aqueous HCl (0.2 mL, 2.2 mmol) was added and stirring continued for 5 h. The mixture was concentrated to dryness in vacuum and separated by means of LCMS (column LUNA 10 µ C18 (2) 00G-4253-V0 250×50 mm) using water—MeCN (0.1% AcOH) as eluent (in gradient; flow 80 mL/min) to afford 48 (41.64 mg, 70%). ¹H NMR (400 MHz; CDCl₃+3 drops of CD₃OD) δ 6.61 (dd, J=1.8, 0.8 Hz, 1H), 7.32 (s, 1H), 7.43 (d, J=2.5 Hz, 1H), 7.45 (dd, J=3.3, 1.7 Hz, 1H), 7.68 (dd, J=2.3, 1.0 Hz, 1H), 7.80 (d, J=2.5 Hz, 1H); MS (ES) m/z 241 (MH⁺+MeCN).

4-Fluoro-N-(3-(furan-3-yl)-1H-pyrrolo[2,3-b]pyridin-5-yl)benzamide (49)

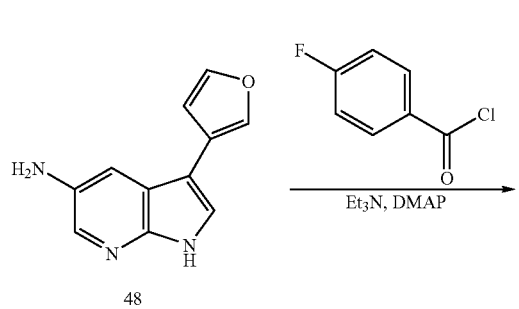

tert-Butyl 3-(1-trityl-1H-pyrazol-4-yl)-1H-pyrrolo[2,3-b]pyridin-5-ylcarbamate (51)

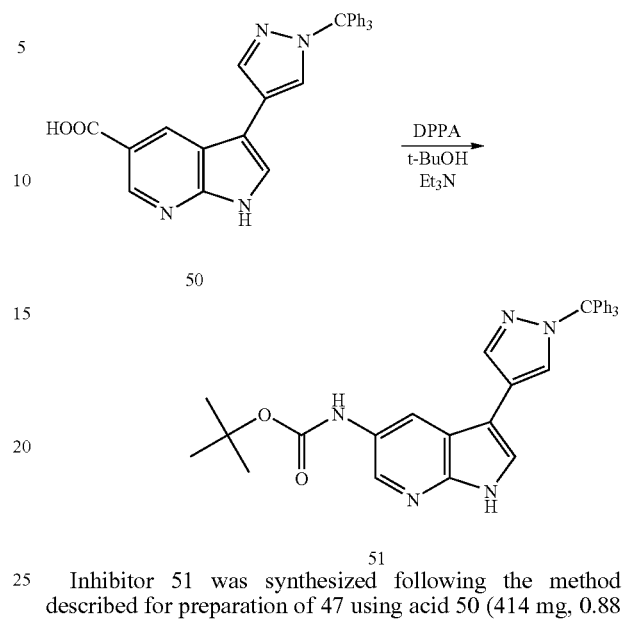

4-Fluorobenzoyl chloride (29.7 mg, 0.19 mmol) was added to a solution of amine 48 (25 mg, 0.125 mmol), DMAP (1.53 mg, 12.5 µmol) and Et$_3$N (12.6 mg, 0.125 mmol) in DMF (0.6 mL). The mixture was stirred at r.t. overnight, concentrated and separated by means of LCMS (column LUNA 10 µ C18 (2) 00G-4253-V0 250×50 mm) using water—MeCN (0.1% AcOH) as eluent (in gradient; flow 80 mL/min) to afford 49 (2.13 mg, 5%). $^1$H NMR (400 MHz; CDCl$_3$+3 drops of CD$_3$OD) δ 6.45 (dd, J=1.9, 0.9 Hz, 1H), 6.91 (t, J=1.8 Hz, 2H), 7.22 (s, 1H), 7.23 (t, J=1.7 Hz, 1H), 7.56 (m, 1H), 7.73-7.76 (m, 2H), 8.15 (d, J=2.1 Hz, 1H), 8.25 (d, J=2.3 Hz, 1H); MS (ES) m/z 363 (MH$^+$+MeCN).

Synthesis of example inhibitors 51-53

Inhibitor 51 was synthesized following the method described for preparation of 47 using acid 50 (414 mg, 0.88 mmol; prepared in analogous way to 46). Yield 476 mg (quant).

tert-Butyl 3-(1H-pyrazol-4-yl)-1H-pyrrolo[2,3-b]pyridin-5-ylcarbamate (52)

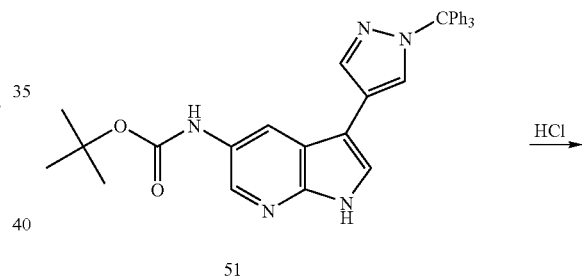

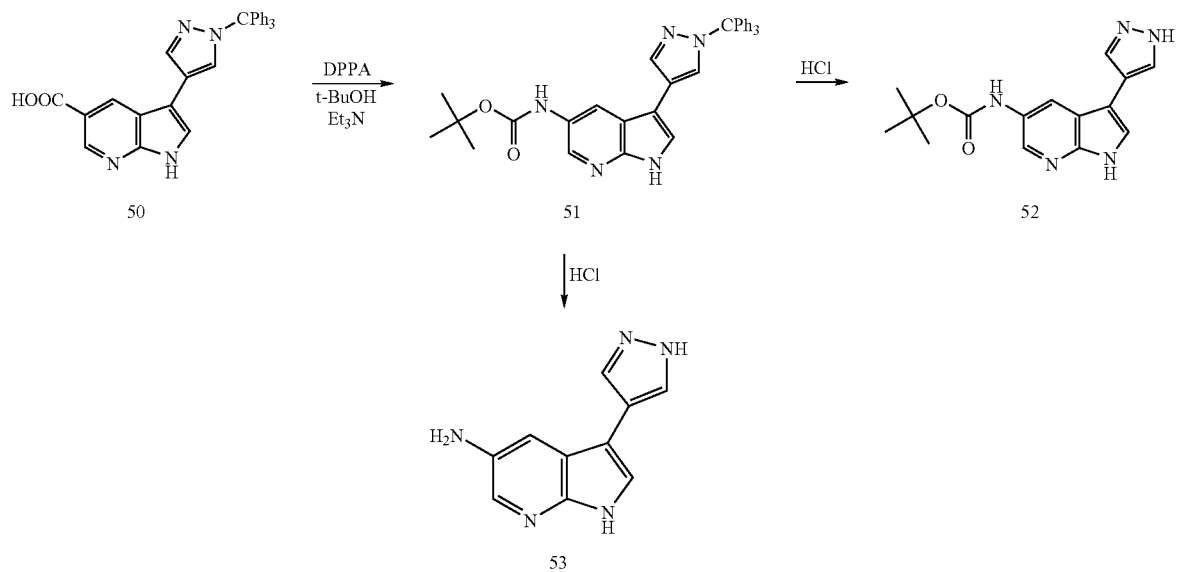

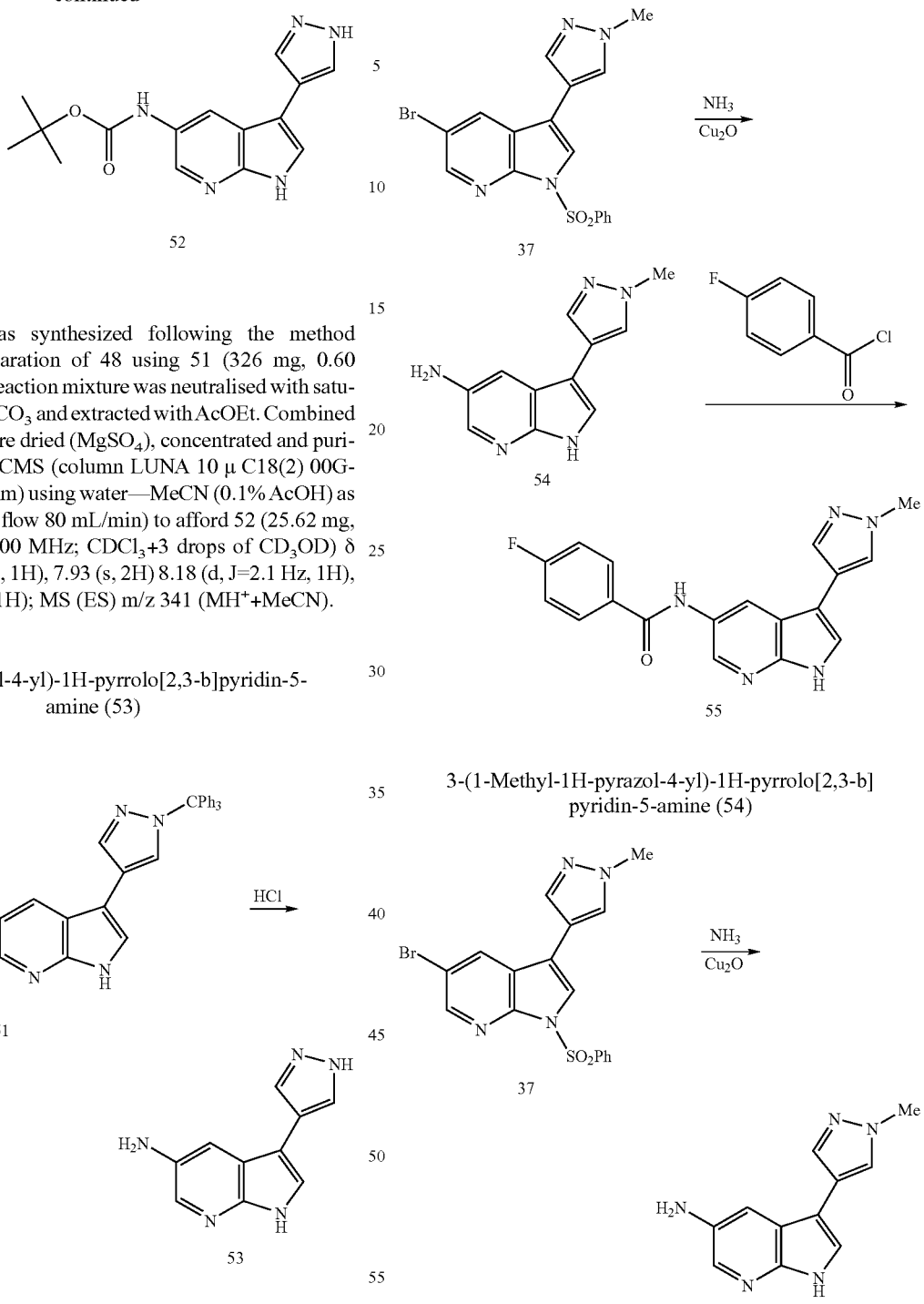

Inhibitor 52 was synthesized following the method described for preparation of 48 using 51 (326 mg, 0.60 mmol). The crude reaction mixture was neutralised with saturated aqueous NaHCO$_3$ and extracted with AcOEt. Combined organic extracts were dried (MgSO$_4$), concentrated and purified by means of LCMS (column LUNA 10 μ C18(2) 00G-4253-V0 250×50 mm) using water—MeCN (0.1% AcOH) as eluent (in gradient; flow 80 mL/min) to afford 52 (25.62 mg, 14%). $^1$H NMR (400 MHz; CDCl$_3$+3 drops of CD$_3$OD) δ 1.54 (s, 9H), 7.54 (s, 1H), 7.93 (s, 2H) 8.18 (d, J=2.1 Hz, 1H), 8.31 (d, J=2.1 Hz, 1H); MS (ES) m/z 341 (MH$^+$+MeCN).

3-(1H-pyrazol-4-yl)-1H-pyrrolo[2,3-b]pyridin-5-amine (53)

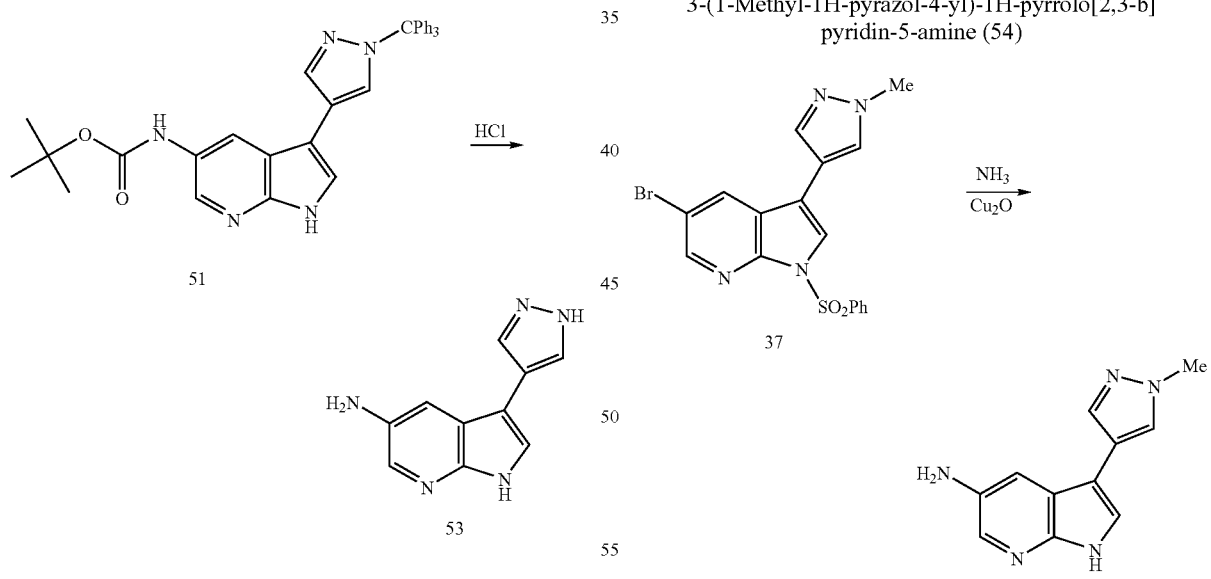

Inhibitor 53 was synthesized following the method described for preparation of 48 using 51 (150 mg, 0.28 mmol). The reaction mixture was concentrated to dryness in vacuum and separated by means of LCMS (column LUNA 10 μ C18(2) 00G-4253-V0 250×50 mm) using water—MeCN (0.1% AcOH) as eluent (in gradient; flow 80 mL/min) to afford 53 (6.07 mg, 11%). $^1$H NMR (400 MHz; CDCl$_3$+3 drops of CD$_3$OD) δ 7.26 (s, 1H), 7.66 (s, 2H), 8.54 (d, J=1.9 Hz, 1H), 8.68 (d, J=1.9 Hz, 1H); MS (ES) m/z 241 (MH$^+$+MeCN).

Synthesis of example inhibitors 54 and 55

3-(1-Methyl-1H-pyrazol-4-yl)-1H-pyrrolo[2,3-b]pyridin-5-amine (54)

A mixture of 37 (100 mg, 0.24 mmol), Cu$_2$O (5.0 mg, 35 μmol), and aqueous ammonium hydroxide (3 mL) in ethylene glycol (2.5 mL) was heated in a sealed tube at 100° C. for a period of 23 h. The mixture was cooled and partitioned between water-AcOEt. The aqueous layer was extracted with AcOEt. Combined organic solutions were dried (MgSO$_4$), concentrated and the residue was purified by means of LCMS (column LUNA 10 μ C18(2) 00G-4253-V0 250×50 mm) using water—MeCN (0.1% AcOH) as eluent (in gradient; flow 80 mL/min) to afford 54 (20.0 mg, 39%). $^1$H NMR (400

MHz; DMSO-d$_6$) δ 3.80 (s, 3H), 7.43 (s, 1H), 7.58 (dd, J=6.0, 1.7 Hz, 2H), 7.70 (m, 1H), 7.93 (m, 1H); MS (ES) m/z 254 (MH$^+$+MeCN).

4-Fluoro-N-(3-(1-methyl-1H-pyrazol-4-yl)-1H-pyrrolo[2,3-b]pyridin-5-yl)benzamide (55)

Indolin-1-yl(3-(1-methyl-1H-pyrazol-4-yl)-1H-pyrrolo[2,3-b]pyridin-5-yl)methanone (58)

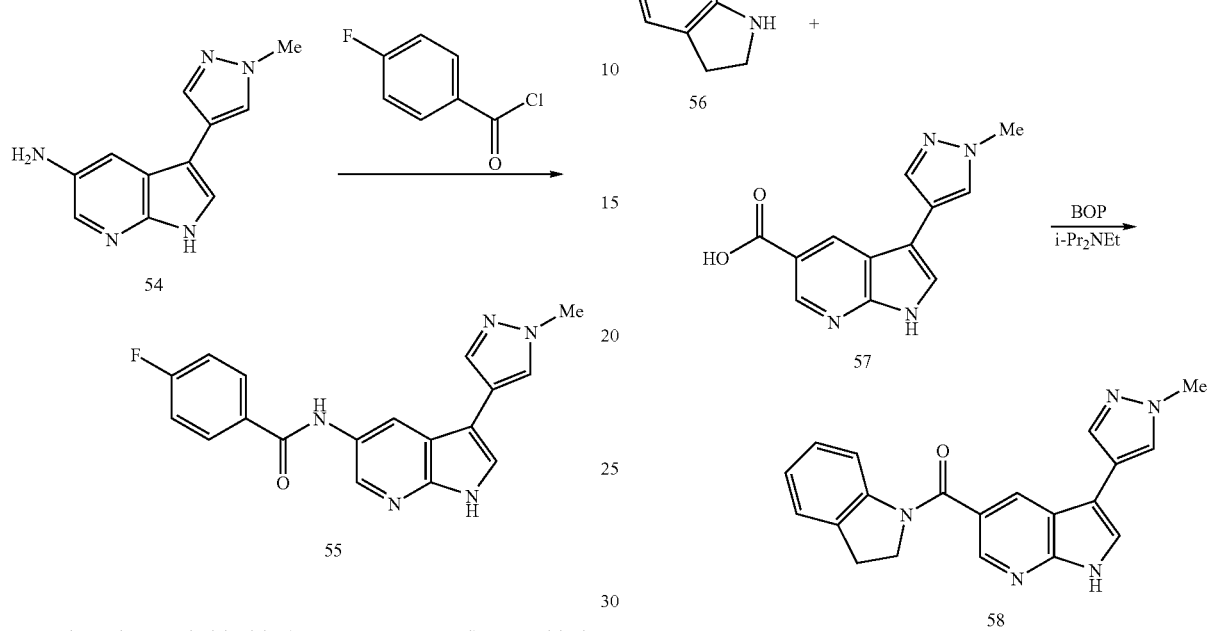

4-Fluorobenzoyl chloride (100 μL, 0.84 mmol) was added to a solution of 54 (20.0 mg, 93.7 μmol) in pyridine (2 mL). The mixture was stirred at r.t. overnight, concentrated and separated by means of LCMS (column LUNA 10 μ C18(2) 00G-4253-V0 250×50 mm) using water—MeCN (0.1% AcOH) as eluent (in gradient; flow 80 mL/min) to afford 55 (3.99 mg, 13%). $^1$H NMR (400 MHz; DMSO-d$_6$) δ 3.87 (s, 3H), 7.38 (t, J=8.8 Hz, 2H), 7.66 (s, 1H), 7.75 (s, 1H), 8.00 (s, 1H), 8.08 (dd, J=8.7, 5.4 Hz, 2H), 8.48 (dd, J=7.0, 2.2 Hz, 2H); MS (ES) m/z 377 (MH$^+$+MeCN).

Synthesis of example inhibitors 59 and 60

A mixture of indoline (56)(184 μL, 1.64 mmol), acid 57 (200 mg, 0.826 mmol; prepared in analogous way to 46), benzotriazole-1-yl-oxy-tris-(dimethylamino)-phosphonium hexafluorophosphate (BOP, 473 mg, 1.07 mmol) and i-Pr$_2$NEt (288 μL, 1.65 mmol) in DMF (4 mL) was stirred at r.t. overnight. The product was isolated by means of preparative LCMS (column LUNA 10, C18(2) 00G-4253-V0 250× 50 mm) using water—acetonitrile (0.1% AcOH) as eluent (in gradient; flow 80 mL/min) to give 58 as a white solid (126.9

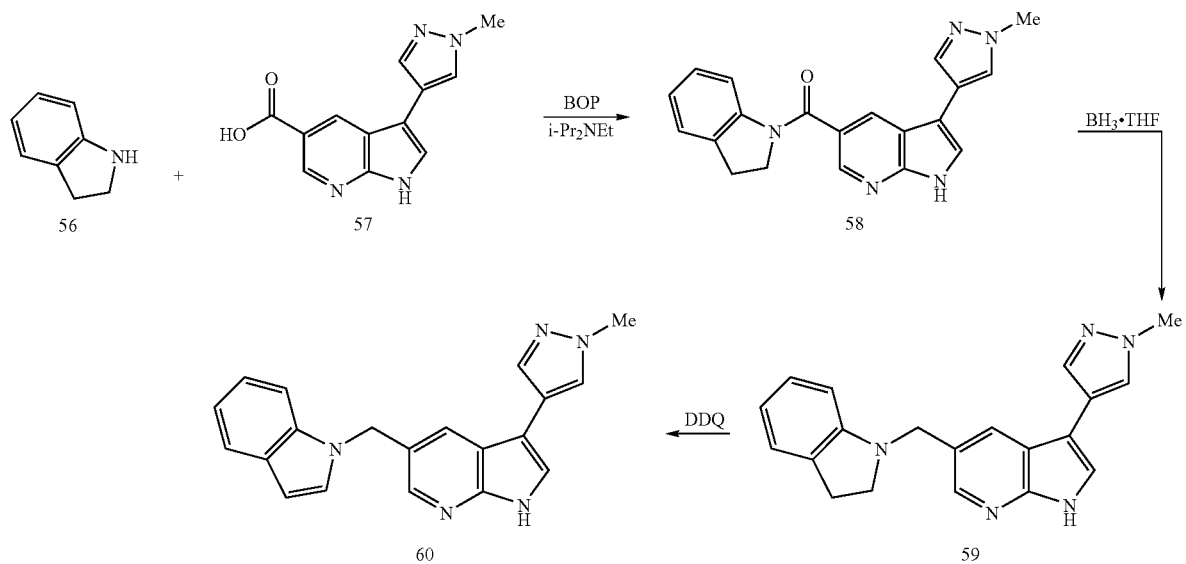

mg, 45%); ¹H NMR (400 MHz, CDCl₃) δ 3.18 (t, J=8.2 Hz, 2H), 3.99 (s, 3H), 4.21 (t, J=8.2 Hz, 2H), 7.06 (t, J=6.7 Hz, 1H), 7.15 (br s, 1H), 7.24-7.30 (m, 2H), 7.49 (d, J=2.2 Hz, 1H), 7.67 (s, 1H), 7.75 (d, J=0.4 Hz, 1H), 8.35 (d, J=1.9 Hz), 8.60 (d, J=1.9 Hz), 9.16 (bs, 1H).

2H), 7.43 (d, J=1.6 Hz, 1H), 7.61 (s, 1H), 7.75 (s, 1H), 8.08 (d, J=1.8 Hz, 1H), 8.38 (d, J=1.8 Hz, 1H), 9.90 (bs, 1H).

5-((1H-indol-1-yl)methyl)-3-(1-methyl-1H-pyrazol-4-yl)-1H-pyrrolo[2,3-b]pyridine (60)

5-(Indolin-1-ylmethyl)-3-(1-methyl-1H-pyrazol-4-yl)-1H-pyrrolo[2,3-b]pyridine (59)

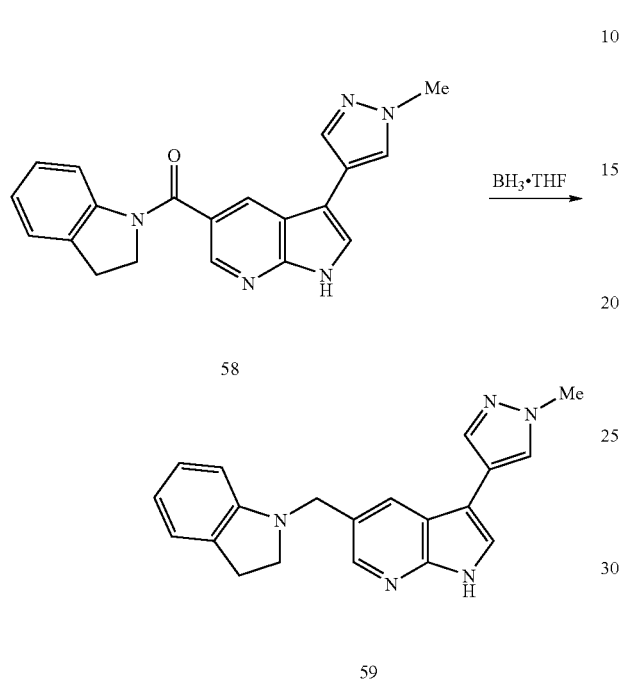

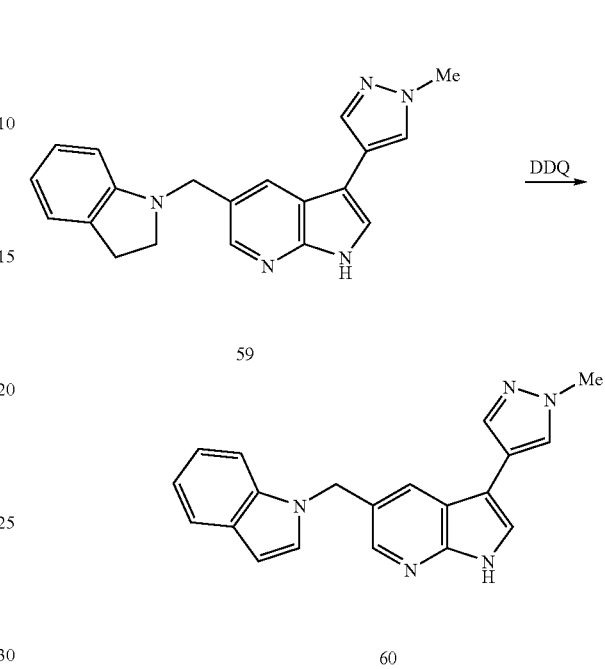

A mixture of 1.0 M BH₃ in THF (1.0 mL, 1.0 mmol) and amide 58 (80.7 mg, 0.235 mmol) in THF (2.0 mL) was refluxed under N₂ for 20 min. The reaction mixture was cooled to r.t., quenched with MeOH (5 mL) and concentrated. The residual solid was treated with 10% aqueous HCl (2.0 mL) and MeOH (2.0 mL). After 1 h stirring at r.t. the mixture was concentrated, basified with NaHCO₃ and extracted with AcOEt (3×10 mL). Combined extracts were dried (MgSO₄), concentrated and purified by means of preparative LCMS (column LUNA 10 μ C18(2) 00G-4253-V0 250×50 mm) using water—acetonitrile (0.1% AcOH) as eluent (in gradient; flow 80 mL/min) to give 59 as a white solid (14.0 mg, 18%); ¹H NMR (400 MHz, CDCl₃) δ 2.97 (t, J=8.3 Hz, 2H), 3.30 (t, J=8.3 Hz, 2H), 3.98 (s, 3H), 4.40 (s, 2H), 6.66 (d, J=7.8 Hz, 1H), 6.72 (td, J=7.4, 0.8 Hz, 1H), 7.08-7.15 (m, 2,3-Dichloro-5,6-dicyano-1,4-benzoquinone (25 mg, 0.11 mmol) was added in small portions over a period of 0.5 h to a stirred solution of 59 (11.0 mg, 33.4 μmol) in CH₂Cl₂ (1.8 mL)-0.2 M aqueous phosphate buffer (pH 7.0) solution (0.05 mL). When the addition was completed, the mixture was stirred for additional 0.5 h and then treated with saturated aqueous NaHCO₃ (2 mL). Stirring continued for 1 h. The organic layer was separated and the aqueous phase extracted with CH₂Cl₂ (5×2 mL). Combined organic solutions were washed with brine, dried (MgSO₄), concentrated and the residue was purified by means of PTLC using AcOEt as eluent to afford 60 (2.9 mg, 26%) as grey solid; ¹H NMR (400 MHz, CDCl₃) δ 3.95 (s, 3H), 5.46 (s, 2H), 6.56 (dd, J=3.2, 0.7 Hz, 1H), 7.12 (td, J=7.5, 1.0 Hz, 1H), 7.16 (d, J=3.2, 1H), 7.20 (td, J=7.5, 1.2 Hz, 1H), 7.37 (d, J=2.4 Hz, 1H), 7.39 (dd, J=8.2, 0.7 Hz, 1H), 7.47 (s, 1H), 7.66 (s, 1H), 7.66 (dd, J=7.8, 0.7 Hz, 1H), 7.82 (d, J=1.9 Hz, 1H), 8.28 (d, J=1.9 Hz, 1H), 8.86 (bs, 1H).

Synthesis of Example Inhibitor 63

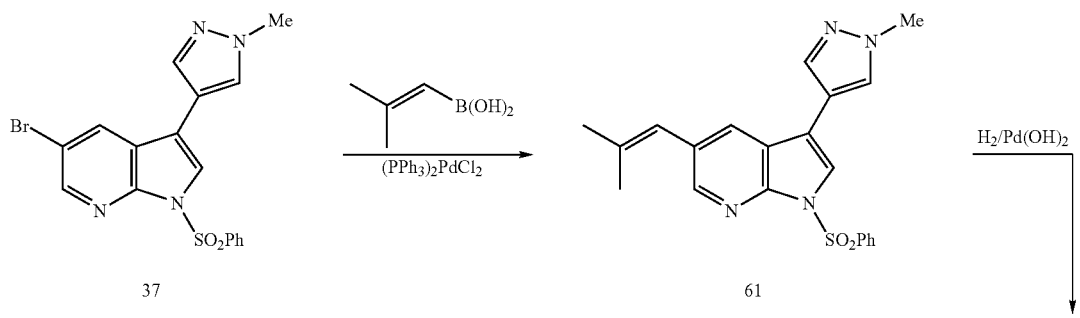

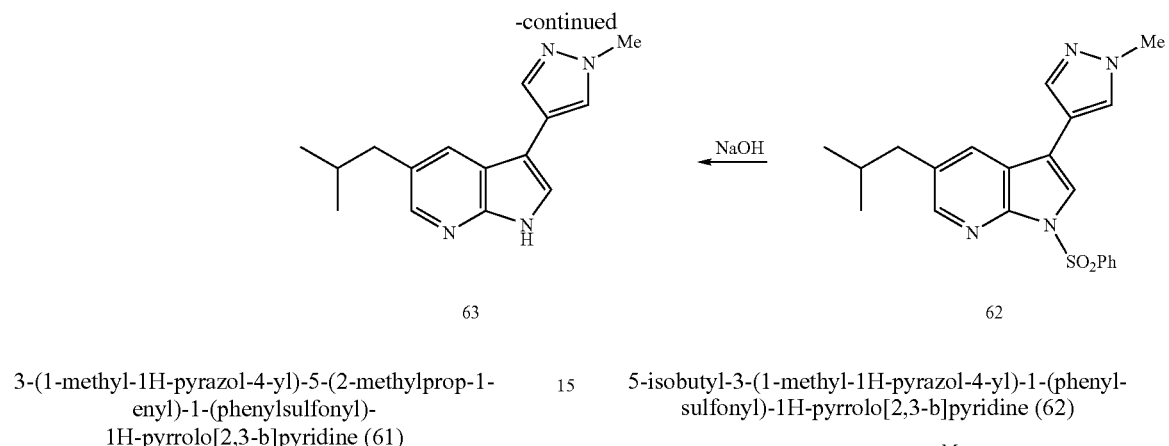

3-(1-methyl-1H-pyrazol-4-yl)-5-(2-methylprop-1-enyl)-1-(phenylsulfonyl)-1H-pyrrolo[2,3-b]pyridine (61)

5-isobutyl-3-(1-methyl-1H-pyrazol-4-yl)-1-(phenylsulfonyl)-1H-pyrrolo[2,3-b]pyridine (62)

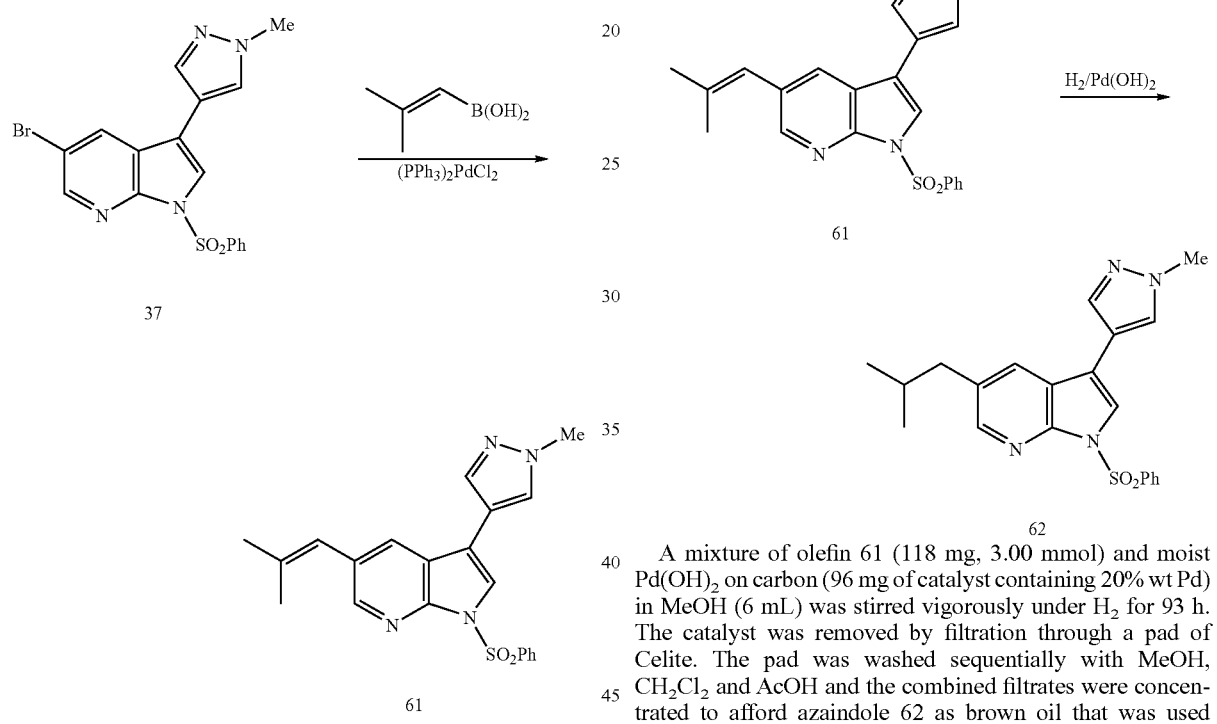

A mixture of bromide 37 (280 mg, 0.67 mmol), 2,2-dimethylethenylboronic acid (101 mg, 1.01 mmol), LiCl (84 mg, 2.02 mmol), (PPh$_3$)$_2$PdCl$_2$ (24 mg, 0.03 mmol), 1.0 M aqueous Na$_2$CO$_3$ (1.68 mL, 1.68 mmol), in toluene (8 mL)—EtOH (8 mL) was stirred in an oil bath (105° C.) for 96 h. The reaction mixture was then cooled to r.t., diluted with AcOEt and saturated brine and partitioned. The aqueous layer was extracted with AcOEt (2×). The combined organic solutions were dried (MgSO$_4$) and concentrated. The residual oil was purified by means of PTLC plates using AcOEt:hexane=1:1 (v/v) as eluent to afford the olefin 61 (118 mg, 45%) as an oil; $^1$H NMR (400 MHz; CDCl$_3$) δ 1.88 (d, J=1.0 Hz, 3H), 1.94 (d, J=1.0 Hz, 3H), 3.96 (s, 3H), 6.37 (s, 1H), 7.39-7.46 (m, 3H), 7.49-7.54 (m, 1H), 7.59 (s, 1H), 7.63-7.68 (m, 2H), 7.75 (s, 1H), 7.90 (d, J=1.8 Hz, 1H), 8.23 (d, J=1.8 Hz, 1H).

A mixture of olefin 61 (118 mg, 3.00 mmol) and moist Pd(OH)$_2$ on carbon (96 mg of catalyst containing 20% wt Pd) in MeOH (6 mL) was stirred vigorously under H$_2$ for 93 h. The catalyst was removed by filtration through a pad of Celite. The pad was washed sequentially with MeOH, CH$_2$Cl$_2$ and AcOH and the combined filtrates were concentrated to afford azaindole 62 as brown oil that was used directly without purification in the next step. $^1$H NMR (400 MHz; CDCl$_3$) δ 0.90 (s, 3H), 0.91 (s, 3H), 1.87 (m, 1H), 2.58 (d, J=7.2 Hz, 2H), 3.96 (s, 3H), 7.34 (s, 1H), 7.41-7.46 (m, 2H), 7.50-7.55 (m, 1H), 7.59 (s, 1H), 7.62-7.67 (m, 2H), 7.73 (s, 1H), 7.86 (d, J=1.8 Hz, 1H), 7.99 (d, J=1.8 Hz, 1H).

5-isobutyl-3-(1-methyl-1H-pyrazol-4-yl)-1H-pyrrolo[2,3-b]pyridine (63)

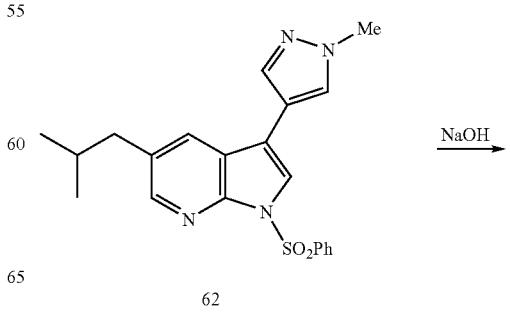

118

(E)-5-(4-(tert-butyldimethylsilyloxy)but-1-enyl)-3-(1-methyl-1H-pyrazol-4-yl)-1-(phenylsulfonyl)-1H-pyrrolo[2,3-b]pyridine (65)

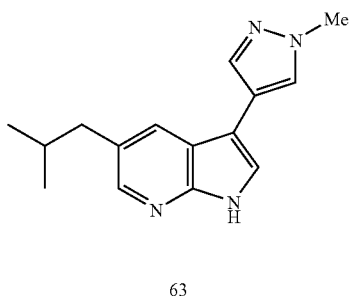

63

To crude azaindole 62 (118 mg) in EtOH (6 mL) was added 10% NaOH (1 mL) and the mixture was stirred in an oil bath (90° C.) for 4.5 h. The mixture was then cooled to r.t., diluted with AcOEt and saturated brine and partitioned. The aqueous layer was extracted with AcOEt (3×). The combined organic solutions were dried (MgSO₄), filtered and concentrated. The residual yellow oil was partially purified by means of PTLC employing AcOEt as eluent to afford a semi-pure azaindole 63 (74 mg). A fraction (14 mg) of this material was further purified by means of preparative LCMS (column LUNA 10 μ C18(2) 00G-4253-V0 250×50 mm) using water—acetonitrile (0.1% AcOH) as eluent (in gradient; flow 80 mL/min) to give the desired azaindole 63 (5.6 mg, 25%); ¹H NMR (400 MHz; CDCl₃) δ 0.92 (s, 3H), 0.94 (s, 3H), 1.90 (m, 1H), 2.59 (d, J=7.2 Hz, 2H), 3.98 (s, 3H), 7.36 (d, J=2.1 Hz, 1H), 7.60 (s, 1H), 7.74 (d, J=0.6 Hz, 1H), 7.81 (d, J=1.8 Hz, 1H), 8.14 (d, J=1.8 Hz, 1H), 9.62 (br s, 1H); MS (CI) m/z 255 (MH⁺).

Synthesis of Example Inhibitor 67

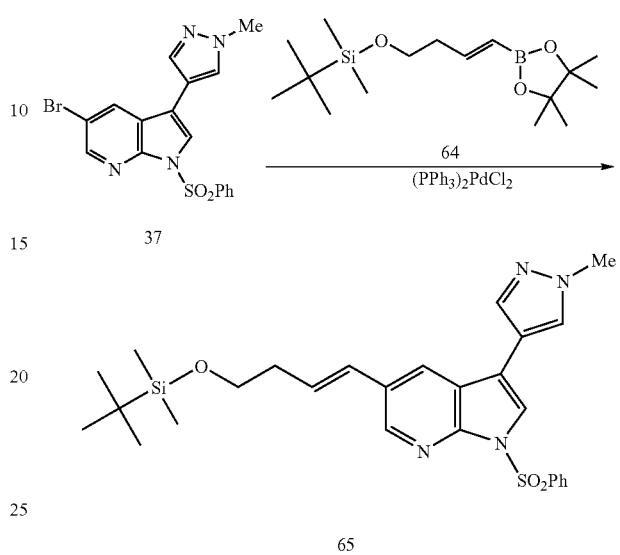

A mixture of bromide 37 (280 mg, 0.67 mmol), boronic pinacol ester 64 (314 mg, 1.01 mmol), LiCl (84 mg, 2.02 mmol), (PPh₃)₂PdCl₂ (24 mg, 0.03 mmol), 1.0 M aqueous Na₂CO₃ (1.68 mL, 1.68 mmol), in toluene (8 mL)-EtOH (8 mL) was stirred in an oil bath (105° C.) for 5.5 h. The reaction mixture was then cooled to r.t., diluted with AcOEt and satu-

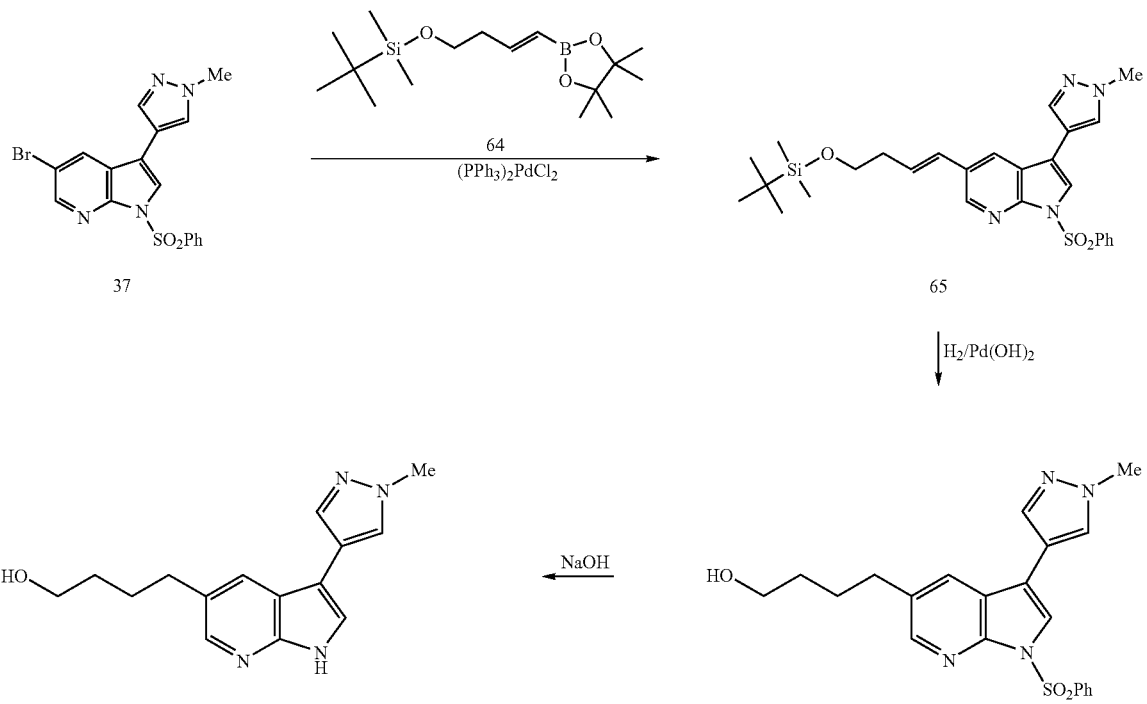

rated brine and partitioned. The aqueous layer was extracted with AcOEt (2×). The combined organic solutions were dried (MgSO$_4$) and concentrated. The residual oil was purified by means of PTLC plates using AcOEt:hexane=1:1 (v/v) as eluent to afford the olefin 65 (198 mg, 56%) as an oil; $^1$H NMR (400 MHz; CDCl$_3$) δ 0.04 (s, 6H), 0.87 (s, 9H), 2.43 (dq, J=6.6, 1.0 Hz, 2H), 3.72 (t, J=6.6 Hz, 2H), 3.96 (s, 3H), 6.26 (d, J=16.4 Hz, 1H), 6.49 (d, J=16.4 Hz, 1H), 7.43-7.47 (m, 2H), 7.52-7.56 (m, 1H), 7.62 (s, 1H), 7.72 (d, J=10.2 Hz, 2H), 7.87 (d, J=1.9 Hz, 1H), 8.15-8.17 (m, 2H), 8.41 (d, J=1.9 Hz, 1H).

4-(3-(1-methyl-1H-pyrazol-4-yl)-1-(phenylsulfonyl)-1H-pyrrolo[2,3-b]pyridin-5-yl)butan-1-ol (66)

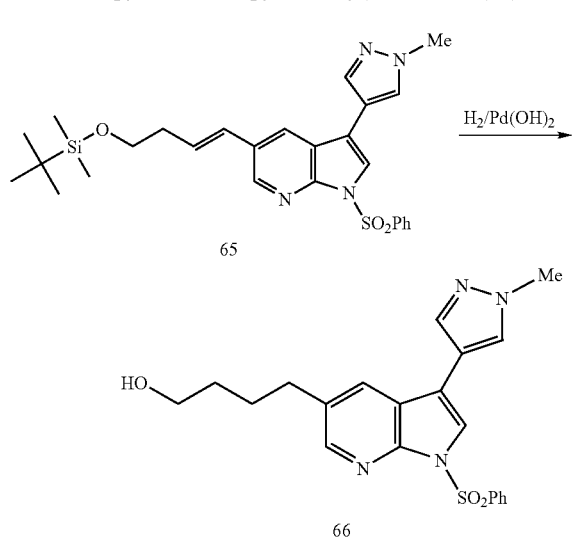

A mixture of olefin 65 (198 mg, 0.38 mmol) and moist Pd(OH)$_2$ on carbon (96 mg of catalyst containing 20% wt Pd) in MeOH (6 mL) was stirred vigorously under H$_2$ for 43 h. The catalyst was removed by filtration through a pad of Celite. The pad was washed sequentially with MeOH, CH$_2$Cl$_2$ and AcOH and the combined filtrates were concentrated to afford azaindole 66 as brown oil that was used directly without purification in the next step; $^1$H NMR (400 MHz; CDCl$_3$) δ 1.55-1.76 (m, 4H), 2.71 (t, J=7.7 Hz, 2H), 3.64 (t, J=6.4 Hz, 2H), 3.97 (s, 3H), 7.43-7.47 (m, 2H), 7.52-7.56 (m, 1H), 7.64 (s, 1H), 7.71 (s, 1H), 7.73-7.75 (m, 2H), 8.16-8.18 (m, 2H), 8.27 (d, J=1.9 Hz, 1H).

4-(3-(1-methyl-1H-pyrazol-4-yl)-1H-pyrrolo[2,3-b]pyridin-5-yl)butan-1-ol (67)

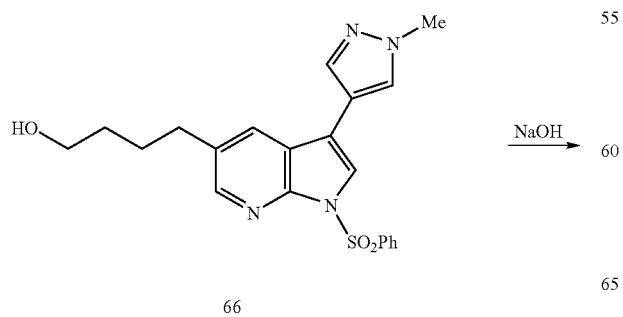

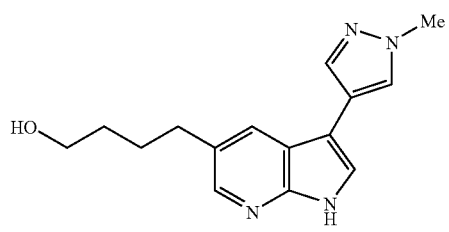

To crude azaindole 66 (76 mg, 0.19 mmol) in EtOH (6 mL) was added 10% NaOH (1 mL) and the mixture was stirred in an oil bath (90° C.) for 2 h. The mixture was then cooled to r.t., diluted with AcOEt and saturated brine and partitioned. The aqueous layer was extracted with AcOEt (3×). The combined organic solutions were dried (MgSO$_4$), filtered and concentrated. The residual yellow oil was purified by means of PTLC employing AcOEt as eluent to afford the azaindole 67 (16 mg, 31%); $^1$H NMR (400 MHz; CDCl$_3$) δ 1.61-1.80 (m, 8H), 2.77 (t, J=7.6 Hz, 2H), 3.67 (t, J=6.6 Hz, 2H), 3.97 (s, 3H), 7.34 (d, J=1.9 Hz, 1H), 7.61 (s, 1H), 7.73 (d, J=0.6 Hz, 1H), 7.85 (d, J=1.8 Hz, 1H), 8.17 (d, J=1.8 Hz, 1H), 9.29 (br s, 1H).

Synthesis of Example Inhibitor 69

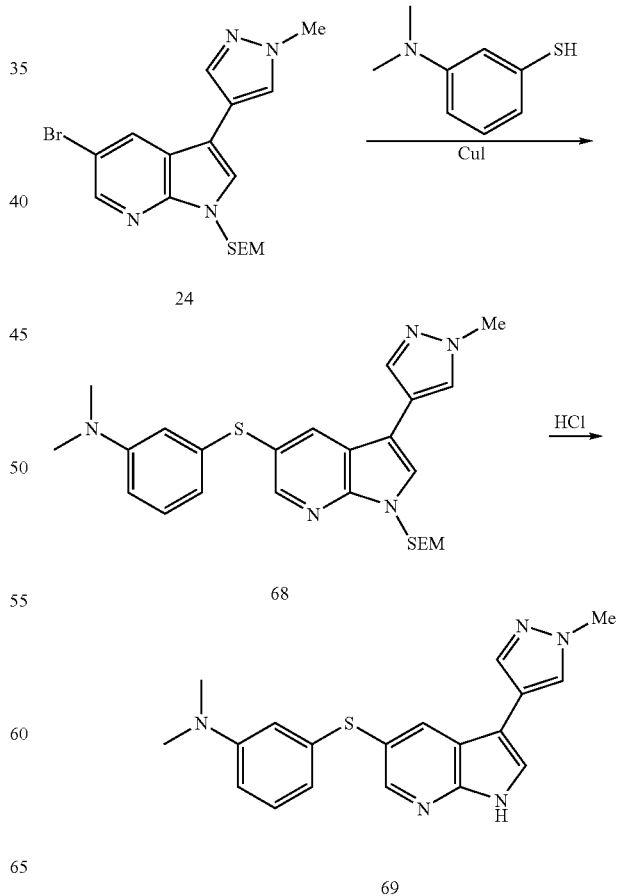

N,N-dimethyl-3-(3-(1-methyl-1H-pyrazol-4-yl)-1-(2-(trimethylsilyl)ethoxy)-1H-pyrrolo[2,3-b]pyridin-5-ylthio)aniline (68)

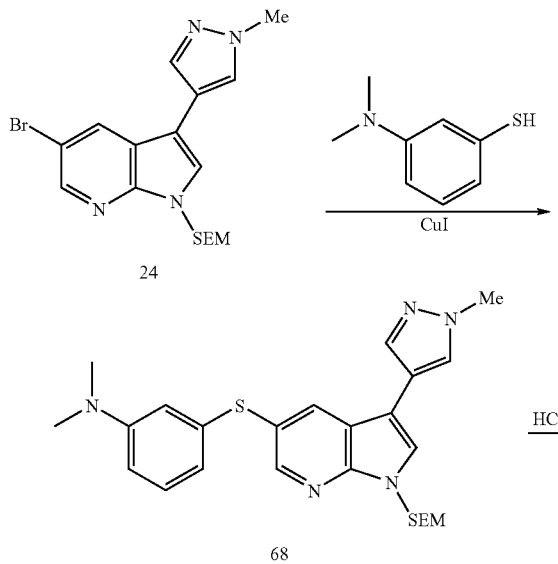

A mixture of bromide 24 (100 mg, 0.245 mmol), 3-(dimethylamino)benzenethiol (94 mg, 0.613 mmol), CuI (9.3 mg, 0.049 mmol), N,N-dimethylglycine (5.1 mg, 0.049 mmol), potassium phosphate (156 mg, 0.736 mmol) and DMF (1.0 mL) was heated to 160° C. using microwave irradiation for 0.5 h then at 180° C. for 1 h. The reaction mixture was cooled and partitioned between AcOEt/brine, the layers separated and the aqueous phase extracted with more AcOEt (2×). The combined organic extracts were dried (MgSO$_4$) and concentrated. The resulting crude residue containing 68 was purified by PTLC using 80% ethyl acetate in hexane as eluent to afford pure 68 as an orange oil (78 mg, 66%); $^1$H NMR (400 MHz, CDCl$_3$) δ -0.055 (s, 9H), 0.95 (t, J=8.2 Hz, 2H), 2.87 (s, 6H), 3.58 (t, J=8.2 Hz, 2H), 3.95 (s, 3H), 5.68 (s, 2H), 6.43 (d, J=7.6 Hz, 1H), 6.51 (tt, J=8.3, 2.0 Hz, 1H), 6.62 (s, 1H), 7.06 (t, J=8.0 Hz, 1H), 7.45 (s, 1H), 7.61 (s, 1H), 7.76 (s, 1H), 8.22 (d, J=1.7 Hz, 1H), 8.48 (d, J=1.6 Hz, 1H).

N,N-dimethyl-3-(3-(1-methyl-1H-pyrazol-4-yl)-1H-pyrrolo[2,3-b]pyridin-5-ylthio)aniline (69)

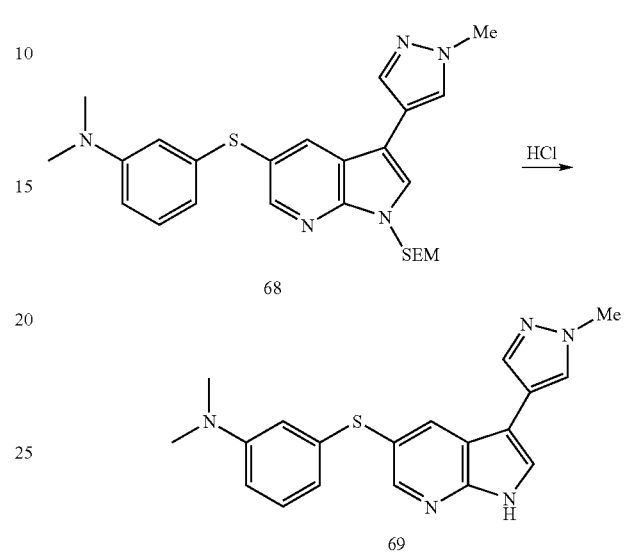

A mixture of 68 (78 mg, 0.163 mmol), 10% aq. HCl (1.0 mL), EtOH (1.0 mL) was heated at 90° C. for 14 h. Purification by PTLC using AcOEt as eluent gave 69 as a white solid (22.8 mg, 40%); $^1$H NMR (400 MHz, CDCl$_3$) δ 2.70 (s, 6H), 3.79 (s, 3H), 7.26 (m, 1H), 6.34 (ddd, J=8.3, 2.5, 0.7 Hz, 1H), 6.44 (t, J=2.1 Hz, 1H), 6.91 (t, J=8.0 Hz, 1H), 7.26 (s, 1H), 7.45 (s, 1H), 7.55 (d, J=0.7 Hz, 1H), 8.10 (d, J=2.0 Hz, 1H), 8.28 (d, J=1.9 Hz, 1H).

Synthesis of Example Inhibitor 77

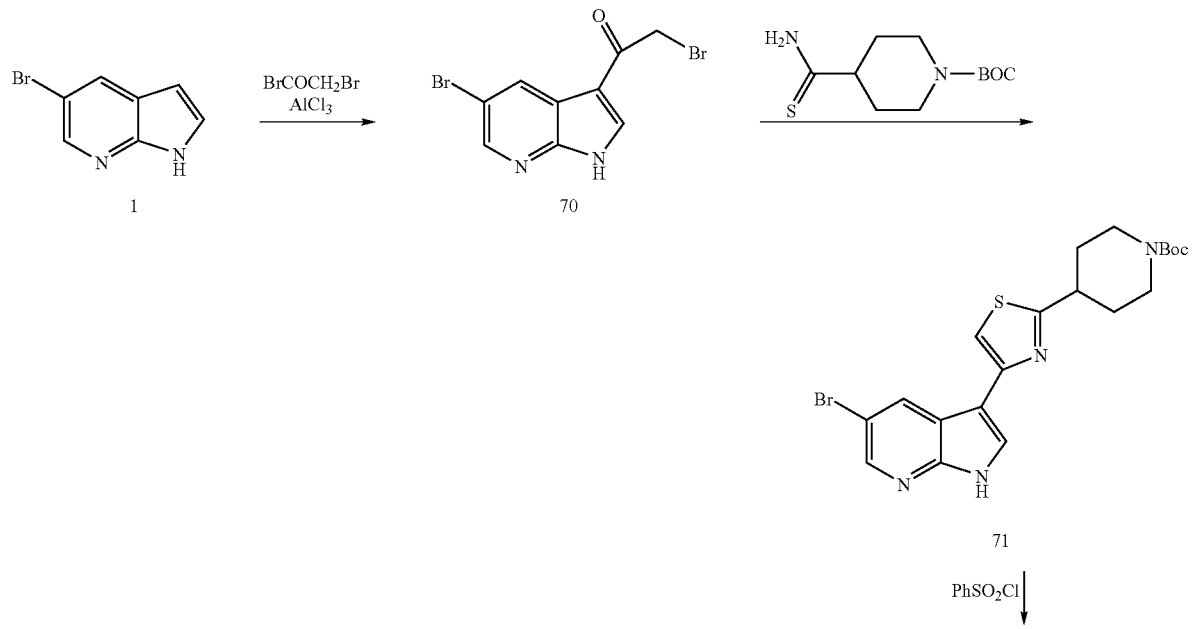

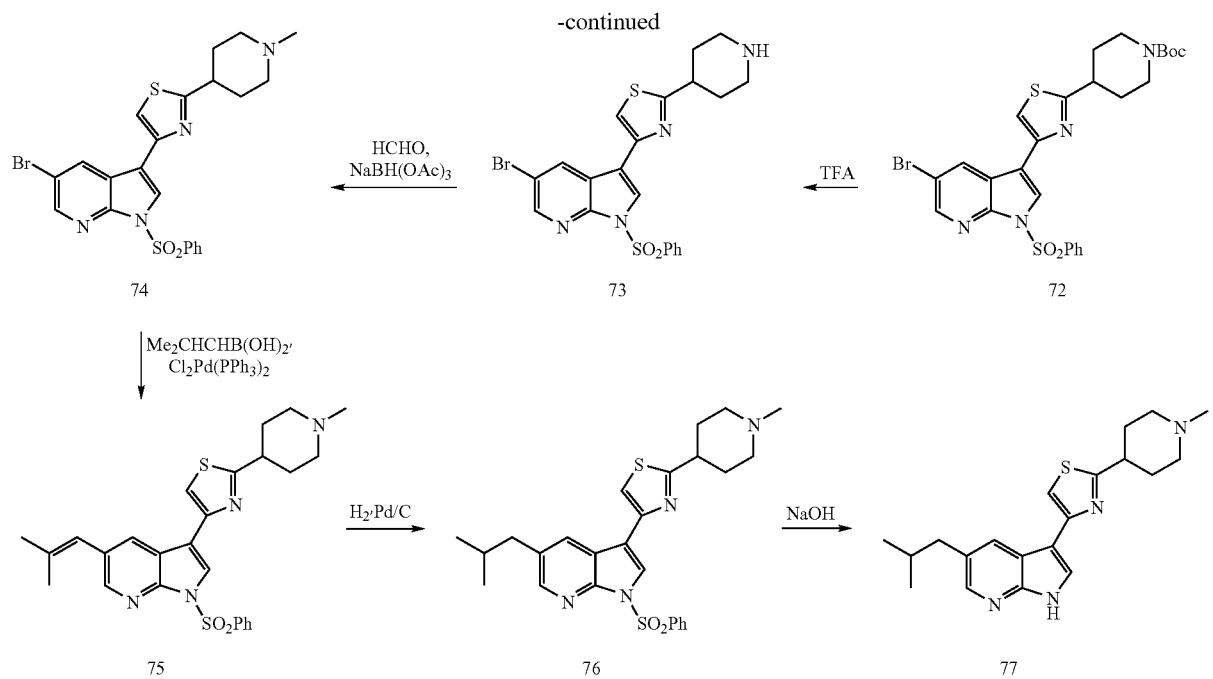

2-Bromo-1-(5-bromo-1H-pyrrolo[2,3-b]pyridin-3-yl)-ethanone (70)

4-[4-(5-Bromo-1H-pyrrolo[2,3-b]pyridin-3-yl)-thiazol-2-yl]-piperidine-1-carboxylic acid tert-butyl ester (71)

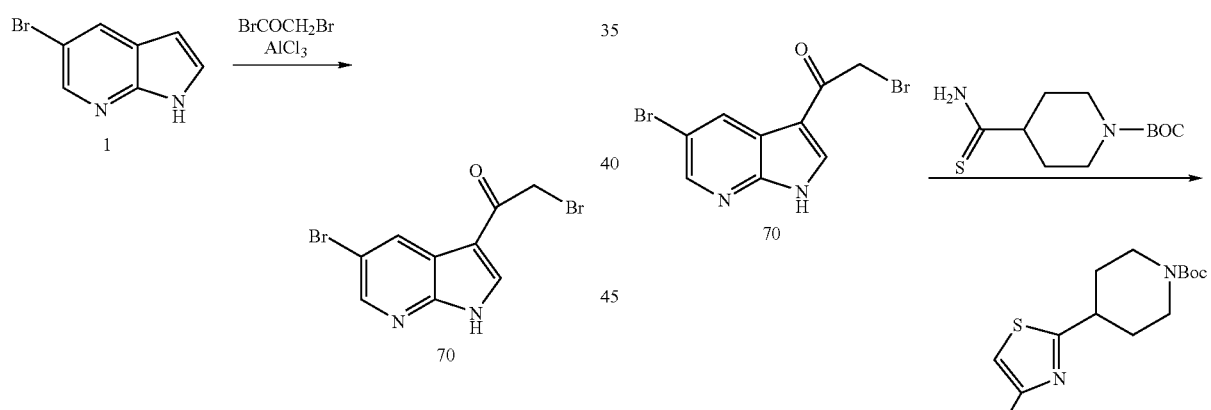

To a stirred solution of 1 (6.65 g, 33.8 mmol) in anh. CS$_2$ (125 mL) was added AlCl$_3$ (15.60 g, 117.0 mmol) in a single portion. The reaction vessel was equipped with a reflux condenser, the temperature was brought to 50° C., and bromoacetyl bromide (3.00 mL, 6.95 g, 34.4 mmol) was added dropwise over 10 min. After stirring at 50° C. for a further 1 h, the reaction mixture was cooled to 0° C., and 100 mL water was added (very cautiously at first). Once effervescence had ceased, AcOEt (300 mL) and THF (100 mL) were added. Solid NaHCO$_3$ was then added to adjust the pH of the aqueous layer from 1 to 3. The layers were separated, and the organic layer washed with saturated aqueous NaHCO$_3$ (150 mL) and brine (150 mL). Solvent was then removed in vacuo to afford a yellow solid (8.32 g), which was further purified by trituration with MeOH (100 mL) to afford 70 as an off-white powder (7.16 g, 22.5 mmol, 67%). $^1$H NMR (400 MHz, CDCl$_3$) δ 4.31 (s, 2H), 8.10 (d, J=3.1 Hz, 1H), 8.48 (d, J=2.2 Hz, 1H), 8.83 (d, J=0.4, 2.2 Hz, 1H), 9.34 (br s, 1H).

To a solution of 70 (1.71 g, 5.38 mmol) in THF (20 mL) was added 1-Boc-4-aminothiocarbonyl piperidine (1.31 g, 5.36 mmol) and the solution was allowed to stir at r.t. for 3 h. The reaction mixture was then poured onto saturated aqueous NaHCO$_3$ (50 mL) and extracted with AcOEt (2×50 mL). The combined organic portions were then evaporated to afford 71 (2.58 g, 5.41 mmol, 100%) as a white powder. $^1$H NMR (400 MHz, CDCl$_3$) δ 1.43 (s, 9H), 1.64-1.84 (m, 4H), 2.07-2.17 (m, 2H), 2.81-2.94 (m, 2H), 3.13-3.24 (m, 1H), 7.17 (s, 1H), 7.74 (d, J=2.4 Hz, 1H), 8.32 (d, J=2.1 Hz, 1H), 8.48 (d, J=2.1 Hz, 1H), 8.97 (br s, 1H).

4-[4-(1-Benzenesulfonyl-5-bromo-1H-pyrrolo[2,3-b]pyridin-3-yl)-thiazol-2-yl]-piperidine-1-carboxylic acid tert-butyl ester (72)

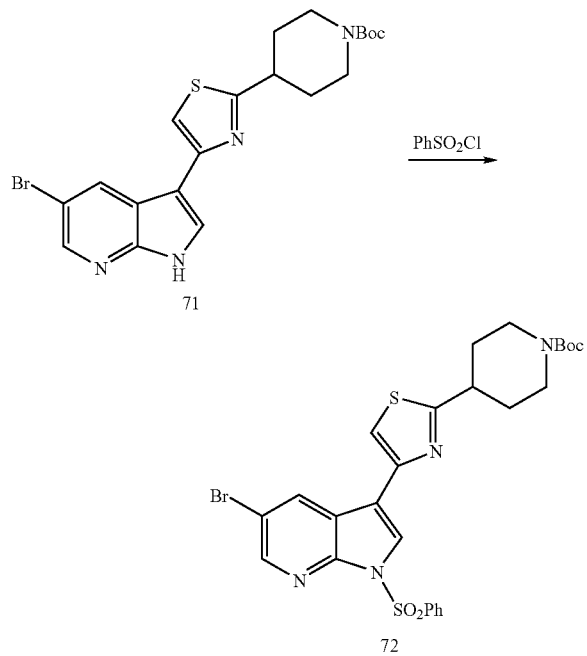

To a vigorously stirred solution of 2 and n-Bu₄NHSO₄ (120 mg, cat.) in CH₂Cl₂ (15 mL) was added 50% aqueous NaOH (0.5 mL), followed by the dropwise addition of PhSO₂Cl (0.50 mL, 690 mg, 3.90 mmol). The reaction mixture was allowed to stir overnight, diluted with AcOEt (100 mL), and washed with saturated aqueous NaHCO₃ (3×25 mL). The organic layer was dried (MgSO₄) and concentrated to afford a pale yellow solid (840 mg). On standing overnight, a precipitate appeared in the aqueous layer, which was filtered to afford a white powder (710 mg). The two solids were combined to afford 72 as an off-white solid (1.55 g, 2.57 mmol, 96%). ¹H NMR (400 MHz, CDCl₃) δ 1.51 (s, 9H), 1.79 and 1.84 (2×dd, 2×J=4.4, 12.6 Hz, 2×1H), 2.19 (br d, J=12.6 Hz, 2H), 2.95 (br t, J=12.3 Hz, 2H), 3.25 (tt, J=3.8, 11.6 Hz, 1H), 4.26 (br s, 2H), 7.37 (s, 1H), 7.52 (t, J=7.8 Hz, 2H), 7.62 (t, J=7.5 Hz, 1H), 8.17 (s, 1H), 8.22 (d, J=7.8 Hz, 1H), 8.52 & 8.54 (2×d, 2×J=2.4 Hz, 1H).

1-Benzenesulfonyl-5-bromo-3-[2-(1-methyl-piperidin-4-yl)-thiazol-4-yl]-1H pyrrolo[2,3-b]pyridine (74)

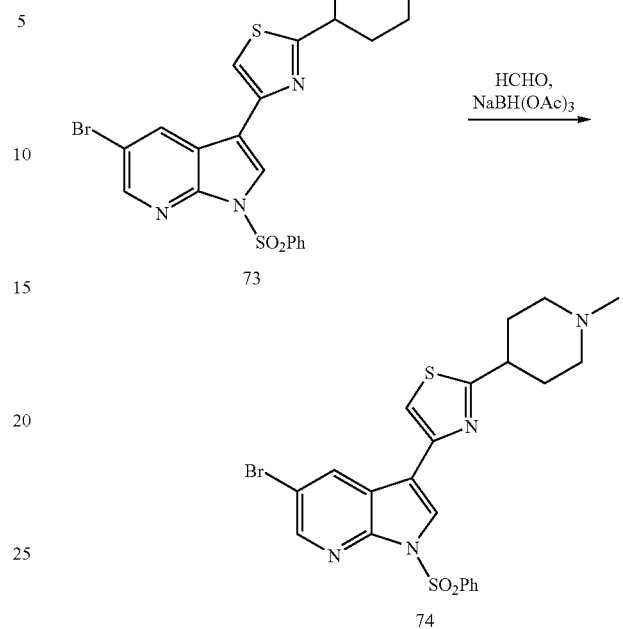

To a stirred solution of 3 (1.55 g, 2.57 mmol) in CH₂Cl₂ (10 mL) was added CF₃COOH (5 mL). After 1 h, the solution was concentrated to dryness and THF (5 mL) was added. To the resulting suspension was added formaldehyde (40% aq., 1 mL, excess), acetic acid (3 drops, cat.) and NaBH(OAc)₃ (800 mg, 3.77 mmol). The reaction mixture was allowed to stir overnight, and was then quenched by the addition of 1.0 N aqueous HCl (10 mL, 10 mmol). The mixture was then neutralised with 1.0 N aqueous NaOH (10 mL) and extracted with AcOEt (3×50 mL). The organic portions were combined, dried over MgSO₄ and concentrated to afford 74 as a pale yellow solid (840 mg, 1.62 mmol, 63%). ¹H NMR (400 MHz, CDCl₃) δ 1.85-2.00 (m, 2H), 2.07-2.23 (m, 4H), 2.33 (s, 3H), 2.93-3.07 (m, 3H), 7.27 (s, 1H), 7.42 (t, J=7.7 Hz, 2H), 7.52 (t, J=7.4 Hz, 1H), 8.06 (s, 1H), 8.12 (d, J=7.7 Hz, 1H), 8.41 & 8.45 (2×d, 2×J=2.0 Hz, 1H).

1-Benzenesulfonyl-3-[2-(1-methyl-piperidin-4-yl)-thiazol-4-yl]-5-(2-methyl-propenyl)-1H-pyrrolo[2,3-b]pyridine (75)

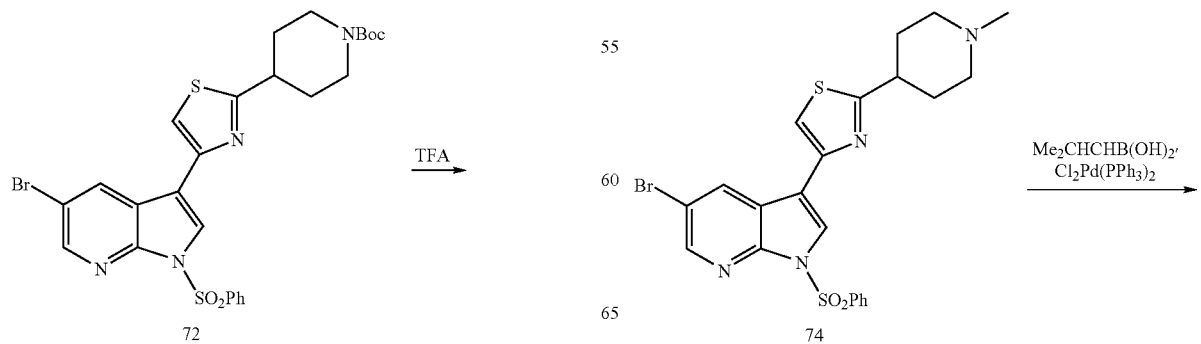

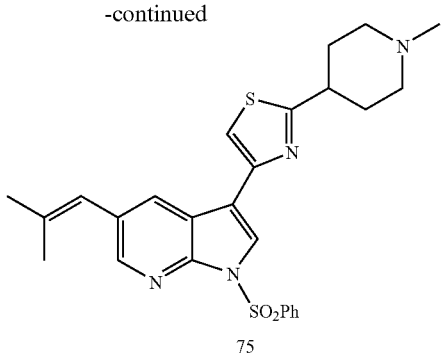

75

To a stirred solution of 74 (202 mg, 0.39 mmol), isobutenyl boronic acid (50 mg, 0.50 mmol) and (PPh$_3$)$_2$PdCl$_2$ (30 mg, 43 μmol) in toluene:EtOH 1:1 (3 mL) was added LiCl (50 mg, 1.19 mmol) and 1.0 M aq. Na$_2$CO$_3$ (0.75 mL, 0.75 mmol). The mixture was heated to reflux (bath temperature 110° C.) and stirred for 1.5 h. Saturated aqueous NaHCO$_3$ (25 mL) was added, and the mixture was extracted with AcOEt (2×40 mL). The combined organic solutions were dried (MgSO$_4$) and concentrated to afford a brown solid (255 mg). The crude product was purified by SGC with 5% MeOH in CH$_2$Cl$_2$ as eluent to afford 75 as an off-white powder (166 mg, 0.34 mmol, 86%). $^1$H NMR (400 MHz, CDCl$_3$) δ 1.88 (s, 3H), 1.96 (s, 3H), 1.92-2.04 (m, 2H), 2.11-2.25 (m, 2H), 2.37 (s, 3H), 2.97-3.11 (m, 3H), 6.33 (1H, s, 1H), 7.34 (s, 1H), 7.48 (t, J=7.5 Hz, 2H), 7.54-7.60 (m, 1H), 8.14 (s, 1H), 8.20-8.25 (m, 3H), 8.36 (d, J=2.0 Hz, 1H).

1-Benzenesulfonyl-5-isobutyl-3-[2-(1-methyl-piperidin-4-yl)-thiazol-4-yl]-1H-pyrrolo[2,3-b]pyridine (76)

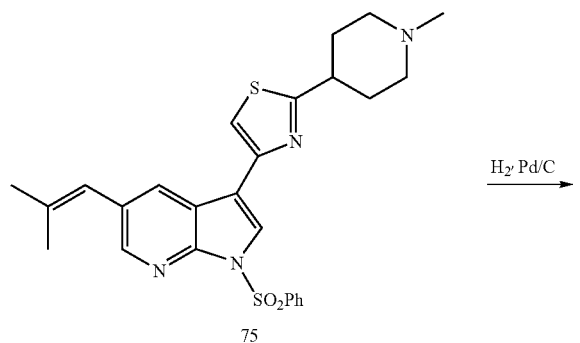

To a solution of 75 (166 mg, 0.34 mmol) in MeOH (10 mL) was added 20% Pd(OH)$_2$ on carbon (50 mg, cat.), and the reaction mixture was stirred vigorously under H$_2$ for 72 h. The mixture was then filtered through Celite, which was then washed with MeOH (100 mL). The filtrate was concentrated to afford 76 as a foam (155 mg, 0.31 mmol, 93%). $^1$H NMR (400 MHz, CDCl$_3$) δ 0.93 (d, J=6.6 Hz, 2H), 1.85-1.97 (m, 1H), 2.06-2.18 (m, 2H), 2.26-2.47 (m, 4H), 2.48 (s, 3H), 2.60 (d, J=7.3 Hz, 2H), 3.10-3.21 (m, 3H), 7.37 (s, 1H), 7.45-7.61 (m, 3H), 8.08 (d, J=2.0 Hz, 1H), 8.15 (s, 1H), 8.21-8.26 (m, 2H), 8.29 (d, J=2.0 Hz, 1H).

5-Isobutyl-3-[2-(1-methyl-piperidin-4-yl)-thiazol-4-yl]-1H-pyrrolo[2,3-b]pyridine (77)

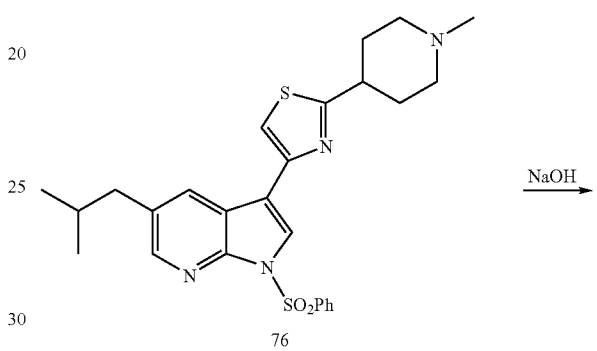

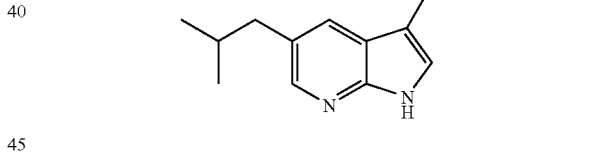

To a stirred solution of 76 (155 mg, 0.31 mmol) in EtOH (4 mL) was added 10% aqueous NaOH (2 mL) and the reaction was heated at reflux for 1.5 h. The mixture was then cooled. Saturated aqueous NaHCO$_3$ (25 mL) was added, and the solution was extracted with AcOEt (2×40 mL) The combined organic extracts were dried (MgSO$_4$) and concentrated to afford a brown solid, which was purified by preparative LCMS (column LUNA 10 μ C18(2) 00G-4253-V0 250×50 mm) using water—acetonitrile (0.1% AcOH) as eluent (in gradient; flow 80 mL/min) to afford 77 as a white solid (54 mg, 0.15 mmol, 49%). $^1$H NMR (400 MHz, CDCl$_3$) δ 0.96 (d, J=6.6 Hz, 2H), 1.94 (nonet, J=6.7 Hz, 1H), 2.07-2.19 (m, 2H), 2.25-2.35 (m, 2H), 2.41-2.52 (m, 5H), 2.64 (d, J=7.1 Hz, 2H), 3.14-3.24 (m, 3H), 7.26 (s, 1H), 7.83 (s, 1H), 8.10 (d, J=1.9 Hz, 1H), 8.18 (d, J=1.9 Hz, 1H), 10.90 (br s, 1H). MS (CI) m/z 355 (MH$^+$).

Synthesis of Example Inhibitor 83
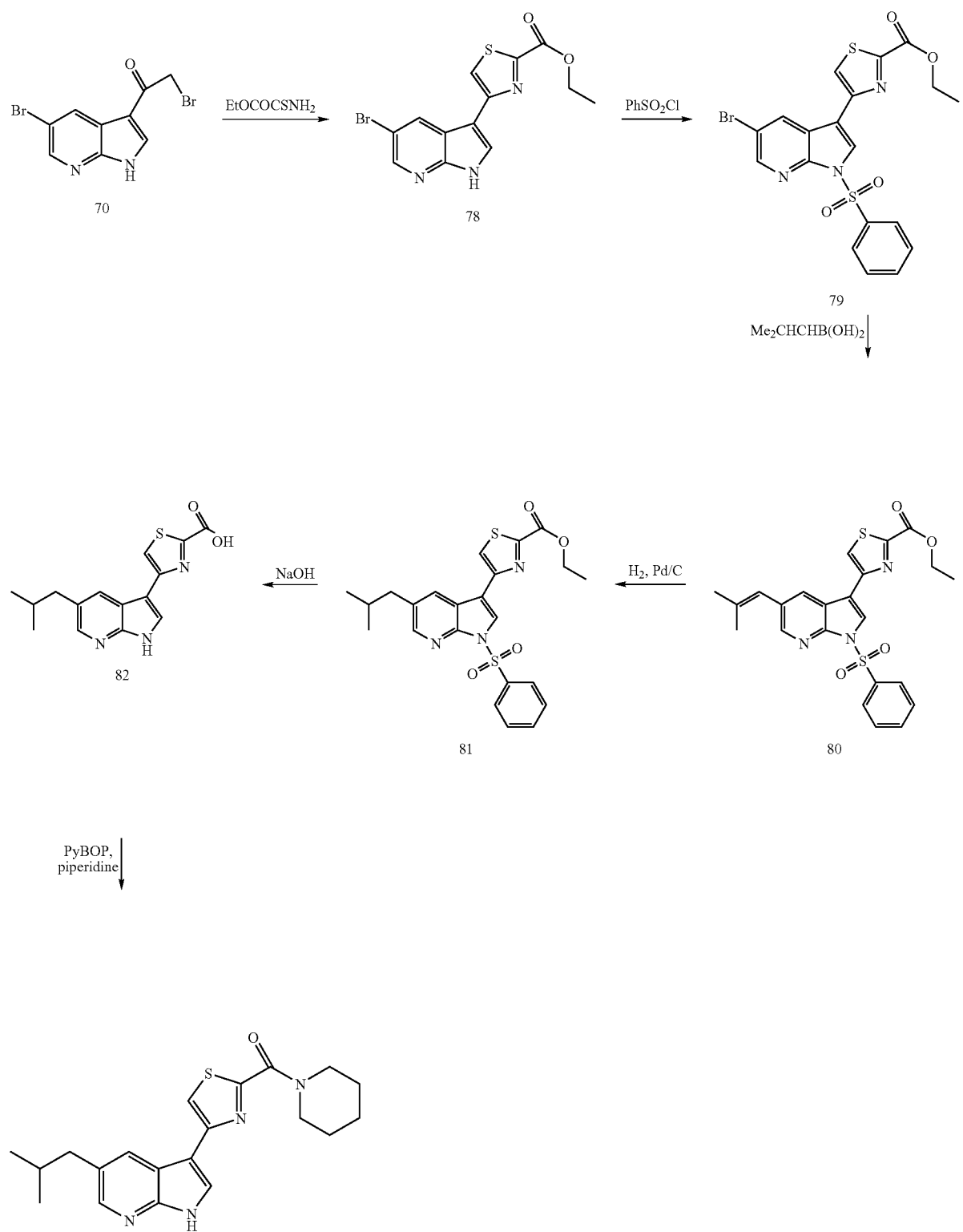

4-(5-Bromo-1H-pyrrolo[2,3-b]pyridin-3-yl)-thiazole-2-carboxylic acid ethyl ester (78)

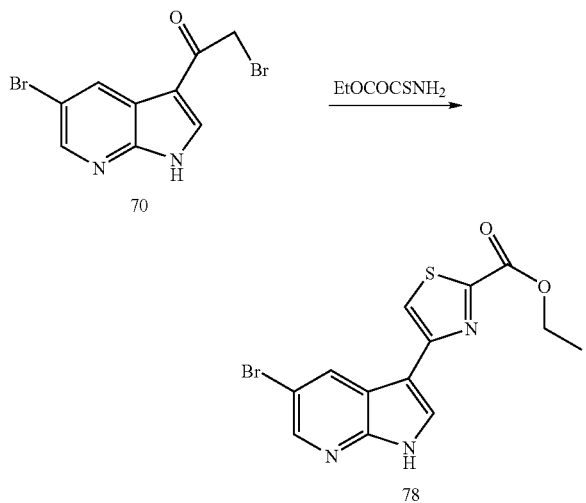

To a stirred solution of 70 (4.97 g, 15.6 mmol) in dioxane (55 mL) was added ethyl thiooxamate (2.29 g, 17.2 mmol). The reaction mixture was stirred vigorously at 95° C. for 18 h. The hot reaction mixture was filtered and the collected product was washed with cold dioxane (25 mL) to afford the hydrobromide salt of 78 as a yellow powder (6.08 g, 14.0 mmol, 90%). $^1$H NMR (400 MHz, CDCl$_3$) δ 1.48 (t, J=7.1 Hz, 3H), 4.52 (q, J=7.1 Hz, 2H), 7.77 (s, 1H), 8.05 (s, 1H), 8.43 (d, J=1.8 Hz, 1H), 9.21 (s, 1H).

4-(1-Benzenesulfonyl-5-bromo-1H-pyrrolo[2,3-b]pyridin-3-yl)-thiazole-2-carboxylic acid ethyl ester (79)

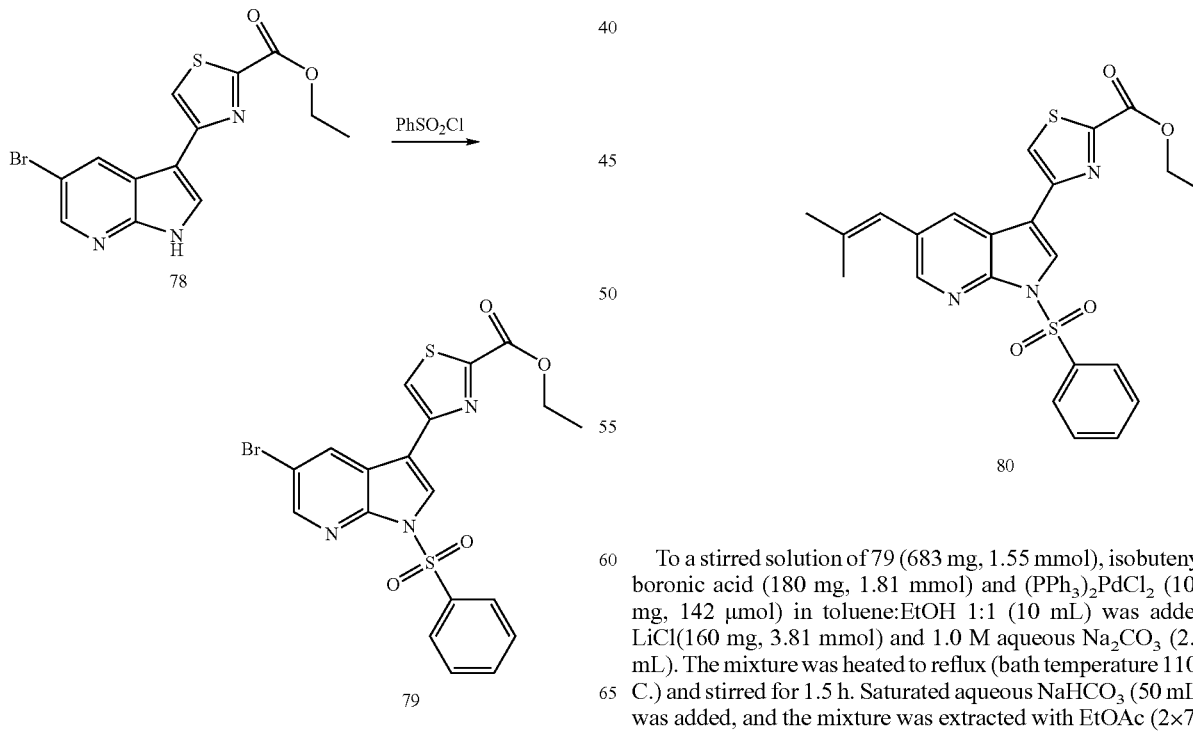

To a stirred solution of 78 (6.08 g, 14.0 mmol) in CH$_2$Cl$_2$ (75 mL) was added n-Bu$_4$NHSO$_4$ (100 mg, cat.) and 50% aqueous NaOH (2 mL). PhSO$_2$Cl (2.50 mL, 19.5 mmol) was then added dropwise, and the reaction stirred at r.t. for 1.5 h. The mixture was then diluted with EtOAc (400 mL) and acetone (20 mL), washed with brine (2×100 mL) and concentrated to give a yellow solid (6.02 g). The crude product was recrystallized from CH$_2$Cl$_2$/hexane to afford pure 79 as a yellow solid (2.33 g). More product was obtained from the mother liquor by SGC using hexane:CH$_2$Cl$_2$:EtOAc (2:1:1, v/v/v) as eluent. Total yield of 79 4.40 g, 8.94 mmol, 57%. $^1$H NMR (400 MHz, CDCl$_3$) δ 1.51 (t, J=7.2 Hz, 3H), 4.55 (q, J=7.1 Hz, 2H), 7.53 (t, J=7.8 Hz, 2H), 7.63 (t, J=7.5 Hz, 1H), 7.74 (s, 1H), 8.24 (d, J=7.8 Hz, 1H), 8.30 (s, 1H), 8.54 (d, J=2.1 Hz, 1H), 8.56 (d, J=2.1 Hz, 1H).

4-[1-Benzenesulfonyl-5-(2-methyl-propenyl)-1H-pyrrolo[2,3-b]pyridin-3-yl]-thiazole-2-carboxylic acid ethyl ester (80)

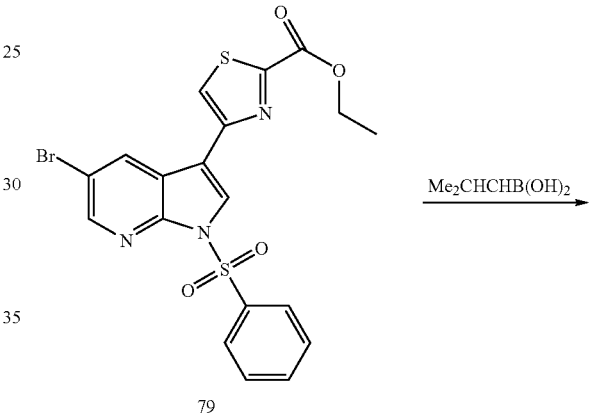

To a stirred solution of 79 (683 mg, 1.55 mmol), isobutenyl boronic acid (180 mg, 1.81 mmol) and (PPh$_3$)$_2$PdCl$_2$ (100 mg, 142 μmol) in toluene:EtOH 1:1 (10 mL) was added LiCl(160 mg, 3.81 mmol) and 1.0 M aqueous Na$_2$CO$_3$ (2.5 mL). The mixture was heated to reflux (bath temperature 110° C.) and stirred for 1.5 h. Saturated aqueous NaHCO$_3$ (50 mL) was added, and the mixture was extracted with EtOAc (2×75 mL). The combined organic solutions were dried (MgSO$_4$)

and concentrated to afford a brown solid (922 mg). The crude product was isolated by means of SGC-using hexane:EtOAc: $CH_2Cl_2$=2:1:1 (v/v/v) as eluent to afford 80 as a foam (548 mg, 1.32 mmol, 85%). $^1$H NMR (400 MHz, $CDCl_3$) δ 1.40 (t, J=7.2 Hz, 3H), 1.80 (d, J=1.1 Hz, 3H), 1.86 (d, J=1.1 Hz, 3H), 4.43 (q, J=7.1 Hz, 2H), 6.24 (s, 1H), 7.40 (t, J=7.8 Hz, 2H), 7.49 (t, J=7.4 Hz, 1H), 7.63 (s, 1H), 8.13-8.17 (m, 3H)), 8.18 (s, 1H), 8.28 (d, J=1.9 Hz, 1H).

4-(1-Benzenesulfonyl-5-isobutyl-1H-pyrrolo[2,3-b]pyridin-3-yl)-thiazole-2-carboxylic acid ethyl ester (81)

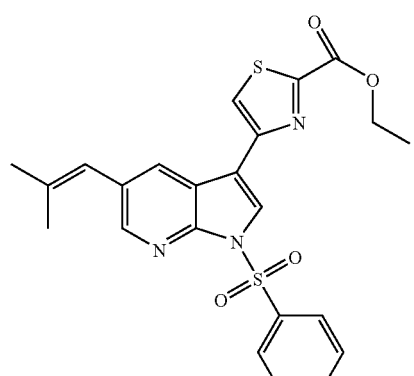

To a solution of 80 (548 mg, 1.32 mmol) in MeOH: $CH_2Cl_2$=3:1 (v/v; 20 mL) was added 20% Pd(OH)$_2$ on carbon (100 mg, cat.), and the reaction mixture was stirred vigorously under H$_2$ for 72 h. The mixture was then filtered through Celite, which was then washed with MeOH:$CH_2Cl_2$=1:1 (v/v; 100 mL). The solutions were combined and concentrated to afford 81 as a foam (412 mg, 0.99 mmol, 75%). $^1$H NMR (400 MHz, $CDCl_3$) δ 0.84 (d, J=6.6 Hz, 2H), 1.40 (t, J=7.1 Hz, 3H), 1.82 (nonet, J=6.7 Hz, 1H), 2.51 (d, J=7.2 Hz, 2H), 4.45 (q, J=7.1 Hz, 2H), 7.41 (t, J=7.8 Hz, 2H), 7.48 (t, J=7.6 Hz, 1H), 7.66 (s, 1H), 8.03 (d, J=1.8 Hz, 1H), 8.15 (d, J=7.5 Hz, 1H), 8.20 (s, 1H), 8.22 (d, J=1.9 Hz, 1H).

4-(5-Isobutyl-1H-pyrrolo[2,3-b]pyridin-3-yl)-thiazole-2-carboxylic acid (82)

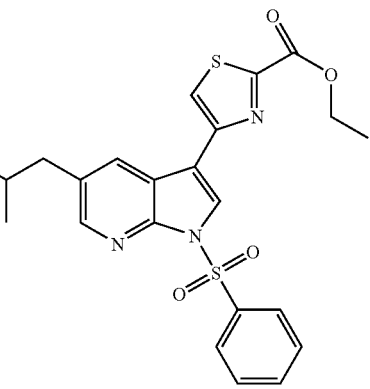

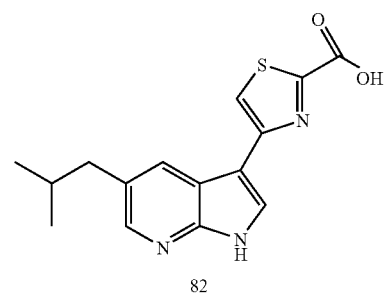

To a stirred solution of 81 (412 mg, 0.99 mmol) in EtOH (10 mL) was added 10% aqueous NaOH (5 mL) and the reaction mixture heated to reflux. After 2 h, the solution was cooled to r.t., and the mixture concentrated to 5 mL under reduced pressure. Acetic acid was then added dropwise with stirring until a precipitate appeared, which was filtered off and dried to afford 82 (267 mg, 0.89 mmol, 90%) as a yellow powder. $^1$H NMR (400 MHz, DMSO-$d_6$) δ 0.91 (d, J=6.6 Hz, 2H), 1.92 (nonet, J=6.6 Hz, 1H), 2.60 (d, J=7.2 Hz, 2H), 7.69 (s, 1H), 7.95 (s, 1H), 8.08 (d, J=1.9 Hz, 1H), 8.27 (s, 1H), 11.73 (s, 1H).

[4-(5-Isobutyl-1H-pyrrolo[2,3-b]pyridin-3-yl)-thiazol-2-yl]-piperidin-1-yl-methanone (83)

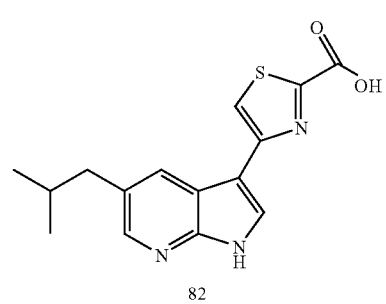

-continued

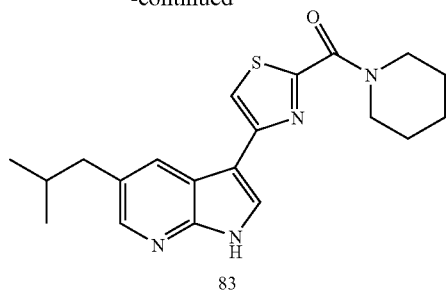

83

To a stirred solution of 82 (60 mg, 0.20 mmol) in DMF (1 mL) was added N,N-diisopropylethylamine (50 mg, 0.39 mmol), piperidine (40 mg, 0.47 mmol) and (benzotriazol-1-yloxy)tripyrrolidinophosphonium hexafluorophosphate (PyBOP; 180 mg, 0.35 mmol). After stirring for 1 h, the reaction mixture was filtered and purified by preparative LCMS (column LUNA 10 g C18(2) 00G-4253-V0 250×50 mm) using water—acetonitrile (0.1% AcOH) as eluent (in gradient; flow 80 mL/min) to afford 83 as a white solid (42 mg, 0.11 mmol, 57%). $^1$H NMR (400 MHz, CDCl$_3$) δ 0.89 (d, J=6.6 Hz, 2H), 1.63-1.76 (m, 6H), 1.86 (nonet, J=6.6 Hz, 1H), 2.56 (d, J=7.2 Hz, 2H), 3.69-3.75 (m, 2H), 4.32-4.39 (m, 2H), 7.45 (s, 1H), 7.70 (d, J=2.6 Hz, 1H), 8.11 (d, J=1.6 Hz, 1H), 8.13 (d, J=1.6 Hz, 1H), 9.26 (s, 1H). MS (CI) m/z 369 (MH$^+$).

Synthesis of Example Inhibitors 89 and 90

8-Bromomethylene-1,4-dioxa-spiro[4.5]decane (85)

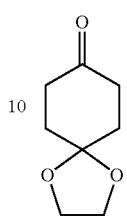
84

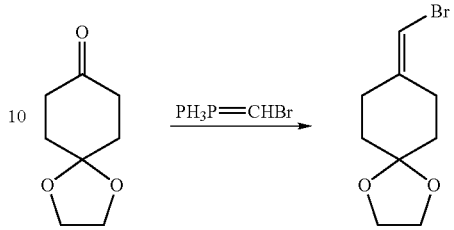
85

1.0 N solution of sodium hexamethyldisilazide (10.8 mL, 1N in THF, 10.8 mmol) was added dropwise to a cooled (−60° C.) solution of bromomethyltriphenylphosphonium bromide (4.71 g, 10.8 mmol) in anhydrous THF (30 mL). After stirring for a further 1 h, 1,4-cyclohexanedione monoethylene acetal (84)(1.40 g, 8.96 mmol) in THF (5 mL) was added over 1 min. The cooling bath was then removed and the reaction mixture allowed to warm to r.t. and stir for a further 1 h. Hexane (50 mL) was then added, and the resulting solution was filtered through a short plug of SiO$_2$. The filtrate was concentrated to

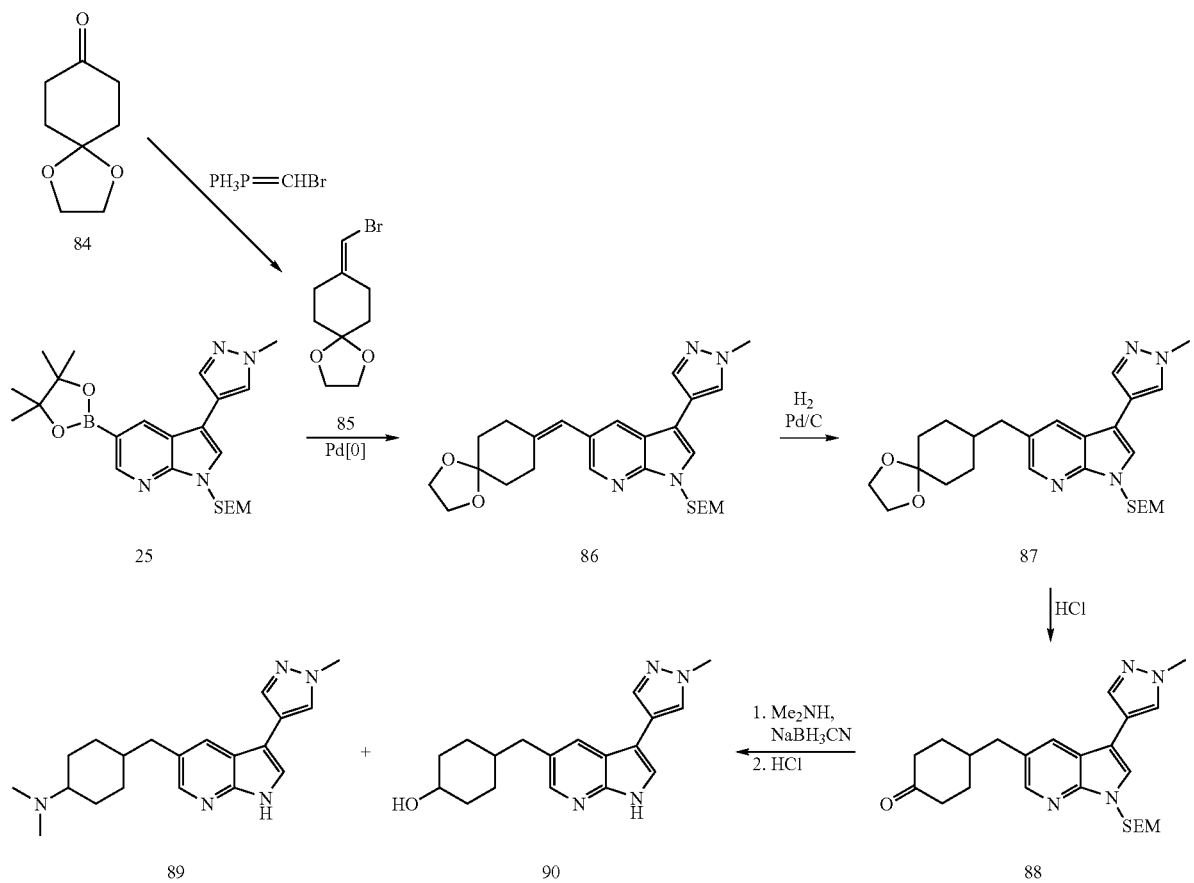

afford yellow oil (2.21 g). Purification by means of SGC with AcOEt:hexane=9:1 (v/v) as eluent afforded 85 as a clear oil (1.32 g, 5.67 mmol, 63%). $^1$H NMR (400 MHz, CDCl$_3$) δ 1.62 (t, J=6.8 Hz, 3H), 1.65 (t, J=7.4 Hz, 3H), 2.27 (ddd, J=1.0, 5.3, 7.3 Hz, 2H), 2.42 (ddd, J=1.0, 5.8, 7.6 Hz, 2H), 3.89-3.92 (m, 4H), 5.85 (pentet, J=1.0 Hz, 1H).

5-(1,4-Dioxa-spiro[4.5]dec-8-ylidenemethyl)-3-(2-methyl-1H-pyrazol-4-yl)-1-(2-trimethylsilanyl-ethoxymethyl)-1H-pyrrolo[2,3-b]pyridine (86)

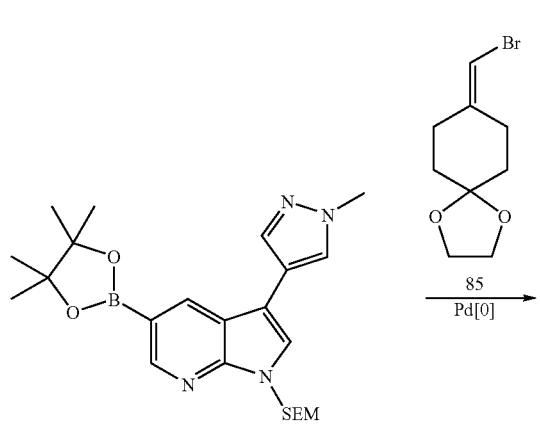

To a stirred solution of 85 (1.50 g, 6.44 mmol), 25 (1.94 g, 4.36 mmol) and (PPh$_3$)$_2$PdCl$_2$ (300 mg, 0.43 mmol) in toluene:EtOH=1:1 (v/v, 20 mL) was added LiCl (650 mg, 14.9 mmol) and 1.0 M aqueous Na$_2$CO$_3$ (5 mL). The mixture was heated to refluxed (bath temperature 110° C.) and stirred for 2.5 h. Saturated aqueous NaHCO$_3$ (100 mL) was added, and the mixture was extracted with AcOEt (2×150 mL). The combined organic solutions were dried (MgSO$_4$) and concentrated to afford a yellow oil (3.46 g). The crude product was purified by SGC using AcOEt:hexane=1:1 (v/v) as eluent to afford 86 as an oil (389 mg, 0.81 mmol, 19%). $^1$H NMR (400 MHz, CDCl$_3$) δ 0.00 (s, 9H), 0.99 (t, J=8.3 Hz, 2H), 1.76 (t, J=6.5 Hz, 2H), 1.89 (t, J=6.5 Hz, 2H), 2.55 (t, J=6.5 Hz, 2H), 2.61 (t, J=6.5 Hz, 2H), 3.63 (t, J=8.3 Hz, 2H), 4.00-4.10 (m, 7H), 5.74 (s, 2H), 6.48 (s, 1H), 7.47 (s, 1H), 7.68 (s, 1H), 7.81 (s, 1H), 7.90 (d, J=1.8 Hz, 1H), 8.29 (d, J=1.8 Hz, 1H).

5-(1,4-Dioxa-spiro[4.5]dec-8-ylmethyl)-3-(2-methyl-1H-pyrazol-4-yl)-1-(2-trimethylsilanyl-ethoxymethyl)-1H-pyrrolo[2,3-b]pyridine (87)

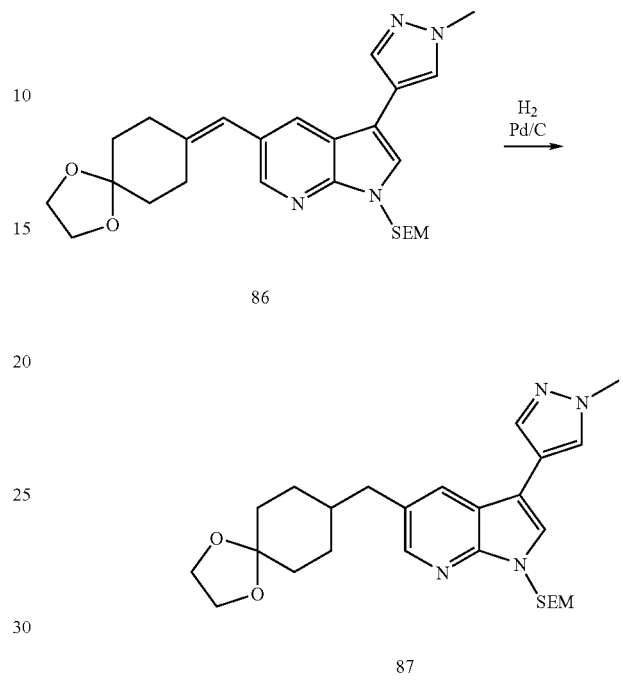

To a solution of 86 (389 mg, 0.81 mmol) in MeOH (15 mL) was added 20% Pd(OH)$_2$ on carbon (50 mg, cat.), and the reaction mixture was stirred vigorously under H$_2$ for 48 h. The mixture was then filtered through Celite, which was then washed with MeOH:CH$_2$Cl$_2$=1:1 (v/v; 200 mL). The solutions were combined and concentrated to afford 87 as a clear oil (307 mg, 0.64 mmol, 79%). $^1$H NMR (400 MHz, CDCl$_3$) δ 0.00 (s, 9H), 0.99 (t, J=8.1 Hz, 2H), 1.34-1.46 (m, 2H), 1.56 (dt, J=13.9, 4.8 Hz, 2H), 1.61-2.12 (m, 5H), 2.74 (d, J=7.1 Hz, 2H), 3.64 (t, J=8.3 Hz, 2H), 4.00 (s, 4H), 4.07 (s, 3H), 5.76 (s, 2H), 7.47 (s, 1H), 7.70 (s, 1H), 7.82 (s, 1H), 7.88 (s, 1H), 8.23 (d, J=1.8 Hz, 1H).

4-[3-(2-Methyl-1H-pyrazol-4-yl)-1-(2-trimethylsilanyl-ethoxymethyl)-1H-pyrrolo[2,3-b]pyridin-5-ylmethyl]-cyclohexanone (88)

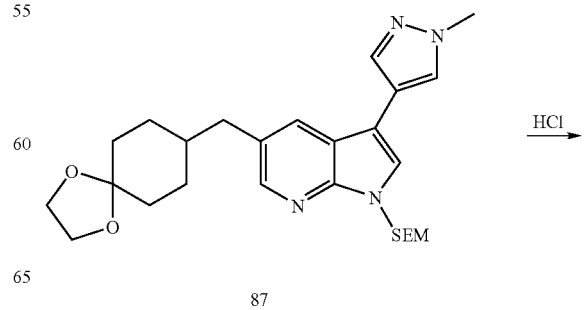

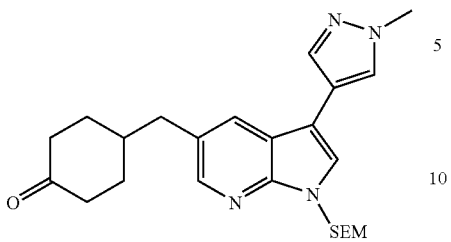

88

To a solution of 87 (307 mg, 0.64 mmol) in THF (20 mL) was added 6.0 N aq. HCl solution (7 mL) and the reaction mixture was allowed to stir at r.t. for 1 h. Water (50 mL) was then added, and the mixture extracted with AcOEt (2×75 mL). The combined organic solutions were dried (MgSO$_4$) and concentrated to afford 88 as a clear oil (261 mg, 0.59 mmol, 93%). $^1$H NMR (400 MHz, CDCl$_3$) δ 0.00 (s, 9H), 0.99 (t, J=8.2 Hz, 2H), 1.49-1.62 (m, 2H), 2.07-2.16 (m, 2H), 2.31-2.49 (m, 5H), 2.82 (d, J=6.7 Hz, 2H), 3.65 (t, J=8.3 Hz, 2H), 4.07 (s, 3H), 5.77 (s, 2H), 7.49 (s, 1H), 7.69 (s, 1H), 7.83 (s, 1H), 7.92 (s, 1H), 8.27 (s, 1H).

Dimethyl-{4-[3-(2-methyl-1H-pyrazol-4-yl)-1H-pyrrolo[2,3-b]pyridin-5-yltmethyl]-cyclohexyl}-amine (89) and 4-[3-(2-Methyl-1H-pyrazol-4-yl)-1H-pyrrolo[2,3-b]pyridin-5-ylmethyl]-cyclohexanol (90)

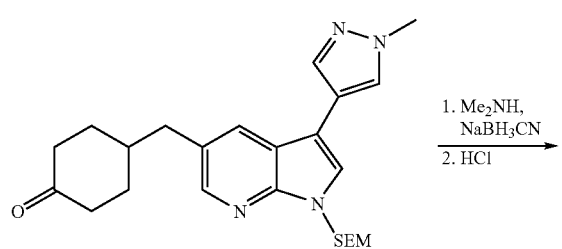

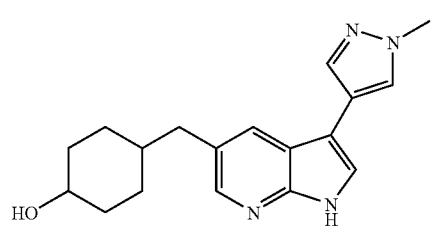

90

To a solution of 88 (89 mg, 0.20 mol) in MeOH (2 mL) was added Me$_2$NH.HCl (100 mg, 1.23 mmol), and the solution was allowed to stir for 10 min. NaBH$_3$CN (30 mg, 0.48 mmol) was then added, and stirring was continued for 22 h. The reaction was then quenched by the addition of saturated aqueous NaHCO$_3$ (25 mL) and extracted with AcOEt (2×25 mL). The combined organic solutions were (MgSO$_4$) and concentrated to afford an oil (84 mg). The oil was dissolved in EtOH (2 mL) and 10% aq. HCl (2 mL) was added. The reaction mixture was heated to 90° C. for 6 h, then evaporated and purified by preparative LCMS (column LUNA 10 μ C18(2) 00G-4253-V0 250×50 mm) using water—acetonitrile (0.1% AcOH) as eluent (in gradient; flow 80 mL/min) to afford two compounds. Eluting first, 89 (22 mg, 65 μmol, 33%), a white powder, as a 1:1 mixture of diastereomers. $^1$H NMR (400 MHz, CDCl$_3$) δ 1.05-2.15 (m, 9H), 2.55-2.90 (m, 3H), 3.98 (s, 3H), 7.35 (s, 1H), 7.60 (s, 0.5H), 7.65 (s, 0.5H), 7.70-7.74 (m, 1H), 7.80 (d, J=1.8 Hz, 0.5H), 7.86 (d, J=1.8 Hz, 0.5H), 8.01 (d, J=1.8 Hz, 0.5H), 8.05, (d, J=1.8 Hz, 0.5H), 10.01 (br s, 0.5H), 10.05 (br s, 0.5H). MS (CI) m/z 338 (MH$^+$). Further elution afforded 90, a white powder (8 mg, 26 μmol, 13%) as an unassigned 4:1 mixture of diastereoisomers. $^1$H NMR (400 MHz, CDCl$_3$) δ 1.01-2.00 (m, 9H), 2.67 (d, J=7.1 Hz, 1.6H), 2.73 (d, J=7.1 Hz, 0.4H) 3.51-3.61 (m, 1H), 4.00 (s, 3H), 7.45 (s, 0.8H), 7.46 (s, 0.2H), 7.63 (s, 0.1H), 7.74 (s, 1H), 8.03 (s, 0.8H), 8.06 (s, 1H), 8.06 (s, 0.2H). MS (CI) m/z 311 (MH$^+$).

4-[3-(2-Methyl-1H-pyrazol-4-yl)-1H-pyrrolo[2,3-b]pyridin-5-ylmethyl]-cyclohexanone (91)

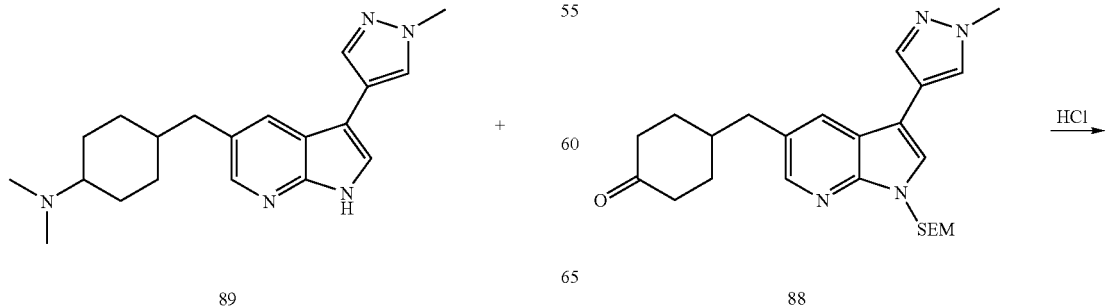

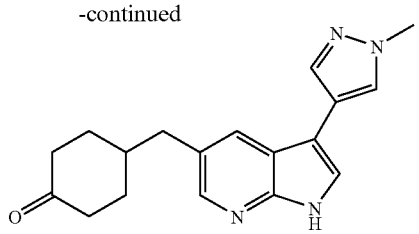

91

To a solution of 88 (19 mg, 42 μmol) in EtOH (1 mL) was added 10% aq. HCl (1 mL) and the reaction mixture heated to reflux (bath temperature 90° C.) for 18 h. The solution was then concentrated and the residue purified by preparative LCMS (column LUNA 10 μ C18(2) 00G-4253-V0 250×50 mm) using water—acetonitrile (0.1% AcOH) as eluent (in gradient; flow 80 mL/min) to afford 91 (8 mg, 26 μmol, 62%) as a white powder. $^1$H NMR (400 MHz, CDCl$_3$) δ 1.49-1.63 (m, 2H), 2.04-2.19 (m, 3H), 2.31-2.50 (m, 4H), 2.92 (d, J=6.9 Hz, 2H), 4.06 (s, 3H), 7.67 (s, 1H), 7.68 (s, 1H), 7.85 (s, 1H), 8.24 (s, 1H), 8.38 (s, 1H), 12.35 (br s, 1H). MS (CI) m/z 309 (MH$^+$).

Synthesis of Example Inhibitor 95

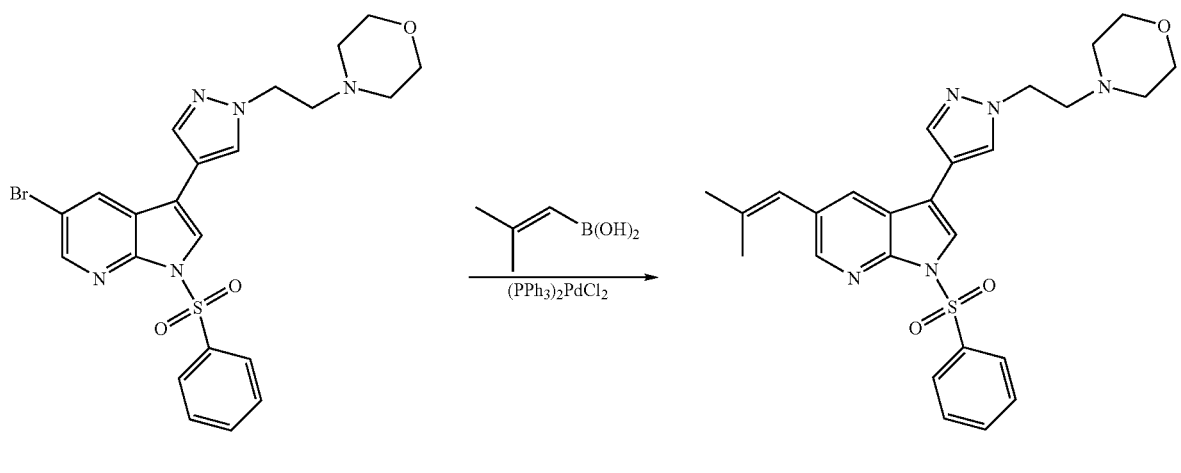

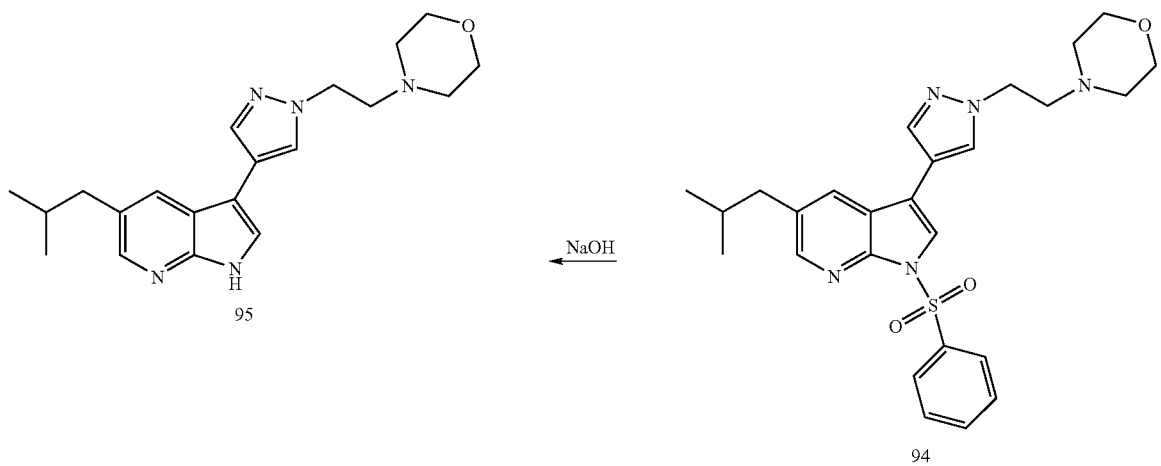

143

1-Benzenesulfonyl-5-(2-methyl-propenyl)-3-[1-(2-morpholin-4-yl-ethyl)-1H-pyrazol-4-yl]-1H-pyrrolo[2,3-b]pyridine (93)

144

1-Benzenesulfonyl-5-isobutyl-3-[1-(2-morpholin-4-yl-ethyl)-1H-pyrazol-4-yl]-1H-pyrrolo[2,3-b]pyridine (94)

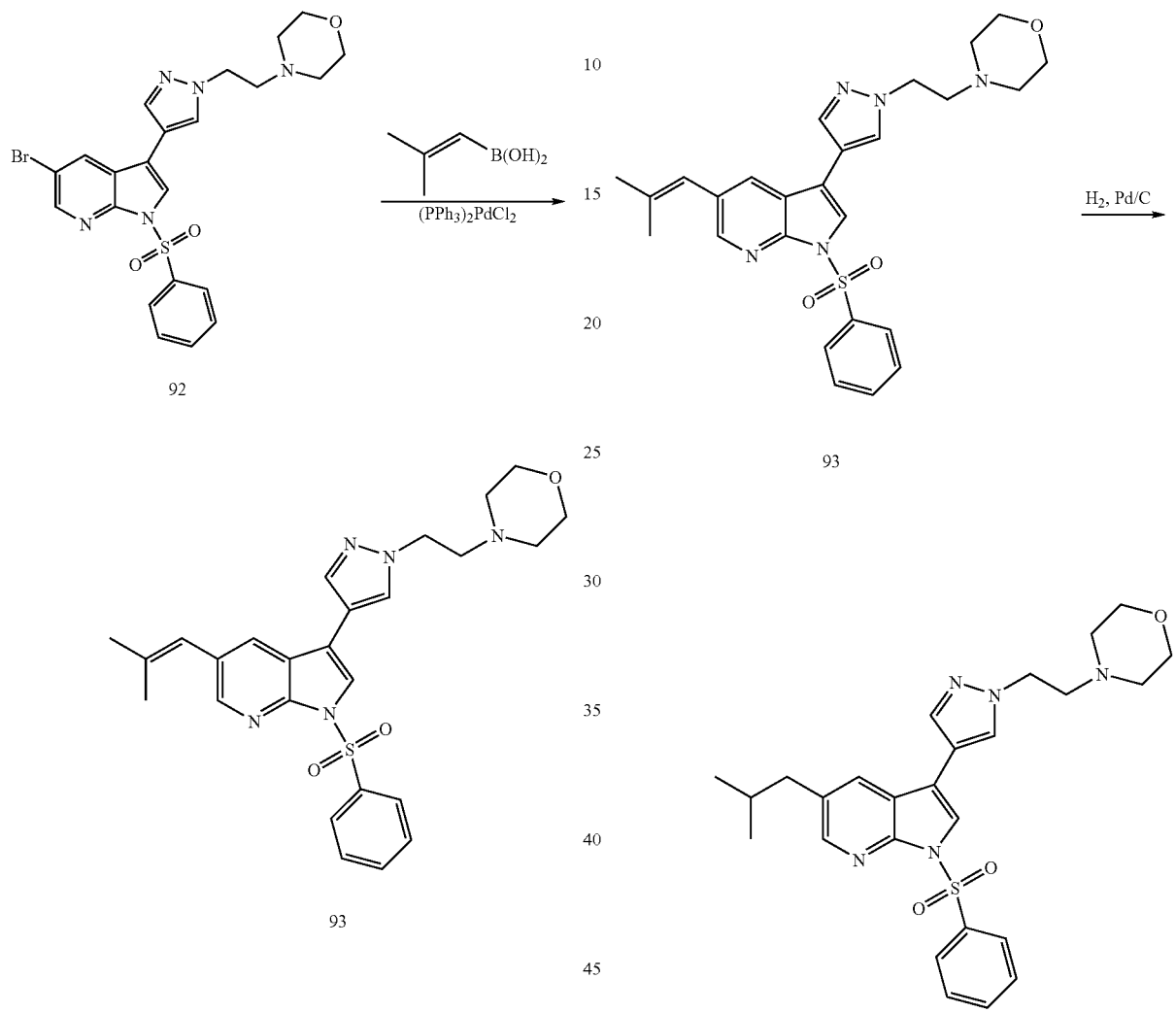

Bromide 92 (158 mg, 0.31 mmol; prepared in analogous way to 20), isobutenyl boronic acid (40 mg, 0.40 mmol) and (PPh$_3$)$_2$PdCl$_2$ (30 mg, 43 µmol) in toluene:EtOH 1:1 (2 mL) was added LiCl (50 mg, 1.18 mmol) and 1.0 M aq. Na$_2$CO$_3$ solution (0.5 mL). The mixture was refluxed (bath temperature 115° C.) for 3 h. Saturated aqueous NaHCO$_3$ (50 mL) was added, and the mixture was extracted with AcOEt (2×75 mL). The combined organic solutions were dried (MgSO$_4$) and concentrated to afford a brown solid (175 mg). The crude product was purified by SGC using MeOH:CH$_2$Cl$_2$:AcOEt=2:49:49 (v/v) as eluent to afford 93 as an off-white powder (99 mg, 0.20 mmol, 66%). $^1$H NMR (400 MHz, CDCl$_3$) δ 1.87 (s, 3H), 1.96 (s, 3H), 2.53 (t, J=4.6 Hz, 4H), 2.88 (t, J=6.6 Hz, 2H), 3.73 (t, J=4.6 Hz, 4H), 4.33 (t, J=6.6 Hz, 2H), 6.32 (1H, s, 1H), 7.51 (t, J=7.8 Hz, 2H), 7.60 (t, J=7.5 Hz, 1H), 7.77 (s, 2H), 7.78 (s, 1H), 7.80 (d, J=1.9 Hz, 1H), 8.23 (d, J=7.6 Hz, 2H), 8.37 (d, J=1.9 Hz, 1H).

To a solution of 93 (80 mg, 0.18 mmol) in MeOH (4 mL) was added 20% Pd(OH)$_2$ on C (30 mg, cat.), and the reaction mixture was stirred vigorously under H$_2$ for 24 h. The mixture was then filtered through Celite, which was then washed with MeOH:CH$_2$Cl$_2$=1:1 (v/v; 50 mL). The solutions were combined and concentrated to afford 94 as a foam (66 mg, 0.15 mmol, 82%). $^1$H NMR (400 MHz, CDCl$_3$) δ 0.84 (d, J=6.6 Hz, 2H), 1.40 (t, J=7.1 Hz, 3H), 1.80 (nonet, J=6.7 Hz, 1H), 2.50 (d, J=7.3 Hz, 2H), 2.49-2.60 (m, 4H), 2.84-3.06 (m, 2H), 3.63-3.76 (m, 4H), 4.29-4.46 (m, 2H), 7.42 (t, J=7.6 Hz, 2H), 7.50 (t, J=7.4 Hz, 1H), 7.66 (d, J=2.0 Hz, 1H), 7.68 (s, 1H), 7.71 (s, 1H), 7.76 (s, 1H), 8.03 (d, J=1.8 Hz, 1H), 8.14 (d, J=7.6 Hz, 1H), 8.20 (d, J=1.9 Hz, 1H).

145

5-Isobutyl-3-[1-(2-morpholin-4-yl-ethyl)-1H-pyrazol-4-yl]-1H-pyrrolo[2,3-b]pyridine (95)

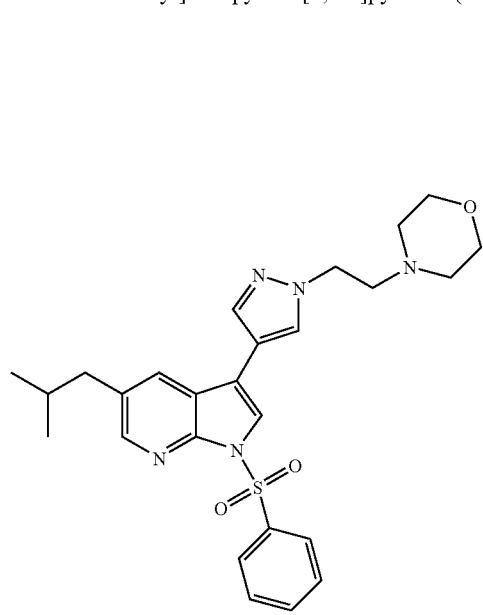

94

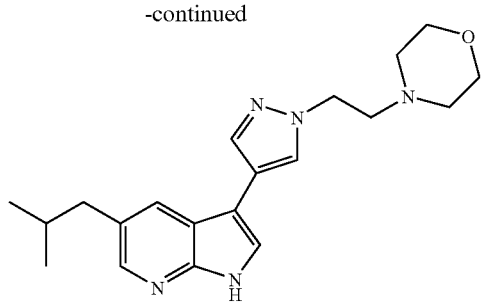

95

To a stirred solution of 94 (66 mg, 0.15 mmol) in EtOH (2 mL) was added 10% aq. NaOH (1 mL) and the reaction mixture heated to reflux for 2 h. The mixture was then cooled, AcOEt (50 mL) added, and the solution was washed with saturated aqueous NaHCO$_3$ (2×25 mL). The organic portion was dried (MgSO$_4$) and concentrated to afford 25 as an off-white solid (44 mg, 0.12 mmol, 83%). $^1$H NMR (400 MHz, CDCl$_3$) δ 0.88 (d, J=6.6 Hz, 2H), 1.85 (nonet, J=6.7 Hz, 1H), 2.46 (t, J=4.5 Hz, 4H), 2.55 (d, J=7.2 Hz, 2H), 2.81 (t, J=6.7 Hz, 2H), 3.66 (t, J=4.6 Hz, 4H), 4.26 (t, J=6.6 Hz, 2H), 7.32 (d, J=2.2 Hz, 1H), 7.68 (s, 1H), 7.70 (s, 1H), 7.76 (d, J=1.7 Hz, 1H), 8.10 (d, J=1.8 Hz, 1H), 9.52 (br s, 1H).

Synthesis of Example Inhibitor 98

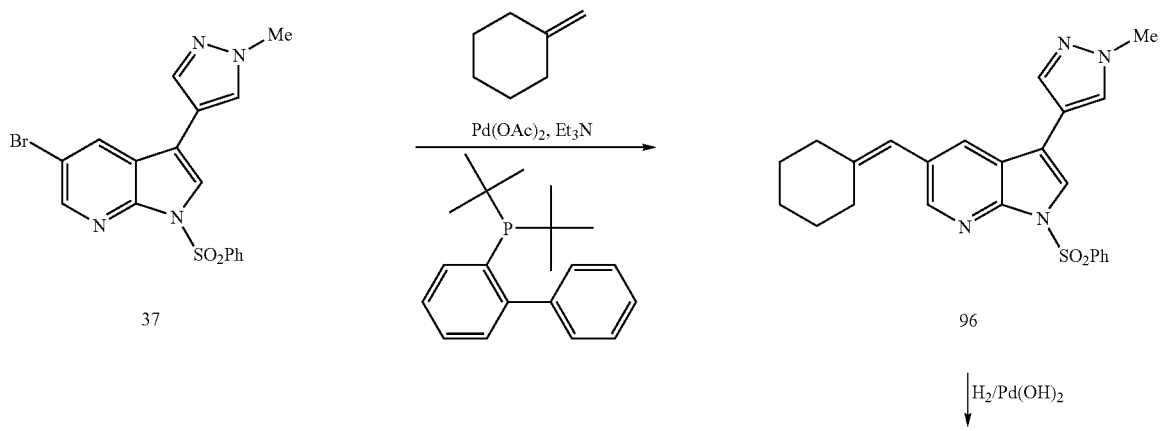

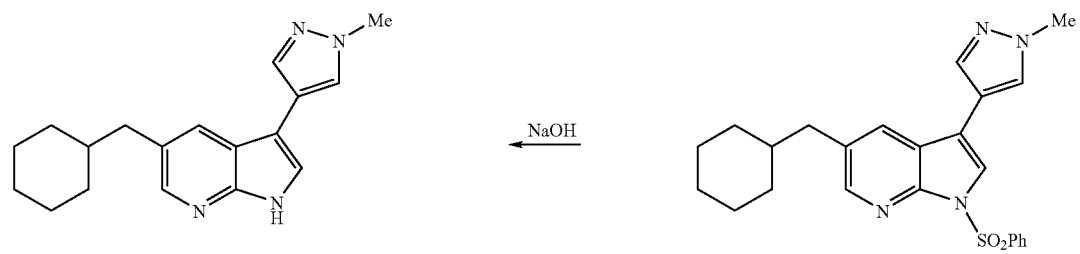

5-(cyclohexylidenemethyl)-3-(1-methyl-1H-pyrazol-4-yl)-1-(phenylsulfonyl)-1H-pyrrolo[2,3-b]pyridine (96)

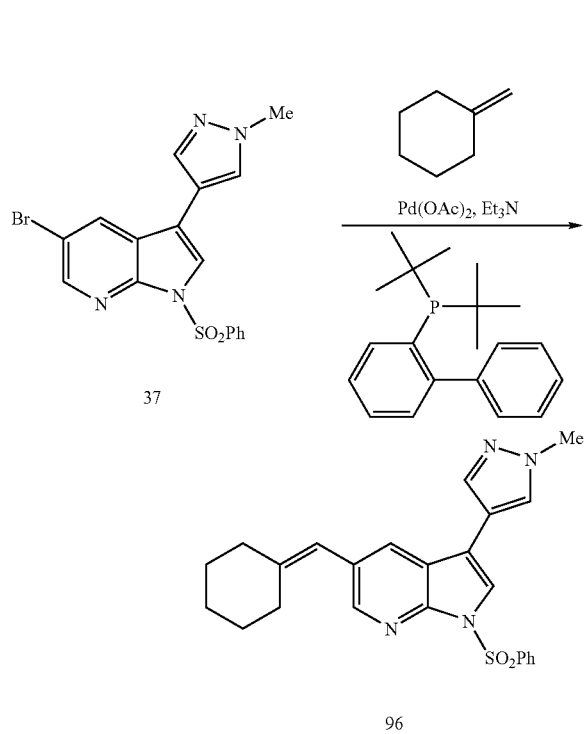

A mixture of 37 (100 mg, 0.24 mmol), methylenecyclohexane (23.1 mg, 0.48 mmol), Pd(OAc)$_2$ (5.39 mg, 0.024 mmol), biphenyl-2-yldi-tert-butylphosphine (14.3 mg, 0.048 mmol) and Et$_3$N (121.4 mg, 1.2 mmol) in DMF (2 mL) was irradiated in a microwave (120° C., 80 W) in a sealed tube for 5-min. The mixture was filtered and the product was isolated by reverse-phase LCMS (column LUNA 10 μ C18(2) 00G-4253-V0 250×50 mm) using water—acetonitrile (0.1% AcOH) as eluent (in gradient; flow 80 mL/min) to afford 96 (32 mg, 31%) as a solid; $^1$H NMR (400 MHz; CDCl$_3$) δ 1.34-1.43 (m, 2H), 1.43-1.56 (m, 4H), 2.11-2.23 (m, 4H), 3.85 (s, 3H), 6.10 (s, 1H), 7.32-7.38 (m, 2H), 7.40-7.46 (m, 1H), 7.49 (s, 1H), 7.59 (s, 1H), 7.60-7.62 (m, 2H), 8.05-8.09 (m, 2H), 8.17-8.19 (d, J=2.09 Hz, 1H). MS (CI) m/z 433 (MH$^+$).

5-(cyclohexylmethyl)-3-(1-methyl-1H-pyrazol-4-yl)-1-(phenylsulfonyl)-1H-pyrrolo[2,3-b]pyridine (97)

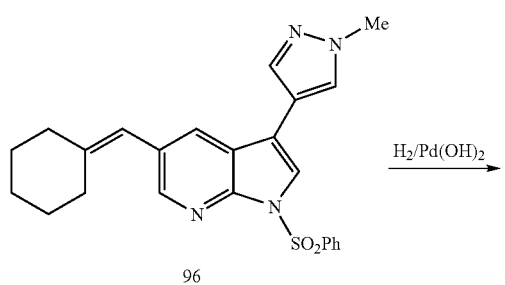

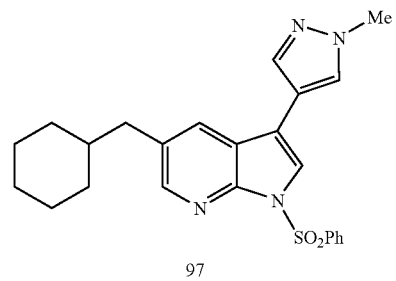

A mixture of 96 (32 mg, 0.073 mmol) and Pd(OH)$_2$ (1.0 mg, 7.3 μmol) in MeOH (2.0 mL) was stirred under H$_2$ at r.t. for 30.5 h. The mixture was filtered through Celite and concentrated to afford 97, which was used in the next step without purification.

5-(cyclohexylmethyl)-3-(1-methyl-1H-pyrazol-4-yl)-1H-pyrrolo[2,3-b]pyridine (98)

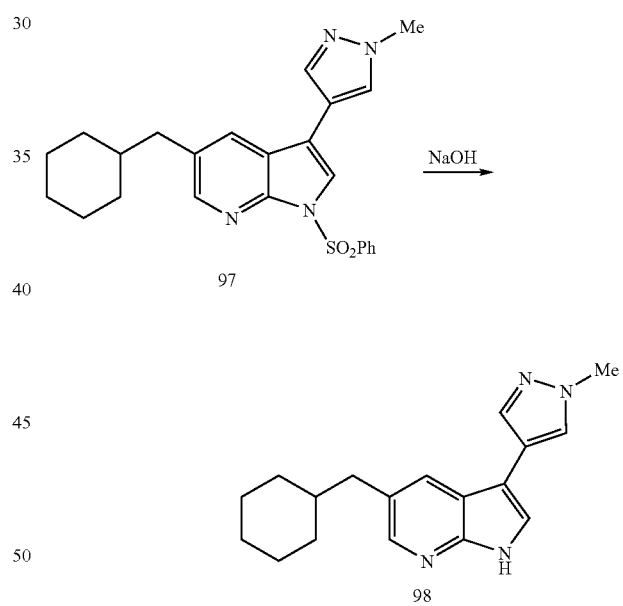

A mixture of 97 (25 mg, 0.0575 mmol) and 10% aq. NaOH (0.32 mL) in EtOH (2 mL) was refluxed (oil bath temperature 105° C.) for 30 min., cooled to r.t. and partitioned between water:AcOEt. The aqueous layer was extracted with AcOEt. The extract was dried (MgSO$_4$), concentrated and separated by means of PTLC using AcOEt as eluent to afford desired inhibitor 98 (2.23 mg, 11% over 2 steps) as a solid. $^1$H NMR (400 MHz; CDCl$_3$) δ 0.86-0.97 (m, 2H), 1.05-1.26 (m, 4H), 1.53-1.73 (m, 5H), 2.54 (d, J=7.1 Hz, 2H), 3.93 (s, 3H), 7.29 (d, J=2.3 Hz, 1H), 7.55 (s, 1H), 7.69 (d, J=0.5 Hz, 1H), 7.74 (d, J=1.9 Hz, 1H), 8.07 (d, J=1.8 Hz, 1H), 9.31 (bs, 1NH); MS (CI) m/z 295 (MH$^+$).

Synthesis of Example Inhibitor 100

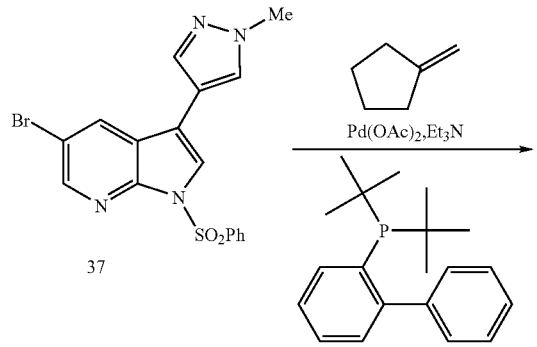

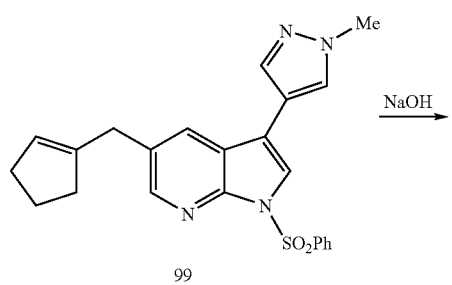

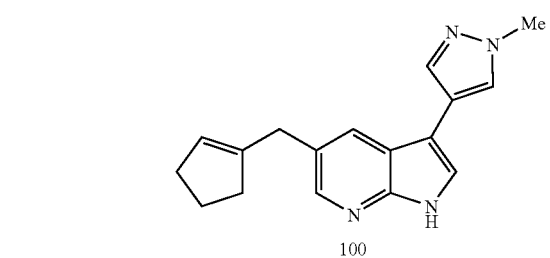

5-(cyclopentenylmethyl)-3-(1-methyl-1H-pyrazol-4-yl)-1-(phenylsulfonyl)-1H-pyrrolo[2,3-b]pyridine (99)

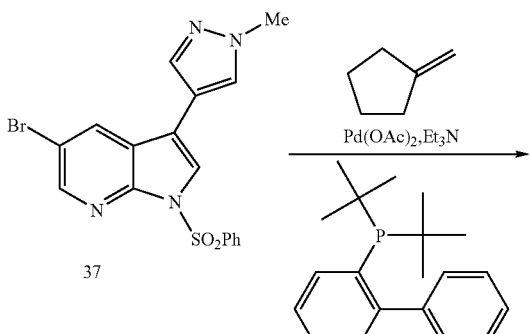

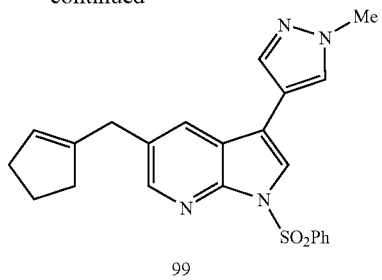

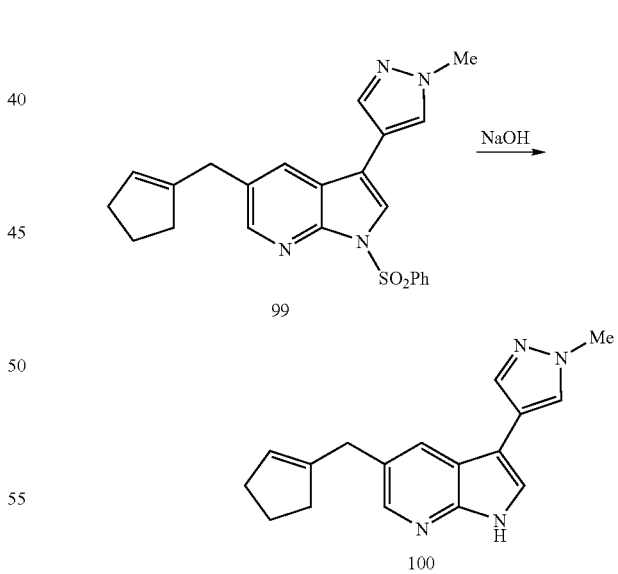

A mixture of 37 (100 mg, 0.24 mmol), methylenecyclopentane (19.72 mg, 0.48 mmol), Pd(OAc)$_2$ (5.39 mg, 0.024 mmol), biphenyl-2-yldi-tert-butylphosphine (14.3 mg, 0.048 mmol) and Et$_3$N (121.4 mg, 1.2 mmol) in DMF (2 mL) was irradiated in a microwave (110° C., 80 W) in a sealed tube for 19 h. The mixture was partitioned between AcOEt (10 mL) saturated aqueous NH$_4$Cl. The aqueous layer was extracted with AcOEt. The combined organic solutions were dried (MgSO$_4$), concentrated and the product was isolated by reverse-phase LCMS (column LUNA 10, C18(2) 00G-4253-V0 250×50 mm) using water—acetonitrile (0.1% AcOH) as eluent (in gradient; flow 80 mL/min) to afford 99 (22.70 mg, 23%) as a solid. $^1$H NMR (400 MHz; CDCl$_3$) δ 1.86-1.91 (m, 2H), 2.17-2.25 (m, 2H), 2.27-2.35 (m, 2H), 3.46-3.50 (m, 2H), 4.01 (s, 3H), 5.30-5.37 (m, 1H), 7.48-7.55 (m, 1H), 7.56-7.61 (m, 1H), 7.65 (s, 1H), 7.52-7.83 (m, 3H), 8.21-8.23 (m, 2H), 8.23-8.25 (m, 1H), 8.32 (d, J=2.1 Hz, 1H). MS (CI) m/z 419 (MH$^+$).

5-(cyclopentenylmethyl)-3-(1-methyl-1H-pyrazol-4-yl)-1H-pyrrolo[2,3-b]pyridine (100)

A mixture of 99 (22.70 mg, 0.054 mmol) and 10% aq. NaOH (0.60 mL) in EtOH (1.43 mL) was refluxed (oil bath temperature 105° C.) for 30 min., cooled to r.t. and partitioned between water:AcOEt. The aqueous layer was extracted with AcOEt. The extract was dried (MgSO$_4$), concentrated and separated by means of PTLC using AcOEt as eluent to afford desired inhibitor 100 (4.29 mg, 44%) as a solid. $^1$H NMR (400 MHz; CDCl$_3$) δ 1.77-1.84 (m, 2H), 2.12-2.21 (m, 2H), 2.21-

2.28 (m, 2H), 3.42-3.46 (m, 2H), 3.92 (s, 3H), 5.25-5.29 (m, 1H), 7.30 (d, J=2.5 Hz, 1H), 7.55 (s, 1H), 7.68 (s, 1H), 7.87 (d, J=1.7 Hz, 1H), 8.12 (d, J=1.8 Hz, 1H), 9.16 (bs, 1NH). MS (CI) m/z 279 (MH$^+$).

Biological Activity

JNK1, JNK2, JNK3—SPA Assay

1. Compound is dissolved in DMSO to a convenient concentration and this is diluted in 10% DMSO to a five times concentrate of the desired starting concentration (frequently 1:100).
2. 10 µl of 500 mM EDTA is added to alternative wells of the Opti-plate row, which will receive kinase reaction plus DMSO. This creates the negative control.
3. For the JNK2 and JNK3 assay, compounds are prepared in six 2-fold dilutions with water and each concentration is tested in duplicate. For the JNK1 assay compounds are prepared in four 5-fold dilutions with water which are tested in triplicate. Controls are treated identically.
4. 20 µl per well of each compound concentration is transferred to an Opti-plate, in duplicate.
5. 30 µl (JNK2/3 SPA) or 50 µl (JNK1 SPA) of substrate solution (25 mM HEPES pH 7.5, 10 mM magnesium acetate with 3.33 µM ATP (JNK2/3) or 2 µM ATP (JNK1), approximately 7.5 kBq [γ-$^{33}$P]ATP, GST-c-Jun, in water) is added to each well.
6. 50 µl (JNK2/3 SPA) or 30 µl (JNK1 SPA) of kinase solution (JNK in 25 mM HEPES pH 7.5, 10 mM Mg Acetate) is added to each well.

| Kinase | Kinase per well (µg) | GST-c-Jun per well (µg) |
|---|---|---|
| JNK1 | 0.25 | 1 |
| JNK2 | 0.2 | 1.2 |
| JNK3 | 0.16 | 1.2 |

7. The plate is incubated for 30 minutes at room temperature.
8. 100 µl of bead/stop solution is added to each well (5 mg/ml glutathione-PVT-SPA beads, 40 mM ATP in PBS).
9. Plates are sealed and incubated for 30 minutes at room temperature, centrifuged for 10 minutes at 2500 g and counted.
10. The IC$_{50}$ values are calculated as the concentration of the compound being tested at which the phosphorylation of c-Jun is decreased to 50% of the control value. Example IC$_{50}$ values for the compounds of this invention are given in Table 1.

p38 ELISA

Active p38 kinase (100 ng; Upstate) was added to 2 µg GST-ATF2 substrate (NEB) in 250 mM Hepes pH 7.5/100 mM MgAc/50 µM ATP (final) in the presence or absence of compounds in 50 µl. The mixture was incubated at 30° C. for 1 hour, and then diluted with 200 µl PBS-Tween (0.05%). From this, duplicate volumes of 100 pt were added to a Reacti-Bind glutathione coated plate (Pierce) and incubated for 1 hour. After washing 3 times with PBS-Tween (0.05%), rabbit anti-phospho-ATF2 (Thr71) antibody (NEB) was added at 1:500, and incubated for another hour at room temperature. After 3 additional washes with PBS-Tween (0.05%), 100 µl of anti-rabbit IgG alkaline phosphatase-conjugated secondary antibody (Sigma) was added at 1:1000, the reaction was incubated for a further hour, washed 3 times, and then phosphatase substrate (Sigma) was added (100 µl per well; 3 tablets in 5 ml water). After incubation in the dark at 37° C. for 1 hour, the reaction mixture was transferred to a clear 96 well plate, and the absorbance at 405 nm was read. The IC$_{50}$ values are calculated as the concentration of the compound being tested at which the phosphorylation of ATF2 is decreased to 50% of the control value. Example IC$_{50}$ values for the compounds of this invention are given in Table 1.

TABLE 1

IC$_{50}$ values for selected compounds against JNK3.

| Compound | JNK3 IC$_{50}$ (nM) | Compound | JNK3 IC$_{50}$ (nM) |
|---|---|---|---|
| (structure) | <500 | (structure) | <200 |
| (structure) | <1000 | (structure) | <200 |
| (structure) | <200 | (structure) | <1000 |
| (structure) | <500 | (structure) | <1000 |

TABLE 1-continued

IC$_{50}$ values for selected compounds against JNK3.

| Compound | JNK3 IC$_{50}$ (nM) | Compound | JNK3 IC$_{50}$ (nM) |
|---|---|---|---|
| (structure) | <500 | (structure) | <500 |
| (structure) | <500 | (structure) | <2000 |
| (structure) | <1000 | (structure) | <500 |
| (structure) | <500 | (structure) | <200 |

TABLE 1-continued
IC$_{50}$ values for selected compounds against JNK3.
| Compound | JNK3 IC$_{50}$ (nM) | Compound | JNK3 IC$_{50}$ (nM) |
|---|---|---|---|
| 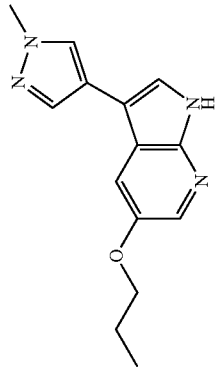 | <500 | 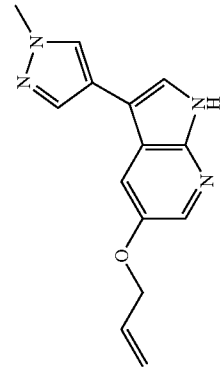 | <500 |
| 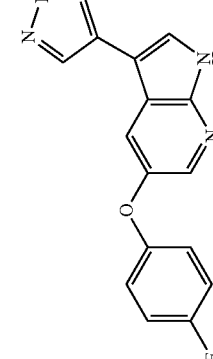 | <2000 | 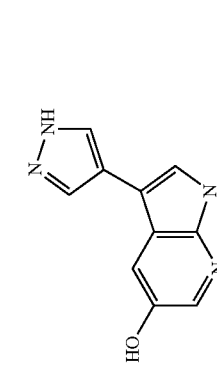 | <500 |
| 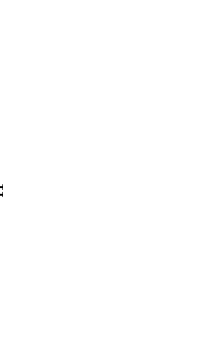 | <200 | 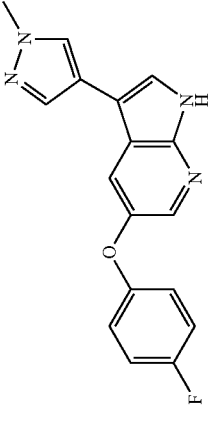 | <1000 |
| 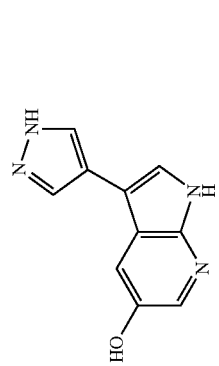 | <500 |  | <2000 |

TABLE 1-continued

IC$_{50}$ values for selected compounds against JNK3.

| Compound | JNK3 IC$_{50}$ (nM) | Compound | JNK3 IC$_{50}$ (nM) |
|---|---|---|---|
| (structure) | <500 | (structure) | <500 |
| (structure) | <500 | (structure) | <100 |
| (structure) | <100 | (structure) | <200 |
| (structure) | <500 | (structure) | <1000 |

TABLE 1-continued

IC$_{50}$ values for selected compounds against JNK3.

| Compound | JNK3 IC$_{50}$ (nM) | Compound | JNK3 IC$_{50}$ (nM) |
|---|---|---|---|
| | <1000 | | <100 |
| | <500 | | <200 |
| | <500 | | <1000 |
| | <200 | | <100 |

TABLE 1-continued
IC$_{50}$ values for selected compounds against JNK3.
| Compound | JNK3 IC$_{50}$ (nM) | Compound | JNK3 IC$_{50}$ (nM) |
|---|---|---|---|
| 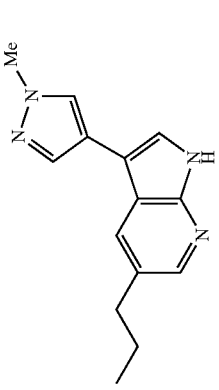 | <100 | 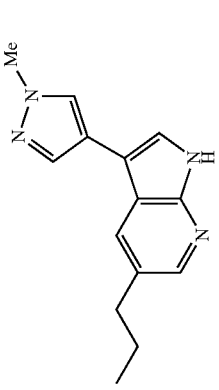 | <100 |
| 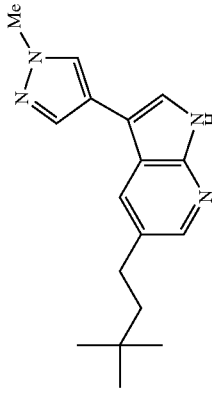 | <200 | 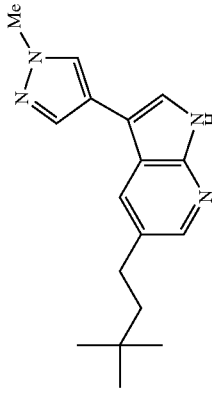 | <500 |
| 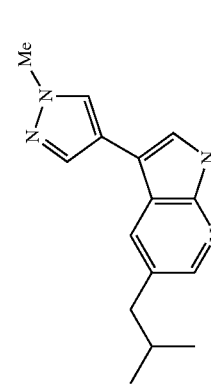 | <1000 | 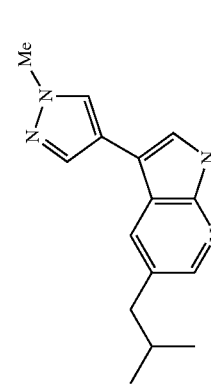 | <100 |
| 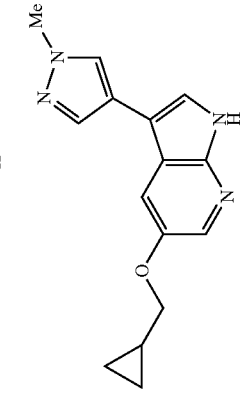 | <200 | 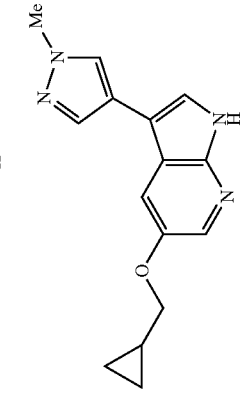 | <500 |

TABLE 1-continued

IC$_{50}$ values for selected compounds against JNK3.

| Compound | JNK3 IC$_{50}$ (nM) | Compound | JNK3 IC$_{50}$ (nM) |
|---|---|---|---|
| (structure) | <500 | (structure) | <1000 |
| (structure) | <500 | (structure) | <200 |
| (structure) | <500 | (structure) | <200 |

TABLE 1-continued

IC₅₀ values for selected compounds against JNK3.

| Compound | JNK3 IC₅₀ (nM) | Compound | JNK3 IC₅₀ (nM) |
|---|---|---|---|
| | <200 | | <200 |
| | <200 | | <200 |
| | <500 | | <100 |

TABLE 1-continued

IC$_{50}$ values for selected compounds against JNK3.

| Compound | JNK3 IC$_{50}$ (nM) | Compound | JNK3 IC$_{50}$ (nM) |
|---|---|---|---|
| (morpholine-ethyl-pyrazole-pyrrolopyridine) | <100 | (N-Me-pyrazole-pyrrolopyridine with cyclohexylmethyl) | <100 |
| (N-Me-pyrazole-pyrrolopyridine with cyclopentylmethyl) | <200 | (N-Me-pyrazole-pyrrolopyridine with cyclobutylmethyl) | <200 |
| (N-Me-pyrazole-pyrrolopyridine with cyclopentenylmethyl) | <200 | (N-Me-pyrazole-pyrrolopyridine with cyclohexenylmethyl) | <200 |
| (N-Me-pyrazole-pyrrolopyridine with N-benzylpiperidinylmethyl) | <200 | | |

The invention claimed is:

1. A compound of formula (I):

(I)

wherein X is O, S, C(R$^4$)$_2$, SO, SO$_2$ or NR$^3$, NR$^3$—C(O)— or NR$^3$—C(O)—O—, in which said NR$^3$, NR$^3$—C(O)— or NR$^3$—C(O)—O— is directly attached via the nitrogen atom to the pyrrolopyridine ring of the compound of formula (I);

R$^1$ is C$_{1-10}$ alkyl, C$_{2-10}$ alkenyl, C$_{2-10}$ alkynyl, phenyl or naphthyl, C$_{3-10}$ cycloalkyl, C$_{3-10}$ cycloalkenyl or indole, indoline, piperdine, piperazine or morpholine;

said R$^1$ group being optionally substituted with one or more of C$_{1-6}$ alkyl, C$_{1-10}$ alkoxy, C$_{3-10}$ cycloalkyl, halo, hydroxy, oxo, CO$_2$R$^5$, C$_{3-10}$aryl, C$_{1-6}$alkylC$_{3-10}$aryl, and NR$^6$$_2$;

and R$^2$ is pyrazole;

said R$^2$ group being optionally substituted with one or more of C$_{1-6}$ alkyl, CO$_2$H, and C$_{1-6}$alkyl morpholinyl;

wherein

R$^3$ is hydrogen or C$_{1-6}$ alkyl;
R$^4$ is hydrogen or C$_{1-6}$ alkyl;
R$^5$ is hydrogen or C$_{1-6}$ alkyl; and
R$^6$ is hydrogen or C$_{1-6}$ alkyl.

2. A compound as claimed in claim 1 wherein R$^1$ is an unbranched alkyl group having 2, 3, 4, 5 or 6 carbon atoms.

3. A compound as claimed in claim 1 wherein R$^1$ is an unbranched alkenyl or alkynyl group having 2, 3, 4, 5 or 6 carbon atoms.

4. A compound as claimed in claim 1 wherein R$^1$ is a C$_5$ or C$_6$ cycloalkyl or phenyl or naphthyl optionally substituted with one or more of C$_{1-4}$ alkyl or a halogen.

5. A compound as claimed in claim 4 wherein R$^1$ is phenyl, in which the phenyl is substituted at the ortho or para position.

6. A compound as claimed in claim 4 wherein R$^1$ is phenyl.

7. A compound as claimed in claim 1 wherein R$^2$ is substituted with C$_{1-6}$ alkyl at any available N.

8. A compound as claimed in claim 1 wherein R$^2$ is optionally substituted with an alkyl group having 1, 2, 3, 4, 5 or 6 carbon atoms.

9. A compound as claimed in claim 8 wherein said optional substitution of claim 10 occurs at any available N in the pyrazole of R$_2$.

10. A compound as claimed in claim 8 wherein R$^2$ is C$_{1-6}$alkylmorpholinyl.

11. A compound of formula II (II)

wherein R$^1$ is phenyl or C$_{1-10}$ alkyl optionally substituted with one or more of halo or CO$_2$R$^4$;

wherein R$^4$ is hydrogen or C$_{1-6}$ alkyl,
R$^3$ is hydrogen or C$_{1-6}$ alkyl,
and R$^2$ is pyrazole optionally substituted with one or more of C$_{1-6}$ alkyl.

12. A compound as claimed in claim 11 wherein R$^1$ is a branched alkyl having 3, 4, 5 or 6 carbon atoms.

13. A compound selected from

-continued
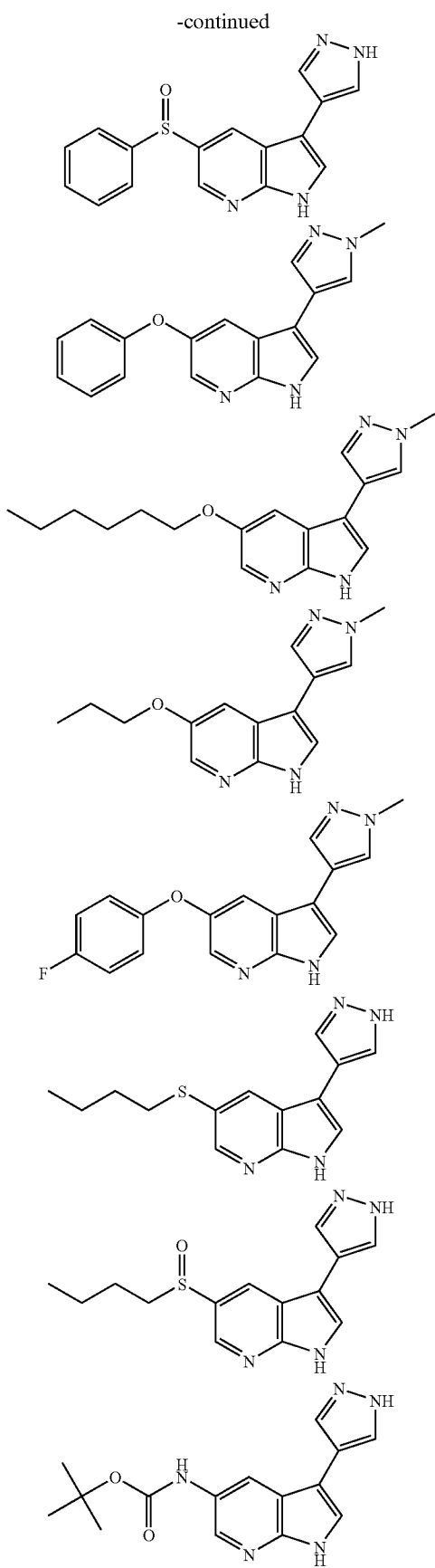
-continued
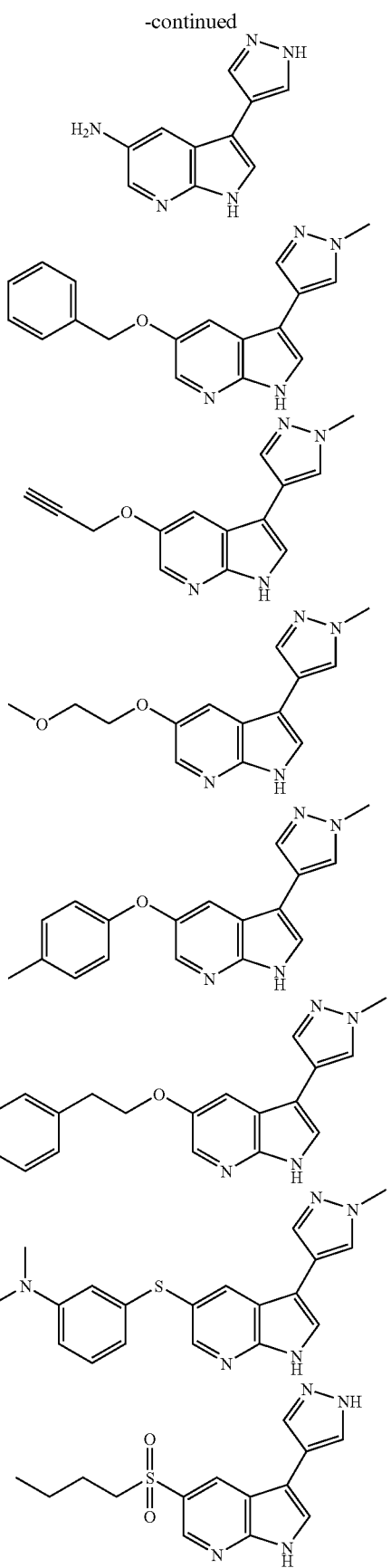

-continued
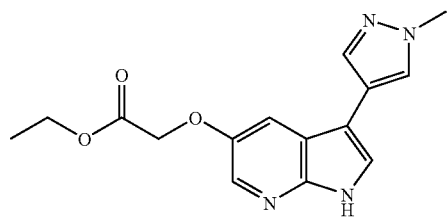
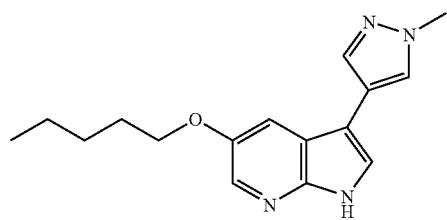
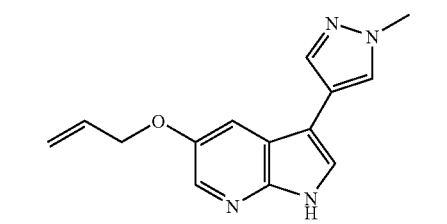
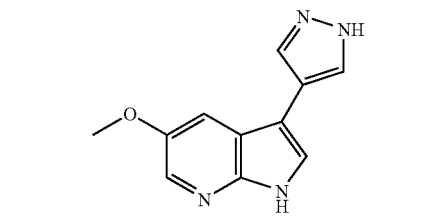
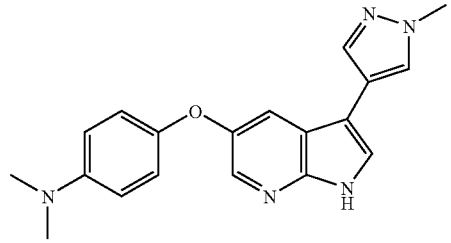
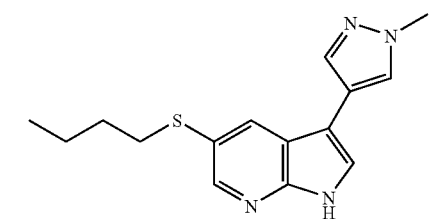
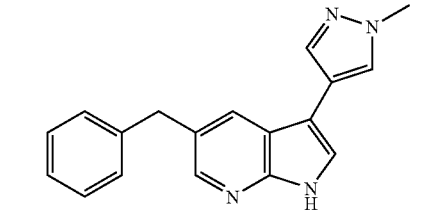
-continued
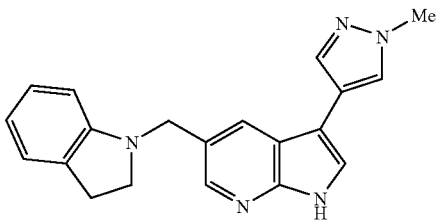
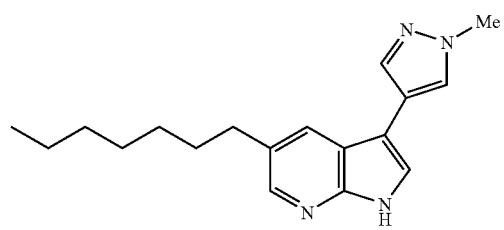
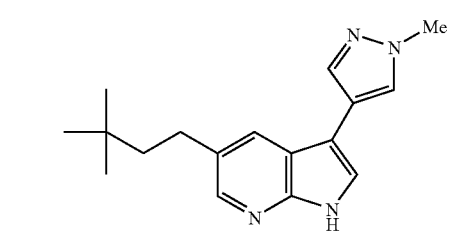
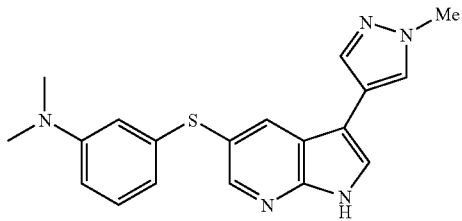
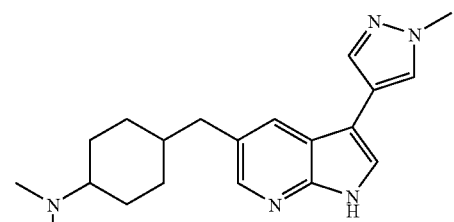
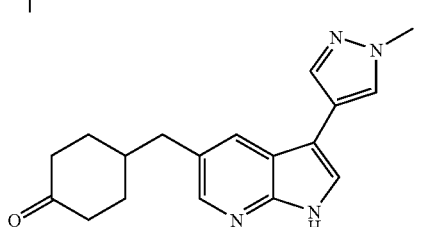
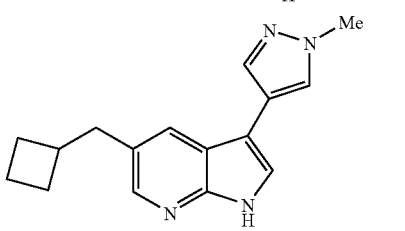

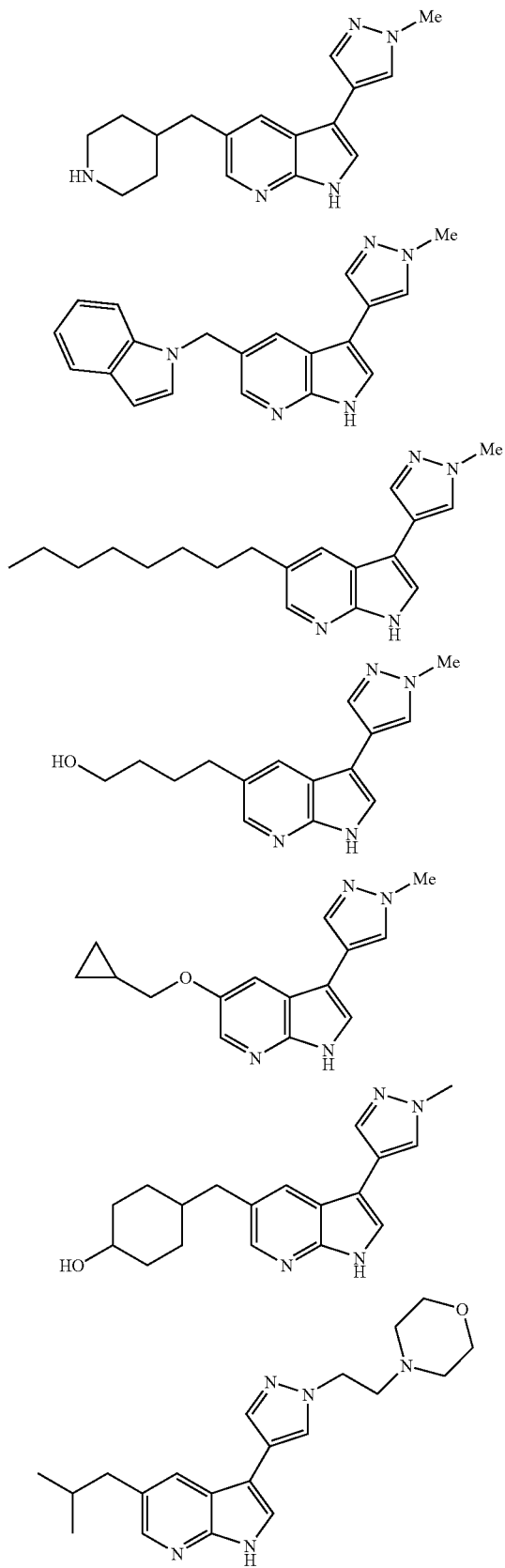
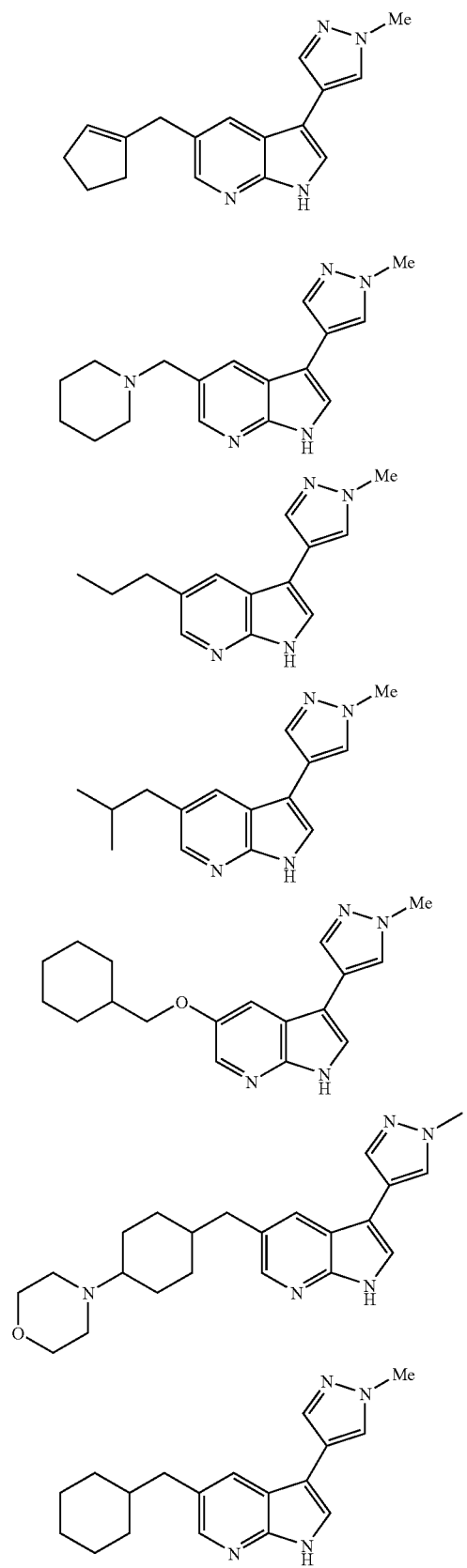

-continued
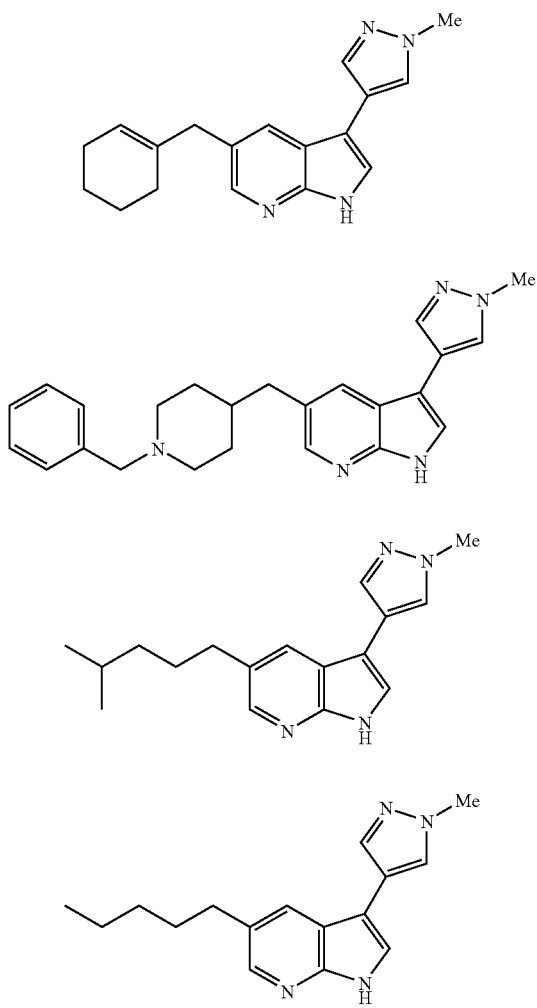
-continued
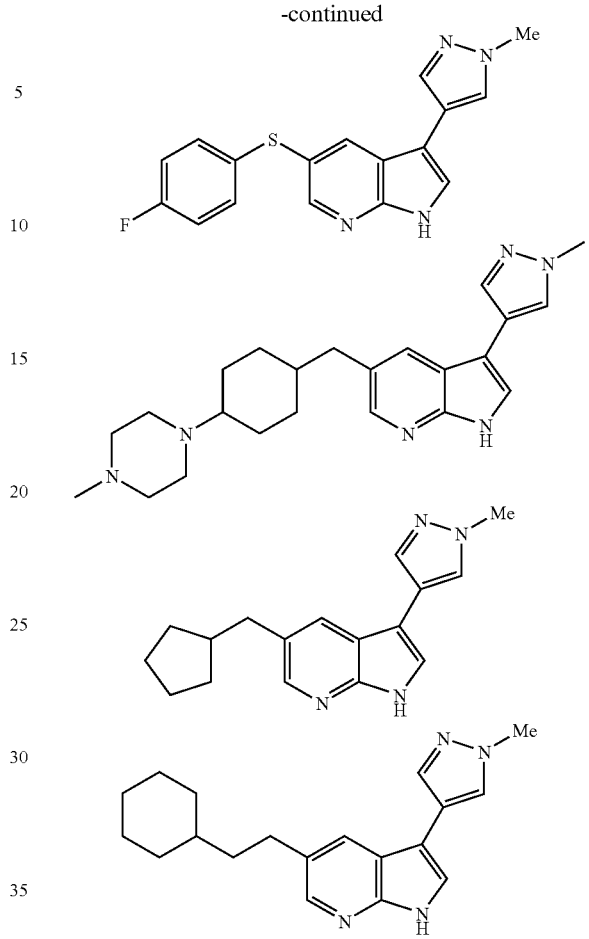
14. A composition comprising a compound as defined in claim 13 in combination with a pharmaceutically acceptable carrier, diluent or excipient.
* * * * *

UNITED STATES PATENT AND TRADEMARK OFFICE
CERTIFICATE OF CORRECTION

PATENT NO. : 7,645,769 B2  Page 1 of 1
APPLICATION NO. : 11/499334
DATED : January 12, 2010
INVENTOR(S) : Khan et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by (97) days Delete the phrase "by 97 days" and insert -- by 135 days --

Signed and Sealed this

Twenty-fourth Day of August, 2010

David J. Kappos
*Director of the United States Patent and Trademark Office*